US006156551A

United States Patent [19]
Neel et al.

[11] Patent Number: 6,156,551
[45] Date of Patent: Dec. 5, 2000

[54] ACTIVATED MUTANTS OF SH2-DOMAIN-CONTAINING PROTEIN TYROSINE PHOSPHATASES AND METHODS OF USE THEREOF

[75] Inventors: Benjamin G. Neel, Wayland; Alana M. O'Reilly, Watertown; Steven Shoelson, Natick; Scott Pluskey, Allston, all of Mass.

[73] Assignees: Beth Israel Deaconess Medical Center; Joslin Diabetes Center, both of Boston, Mass.

[21] Appl. No.: 09/092,443

[22] Filed: Jun. 5, 1998

[51] Int. Cl.$^7$ .................................................. C12N 9/16
[52] U.S. Cl. ............................................................ 435/196
[58] Field of Search ............................................. 435/196

[56] References Cited

U.S. PATENT DOCUMENTS

| | | | |
|---|---|---|---|
| 5,536,636 | 7/1996 | Freeman, Jr. et al. | 435/6 |
| 5,589,375 | 12/1996 | Ullrich et al. | 435/240.2 |
| 5,659,012 | 8/1997 | Klingmüller et al. | 530/327 |

FOREIGN PATENT DOCUMENTS

| | | |
|---|---|---|
| WO 98/04712 | 2/1998 | European Pat. Off. . |
| WO 98/14596 | 4/1998 | European Pat. Off. . |

OTHER PUBLICATIONS

Rudinger, p. of Peptide Hormones, Parsons, Ed., University Park Press, Jun. 1976.

Matthews et al., "Characterization of hematopoietic intracellular protein tyrosine phosphatases: description of a phosphatase containing an SH2 domain and another enriched in proline–, glutamic acid–, serine–, and threonine–rich sequences," Mol. Cell. Bi, 1992.

Bastien et al., "Cloning, expression and mutational analysis of SH–PTP2, human protein–tyrosine phosphatase," Biochem. Biophys. Res. Commun. 196, 124–133, 1993.

Thornton et al., "Protein engineering," Cur. Opinion Biotech., vol. 6, No. 4, pp. 367–369, Aug. 1995.

Aoki et al., EMBL accession No. P81718, submitted Nov. 1996.

Neel, B. G. et al., "Protein tyrosine phosphatases in signal transduction," Current Opinion in Cell Biology, 9:193–204 (1997).

Freeman, R. M. et al., "Indentification of a human src homology 2–containing protein–tyrosine–phosphatase: A putative homolog of Drosophila corkscrew," Proc. Natl. Acad. Sci. USA, 89:11239–11243 (1992).

Tang, T. L. et al., "The SH2–containing protein–tyrosine phosphatase SH–PTP2 is required upstream of MAP kinase for early Xenopus development," Cell, 80:473–483 (1995).

O'Reilly, A. M. et al., "Structural determinants of SHP–2 function and specificity in Xenopus mesoderm induction," Molecular and Cellular Biology, 18:161–177 (1998).

Hof, P. et al., "Crystal structure of the tyrosine phosphatase SHP–2," Cell, 92:441–450 (1998).

Schlessinger, J. et al., "Growth factor signaling by receptor tyrosine kinases," Neuron, 9:383–391 (1992).

Denu, J. M. et al., "Form and function in protein dephosphorylation," Cell, 87:361–364 (1996).

Lorenz, U. et al., "Genetic analysis reveals cell type–specific regulation of receptor tyrosine kinase c–Kit by the protein tyrosine phosphatase SHP1," J. Exp. Med., 184:1111–1126 (1996).

Paulson, R. F. et al., "Signalling by the W/Kit receptor tyrosine kinase is negatively regulated in vivo by the protein tyrosine phosphatase Shpl," Nature Genetics, 13:309–315 (1996).

Neel, B. G., "Structure and function of SH2–domain containing tyrosine phosphatases," Seminars in Cell Biology, 4:419–432 (1993).

Flint, A. J. et al., "Development of "substrate–trapping" mutants to identify physiological substrates of protein tyrosine phosphatases," Proc. Natl. Acad. Sci. USA, 94:1680–1685 (1997).

Feng, G. S. et al., "Phosphotyrosine phosphatases with SH2 domains: regulators of signal transduction," TIG, 10:54–58 (1994).

Lechleider, R. J. et al., "Activation of the SH2–containing phosphotyrosine phosphatase SH–PTP2 by its binding site, phosphotyrosine 1009, on the human platelet–derived growth factor receptor $\beta^*$," J. Biol. Chem., 268:21478–21481 (1993).

Garton, A. J. et al., "Identification of P130$^{cas}$ as a substrate for the cytosolic protein tyrosine phosphatase PTP–PEST," Molecular and Cellular Biology, 16:6408–6418 (1996).

Barford, D. et al., "Revealing mechanisms for SH2 domain–mediated regulation of the protein tyrosine phosphatase SHP–2," Structure, 6:249–254 (1998).

Amaya, E. et al., "Expression of a dominant negative mutant of the FGF receptor disrupts mesoderm formation in Xenopus embryos," Cell, 66:257–270 (1991).

Lamb, T. M. et al., "Fibroblast growth factor is a direct neural inducer, which combined with noggin generates anterior–posterior neural pattern," Development 121:3627–3636 (1995).

Nieuwkoop, P. D., "Inductive interactions in early amphibian development and their general nature," J. Embryol. Exp. Morph. Suppl. 89:333–347 (1985).

(List continued on next page.)

Primary Examiner—Ponnathapu Achutamurthy
Assistant Examiner—Christian L. Fronda
Attorney, Agent, or Firm—Hamilton, Brook, Smith & Reynolds, P.C.

[57] ABSTRACT

The invention relates to novel mutant SH2 domain containing protein tyrosine phosphatases wherein the phosphatase is partially or constitutively active; and whose ability to regulate biological processes are different from the wildtype protein tyrosine phosphatases. The invention also relates to methods of use of the novel mutants, for example, in in vitro assays to screen for binding partners and inhibitors of protein tyrosine phosphatases and in the treatment of protein tyrosine phosphatase mediated diseases or conditions.

58 Claims, 32 Drawing Sheets

OTHER PUBLICATIONS

Amaya, E. et al., "FGF signalling in the early specification of mesoderm in Xenopus," *Development* 118:477–487 (1993).

Klein, P. S. et al., "Hormonal regulation of embryogenesis: The formation of mesoderm in *Xenopus laevis*," *Endocrine Reviews* 15:326–341 (1994).

Smith, J. C. et al., "Mesoderm–inducing factors and mesodermal patterning," *Current Opinion in Cell Biology*, 7:856–861 (1995).

Isaacs, H. V., "New perspectives on the role of the fibroblast growth factor family in amphibian development," *Cell. Mol. Life Sci.* 53: 350–361 (1997).

Kroll, K. L. et al., "Transgenic Xenopus embryos from sperm nuclear transplantations reveal FGF signalling requirements during gastrulation," *Development*, 122:3173–3183 (1996).

Kengaku, M. et al., "bFGF as a possible morphogen for the anteroposterior axis of the central nervous system in Xenopus," *Development* 121:3121–3130 (1996).

```
1         11        21        31        41        51        61        71        81
MTSRRWFHPNITGVEAENLLLTRGVDGSFLARPSKSNPGDFTLSVRRNGAVTHIKIQNTGDYYDLYGGEKFATLAELVQYYMEH
   MVRWFHRDLSGLDAETLLKGRGVHGSFLARPSRKNQGDFSLSVRVGDQVTHIRIQNSGDFYDLYGGEKFATLTELVEYYTQQ
MSSRRWFHPTISGIEAEKLLQEQGFDGSFLARLSSSNPGAFTLSVRRGNEVTHIKIQNNGDFFDLYGGEKFATLPELVQYYMEN 101       111       121       131       141       151       161
HGQLKERNGDVIELKYPLNCADPTSERWFHGHLSGKEAEKLLTEKGKHGSFLVRESQSHPGDFVLSVRTGDDKGESNDGKSXVT
QGVLQDRDGTIIHLKYPLNCSDPTSERWYHGHMSGGQAETLLQAKGEPWTFLVRESLSQPGDFVLSVLSDQPKAGPGSPL.RVT
.GELKEKNGIAIELKQPLICAEPTTERWFHGNLSGKEAEKLILERGXNGSFLVRESQSKPGDFVLSVRT.DD.........KVT 171       181       191       201       211       221       231       241       251
HVMIRCQELKYDVGGGERFDSLTDLVEHYKKNPMVETLGTVLQLKQPLNTTRINAAEIESRVRELSKLAETTDKVKQGFWEEFE
HIKVMCEGGRYTVGGLETFDSLTDLVEHFKKTGIEEASGAFVYLRQPYYATRVNAADIENRVLELNKKQESEDTAKAGFWEEFE
HVMIRWQDKKYDVGGGESFGTLSELIDHYKRNPMVETCGTVVHLRQPFNATRITAAGINARVEQL.........VKGGFWEEFE

-  -         -         -           ----   -
TLQQQECKL.....LYSRKEGQRQENKNKNRYKNILPFDHTRVVLHDGDPNEPVSDYINANIIMPEFETKCNNSKPKKSYIATQ
SLQKQEVRN.....LHQRLEGQRPENKGKNRYKNILPFDHSRVILQGRDSNIPGSDYINANYIKNQLLGPDENAK...TYIASQ
SLQQDSRD......TFSRNEGYKQENRLKNRYRNILPYDHTRVKLLDVEHSVAGAEYINANYRIL -- (158) -- GCLLTQ 341       351       361       371       381       391       401       411
GCLQNTVNDFWRMVFQENSRVIVMTTKEVERGKSKCVKYWPDEY.ALKEY..GVMRVRNYKESAAHDYTLRELKLSKVGQGNT.
GCLEATVNDFWQMAWQENSRVIVMTTREVEKGRNKCVPYWPEVG.MQRAY..GPYSVTNCGEHDTTEYKLRTLQVSPLDNGDL.
..QVNTVTDFWNMVWQENTRVIYMTTKEYERGKEKCARYWPDEG.RSEQF..GHARIQCVSENSTSDYTLREFLVS...WRDQ.

421       431       441       451        471       481
..ERTVMQYHFRTWPDHGVPSDPGGVLDFLEEVHHKQEST....MDAGPVVVHCSAGIGRTGTFIVIDILIDIIREKGVDCDID
..IREIWHYQYLSWPDHGVPSEPGGVLSFLDQINQRQESL....PHAGPIIVHCSAGIGRTGTIIVIDMLMENISTKGLDCDID
.PARRIFHYHFQVWPDHGVPADPGCVLNFLQDVNTRQSHLAQAGEKPGPICVHCSAGIGRTGTFIVIDMILDQIVRNGLDTEID 491        511       521
VPKTIQMVRSQRSGMVQTEAQYRFIYMAVQHYIET
IQKTIQMVRAQRSGMVQTEAQYKFIYVAIAQFIET
IQRTIQMVRSQRSGLVQTEAQYKFVYYAVQHYIQT
```

Figure 2A

```
              1        ▪  ▪▪▪                                                        50
SHP-2   MTSRRWFHPN  ITGVEAENLL  LTRGVDGSFL  ARPSKSNPGD  FTLSVRRNGA
SHP-1   ..MVRWFHRD  LSGLDAETLL  KGRGVHGSFL  ARPSRKNQGD  FSLSVRVGDQ
Csw     MSSRRWFHPT  ISGIEAEKLL  QEQGFDGSFL  ARLSSSNPGA  FTLSVRRGNE

51    ▪▪▪  ▪▪▪         ▪▪  ▪▪▪▪▪▪▪                                     100
SHP-2   VTHIKIQNTG  DYYDLYGGEK  FATLAELVQY  YMEHHGQLKE  KNGDVIELKY
SHP-1   VTHIRIQNSG  DFYDLYGGEK  FATLTELVEY  YTQQQGVVQD  RDGTIIHLKY
Csw     VTHIKIQNNG  DFFDLYGGEK  FATLPELVQY  YME.NGELKE  KNGQAIELKQ

101
SHP-2   PLNC
SHP-1   PLNC
Csw     PLIC
```

SHP-1 D59A/C453S sequence

ACTIVATED MUTANTS OF SH2-DOMAIN-CONTAINING PROTEIN TYROSINE PHOSPHATASES AND METHODS OF USE THEREOF

GOVERNMENT SUPPORT

The invention was supported, in whole or in part, by grants R01 CA49152, R01 CA66000 and R01 DK50693 from the National Institutes of Health. The Government has certain rights in the invention.

BACKGROUND OF THE INVENTION

Cell signaling molecules, such as hormones, neurotransmitters and cytokines, mediate cell—cell communication by acting through specific receptors on the plasma membrane or in the cytoplasm of target cells to ultimately transduce the signal into a cellular response. A delicate balance between activation and termination of signal transduction pathways is critical to maintaining homeostasis of the cell and organism.

Tyrosyl-phosphorylation regulates cell proliferation, migration and differentiation in complex biological processes such as embryonic development. Following binding of a signaling molecule to a cell surface receptor, tyrosine phosphorylation of target substrates, including some receptors, takes place by the activation of protein-tyrosine kinases. Termination of the signal is the result of activation of protein-tyrosine phosphatases and accompanying de-phosphorylation of tyrosine residues on the target substrates. Protein tyrosine phosphatases can have signal-enhancing or signal-attenuating properties.

SH2-domain-containing protein tyrosine phosphatases (e.g., SHP-1, SHP-2, and corkscrew in *Drosophilia melanogaster*) are a family of protein tyrosine phosphatases that share a common structure consisting of two SH2 ("S"rc "H"omology-2) domains, a protein tyrosine phosphatase catalytic domain containing the conserved I/VHCxAGxxR (S/T)G SEQ ID NOS: 1–70 amino acid sequence and a carboxy-terminal extension (Neel, B. G., *Sem. Cell Biol.* 4:419–432 (1993); Perkins, L. A., et al., *Dev. Biol.* 180:63–81 (1996); Neel, B. G., et al., *Curr. Op. Cell Biol.* 9:193–204 (1997)) (FIG. 1). The two SH2 domains are referred to as amino-(N-SH2) and carboxy-SH (C-SH2) domains relative to their position to the amino-terminus of the phosphatase protein.

Protein-tyrosine phosphatases, including SH2-containing phosphatases, are highly conserved among eukaryotes from such diverse species as mammals, including humans, to yeast and Xenopus. Mutations and altered expression of protein-tyrosine phosphatases have been implicated in neoplastic diseases and developmental abnormalities (Tonks, N. K., et al., *Cell* 87:365–368 (1996); Neel, B. G., et al., *Curr. Op. Cell Biol.* 9:193–204 (1997); Li, J. et al., *Science* 275:1943–1947 (1997)).

Thus, due to their widespread phylogenetic distribution and importance in the homeostasis of organisms a clearer understanding of the role of structural determinants in the catalytic activity of SH2-containing protein tyrosine phosphatases in cells and developmental events (such as embryonic shaping, patterning and organogenesis) can provide new and meaningful insights into their function and their role in disease.

SUMMARY OF THE INVENTION

The present invention relates to activated mutants of SH2-domain-containing protein tyrosine phosphatases. The present invention is based upon the discovery that the N-terminal SH2 (N-SH2) domain of SH2-domain phosphatases, for example SHP-1, SHP-2 and csw, is a conformational (e.g., allosteric) switch. The N-SH2 domain either binds the protein tyrosine phosphatase domain (also referred to herein as the catalytic domain) and directly blocks its active site, or, upon interaction of N-SH2 with a phosphotyrosine peptide, binding of the N-SH2 domain to the catalytic domain is disrupted and the phosphatase is activated. Thus, phosphotyrosine peptide binding to the SH2 domain of the protein tyrosine phosphatase stimulates, or activates, phosphatase activity.

As described herein, for the first time, are provided SH2-domain-containing protein tyrosine phosphatases that are biologically active without requiring phosphotyrosine peptide binding. As defined herein, the biological activity of phosphatases encompasses either their phosphatase activity (e.g., their ability to dephosphorylate a substrate) or their binding activity (e.g., their ability to interact with a binding partner such as a protein), or both. Specifically, the present invention encompasses biologically active SH2-domain-containing protein tyrosine phosphatases comprising one, or more, mutations, in the N-SH2 domain. These activated mutant SH2-domain Protein tyrosine phosphatases are also referred to herein as being in the "open" conformation, while inactive mutants are referred to as being in the "closed" conformation. The activated mutants of the present invention bind substrates or inhibitors in the absence of SH2 domain binding to phosphotyrosine residues.

The activated mutants of the present invention include SH2-domain-containing Protein tyrosine phosphatases with one, or more, mutations occurring in the N-terminal SH2 domain. Additional mutations can occur elsewhere in the protein tyrosine phosphatase, for example, in the catalytic domain. In one embodiment, the mutation(s) occurs in portions (or loops) of the SH2 domain that contact the Protein tyrosine phosphatase catalytic domain. Such loops are also referred to herein as "backside loops". Encompassed are mutants wherein one, or more, of the amino acid residues comprising the backside loop of the SH2 domain of SHP-2 (SEQ ID NOS:5 and 6), SHP-1 (SEQ ID NOS:7 and 8) or csw (SEQ ID NOS: 9 and 10) are mutated. Specifically encompassed are activated mutants of SHP-2 wherein the aspartic acid at position 61 (SEQ ID NOS:1 and 2) or the glutamic acid at position 76 (SEQ ID NOS:3 and 4) is replaced with an alanine residue.

The invention also relates to isolated nucleic acids encoding activated mutant SH2-containing protein tyrosine phosphatases and the polypeptides encoded by the isolated nucleic acid sequence. Specifically encompassed are nucleic acids encoding activated mutants of SHP-2, SHP-1 or corkscrew. For example, a nucleic acid encodes a SH2-containing protein tyrosine phosphatase (such as SHP-1 or SHP-2, respectively) wherein the aspartic acid at position 59 or 61 is replaced with an alanine (such as the D61A mutant of SHP-2; SEQ ID NO:1); or a nucleic acid encodes a SH2-containing protein tyrosine phosphatase wherein the glutamic acid at position 74 or 76 is replaced with an alanine (such as the E76A mutant of SHP-2; SEQ ID NO:3); or a nucleic acid encodes a SH2-containing phosphatase wherein the aspartic acid at position 59 is replaced with an alanine (such as the D59A mutant of SHP-1; SEQ ID NO: 60); or a nucleic acid encodes a SH2-containing phosphatase wherein the glutamic acid at position 74 is replaced with an alanine (such as the E74A mutant of SHP-1; SEQ ID NO: 62).

In another embodiment the isolated nucleic acid sequence encodes for a polypeptide which differs from a wildtype SH2-containing protein tyrosine phosphatase (such as SHP-2) by substitution of arginine at position 4, or phenylalanine at position 7, or histidine at position 8, or proline at position 9, or asparagine at position 58, or threonine at position 59, or glycine at position 60, or aspartic acid at position 61, or tyrosine at position 62, or tyrosine at position 63, or glutamic acid at position 69, or lysine at position 70, or phenylalanine at position 71, or alanine at position 72, or threonine at position 73, or leucine at position 74, or alanine at position 75, or glutamic acid at position 76 or leucine at position 77 or any combination thereof.

In yet another embodiment the nucleic acid sequence encodes for a polypeptide which differs from a wild type SH2-containing protein tyrosine phosphatases (such as SHP-1) by substitution of valine at position 2, or phenylalanine at position 5, or histidine at position 6, or arginine at position 7, or asparagine at position 56, or serine at position 57, or glycine at position 58, or aspartic acid at position 59, or phenylalanine at position 60, or tyrosine at position 61, or glutamic acid at position 67, or lysine at position 68, or phenylalanine at position 69, or alanine at position 70, or threonine at position 71, or leucine at position 72, or threonine at position 73, or glutamic acid at position 74 or leucine at position 75 or any combination thereof.

In another embodiment the present invention relates to activated compound mutants of SH2-domain containing protein tyrosine phosphatases. The activated compound mutants of the invention include SH2-containing protein tyrosine phosphatases with at least one mutation in the SH2 domain of the phosphatase as described herein and at least one additional mutation in the catalytic domain of the phosphatase. In one embodiment the activated compound mutants comprise double mutants of SHP-1 (SEQ ID NO: 6), SHP-2 (SEQ ID NO: 8) and corkscrew (SEQ ID NO: 10). For example, the activated compound mutant can be a mutant of SHP-2 wherein the cysteine residue at position 459 in the catalytic domain is substituted with an alanine or serine residue; or the aspartic acid at position 425 is replaced with alanine or both. The activated compound mutant can also be a mutant of SHP-1 wherein the cysteine residue at position 453 in the catalytic domain is substituted with an alanine or serine residue or the aspartic acid at position 419 is replaced with alanine or both. As describe herein, the activated compound mutant phosphatase can be D61A/D425A of SHP-2 (SEQ ID NO: 12) which has a substitution in the N-SH2 domain wherein the asparatic acid 61 is replaced with alanine and in the catalytic domain wherein the aspartic acid 425 is replaced with alanine. The activated compound double mutant can also be a mutant of SHP-1, for example, the D59A/D419A (SEQ ID NO: 32), or D59A/C453S (SEQ ID NO: 34), or E74A/C453S (SEQ ID NO: 36), or E74A/D419A (SEQ ID NO: 38).

In another embodiment of the present invention, the activated compound mutant is a triple mutant of a SH2-domain containing protein tyrosine phosphatase. For example, the activated triple mutant can have two mutations in the N-SH2 domain as well as a mutation in the catalytic domain of the protein tyrosine phosphatase. As described herein, the triple mutant can be an activated compound mutant of SHP-2, such as R32K/R138K/D61A (SEQ ID NO: 20), or R32K/R138K/E76A (SEQ ID NO: 22); or a triple mutant of SHP-1, such as R30K/R136K/D59A (SEQ ID NO: 40), or R30K/R136K/E74A (SEQ ID NO: 42).

A further embodiment of the present invention is an activated compound quadruple mutant of a SH2-domain containing protein tyrosine phosphatase. For example, the quadruple mutant can have three mutations in the SH2 domain (e.g., N-SH2, or C-SH2, or backside loop) as well as a mutation in the catalytic domain. As described herein, the quadruple mutant can be a mutant of SHP-2, such as R32K/R138K/D61A/C459S (SEQ ID NOS:23 and 24), or R32K/R138K/D61A/D425A (SEQ ID NOS:25 and 26), or R32K/R138K/E76A/C459S (SEQ ID NOS:27 and 28), or R32K/R138K/E76A/D425A (SEQ ID NOS:29 and 30). The activated compound quadruple mutant can also be a mutant of SHP-1, such as R30K/R136K/D59A/C453S (SEQ ID NO: 44), or R30K/R136K/D59A/D419A (SEQ ID NO: 46), or R30K/R136K/E74A/C453S (SEQ ID NO: 48), or R30K/R136K/E74A/D419A (SEQ ID NO: 50).

The invention also provides methods of identifying a substance which alters the interaction between a SH2-domain-containing protein tyrosine phosphatase and its substrate (e.g., tyrosine phosphorylated protein or peptide), comprising the steps of providing a tyrosine phosphorylated protein, or peptide, which is a substrate of a protein tyrosine phosphatase; combining (or admixing) the tyrosine phosphorylated protein and an activated mutant protein tyrosine phosphatase and a test substance under conditions suitable for interaction between the tyrosine phosphorylated protein and an activated mutant SH2-domain containing protein tyrosine phosphatase, thereby producing a combination; determining the amount of interaction in the combination; and comparing the amount of interaction determined in the presence of the test substance with the amount of interaction in the absence of the test substance, wherein a difference in the interaction indicates that the test substance alters the interaction between a SH2-domain containing protein tyrosine phosphatase and the tyrosine phosphorylated protein.

In one embodiment of the methods for identifying substances which alter the activity of the SH2-domain activated mutant phosphatases of the present invention, the activated mutant phosphatase is a mutant of SHP-2 or SHP-1 or corkscrew. For example, the activated mutant which results from a substitution of aspartic acid at position 61 with alanine or substitution of glutamic acid at position 76 with alanine, can be used. In one embodiment the substance inhibits, completely or partially, phosphatase or binding activity; in another embodiment, the substance stimulates, or enhances, phosphatase or binding activity.

A further embodiment of the present invention relates to a method of identifying binding partners (also referred to herein as substrates) for SH2-domain-containing protein tyrosine phosphatases, comprising combining a candidate binding partner and an activated mutant protein tyrosine phosphatase under conditions suitable for interaction between the binding partner and the activated mutant phosphatase resulting in the formation of a complex, thereby producing a combination; and determining the presence or absence of a complex in the combination wherein the presence of a complex in the combination indicates that the binding partner binds a SH2-domain-containing protein tyrosine phosphatase with which it forms a complex.

As used herein, a binding partner is a substance (e.g., protein, peptide, peptidomimetic or other organic molecule) that binds to the Protein tyrosine phosphatase, in particular, to the catalytic domain of the Protein tyrosine phosphatase. In one embodiment of the method for identifying binding partners, the activated compound mutant is a mutant of SHP-1, SHP-2 or corkscrew. For example, the activated compound mutant which results from one or more mutations in the SH2 domains as described herein (e.g., asparatic acid 61 replaced with alanine) combined with at least one additional substitution in the catalytic domain such as replacement of a cysteine at position 453 or 459 with an alanine or serine residue; or substitution of aspartic acid 425 with an alanine residue, can be used. In another embodiment of the method for identifying binding partners the interaction between a candidate binding partner and an activated compound mutant can occur in the presence of phosphotyrosine peptides.

Another aspect of the invention relates to a method of altering SH2-domain-containing protein tyrosine phosphatase activity in a target cell comprising introducing an activated mutant SH2-domain containing protein tyrosine phosphatase of the invention, or a nucleic acid encoding an activated mutant phosphatases described herein, into the target cell, wherein the amount of activated mutant phosphatase introduced effectively alters the phosphatase activity of the cell.

The invention also relates to a method of altering SH2-domain containing protein tyrosine phosphatase in a target cell, comprising introducing into the target cell a substance wherein the amount of the substance introduced effectively alters the phosphatase activity. In one embodiment the substance inhibits, completely or partially, phosphatase activity; in another embodiment, the substance stimulates, or enhances, phosphatase activity.

The present invention further relates to a method of treating a protein tyrosine phosphatase-mediated condition in a mammal, wherein the condition results from alteration in the regulation of SH2-domain containing protein tyrosine phosphatase activity, comprising introducing into the mammal an amount of substance effective to regulate the SH2-domain containing phosphatase activity in the mammal, thereby alleviating the condition. Regulation of phosphatase activity can be up-regulation (e.g., an increase or enhancement in phosphatase activity) or down-regulation (e.g., a decrease or inhibition in phosphatase activity).

The invention also provides methods of treating protein tyrosine phosphatase-mediated condition or disease in a mammal, wherein the condition or disease results from an alteration in the regulation of SH2-domain-containing protein tyrosine phosphatase activity, comprising introducing an activated mutant SH2-domain protein tyrosine phosphatase, or a nucleic acid encoding an activated mutant phosphatase, into a mammal, wherein the amount of activated mutant phosphatase introduced effectively alters the phosphatase activity in a target cell in a mammal.

The activated mutants of SH2-domain-containing protein tyrosine phosphatases described herein provide the basis for methods of screening inhibitors or stimulators of phosphatase activity and for identifying binding partners or substrates of protein tyrosine phosphatases. Such methods are extremely useful in high throughput assays to identify agents, or substances, for therapeutic and diagnostic use. For example, the activated mutants described herein can be used to identify inhibitors for the treatment of cancer, immunosuppression, immunostimulation, hematopoietic stimulation and anti-allergy treatment. The mutants of the present invention are also useful to identify and characterize signaling pathways involving SH2-containing protein tyrosine phosphatases and for the treatment of diseases attributed to perturbations in signaling pathways mediated by protein tyrosine phosphatases.

BRIEF DESCRIPTION OF THE FIGURES

FIG. 2A depicts the alignment of the amino acid sequences of SHP-2 (SEQ ID NO:63), SHP-1 (SEQ ID NO: 64) and corkscrew (csw) (SEQ ID NO:65).

FIG. 2B depicts the alignment of amino acid sequences of SHP-2 (SEQ ID NO:66), SHP-1 (SEQ ID NO:67) and corkscrew (csw) (SEQ IS NO: 68). Potential sites of amino acid substitution are indicated by the blackened squares (■).

FIG. 3 depicts the nucleotide sequence (SEQ ID NO: 1) and the deduced corresponding amino acid sequence (SEQ ID NO: 2) of the D61A SHP-2 mutant. The D61A mutant was generated by an oligonucleotide PCR based point mutation scheme which substituted aspartic acid at position 61 with an alanine residue.

FIG. 4 depicts the nucleotide sequence (SEQ ID NO: 3) and the deduced corresponding amino acid sequence (SEQ ID NO: 4) of the E76A SHP-2 mutant. The E76A mutant was generated by an oligonucleotide PCR based point mutation scheme which substituted glutamic acid at position 76 with an alanine residue.

FIG. 5 depicts the nucleotide sequence (SEQ ID NO: 5) and the deduced corresponding amino acid sequence (SEQ ID NO: 6) of SHP-2.

FIG. 6 depicts the nucleotide sequence (SEQ ID NO: 7) and the deduced corresponding amino acid sequence (SEQ ID NO: 8) of SHP-1.

FIGS. 7A and 7B depict the nucleotide sequence (SEQ ID NO: 9) and the deduced corresponding amino acid sequence (SEQ ID NO: 10) corkscrew.

FIG. 8 depicts the nucleotide sequence (SEQ ID NO: 11) and the deduced corresponding amino acid sequence (SEQ ID NO: 12) of the D61A/D425A activated compound double mutant of SHP-2.

FIG. 9 depicts the nucleotide sequence (SEQ ID NO: 13) and the deduced corresponding amino acid sequence (SEQ ID NO: 14) of the D61A/C459S activated compound double mutant of SHP-2.

FIG. 10 depicts the nucleotide sequence (SEQ ID NO: 15) and the deduced corresponding amino acid sequence (SEQ ID NO: 16) of the E76A/C459S activated compound double mutant of SHP-2.

FIG. 11 depicts the nucleotide sequence (SEQ ID NO: 17) and the deduced corresponding amino acid sequence (SEQ ID NO: 18) of the E76A/D425A activated compound double mutant of SHP-2.

FIG. 12 depicts the nucleotide sequence (SEQ ID NO: 19) and the deduced corresponding amino acid sequence (SEQ ID NO: 20) of the R32K/R138K/D61A activated compound triple mutant of SHP-2.

FIG. 13 depicts the nucleotide sequence (SEQ ID NO: 21) and the deduced corresponding amino acid sequence (SEQ ID NO: 22) of the R32K/R138K/E76A activated compound triple mutant of SHP-2.

FIG. 14 depicts the nucleotide sequence (SEQ ID NO: 23) and the deduced corresponding amino acid sequence (SEQ ID NO: 24) of the R32K/R138K/D61A/C459S activated compound quadruple mutant of SHP-2.

FIG. 15 depicts the nucleotide sequence (SEQ ID NO: 25) and the deduced corresponding amino acid sequence (SEQ ID NO: 26) of the R32K/R138K/D61A/D425A activated compound quadruple mutant of SHP-2.

FIG. 16 depicts the nucleotide sequence (SEQ ID NO: 27) and the deduced corresponding amino acid sequence (SEQ ID NO: 28) of the R32K/R138K/E76A/C459S activated compound quadruple mutant of SHP-2.

FIG. 17 depicts the nucleotide sequence (SEQ ID NO: 29) and the deduced corresponding amino acid sequence (SEQ ID NO: 30) of the R32K/R138K/E76A/D425A activated compound quadruple mutant of SHP-2.

FIG. 18 depicts the nucleotide sequence (SEQ ID NO: 31) and the deduced corresponding amino acid sequence (SEQ ID NO: 32) of the D59A/D419A activated compound double mutant of SHP-1.

FIG. 19 depicts the nucleotide sequence (SEQ ID NO: 33) and the deduced corresponding amino acid sequence (SEQ ID NO: 34) of the D59A/C453S activated compound double mutant of SHP-1.

FIG. 20 depicts the nucleotide sequence (SEQ ID NO: 35) and the deduced corresponding amino acid sequence (SEQ ID NO: 36) of the E74A/C453S activated compound double mutant of SHP-1.

FIG. 21 depicts the nucleotide sequence (SEQ ID NO: 37) and the deduced corresponding amino acid sequence (SEQ ID NO: 38) of the E74A/D419A activated compound double mutant of SHP-1.

FIG. 22 depicts the nucleotide sequence (SEQ ID NO: 39) and the deduced corresponding amino acid sequence (SEQ ID NO: 40) of the R30K/R136K/D59A activated compound triple mutant of SHP-1.

FIG. 23 depicts the nucleotide sequence (SEQ ID NO: 41) and the deduced corresponding amino acid sequence (SEQ ID NO: 42) of the R30K/R136K/E74A activated compound triple mutant of SHP-1.

FIG. 24 depicts the nucleotide sequence (SEQ ID NO: 43) and the deduced corresponding amino acid sequence (SEQ ID NO: 44) of the R30K/R136K/D59A/C453S activated compound quadruple mutant of SHP-1.

FIG. 25 depicts the nucleotide sequence (SEQ ID NO: 45) and the deduced corresponding amino acid sequence (SEQ ID NO: 46) of the R30K/R136K/D59A/D419A activated compound quadruple mutant of SHP-1.

FIG. 26 depicts the nucleotide sequence (SEQ ID NO: 47) and the deduced corresponding amino acid sequence (SEQ ID NO: 48) of the R30K/R136K/E74A/C453S activated compound quadruple mutant of SHP-1.

FIG. 27 depicts the nucleotide sequence (SEQ ID NO: 49) and the deduced corresponding amino acid sequence (SEQ ID NO: 50) of the R30K/R136K/E74A/D419A activated compound quadruple mutant of SHP-1.

FIG. 28 depicts the nucleotide sequence (SEQ ID NO: 59) and the deduced corresponding amino acid sequence (SEQ ID NO: 60) of the D59A SHP-1 mutant. The D59A mutant substitutes an aspartic acid at position 59 with an alanine residue.

FIG. 29 depicts the nucleotide sequence (SEQ ID NO: 61) and the deduced corresponding amino acid sequence (SEQ ID NO: 62) of the E74A SHP-1 mutant. The E74A mutant substitutes glutamic acid at position 74 with an alanine residue.

DETAILED DESCRIPTION OF THE INVENTION

Figure 1:
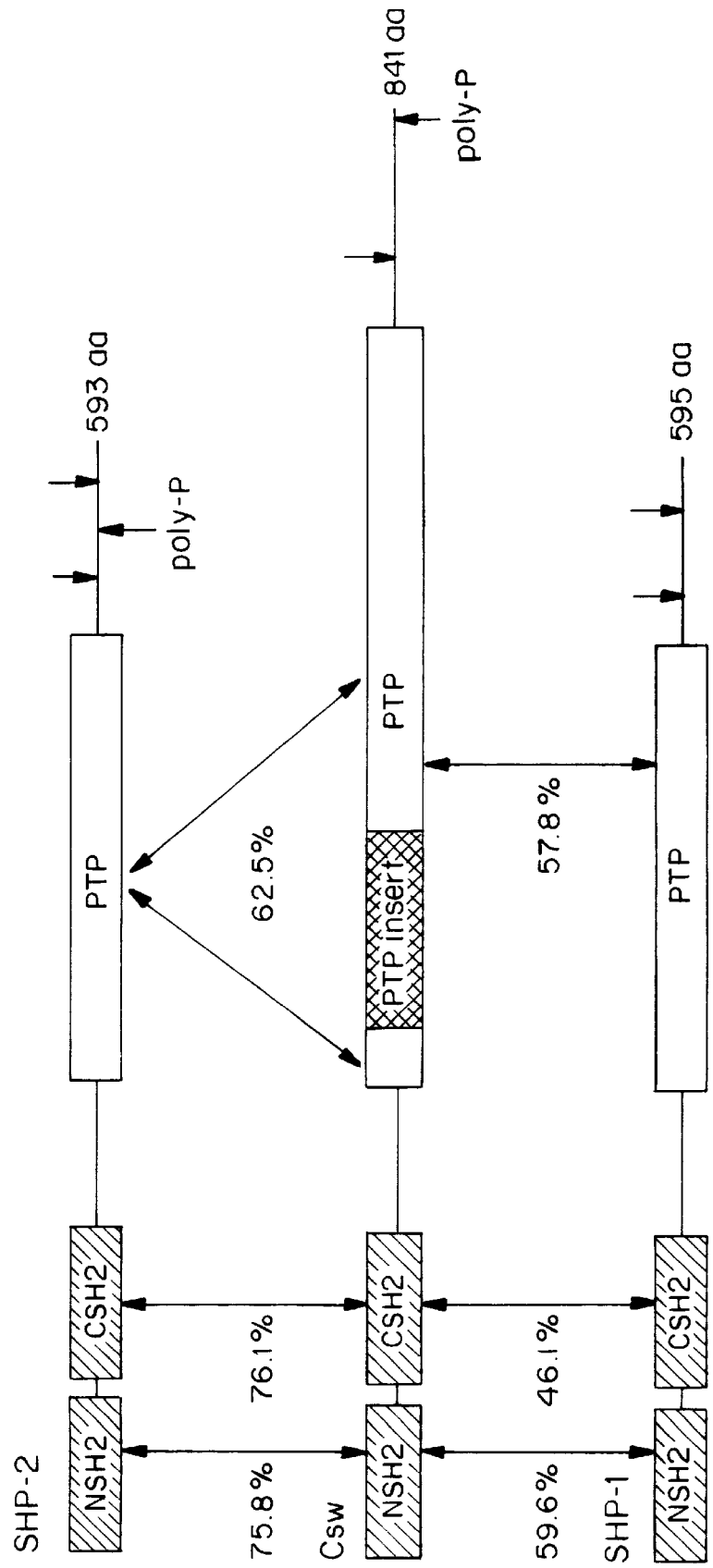
FIG. 1 depicts a schematic representation of the SH2-containing protein tyrosine phosphatases: SHP-2, Drosophila corkscrew (Csw), and SHP-1. SH2-containing protein tyrosine phosphatases consist of an amino-SH2 (NSH2) and carboxy-SH2 (CSH2) domain; a catalytic protein tyrosine phosphatase domain (PTP); carboxy-terminus tyrosyl phosphorylation sites (arrows); and, in the case of Csw and SHP-2, a poly-proline-rich region (poly-P). The percent identities of the phosphatase domains of Csw and SHP-1 are relative to SHP-2.

The present invention relates to the discovery that mutations of SH2-containing protein tyrosine phosphatases result in the formation of activated phosphatases. The activated mutant phosphatases of the present invention induce phenotypic (such as animal cap elongation in Xenopus) and molecular (such as mesoderm-specific muscle actin in Xenopus) changes in cells and embryos. In a preferred embodiment the mutant SH2-containing protein tyrosine phosphatases comprise mutations in the SH2-domain, most preferably in the amino-SH2-domain (also referred to herein as the N-terminal SH2 domain, or N-SH2).

The present invention also encompasses the use of the mutant SH2-containing protein tyrosine phosphatases in screening assays for identifying binding partners, or substrates, of protein tyrosine phosphatases or substances which alter (e.g., inhibit) phosphatase activity. The invention also pertains to the nucleic acid constructs encoding the mutant SH2-containing protein tyrosine phosphatases and their encoded activated mutant SH2-phosphatase polypeptides.

The term "protein tyrosine phosphatase" as used herein refers to a polypeptide, including posttranslationally modified polypeptides (e.g., myristylated, acetylated, glycosylated, phosphorylated), which remove phosphate groups from tyrosine residues of substrates (e.g., SIRPa/SHPS-1, FRS-2/SNT, GAB1, GAB2, PDGF, EGFR, cSRC and other Src family protein tyrosine kinases. The removal of a phosphate can result in deactivation (e.g., fibroblast growth factor receptor) or activation (e.g., Src family kinase) of the substrate. SH2-containing protein tyrosine phosphatases can have signal-enhancing or signal-attenuating activity. As used herein "signal-enhancing activity" refers to an augmentation of the signaling pathways of certain receptors (e.g., FGFR). Conversely, "signal-attenuating" activity is meant to refer to a diminution of the signal pathways of certain receptors (e.g., B-cell antigen receptor, IL-3 and erythropoietin receptors).

As used herein "SH2-containing protein tyrosine phosphatases" are meant to include any protein tyrosine phosphatase which contains at least one discrete contiguous part of a nucleotide sequence which encodes an amino acid sequence with homology to c-Src cytosolic tyrosine kinase (e.g., SHP-2, SHP-1, corkscrew). For example, the SH domains can be SH2. In a preferred embodiment the SH2-containing protein tyrosine phosphatase is SHP-1, SHP-2 or corkscrew (FIGS. 2A and 2B).

The SH2-domain of wildtype SH2-containing protein tyrosine phosphatases interacts with a ligand thereby resulting in an allosteric alteration that exposes the catalytic domain which then dephosphorylates a substrate. The term "ligand" as used herein refers to any molecule (e.g., polypeptide, peptidomimetic, anion or cation, organic molecule, lipid or carbohydrate) that interacts with the SH2 domains. The term "substrate" is intended to refer to any molecule (e.g., polypeptide, peptidomimetic, anion or cation, organic molecule, lipid, carbohydrate) on which the phosphatase acts (e.g., activates or dephosphorylates). The ligand and substrate can be the same molecule. Alternatively, the substrate can be a different molecule than the ligand. For example, the PDGF receptor is both a ligand and substrate for SHP-2.

The term "activated" is used herein to describe polypeptides, e.g., mutants, with biological activity comparable to or greater than the activity of the wildtype or naturally occurring SH2-containing protein tyrosine phosphatase in the presence or absence of phosphotyrosine substrate or peptides.

The term "biological activity" refers to any effect which mimics or simulates an effect of the wildtype or naturally occurring SH2-containing protein tyrosine phosphatase (e.g., dephosphorylation of phosphotyrosine substrates; interaction with specific binding partners; or induction of animal cap elongation and mesoderm-specific actin mRNA in Xenopus explants). In vitro activity can be measured as described in Example 3, or by binding assays as well known to those of skill in the art, and in vivo activity can be measured as described in Example 5.

Figure 3:
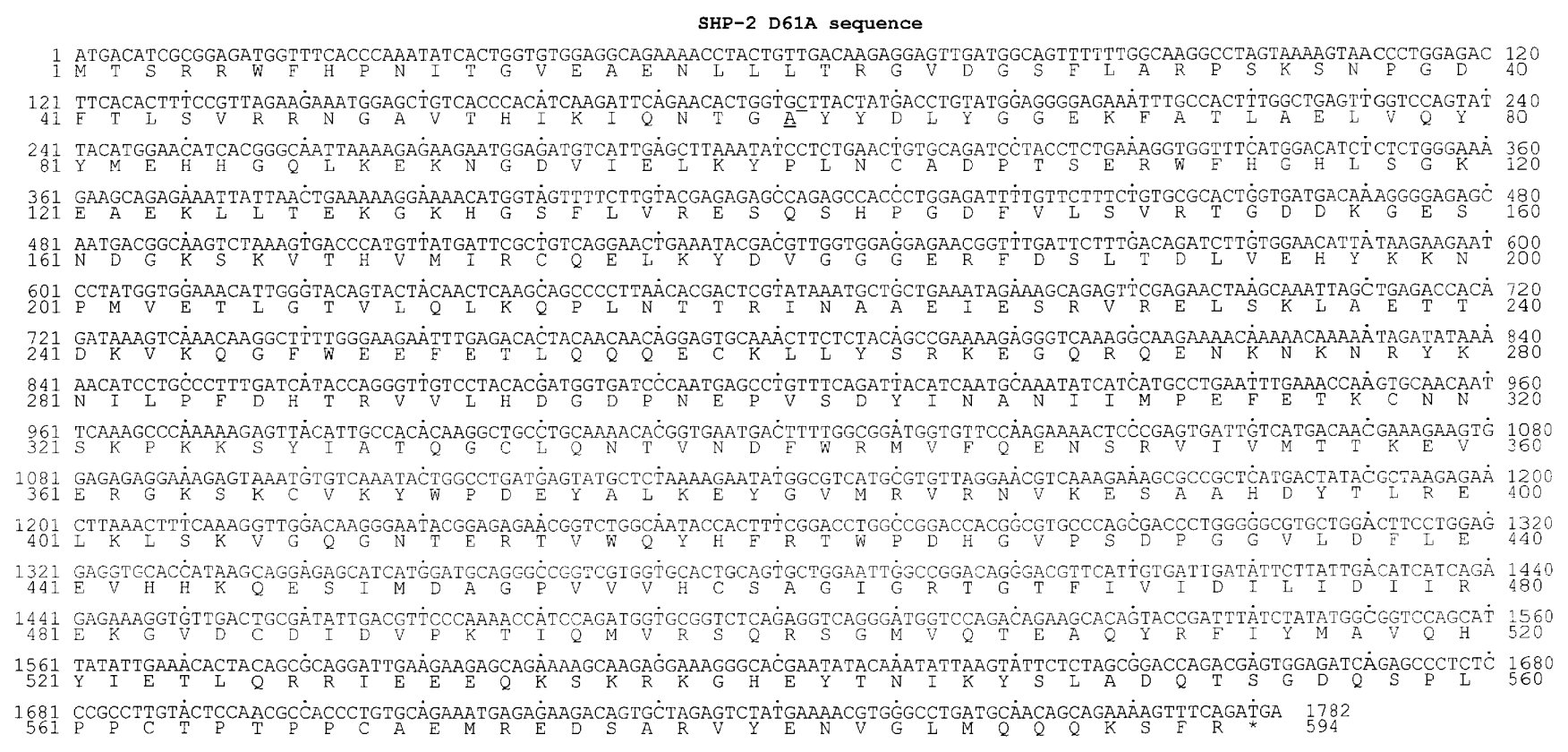
Figure 4:
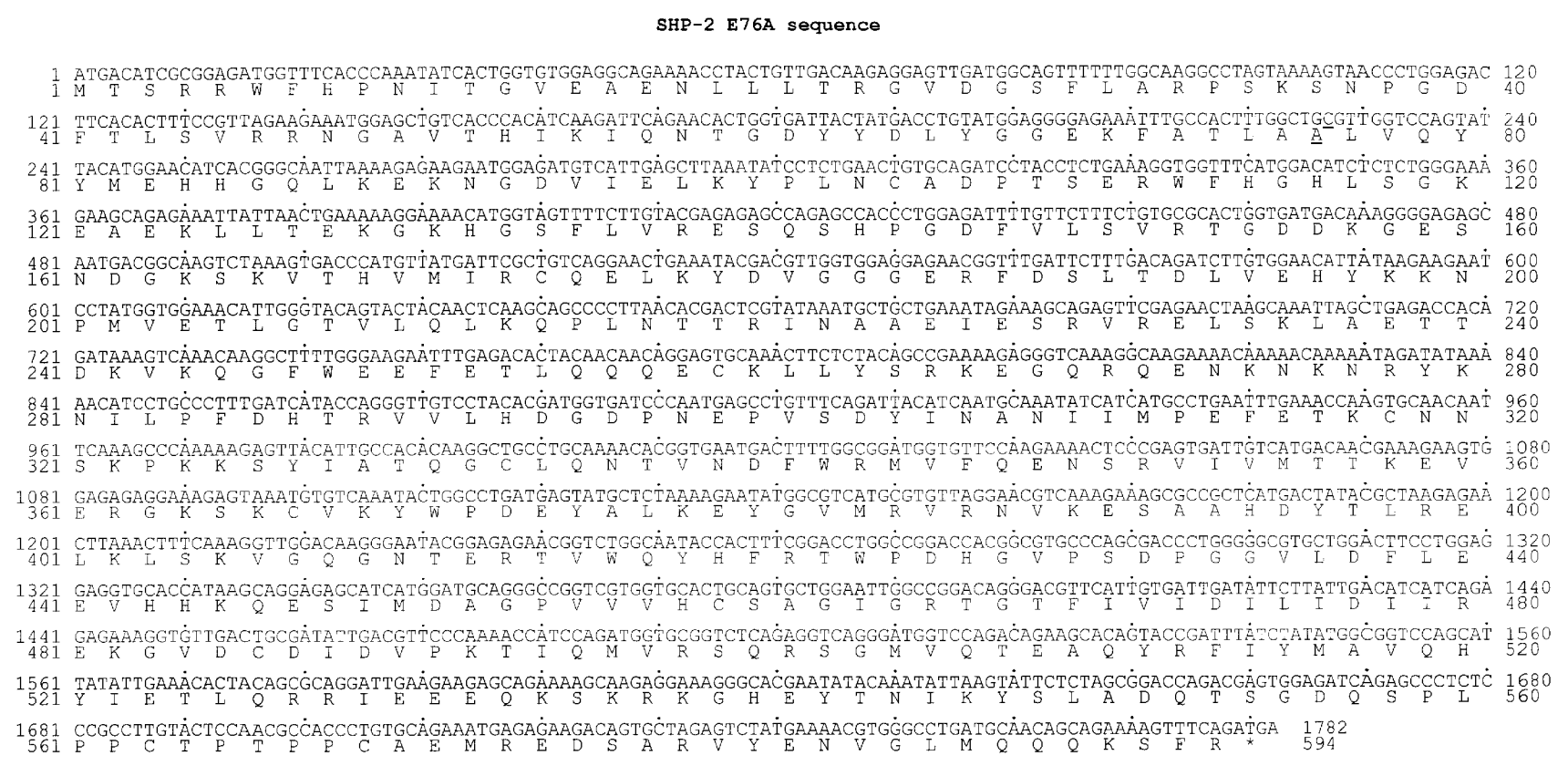

Specifically encompassed in the present invention are activated mutants of SHP-2 with phosphatase activity in the absence of phosphotyrosine peptides, D61A, FIG. 3; E76A, FIG. 4. For example, in the absence of phosphotyrosine peptide ligands, the wildtype SHP-2 phosphatase has low basal levels of phosphatase activity (e.g., ability to liberate $^{32}$P from [$^{32}$P]RCM-lysozyme in in vitro assays. See Example 3). However, an "activated" mutant of SHP-2 (e.g., D61A or E76A, FIGS. 3 and 4, respectively) exhibits phosphatase activity in the absence of phosphotyrosine peptides. In the case of a constitutively active mutant (e.g., the E76A mutant of SHP-2), the phosphatase activity is comparable to or greater than the maximum activity of the wildtype phosphatase, and in the case of a partially activated mutant (e.g., D61A mutant of SHP-2) the phosphatase activity is any amount of phosphatase activity above the basal level and that can be further activated by the addition of phosphotyrosine peptide ligand for its SH2 -domains. In wildtype SHP-2, the amino-SH2 domain undergoes a conformational change following ligand binding (e.g., phosphotyrosine peptides) before it can be enzymatically active (Hof, P., et al., Cell 92:441–450 (1998)). An "activated" mutant does not require ligand binding for enzymatic activity.

The term "mutation", as used herein, refers to any modification in a nucleic acid sequence encoding an SH2-containing protein tyrosine phosphatase. For example, the mutation can be a point mutation or the addition, deletion, insertion and/or substitution of one or more nucleotides or any combination thereof. Modifications can be, for example, conserved or non-conserved, natural or unnatural.

As used herein a mutant also refers to the polypeptide encoded by the mutated nucleic acid. That is, the term "mutant" also refers to a polypeptide which is modified at one, or more, amino acid residues from the wildtype (naturally occurring) polypeptide. In a preferred embodiment mutants are generated by mutations in the backside loop of SH2-containing protein tyrosine phosphatases. SH2-containing protein tyrosine phosphatases fold into three dimensional structures. "Backside loop" as used herein refers to the region of the amino-SH2 domain of an SH2-containing protein tyrosine phosphatase which protrudes into the protein tyrosine phosphatase domain and is opposite the phosphotyrosine peptide binding cleft. The backside loop of an SH2-containing protein tyrosine phosphatase (e.g., SHP-2) can physically impede substrate access and chemically inactivate critical residues in the protein tyrosine phosphatase domain which impart catalytic activity (Hof, P., et al., Cell 92:441–450 (1998)).

Figure 6:
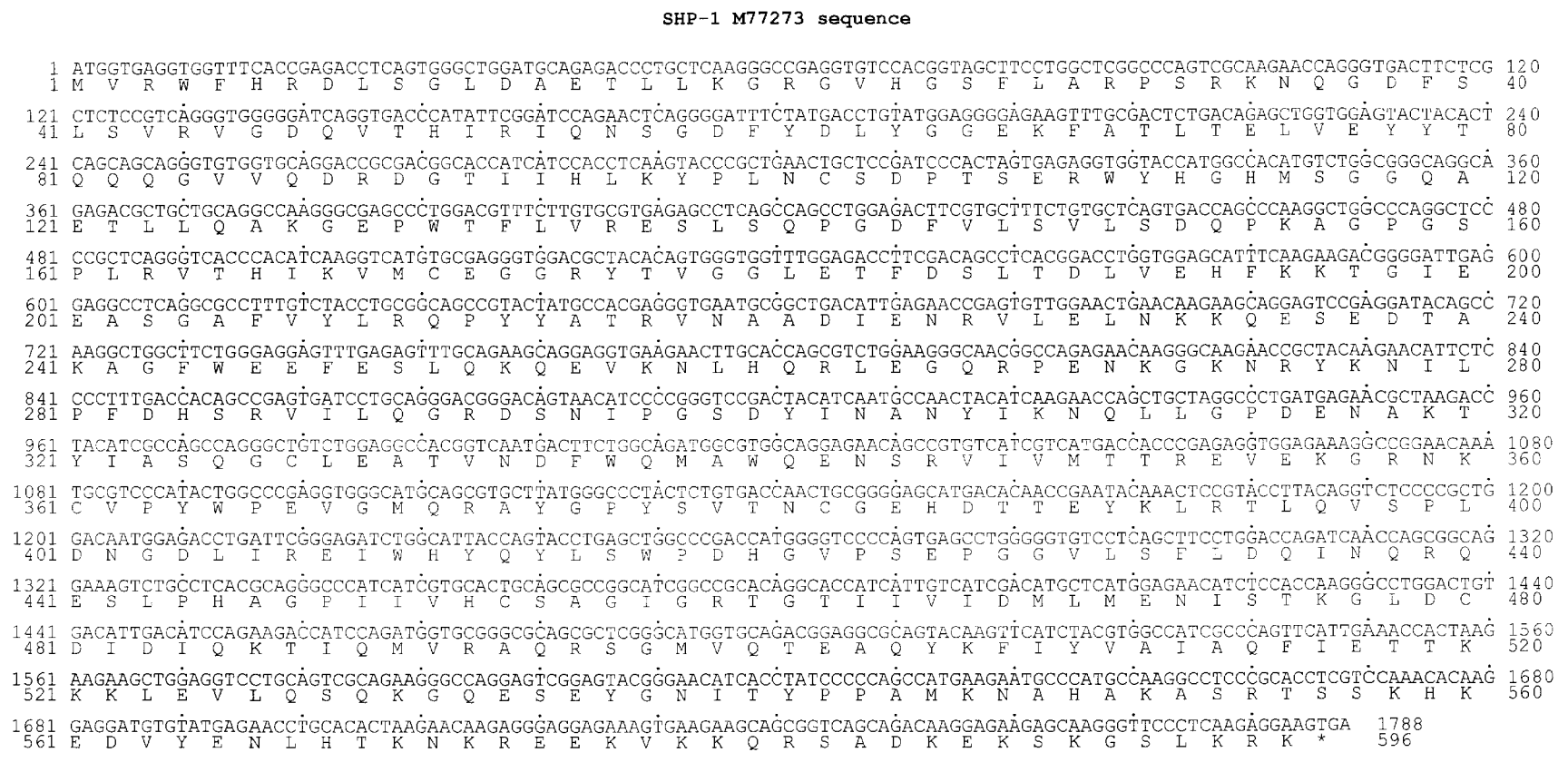
Figure 7A:
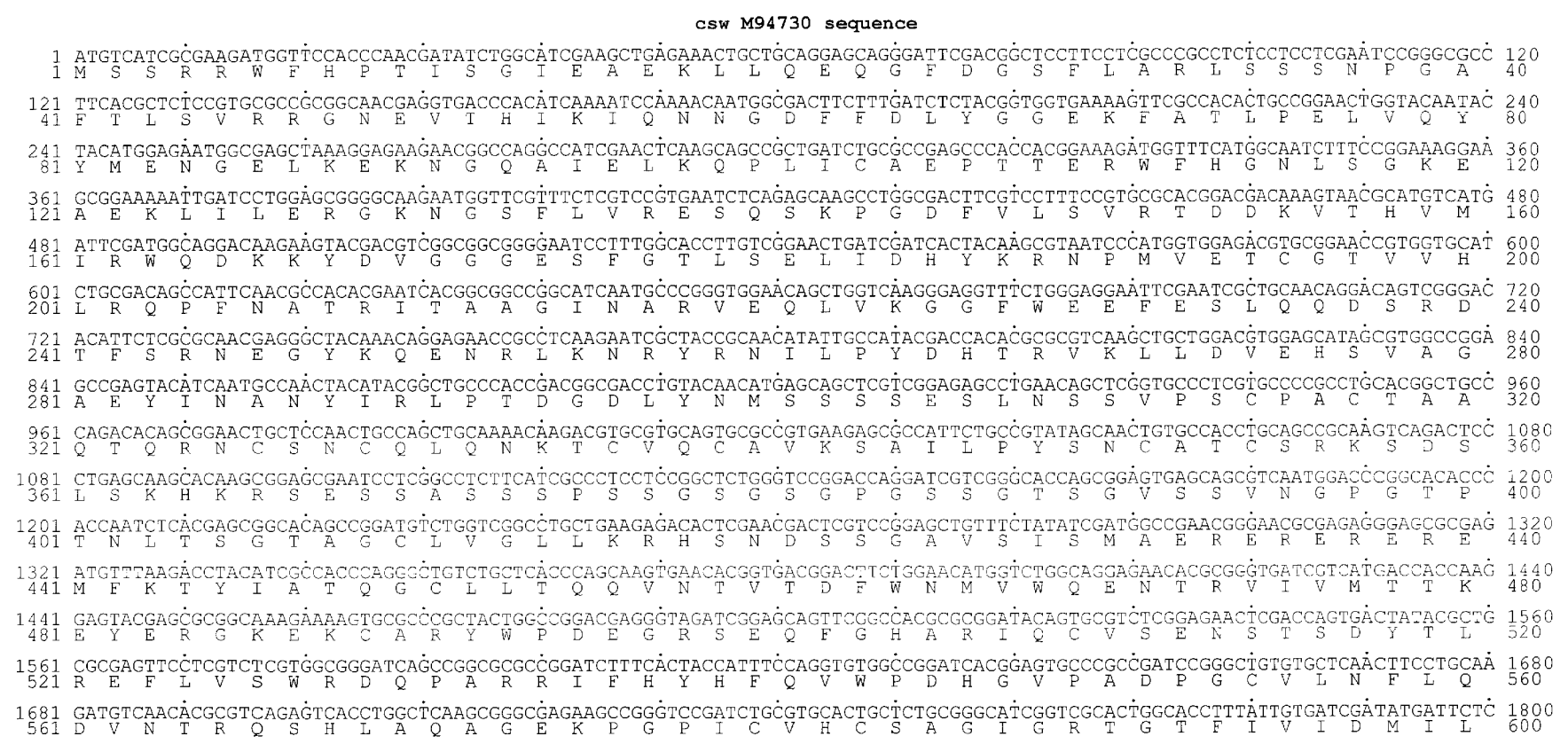
Figure 7B:
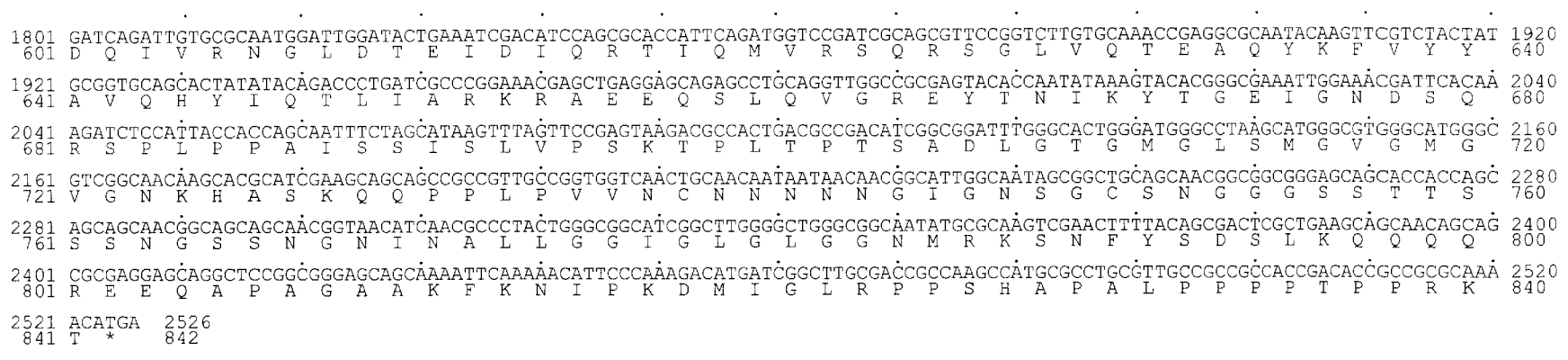

In one embodiment the mutations are made to SHP-2 (FIG. 5), SHP-1, (FIG. 6), or corkscrew (FIG. 7). In a particular embodiment, the amino-SH2 domain (N-SH2) of the SH2-containing protein tyrosine phosphatase, as described herein, has a mutation resulting in a constitutively activated SHP-2 protein. For example, in this embodiment the constitutively active mutant D61A is a mutant of SHP-2 resulting from a point mutation substituting the aspartic acid at position 61 (D61) in the backside loop of SHP-2 with an alanine residue to generate the D61A mutant (FIG. 3). In the wildtype SHP-2 D61 forms a hydrogen bond through a water molecule with a cysteine residue at position 459 in the catalytic domain. The D61A mutant is unlikely to form a hydrogen bond with the critical cysteine residue in the protein tyrosine phosphatase domain, thereby "opening up" the catalytic domain which results in an active phosphatase (Hof, P., et al., Cell 92:441–450 (1998)).

SHP-2 mutants can also be made in the backside loop of the wildtype SH2-containing protein tyrosine phosphatase (FIG. 5) by mutations to one, or more, amino acid residues selected from a group consisting of arginine at position 4, or phenylalanine at position 7, or histidine at position 8, or proline at position 9, or asparagine at position 58, or threonine at position 59, or glycine at position 60, or aspartic acid at position 61, or tyrosine at position 62, or tyrosine at position 63, or glutamic acid at position 69, or lysine at position 70, or phenylalanine at position 71, or alanine at position 72, or threonine at position 73, or leucine at position 74, or alanine at position 75, or glutamic acid at position 76 or leucine at position 77 or any combination thereof.

Figure 28:
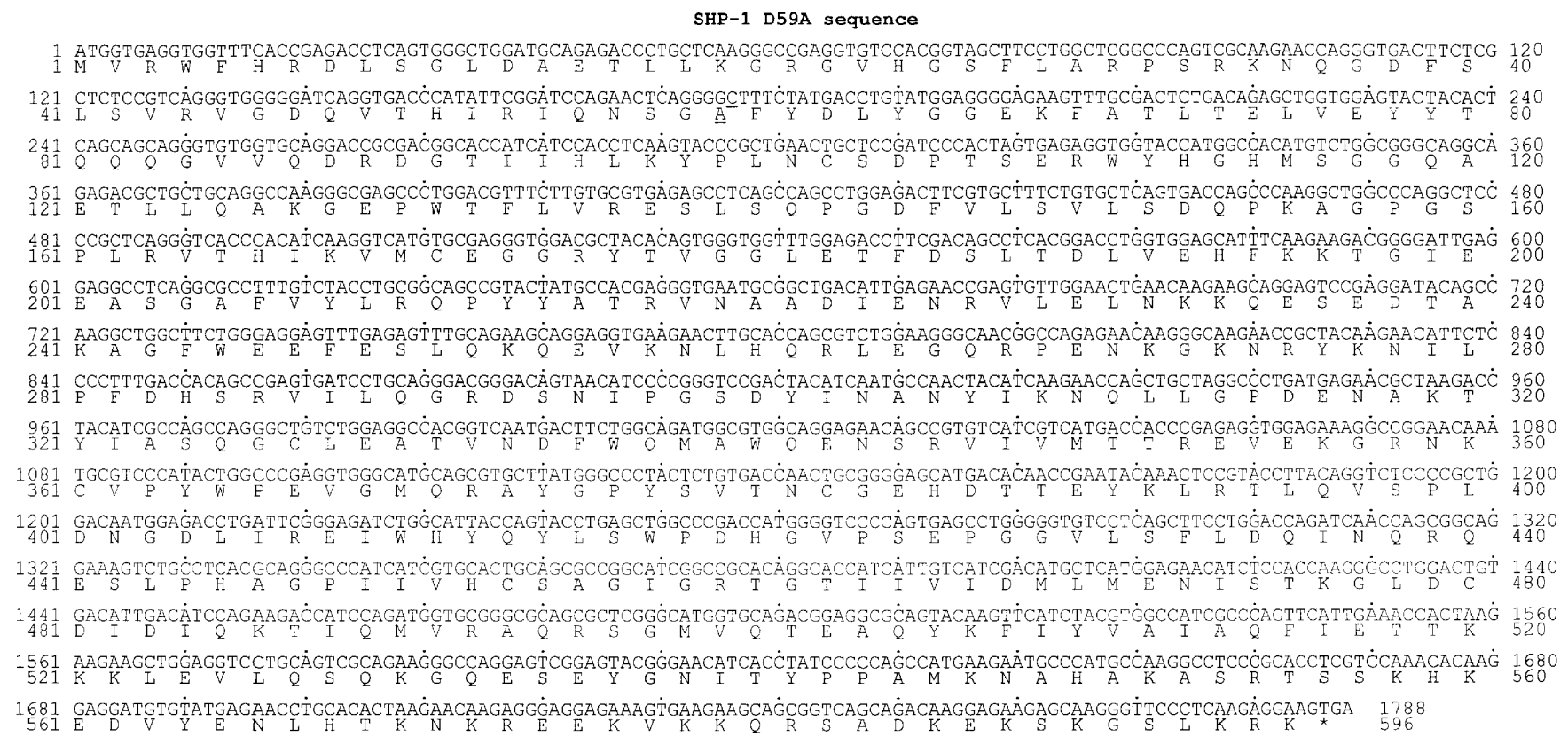
Figure 29:
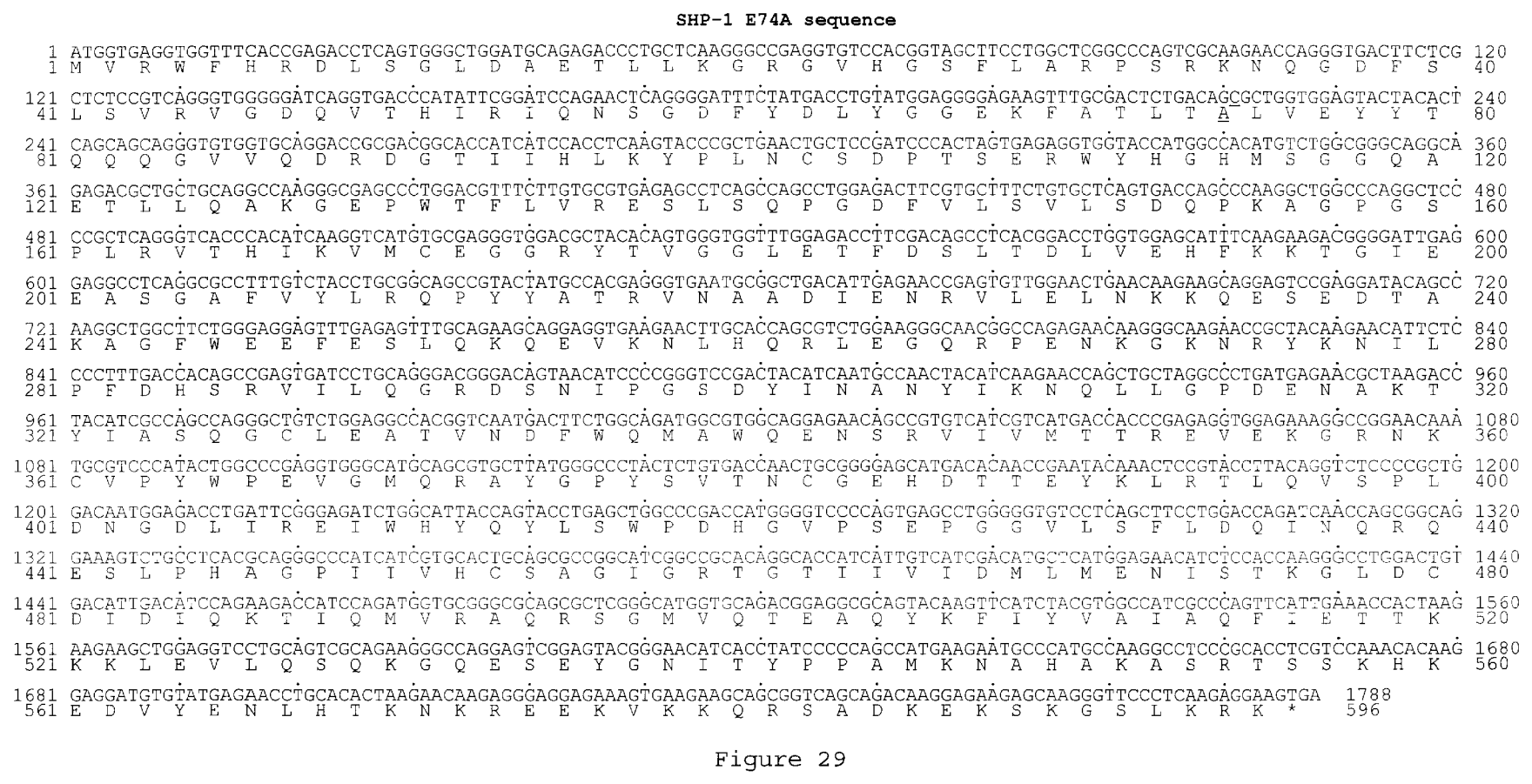

Using the amino acid alignment (FIG. 2), amino acid residues suitable for mutation as described herein for SHP-2 can be determined for other SH2-domain-containing protein tyrosine phosphatases such as SHP-1 (FIG. 6) or corkscrew (FIG. 7). For example, activated SHP-1 mutants can be the D59A mutant (FIG. 28; SEQ ID NO: 60) where the aspartic acid at position 59 is replaced with an alanine residue; or the E74A mutant (FIG. 29; SEQ ID NO: 61) where the glutamic acid at position 76 is replaced with an alanine. Nucleic acid sequences encoding the SH2-domain-containing protein tyrosine phosphatases can be mutated; the mutated nucleic acid constructs expressed under standard experimental conditions well known to the skilled artisan; and the resulting mutant polypeptide evaluated for phosphatase activity as described herein. Appropriate amino acid residues can be substituted as described for SHP-2 using routine, art-recognized techniques.

The coding regions of the nucleic acid molecule code for SH2-containing protein tyrosine phosphatases and activated mutants described herein. Because many amino acids are encoded by a plurality of different codons, the mutant SH2-containing protein tyrosine phosphatase, or a catalytically active fragment thereof, can be altered to produce a codon encoding the same amino acid. For example, the amino acid alanine is encoded by the nucleotide triplet GCA or GCC or GCG or GCU. This can be advantageous where a codon is preferred by a selected host cell.

Mutations to the nucleic acid sequence of SH2-containing protein tyrosine phosphatase can be conserved or nonconserved. The phrase "conserved substitution" is intended to mean a nucleic acid sequence mutation which encodes an amino acid which possesses similar side chains and properties (e.g., hydrophilic, hydrophobic, aromatic) as the amino acid encoded by the non-mutated nucleic acid sequence. In one embodiment, the nucleic acid molecule is mutated outside the catalytic domain, preferably, in the SH2 domains of the native phosphatase. In a more preferred embodiment, the amino-SH2 domain is mutated.

Figure 8:
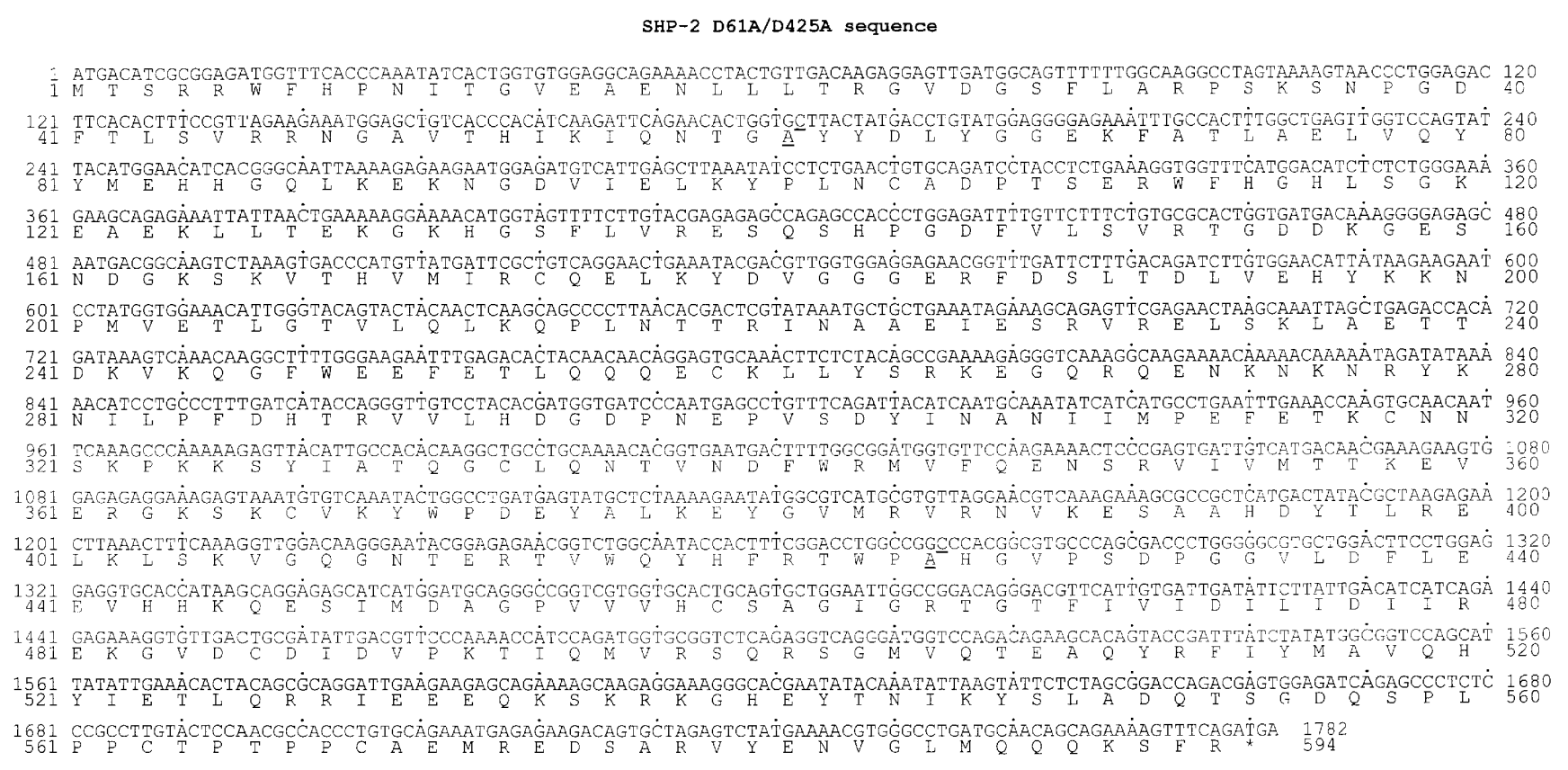
Figure 9:
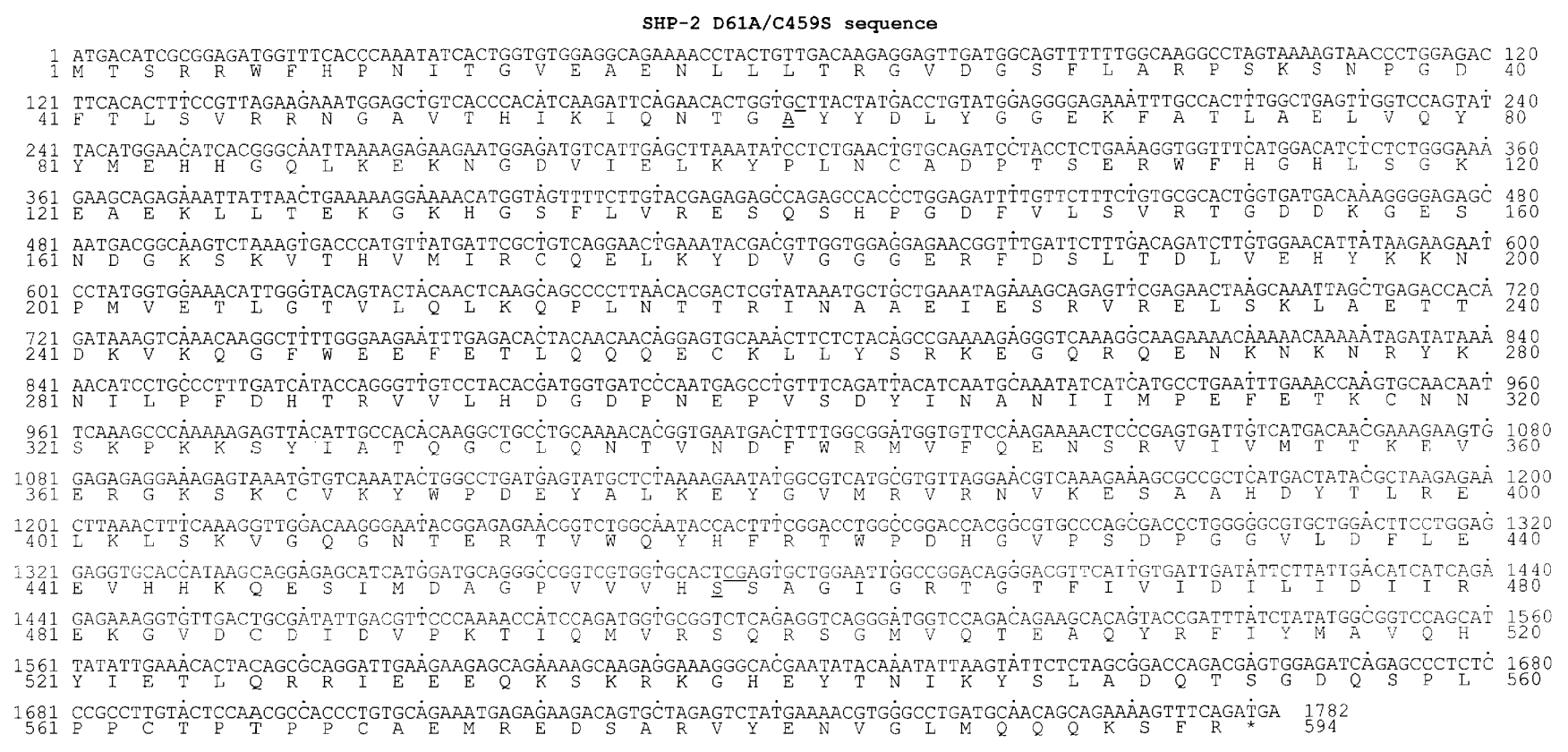
Figure 10:
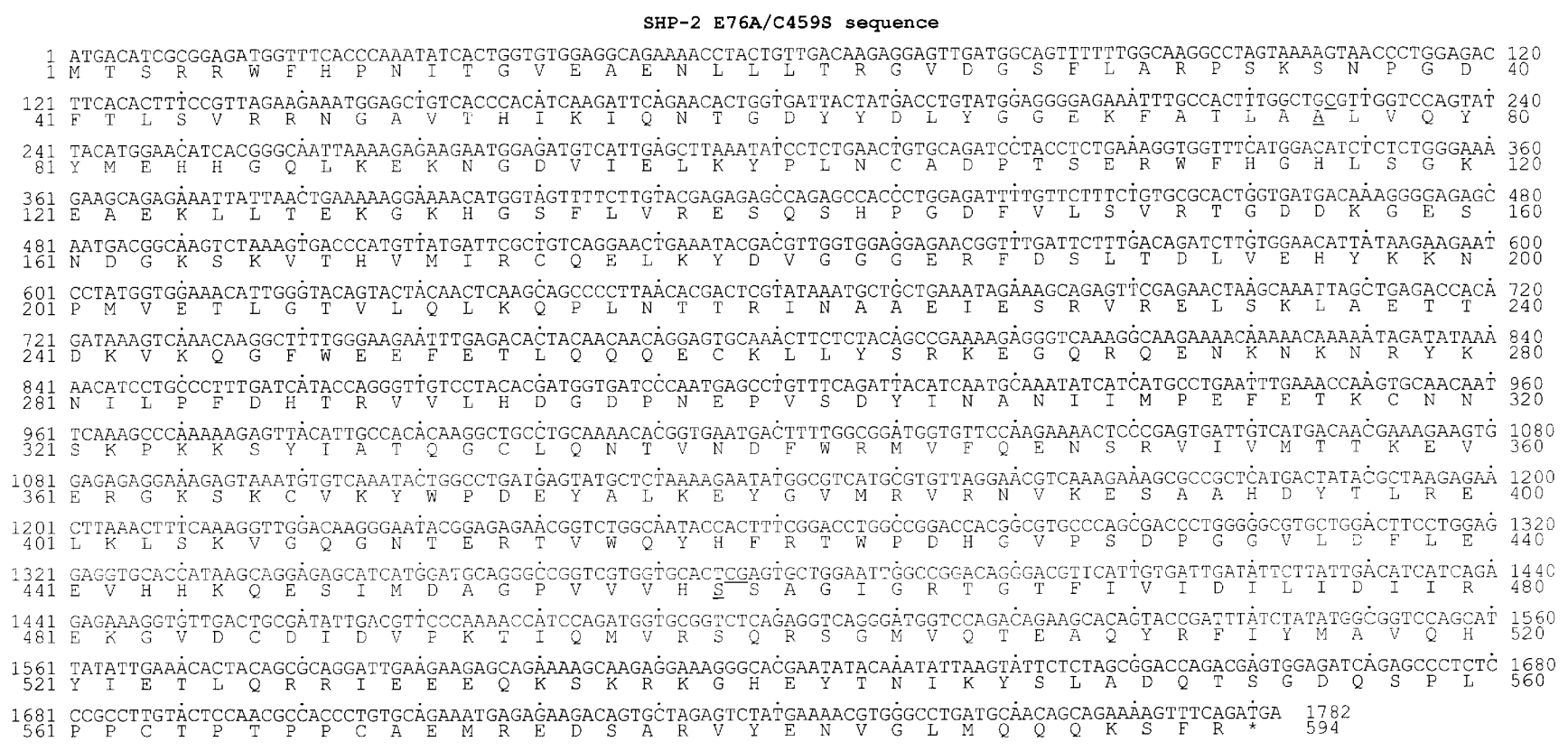
Figure 11:
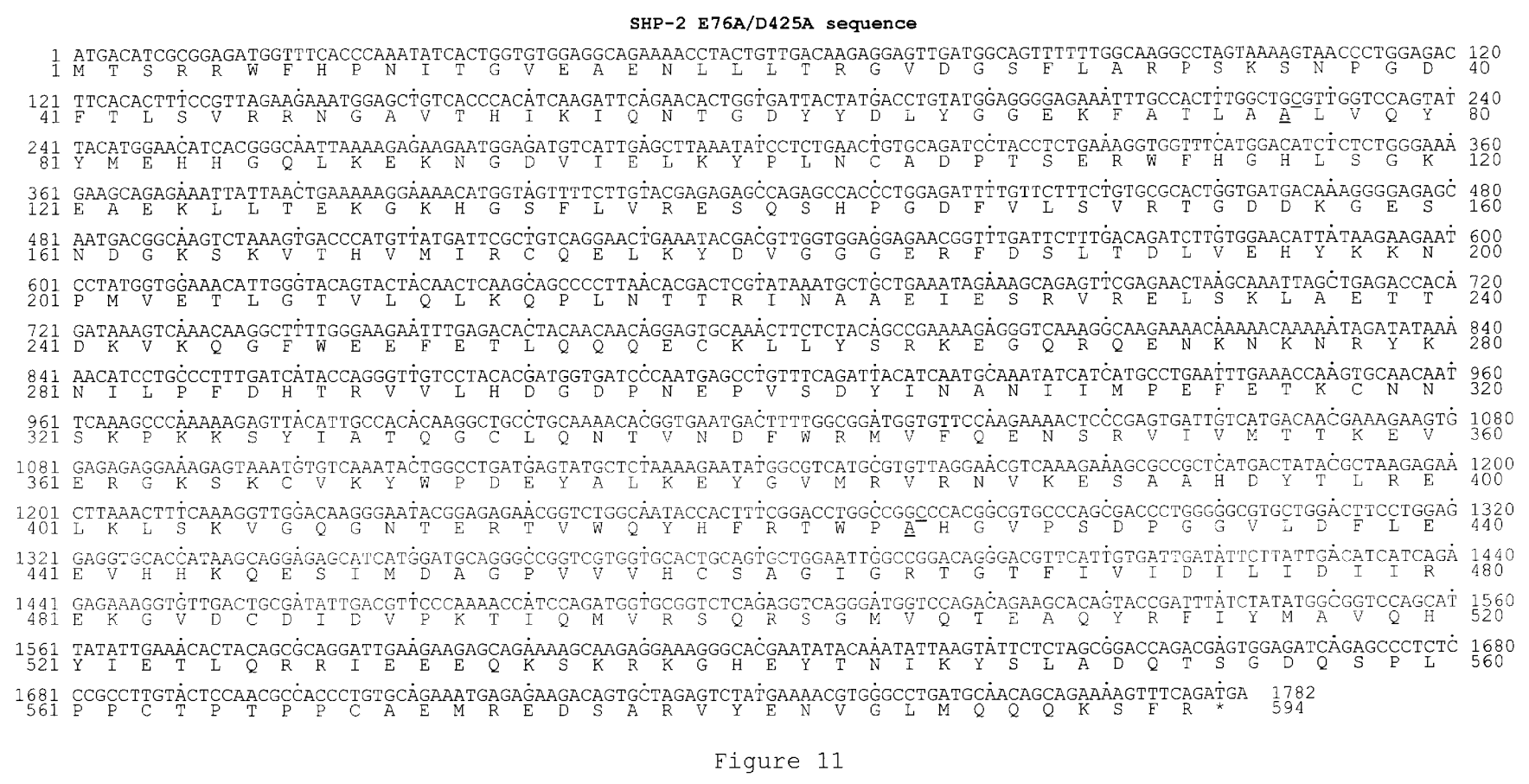
Figure 18:
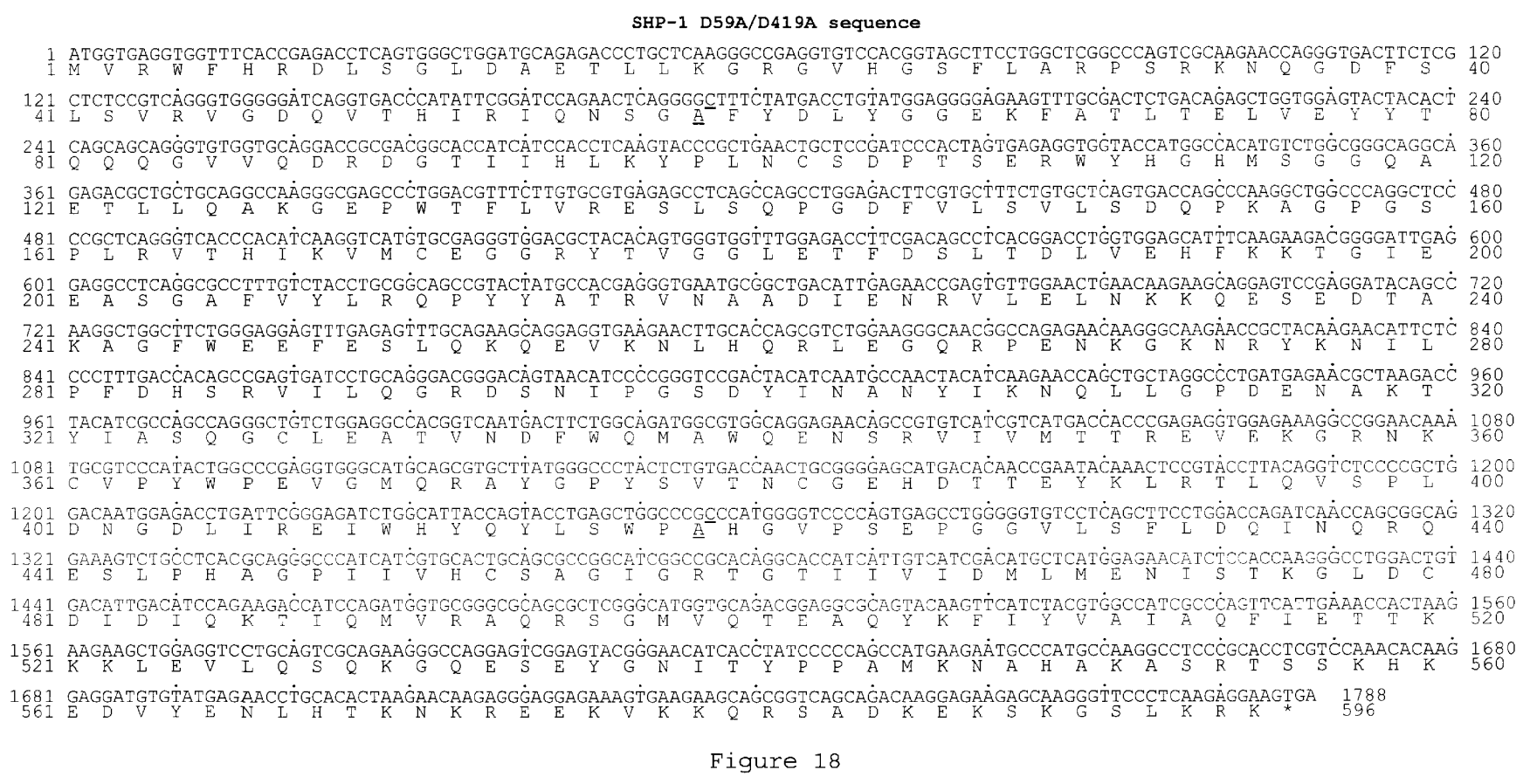
Figure 19:
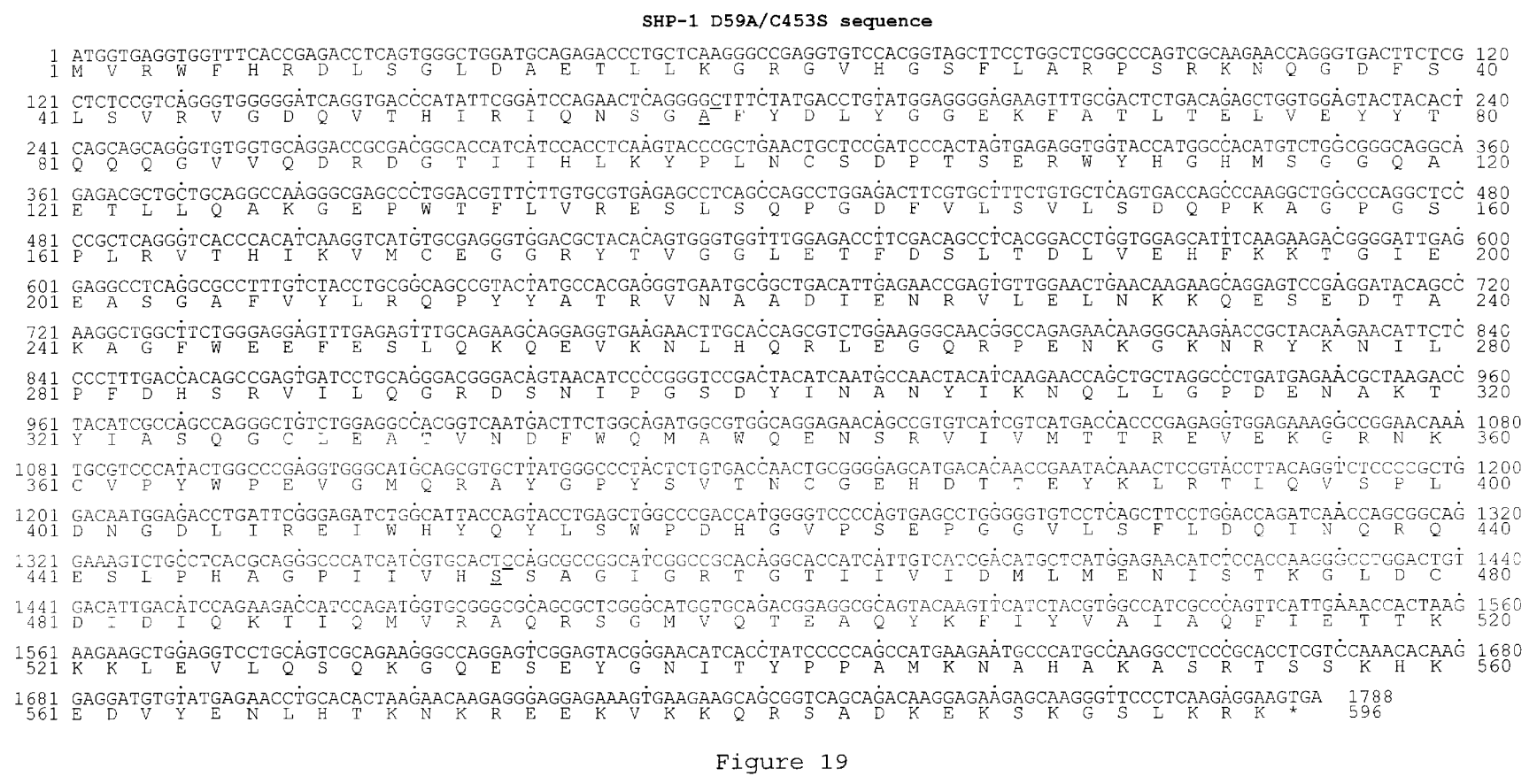
Figure 20:
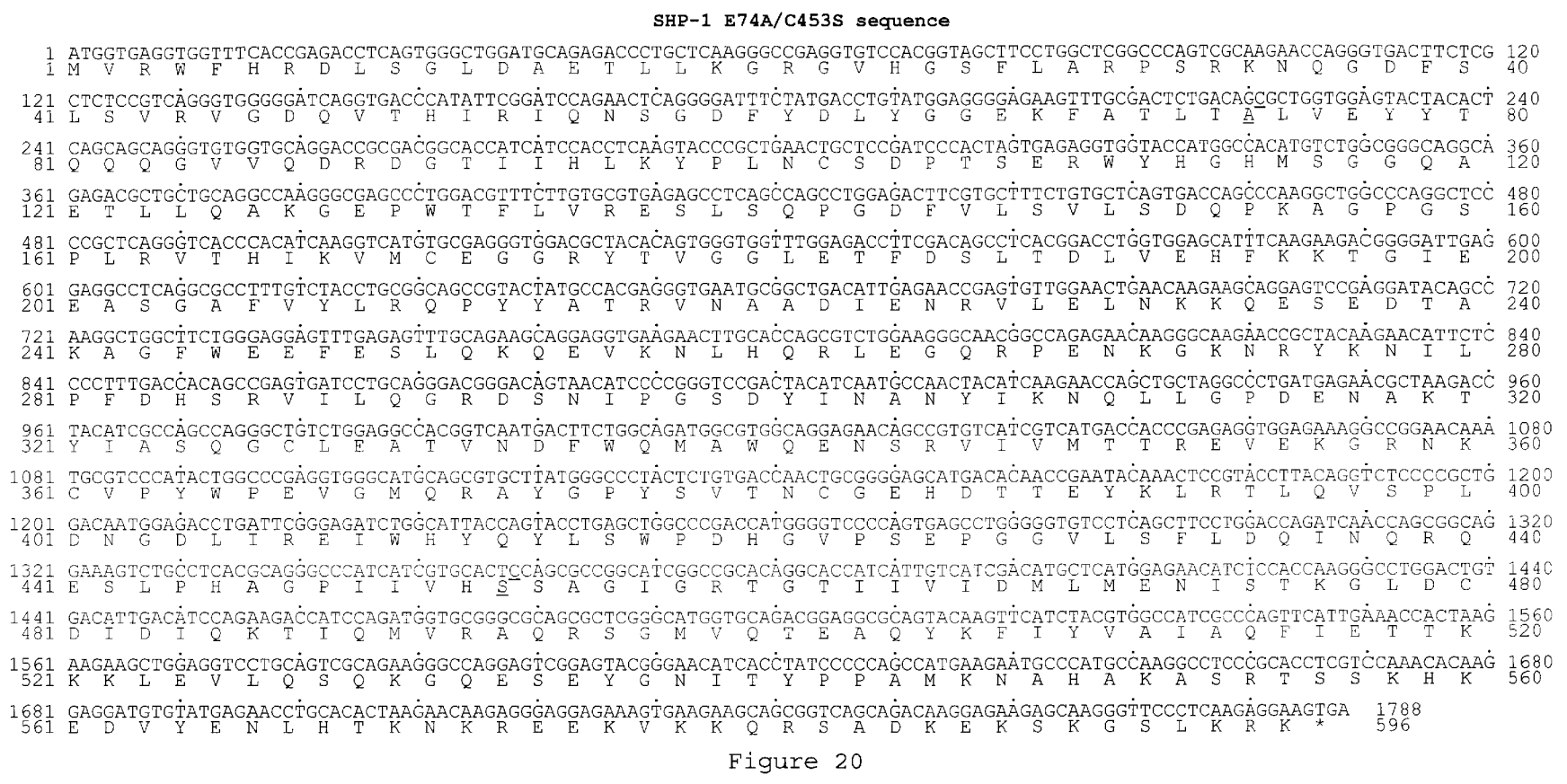
Figure 21:
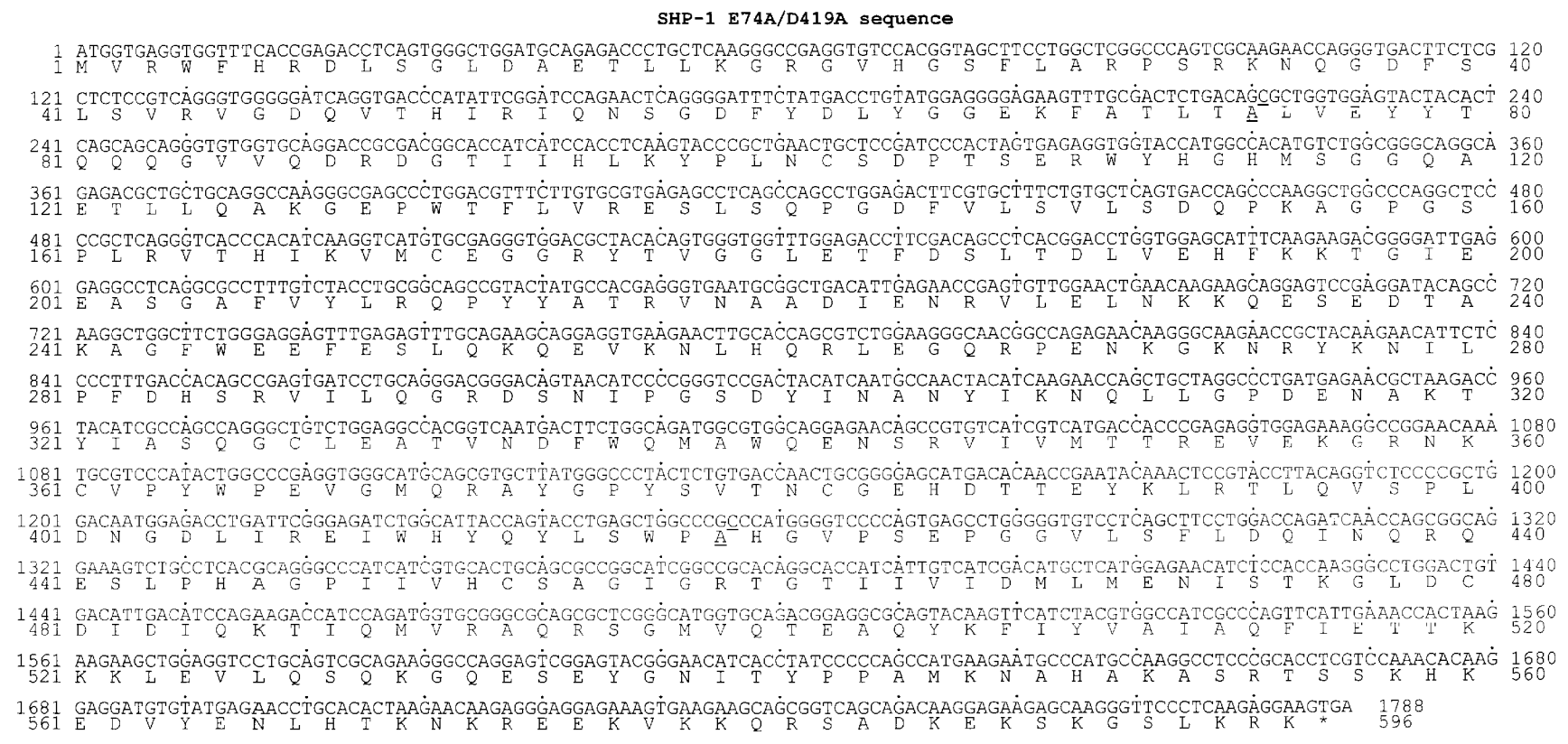

In another embodiment the nucleic acid molecule has a compound mutation (e.g., a double, triple, quadruple or ore mutation) and encodes a activated compound mutant SH2-domain-containing protein tyrosine phosphatase. The term "compound mutation" as used herein refers to at least one mutation in the SH2 domain of the phosphatase as described herein and at least one additional mutation in the catalytic domain of the phosphatase. For example, in the case of a double mutant (e.g., D61A/D425A), due to the mutation in the catalytic domain, a substrate, or binding partner can still bind to the activated mutant protein tyrosine phosphatase but the catalytic domain is enzymatically inactive (e.g., cannot dephosphorylate a substrate). For example, in this embodiment for a double activated mutant, an additional mutation in the catalytic domain can substitute a cysteine at position 459 or 453 with an alanine or serine residue; or an asparatic acid at position 425 or 419 with an alanine residue. In a preferred embodiment the activated compound double mutant is the D61A/D425A mutant (FIG. 8; SEQ ID NO: 12) of SHP-2 made by substituting the aspartic acid at position 61 and 425 with an alanine (See Example 8). In one embodiment the activated compound double mutant is the D61A/C459S (FIG. 9; SEQ ID NO: 14), or E76A/C459S (FIG. 10; SEQ ID NO: 16), or E76A/D425A (FIG. 11; SEQ ID NO: 18) of SHP-2. In another embodiment the activated compound double mutant is the D59A/D419A (FIG. 18; SEQ ID NO: 32), or D59A/C453S (FIG. 19; SEQ ID NO: 34), or E74A/C453S (FIG. 20; SEQ ID NO: 36), or E74A/D419A (FIG. 21; SEQ ID NO: 38) of SHP-1. The phosphatase activity of the activated compound mutants can be determined by methods described herein (see Example 3). Techniques to assess ligand binding to a SH2-domain-containing protein tyrosine phosphatase are known in the art. Exemplary methods are described in Klingmüller, U., et al., U.S. Pat. No. 5,659,012 (1997), the teachings of which are incorporated herein by reference.

Figure 12:
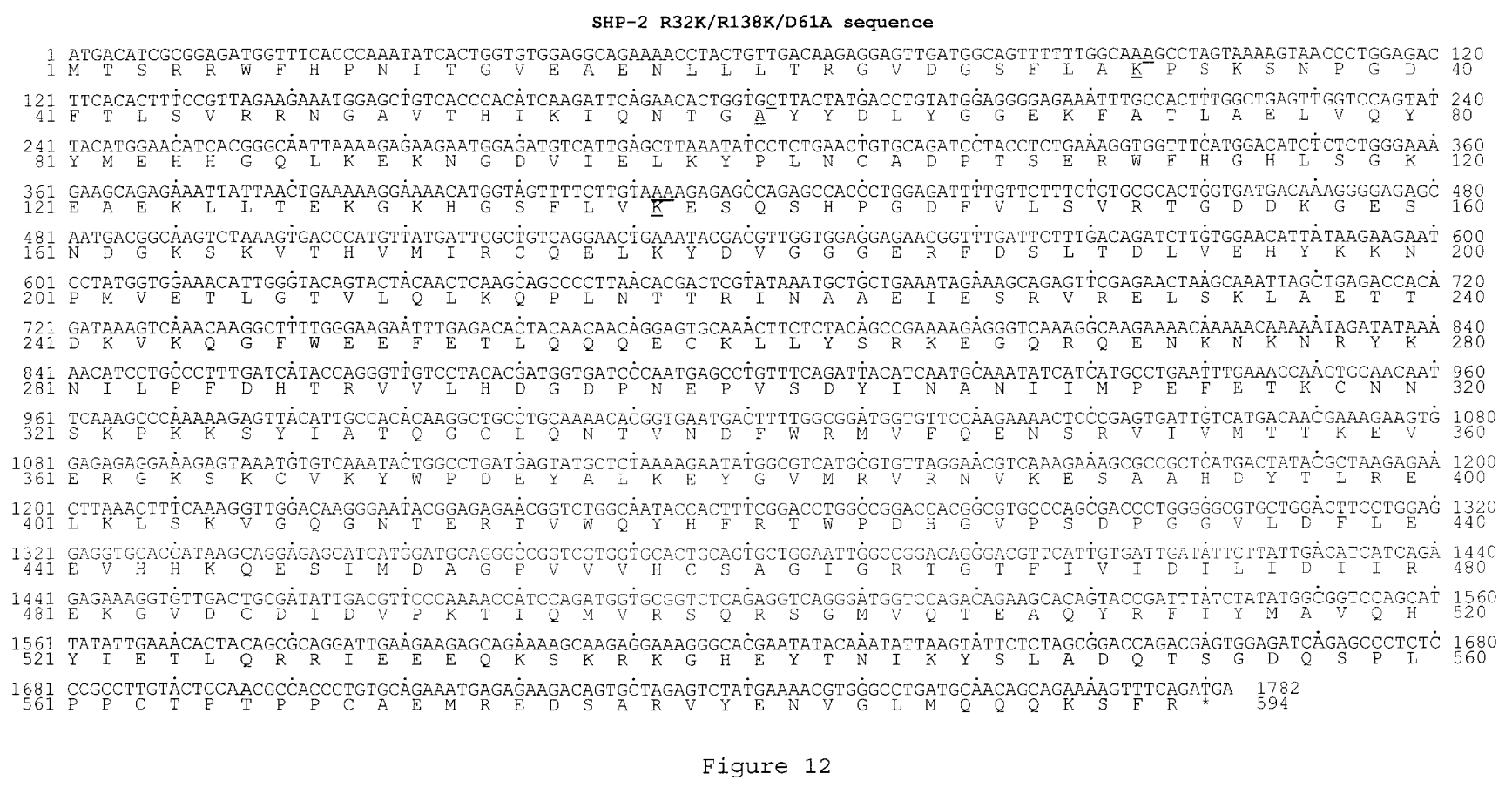
Figure 13:
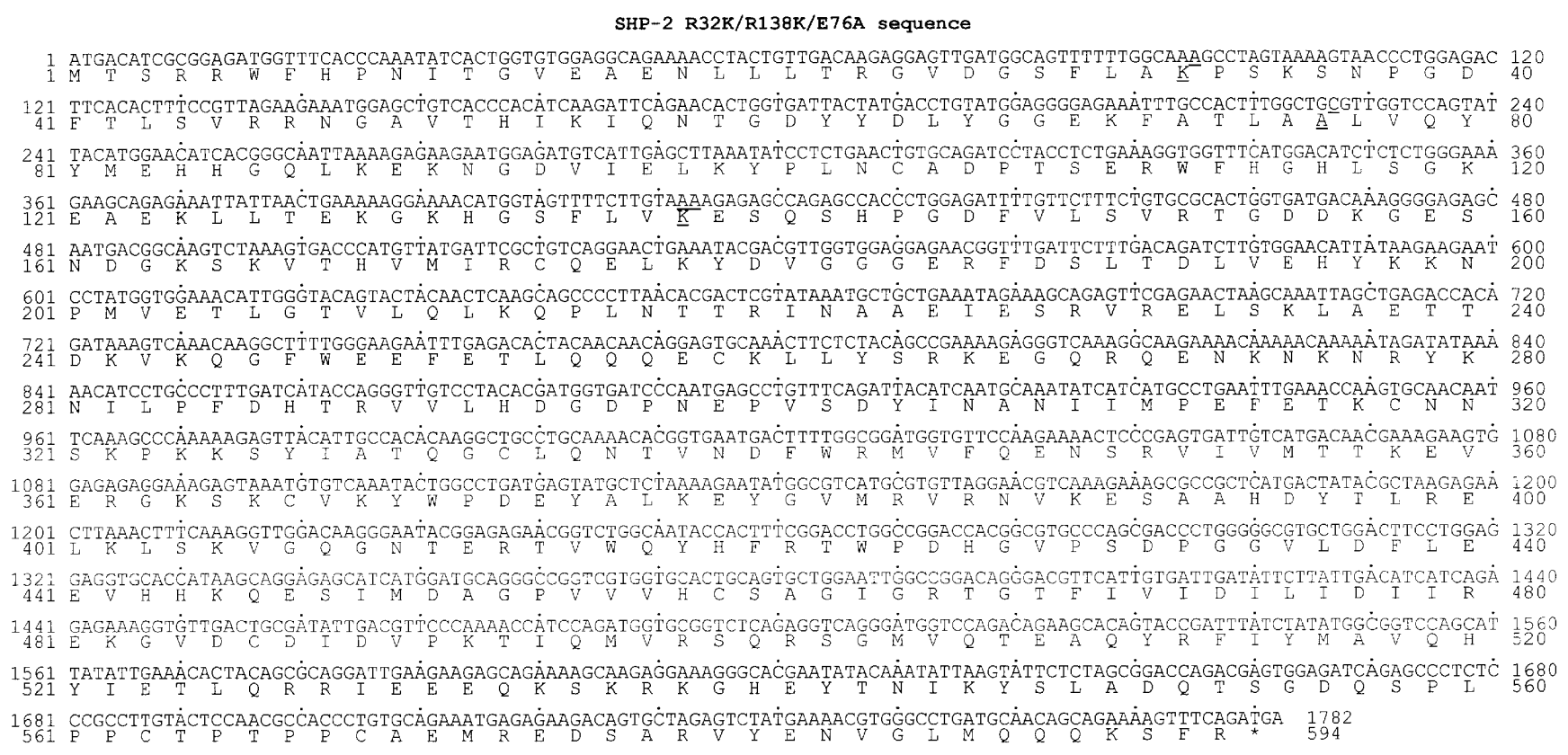

In yet another embodiment, the activated compound mutant is a triple mutant SH2-domain containing protein tyrosine phosphatase as described herein. For example, the triple SHP-2 mutants R32K/R138K/D61A (FIG. 12; Examples 8 and 9; SEQ ID NO: 20) or R32K/R138K/E76A (FIG. 13; SEQ ID NO: 22) due to mutations in the N-SH (e.g., R32K), and the C-SH (e.g., R138K) domains are unable to bind ligand. The additional mutation in the backside loop (e.g., D61A or E76A) results in a triple mutant which can not bind ligand (e.g., phosphotyrosine peptides) yet dephosphorylates substrates thereby providing a mutant which can be used to distinguish candidate ligands from candidate substrates.

As used herein the designation for the amino acid substitutions for activated mutants are depicted as, for example, R32K wherein the letter to the right of the number depicts the amino acid in the wildtype phosphastase (e.g., R or arginine); the number depicts the position of the amino acid in the wildtype phosphatase (e.g., position 32); and the letter to the left of the number depicts the amino acid residue which replaces the wildtype (e.g., K or lysine). Therefore, the R32K/R138K/D61A mutant comprises substituting the arginine at position 32 with a lysine residue; the arginine at position 138 with a lysine; and the asparatic acid at position 61 with an alanine residue.

Figure 22:
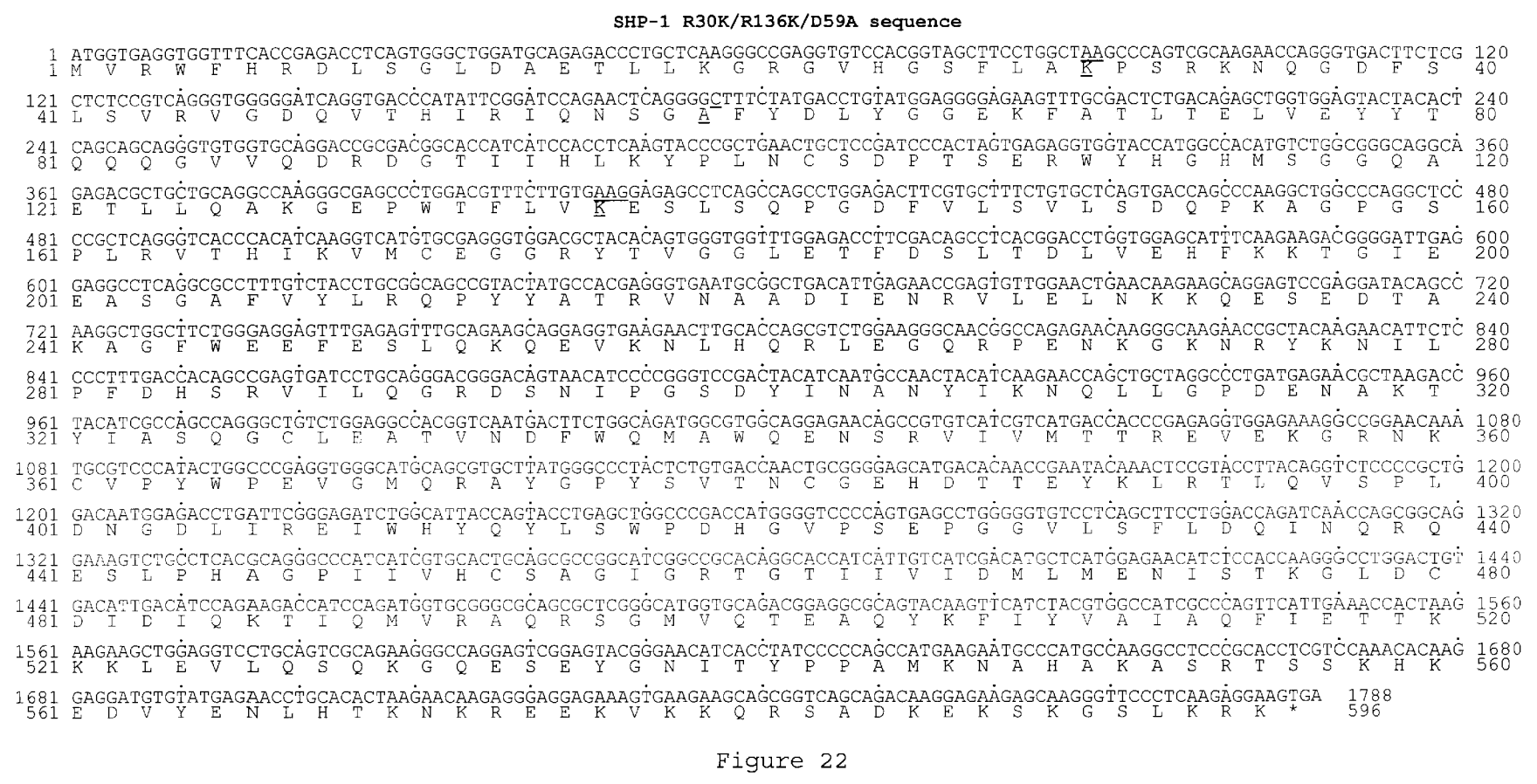
Figure 23:
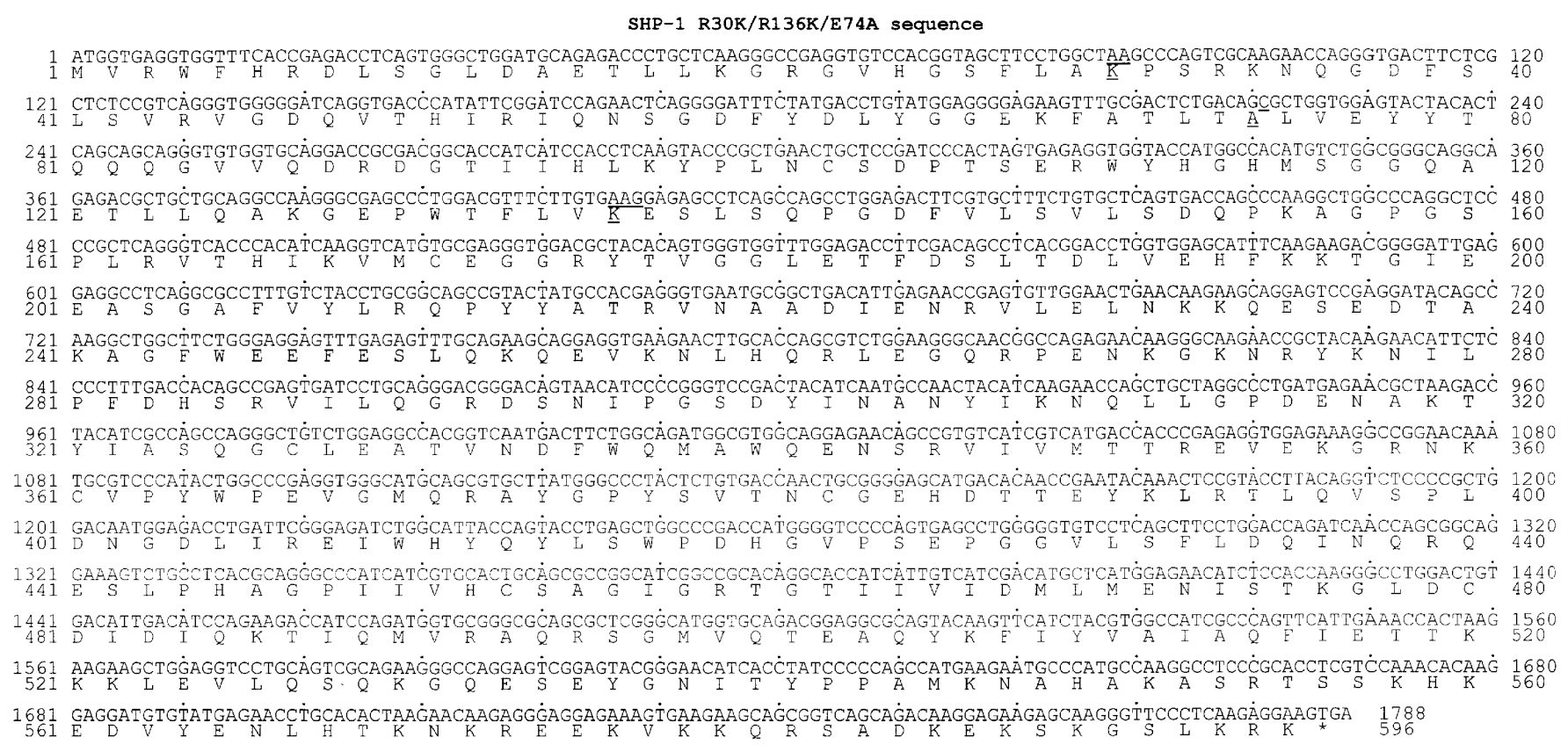

The activated compound triple mutants can also be triple mutants of SHP-1, for example, R30K/R136K/D59A (FIG. 22; SEQ ID NO: 40), or R30K/R136K/E74A (FIG. 23; SEQ ID NO: 42).

Figure 14:
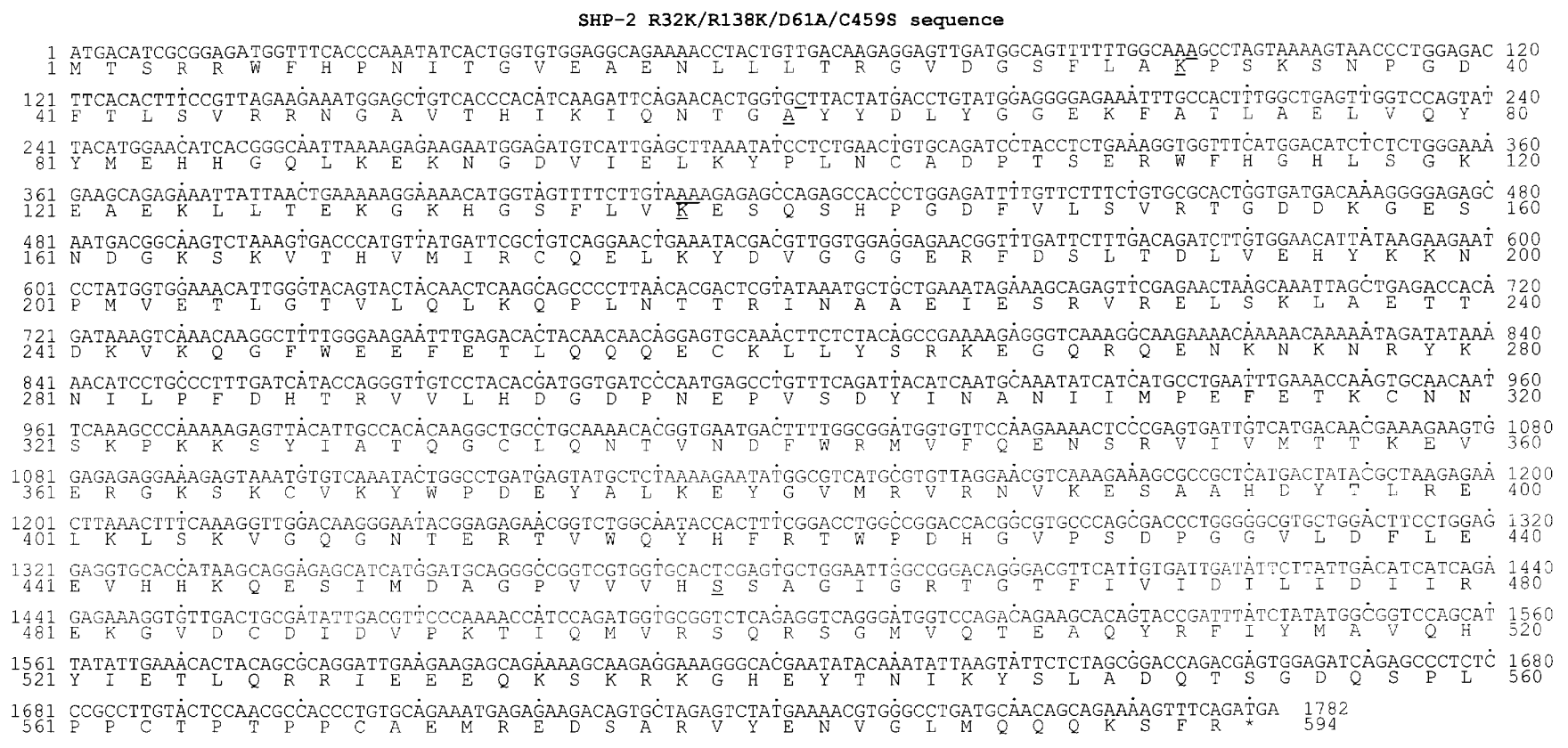
Figure 15:
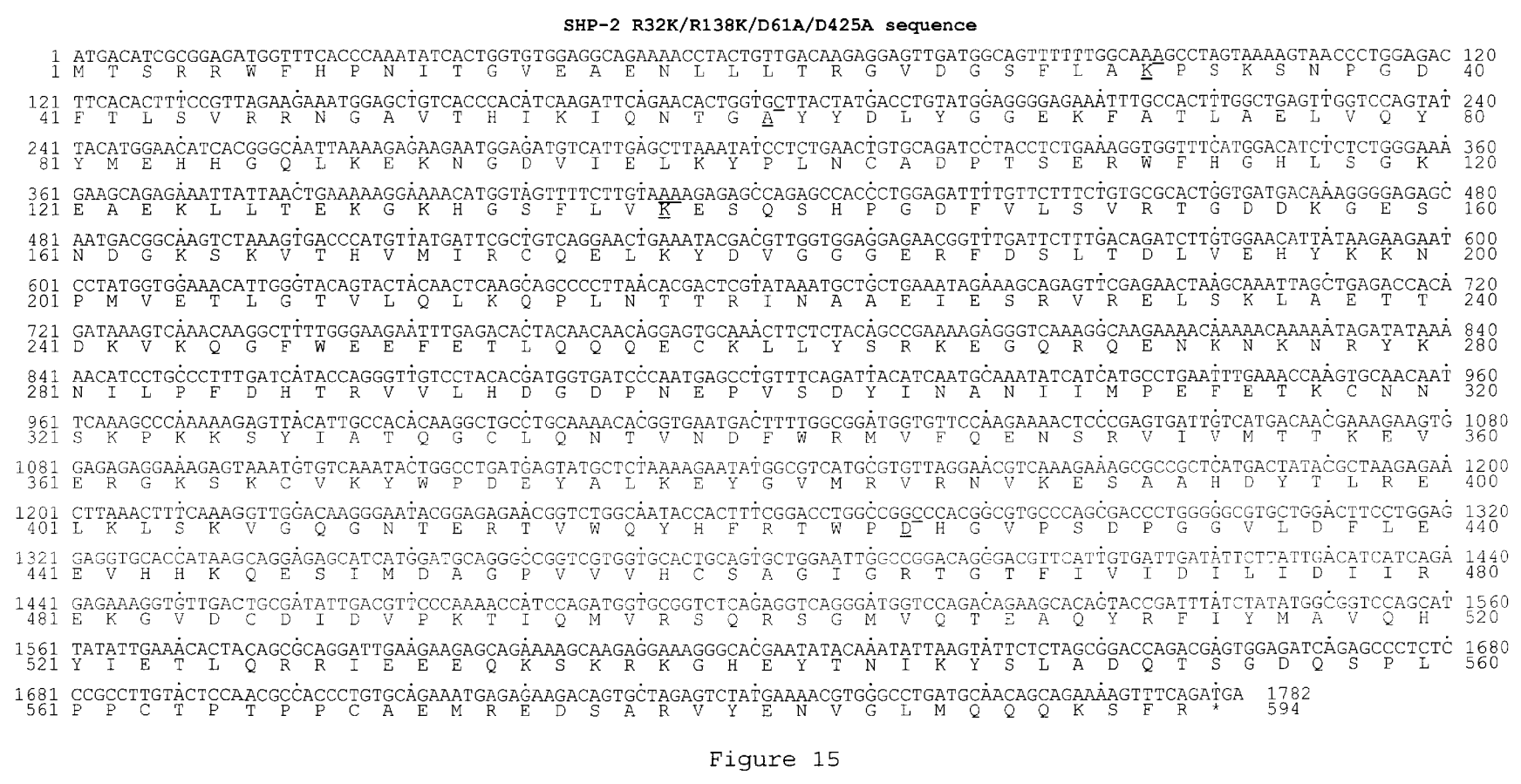
Figure 16:
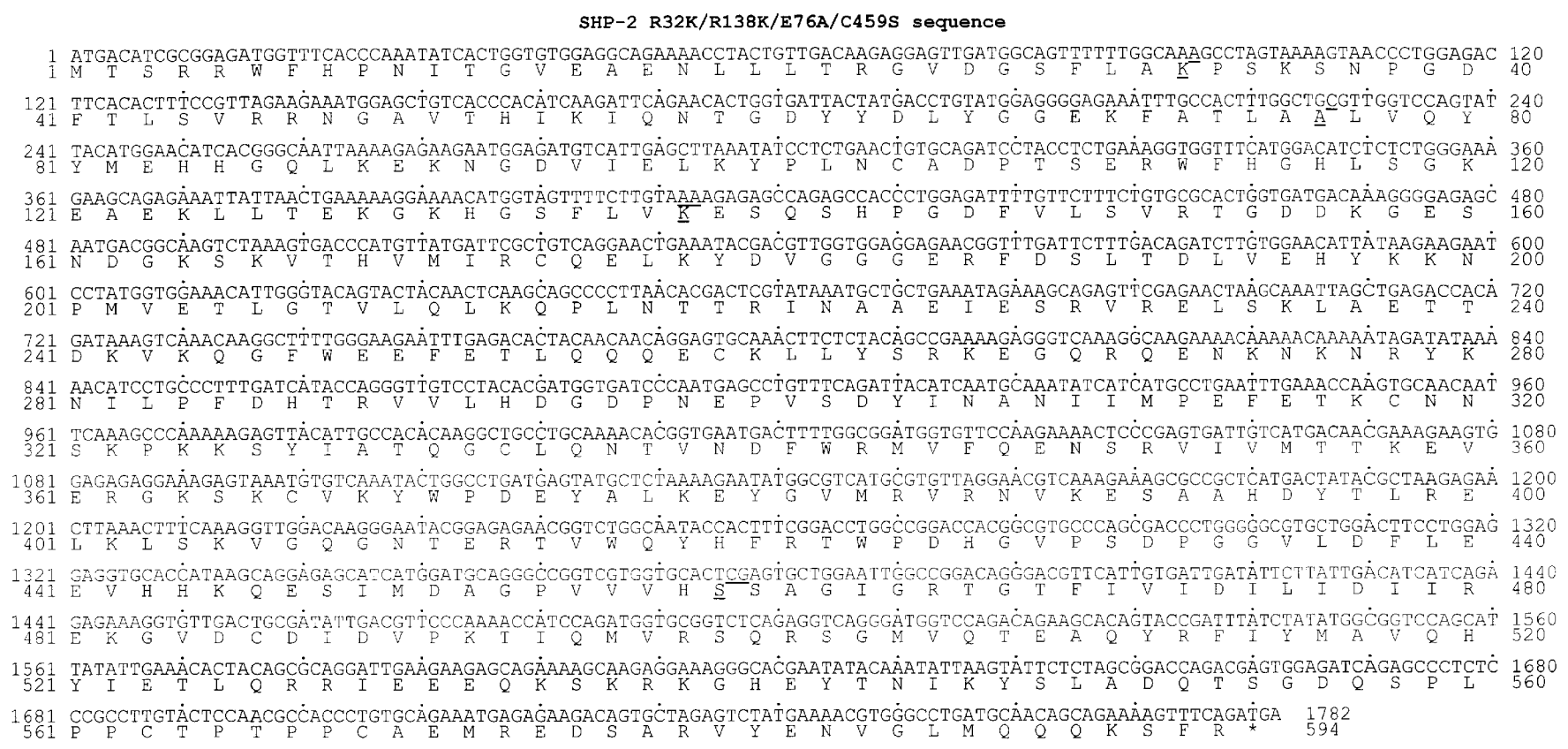
Figure 17:
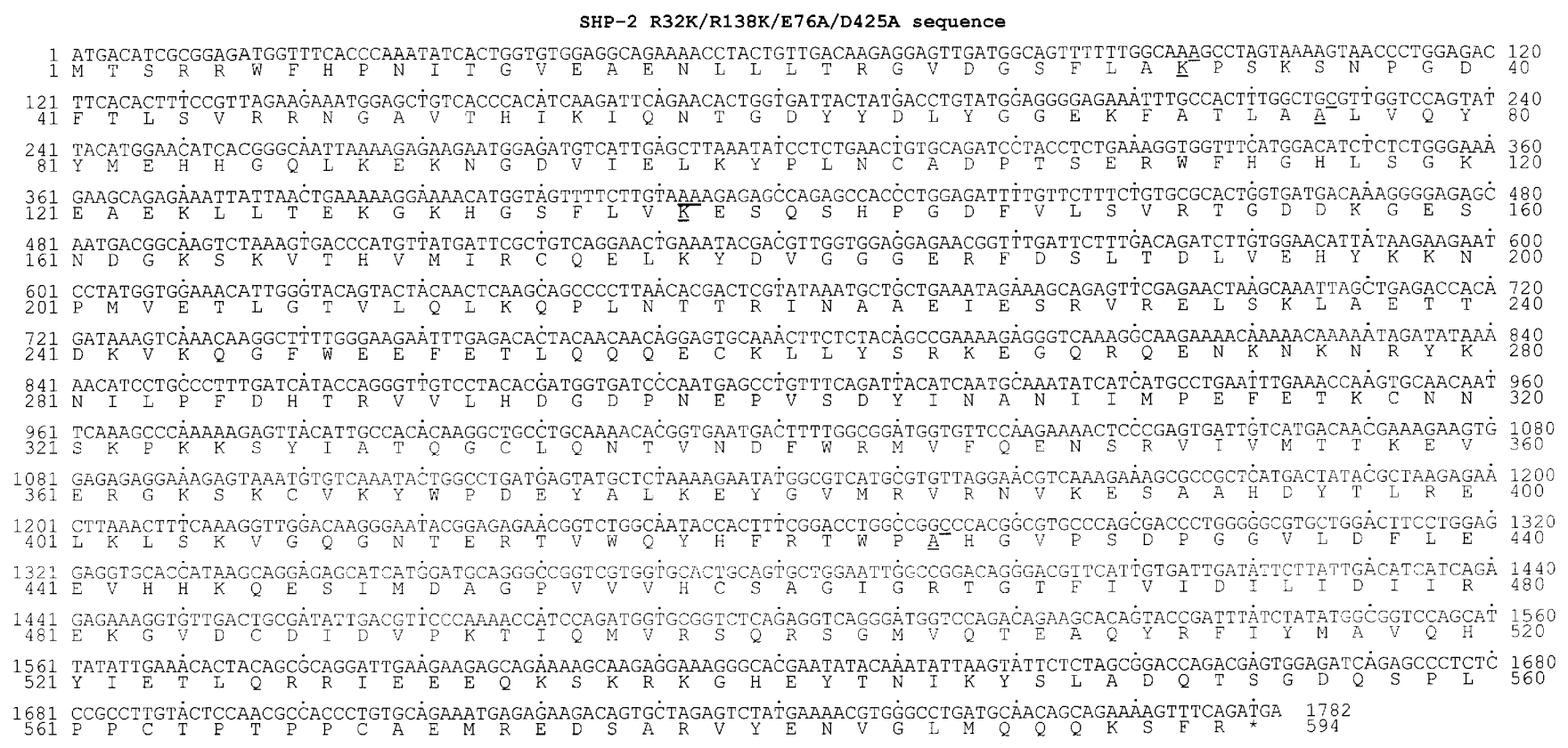

In a further embodiment the activated compound mutant is a quadruple mutant. Examples of quadruple mutants include activated compound mutants of SHP-2 such as (e.g., R32K/R138K/D61A/C459S (FIG. 14; SEQ ID NO: 24), or R32K/R138K/D61A/D425A (FIG. 15; SEQ ID NO: 26), or R32K/R138K/E76A/C459S (FIG. 16; SEQ ID NO: 28), or R32K/R138K/E76A/D425A (FIG. 17; SEQ ID NO: 30). As described herein for single and double activated compound mutants, suitable sites for making triple and quadruple mutants for other SH2-domain containing phosphatases, such as SHP-1 (FIG. 6; SEQ ID NOS: 7 and 8), can also be determined.

Figure 24:
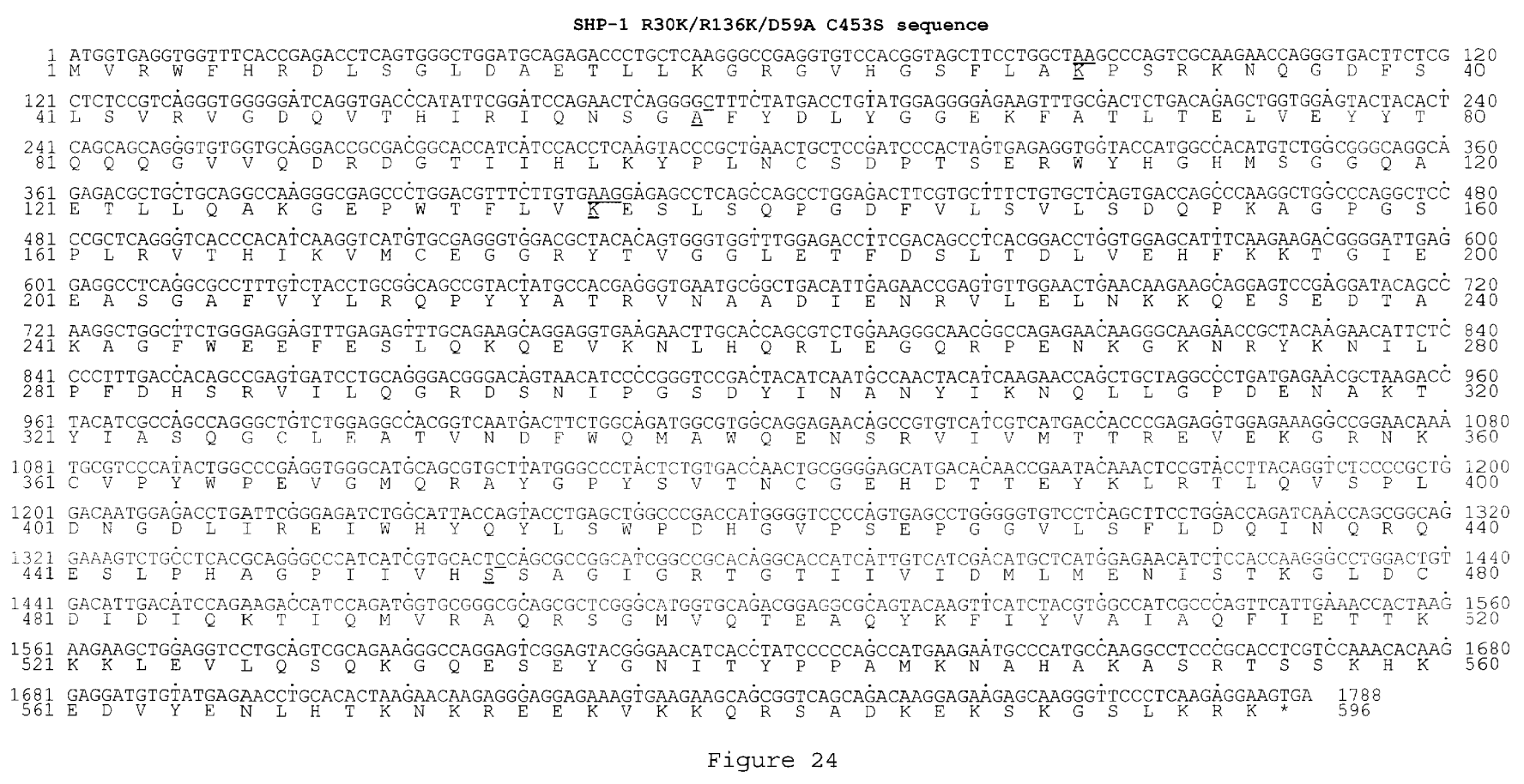
Figure 25:
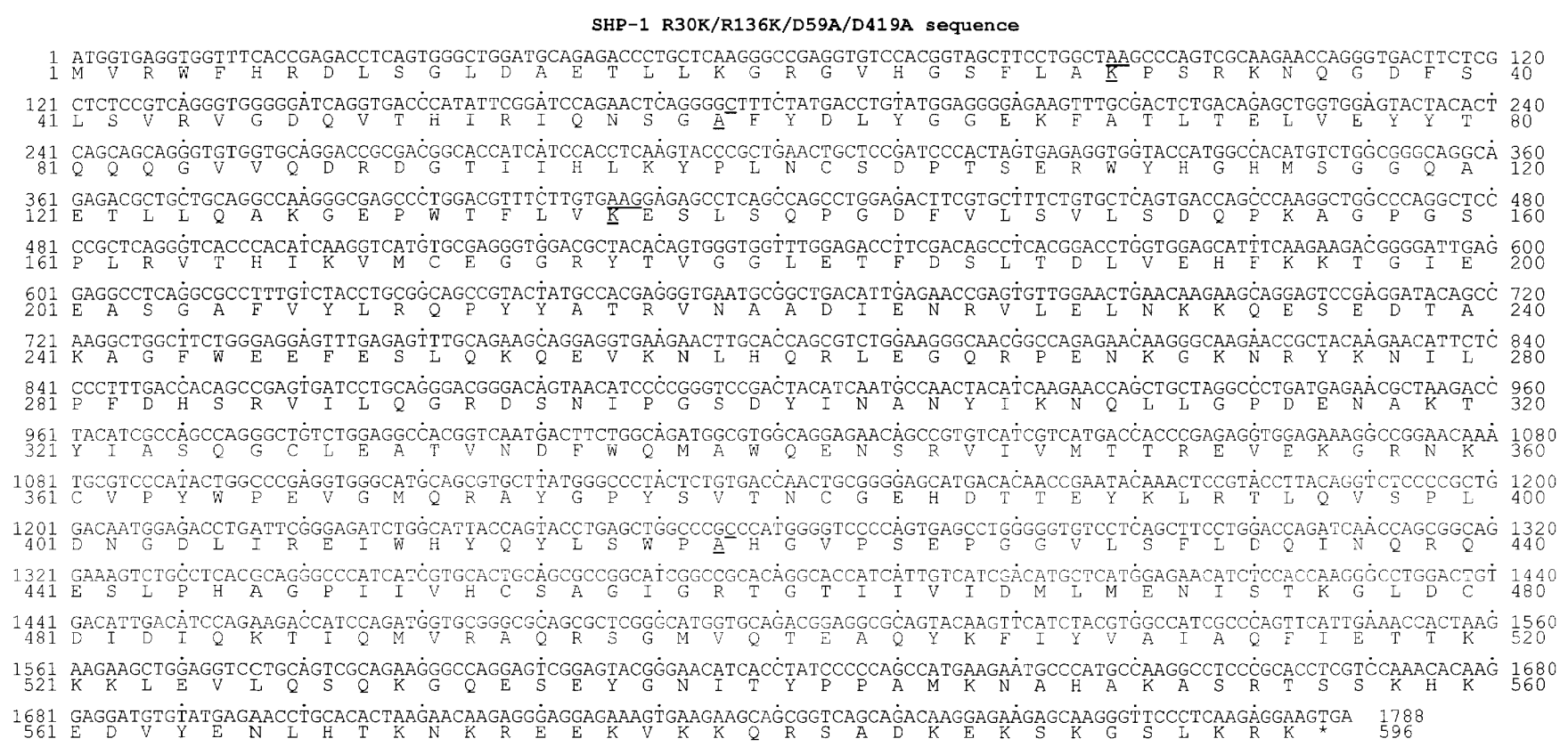
Figure 26:
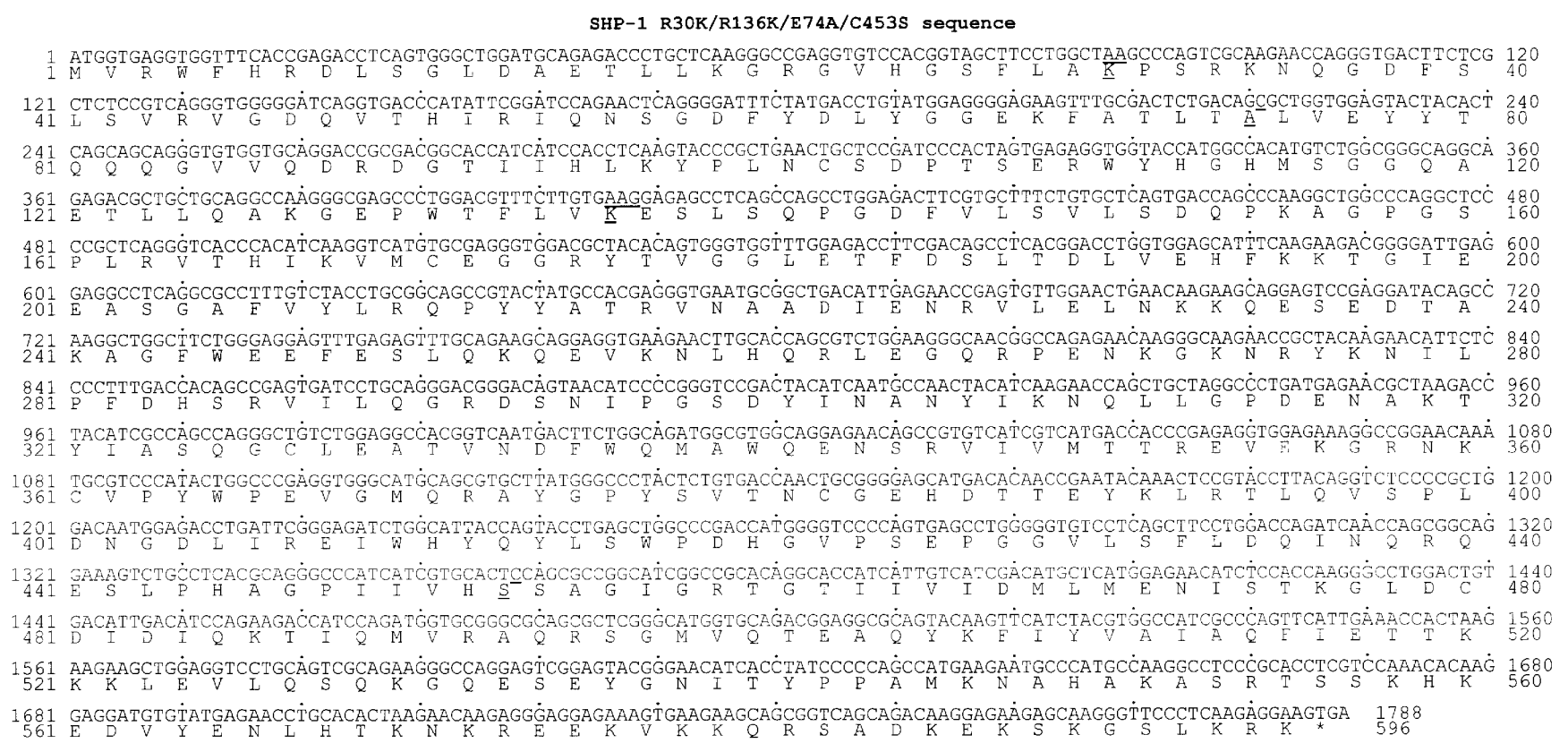
Figure 27:
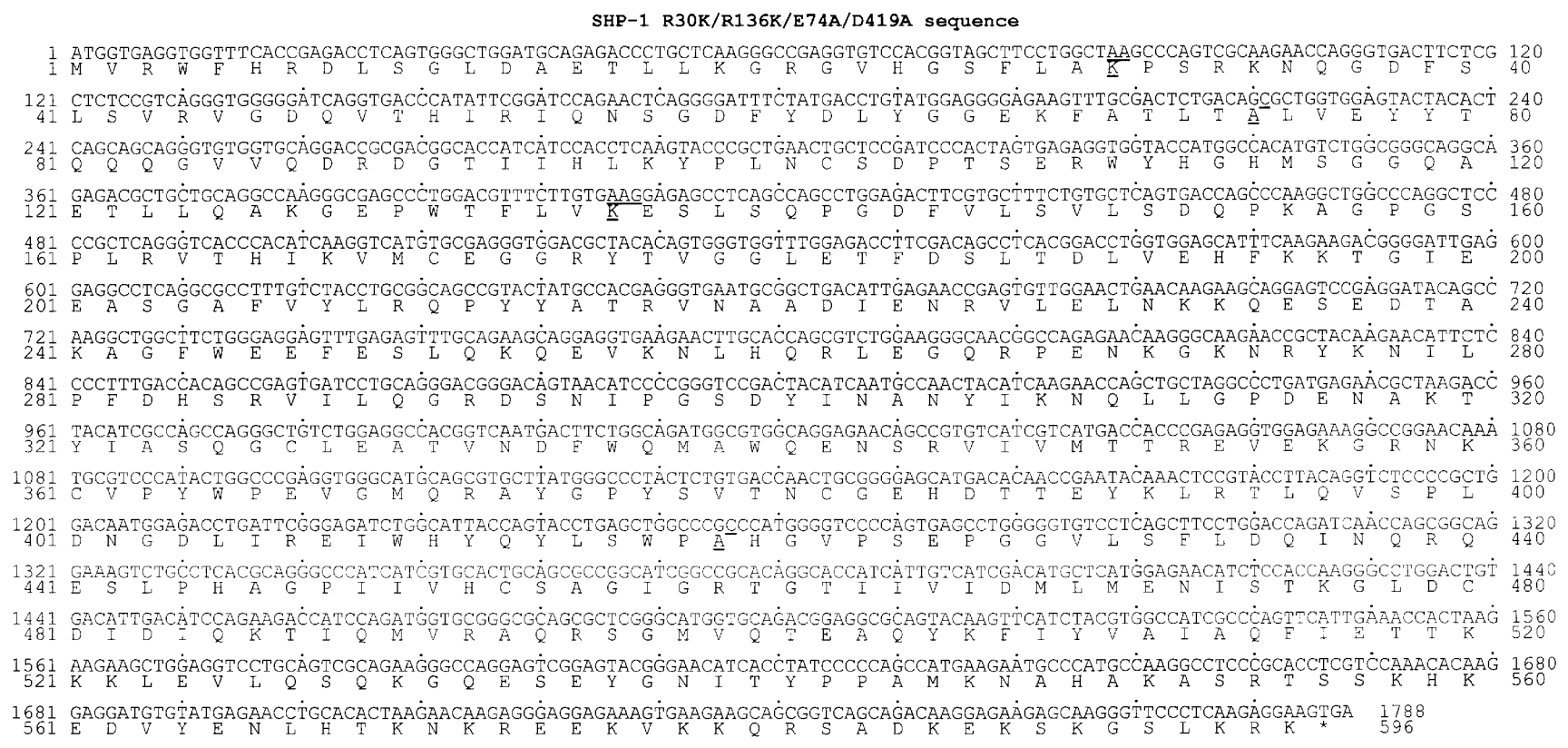

The activated compound quadruple mutants can also be quadruple mutants of SHP-1, for example, R30K/R136K/D59A/C453S (FIG. 24; SEQ ID NO: 44), or R30K/R136K/D59A/D419A (FIG. 25; SEQ ID NO: 46), or R30K/R136K/E74A/C453S (FIG. 26: SEQ ID NO: 48), or R30K/R136K/E74A/D419A (FIG. 27: SEQ ID NO: 50).

In another embodiment of the invention the SH2-containing protein tyrosine phosphatase has a mutation resulting in a partially active mutant. A "partially active" mutant is intended to refer to a mutant that has any amount of phosphatase activity greater than basal activity but activity that can be further activated by the addition of phosphotyrosine ligand for its SH2 domains (e.g., phosphatase activity in the absence of ligand or substrate). In one embodiment a point mutation substituting aspartic acid at position 61 in the backside loop of SHP-2 with alanine results in the partially active D61A mutant (FIG. 3).

The SH2-containing protein tyrosine phosphatases of the invention can be produced by recombinant DNA technologies using nucleic acid constructs. Nucleic acid constructs are defined herein as heteropolymers of nucleic acid molecules. Nucleic acid molecules are meant to refer to chains of nucleotides joined together by phosphodiester bonds to form a nucleic acid heteropolymer. The nucleic acid molecules can be double stranded or single stranded and can be deoxyribonucleotide (DNA) molecules, such as cDNA or genomic DNA, or ribonucleotide (RNA) molecules. As such, the nucleic acid molecule can include one or more exons, with or without, as appropriate, introns. In one example, the nucleic acid molecule contains a single open reading frame which encodes the SH2-containing protein tyrosine phosphatase. The generation of nucleic acid constructs are standard molecular biological procedures and well known in the art. (See, for example, Ausubel et al., "Current Protocols in Molecular Biology", John Wiley & Sons, Inc. (1998)). Alternative combinations or modifications of the nucleic acid constructs according to the present invention would be apparent to the person of skill in the art.

Thus, the nucleic acid molecules of the invention can include nucleotide sequences which encode activated mutant SH2-containing protein tyrosine phosphatases, as well as one or more of the following optional sequences, in a functional relationship: regulatory sequences, a start codon, splice donor sites, splice acceptor sites, introns, stop codon, transcription termination sequences, 5' and 3' untranslated regions, polyadenylation sequences, negative and/or positive selective markers, and replication sequences.

The nucleic acid molecules preferably comprise regulatory sequences. Regulatory sequences are art-recognized and include cis-acting elements that control transcription and regulation, such as promoter sequences, enhancers, ribosomal binding sites, and transcription binding sites. Selection of the promoter will generally depend upon the nucleic acid construct and desired expression properties. In a preferred embodiment, promoter sequences are selected which are functional in bacteria (e.g., *E. coli*), mammalian cells (e.g., COS, CHO cells), yeast (e.g., *Pichia pastorius, Saccharomyces cerevisae*), and insect cells (e.g., *Spodoptera frugiperda,* Sf9 cells). Examples of suitable promoters include polyhedrin, β-galactosidase, 3-phosphoglycerate kinase, metallothionein, retroviral LTR, SV40 and TK promoters and are described in detail in art-recognized technical laboratory texts including Ausubel, F. M. et al., "*Current Protocols in Molecular Biology*", John Wiley & Sons, Inc. (1998) and Sambrook et al., "*Molecular Cloning: A Laboratory Manual*", Second Edition (1989).

The nucleotides which comprise the nucleic acid molecule can be isolated from nature, modified from native sequences or manufactured de novo, as described, for example, in Ausubel, F. M., et al., "Current Protocols in Molecular Biology", John Wiley & Sons (1998) and Sambrook, et al., "Molecular Cloning: A Laboratory Manual", Second Edition (1989). The nucleotides can then be isolated by methods known in the art, such as exploiting and manufacturing compatible cloning or restriction sites. Accordingly, the invention pertains to the production of activated mutant SH2-containing protein tyrosine phosphatases by recombinant technologies.

As used herein, an "isolated" gene or nucleotide sequence is intended to mean a gene or nucleotide sequence which is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Thus, nucleic acid constructs contained in a vector are included in the definition of "isolated" as used herein. Also, isolated nucleotide sequences include recombinant nucleic acid molecules in heterologous host cells, as well as partially or substantially purified nucleic acid molecules in solution. In vivo and in vitro RNA transcripts of the DNA molecules of the present invention are also encompassed by "isolated" nucleotide sequences. Such isolated nucleotide sequences are useful in the manufacture of the encoded activated mutant SH2-domain-containing protein tyrosine phosphatases, as probes for isolating homologous sequences (e.g., from other mammalian species or other organisms), for gene mapping (e.g., by in situ hybridization), or for detecting the presence (e.g., by Southern blot analysis) or expression (e.g., by Northern blot analysis) of related SH2-containing protein tyrosine phosphatase genes in tissue. As such, a further aspect of the invention relates to novel, previously unknown and unidentified SH2-containing protein tyrosine phosphatases from tissues or organisms which are activated mutants. The biological activity of the nucleic acid constructs described herein can be determined, for example, by microinjection of mRNA encoding an activated mutant phosphatase which leads to animal cap elongation and induction of cardiac mesoderm specific mRNA in Xenopus explants as described in Example 5. Biological activity can also be evaluated by expressing nucleic acid constructs in host cells, such as mammalian cells, and monitoring alterations in cell proliferation.

This invention also pertains to isolated, purified activated mutant SH2-containing protein tyrosine phosphatases. The activated mutant SH2 containing phosphatase is characterized by the ability to dephosphorylate substrate in the absence of phosphotyrosine peptides (see Example 3). Mutations resulting in activated mutant SH2-protein tyrosine phosphatases can include conservative or non-conservative amino acid substitutions, additions and deletions of one or more amino acids; however, such mutations should preserve at least the catalytic domain of the phosphatase. For example, the mutation(s) can preferably preserve the three dimensional configuration and accessibility and integrity of the binding and/or catalytic site as is present in the wildtype phosphatase. In a preferred embodiment, the mutations are in the SH2 domains of the protein tyrosine phosphatase, most preferably in the amino SH2 domain which has been shown to contribute binding energy, specificity and catalytic activation of the SH2-containing protein tyrosine phosphatase SHP-2 (Hof, P., et al., Cell 92:441–450 (1998)).

The invention also relates to fragments of the nucleic acid molecules and polypeptides described above. The term "fragment" is intended to encompass a portion of the activated mutant polypeptide; or a nucleotide sequence described herein which is at least approximately 25 contiguous nucleotides to at least approximately 50 contiguous nucleotides or longer in length. Such fragments are useful as probes for diagnostic purposes, experimental tools or, in the case of nucleic acid fragments, as primers. Particularly preferred primers and probes selectively hybridize to the nucleic acid construct encoding a wildtype or activated mutant SH2-containing protein tyrosine phosphatase as described herein. For example, nucleic acid fragments which encode the amino-SH2 (N-SH2) domain or polypeptide fragments of the SH2-domains of the activated mutant SH2-containing protein tyrosine phosphatase are useful wherever full-length sequences are described herein.

The nucleic acid molecules can be inserted into a construct which can, optionally, replicate and/or integrate into a recombinant host cell, by known methods. The host cell can be a eukaryotic or prokaryotic cell and includes, for example, yeast (such as *Pichia pastorius* or *Saccharomyces cerevisa*), bacteria (such as Escherichia or Bacillus) expression systems; animal cells or tissue, including insect (such as baculoviruses) or mammalian cells (such as somatic or embryonic cells, Chinese hamster ovary cells, HeLa cells, human 293 cells and monkey COS-7 cells).

The invention also provides vectors containing the mutant SH2-containing protein tyrosine protein phosphatases. Suitable vectors for use in eukaryotic and prokaryotic cells are well known in the art and are, generally commercially available, or readily prepared by the skilled artisan. For example, suitable plasmids for use include pGEX 2T/3X/4T or pET series vectors. Additional vectors can also be found in, for example, Ausubel et al., "Current Protocols in Molecular Biology", John Wiley & Sons, (1998) and Sambrook et al., "Molecular Cloning: A Laboratory Manual", 2nd Ed. (1989), the teachings of which are incorporated herein by reference.

The nucleic acid molecule can be incorporated or inserted into the host cell, also, by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a polypeptide. Methods for preparing such recombinant host cells and incorporating nucleic acids are described in more detail in Sambrook et al., "Molecular Cloning: A Laboratory Manual," Second Edition (1989) and Ausubel, et al. "Current Protocols in Molecular Biology," (1992), for example.

The host cell is then maintained under suitable conditions for expression and recovering the mutant SH2-containing protein tyrosine phosphatase. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The selection of a buffer is not critical to the invention. The pH which can be selected is generally one tolerated by or optimal for growth for the host cell.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be for example, between about 13°–40° C.

The SH2-containing protein tyrosine phosphatases produced by the processes described herein can be isolated and purified (e.g., to homogeneity) by known means. Examples of suitable purification and isolation processes are generally known and include ammonium sulfate precipitation; dialysis; gel filtration, immunoaffinity, high performance liquid or ion exchange chromatography; electrophoresis; ethanol or acetone precipitation; phosphotyrosine agarose affinity chromatography; ultrafiltration, microfiltration or diafiltration or any combination thereof. The particular method will depend upon the mutations and the properties of the resulting polypeptide and the selection of a host cell. Appropriate methods will be readily apparent to one of ordinary skill in the art.

The mutant SH2-containing protein tyrosine phosphatase is preferably purified substantially prior to use, particularly where the mutant phosphatase is employed in in vitro screens of agents which alter phosphatase activity although the degree of purity is not necessarily critical where the mutant protein phosphatase is to be used in vitro. It is most preferred to employ a mutant SH2-containing protein tyrosine phosphatases which is essentially pure (e.g., about 99% by weight or to homogeneity).

Mutant SH2-containing protein tyrosine phosphates which are prepared according to the above method can be screened for activity. To screen the mutant SH2-containing protein tyrosine phosphatases for phosphatase activity, for example, the mutant phosphates are used in in vitro assays with radiolabeled substrate in the presence or absence of phosphotyrosine peptides (see Example 3).

The activated mutant SH2-containing protein tyrosine phosphatases produced by the methods described herein can be tested for particular biologic activities such as phosphatase activity (See Example 3) and "animal cap assays" (See Examples 5 and 9) (Freeman, R. M., et al., *Proc. Natl. Acad. Sci. USA* 89:11239–11243 (1992); Tang, T. L., et al., *Cell* 80:473–483 (1995); O'Reilly, A. M., et al., *Molec. Cell. Biol.* 18:161–177 (1998)), as well as immunogenicity and antigenicity.

The Xenopus FGF receptor is essential for normal embryogenesis (Amaya, E., et al., *Cell* 66:257–260 (1991); Amaya, E., et al., *Development* 118:477–487 (1993)). Vegetal pole cells in the blastulae send signals to the marginal zone, instructing these cells to differentiate into mesoderm ("mesoderm induction") (Nieuwkoop, P. D., *Wilhelm Roux' Arch* 162:341–373 (1969); Nieuwkoop, P. D., *J. Embryol. Exp. Morph.* 89 *Suppl.*:333–347 (1985)). This phenomenom is the basis for the "animal cap assay", in which various peptide growth factors (e.g., bFGF) induce animal cap cells to become mesoderm (Klein, P. S., et al., *Endocrine Rev.* 15:326–341 (1994); Smith, J. C., *Curr. Opin. Cell Biol.* 7:856–861 (1995).

Elongation of animal cap explants can be induced by activated SHP-2 mutants in the absence of basic FGF (bFGF) (See Examples 5 and 9). As such, a functionally equivalent activated mutant SH2-containing protein tyrosine phosphatase would result in similar phenotypic changes. Methods to assess "animal cap elongation" in Xenopus explants including microinjection, culturing and staging of embryos as well as assays to evaluate phosphatase activity in vitro are art-recognized and well known to one of ordinary skill in the art. See, for example, Ullrich, A., et al., U.S. Pat. No. 5,589,375 (1996); Klingmüller, U., et al., U.S. Pat. No. 5,659,012 (1997); Tonks, N., et al., PCT publication WO 98/04712 (1998); O'Reilly, A. M., et al., *Molec. Cell. Biol.* 18:161–177 (1998); Newport J., et al., *Cell* 30: 675–686 (1982); Tang, T. L., et al., *Cell* 80:473–483 (1995), the teaching of which are incorporated herein in their entirety. Additional techniques include, for example in the case of SHP-1 activated mutants, blocking of B-cell, erythropoietin and IL-3 receptor activation (Neel, B. G., et al., *Curr. Opinion Cell Biol.* 9:193–204 (1997); Klingmüller, U., et al., U.S. Pat. No. 5,659,012 (1997)).

Figure 5:
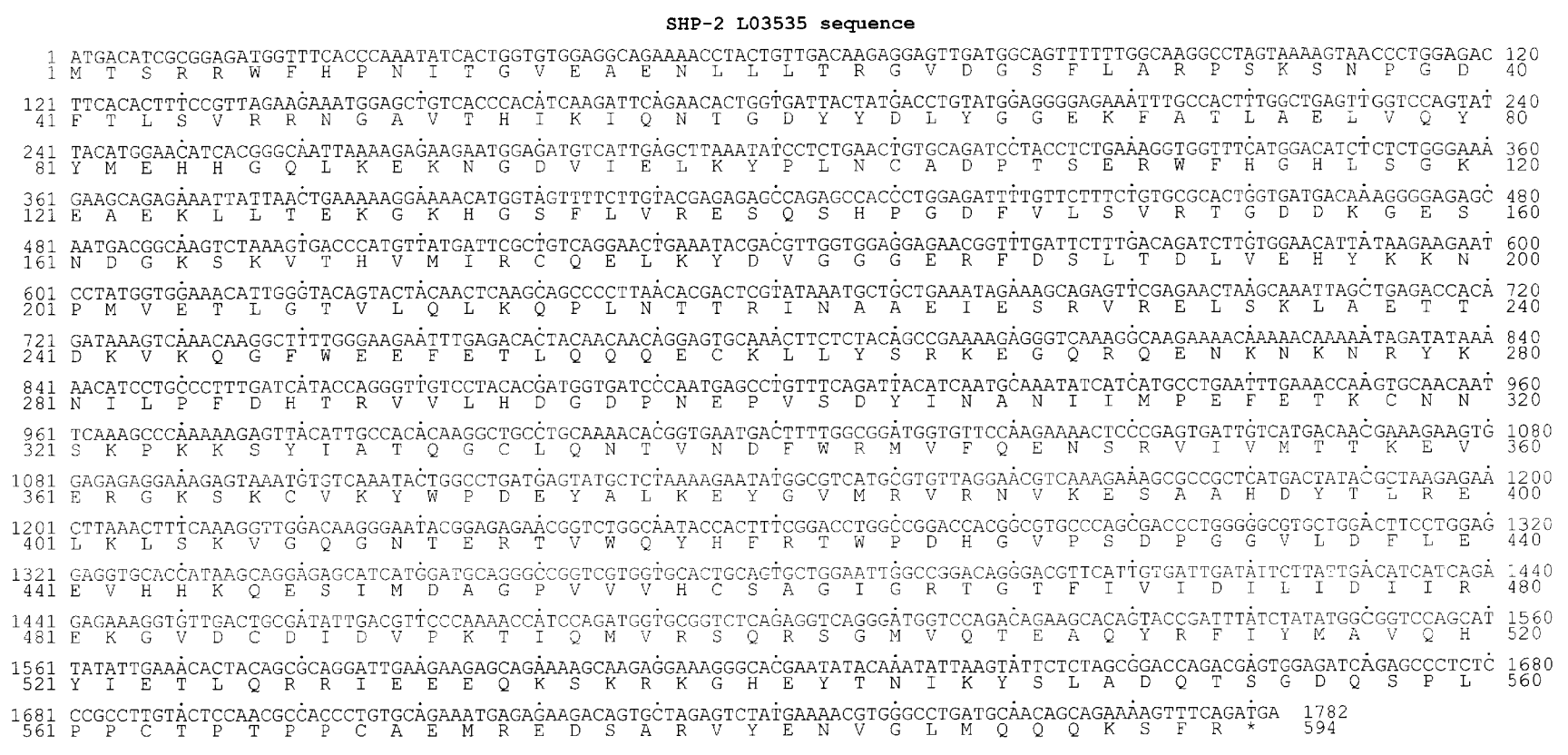

Nucleic acid molecules coding for suitable SH2-containing protein tyrosine phosphatases which can be mutated, e.g., SHP-2 (FIG. 5; SEQ ID NO:5), SHP-1 (FIG. 6; SEQ ID NO: 7) and corkscrew (FIG. 7; SEQ ID NO:9), are known in the art and can be obtained from, for example, the EMBL/GenBank data bases, such as Accession numbers for SHP-1 (M77273), SHP-2 (L03535) and corkscrew (M94730). Alternatively, other sequences can be employed, such as homologs or relatives of related genes which are structurally or functionally equivalent to known SH2-containing protein tyrosine phosphatases.

The phrase "functionally equivalent" as used herein refers to any nucleic acid sequence and its corresponding protein which mimics the biological activity of SH2-containing protein tyrosine phosphatases (such as SHP-2 induced phenotypic changes or alterations in the transcription of responsive genes such as muscle actin in Xenopus explants) or which exhibit nucleotide or amino acid sequence identity to SH2-containing protein tyrosine phosphatases such as SHP-2, SHP-1 or corkscrew. In one embodiment, the nucleic acid or amino acid sequence shares at least about 20% sequence identity with the corresponding native sequence, preferably, at least about 25% sequence. In a more preferred embodiment, the percent sequence identity is at least about 30–50%, and still more preferably, at least about 60–75%.

For example, SHP-1 and SHP-2 homologs or relatives (e.g., corkscrew) have critical roles in several receptor tyrosine kinase, cytokine signaling pathways (Neel, B. G., et al., *Cell Biol.* 9:193–204 (1997); Van Vactor, D, et al., *Curr. Op. Gen. Develop.* 8:112–126.(1998), Perkins, L. A., et al., *Cell* 70:225–236 (1992)) as well as vertebrate development (Tang, T L, et al., *Cell* 80:473–483 (1995)). The terms "homolog" or "relative" are used herein equivalently and are intended to refer to SH2-containing protein tyrosine phosphatases which share structural (e.g., nucleotide or amino acid sequence or three dimensional structure) or enzymatic (e.g., in vitro phosphatase activity) or biological (e.g., animal cap elongation in Xenopus) characteristics.

The presence or absence of phosphatase activity or activities can be determined by various functional assays as described herein (See Examples 3, 5, and 9). Moreover, amino acids which are essential for the function (e.g., substrate binding and enzymatic activity) of the phosphatase can be identified by methods known in the art. Particularly useful methods include crystallization data (e.g., for SHP-2 as described by Hof, P., et al., *Cell* 92:441–450 (1998)), the identification of conserved amino acids in the family or subfamily of SH2-containing protein tyrosine phosphatases, site-directed mutagenesis, alanine-scanning mutagenesis (see, for example, Cunningham and Wells, *Science* 244:1081–1085 (1989)), and nuclear magnetic resonance.

Specifically, appropriate amino acid mutations can be made on the basis of several criteria, including catalytic domain interactions (such as formation of hydrogen bonds between residues in the amino SH2 domain and the catalytic domain), hydrophobicity, basic or acidic character, charge, polarity, size, and aromatic character. Assignment of various amino acids to similar groups based on the properties above and mutagenesis protocols are readily apparent to the skilled artisan. Mutagenesis, for example, can be performed using commercially available kits such as the Altered Sites™ In Vitro Mutagenesis System (Promega Corporation, Madison, Wis.) or using an oligonucleotide PCR based procedure as previously described (Tang, T. L., et al., *Cell* 80:473–483 (1995); O'Reilly, A. M., et al., *Molec. Cell. Biol.* 18:161–177 (1998)) and discussed in the Example 1.

The present invention also provides methods of dentifying a substance which alters the interaction of SH2-domain-containing protein tyrosine phosphatases and its substrate (e.g., tyrosine phosphorylated protein or peptide) comprising the steps of providing a tyrosine phosphorylated protein, or peptide, which interacts with the protein tyrosine phosphatase and an activated mutant protein tyrosine phosphatases described herein; combining (or admixing) the tyrosine phosphorylated protein and an activated mutant protein tyrosine phosphatase and a test substance under conditions suitable for interaction between the tyrosine phosphorylated protein and an activated mutant SH2-domain containing protein tyrosine phosphatase, thereby producing a combination; determining the amount of interaction in the combination; and comparing the amount of interaction determined in the presence of the test substance with the amount of interaction in the absence of the test substance, wherein a difference in the interaction indicates that the test substance alters the interaction between a SH2-domain containing protein tyrosine phosphatase and the tyrosine phosphorylated protein.

Figure 30:
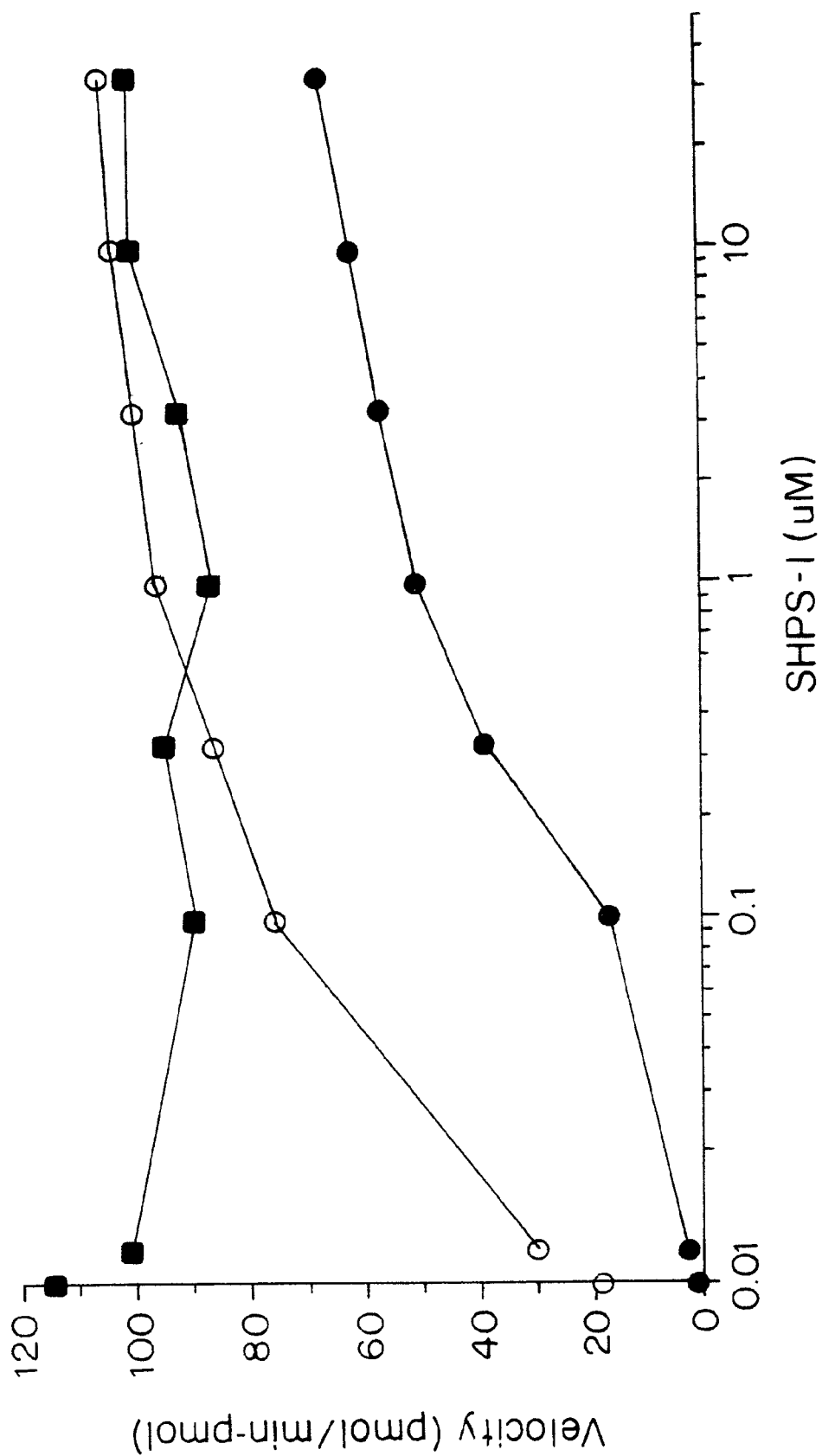
FIG. 30 depicts the phosphatase activity of wildtype SHP-2 phosphatase (● - - ●); and the D61A (○ - - ○) and E76A (■ - - ■) SHP-2 mutants.

The term "alteration" in regard to activity or "altered activity" is defined herein as activity different from that of the protein tyrosine phosphatase in the absence of the test substance. For example, 10 $\mu$M of the E76A mutant of SHP-2 catalyzes the conversion of phosphorylated reduced carboxyamidomethylated lysozyme (RCM-lysozyme) to inorganic phosphate at a velocity of approximately 100 pmol/min-pmol in the absence of phosphotyrosine peptides (FIG. 30). An alteration can result in a decreased velocity of 50 pmol/min-pmol or an increased velocity of 150 pmol/min-pmol. Experimental protocols to assess phosphatase activity are art recognized and described in Example 3.

For example, the tyrosine phosphorylated protein is combined with an activated mutant protein tyrosine phosphatase of the invention and the substance to be tested under conditions suitable for interaction between the tyrosine phosphorylated protein and the activated mutant SH2-domain containing protein tyrosine phosphatase, thereby forming a combination. The amount of enzymatic activity determined after the addition of the test substance to the combination of the protein tyrosine phosphatase and tyrosine phosphate is compared with the amount of enzymatic activity in the absence of the substance to be tested, wherein a difference in the enzymatic activity indicates that the test substance alters the interaction between an activated mutant SH2-domain containing protein tyrosine phosphatase and the tyrosine phosphorylated protein. The amount of enzymatic activity in the combination before and after the addition of the test substance can be determined using well-known art recognized methods including in vitro assays as discussed in Example 3; or as described in Hof, P., et al., *Cell* 92:441–450 (1998); O'Reilly, A. M., et al., *Molec. Cell. Biol.* 18:161–177 (1998); Klingmüller, U., et al., U.S. Pat. No. 5,659,012 (1997); and Tonks, N., et al., WO 98/04712 (1998), the teachings of which are incorporated herein in their entirety.

The test substance (e.g., an inhibitor or stimulator) can be added to the activated mutant SH2-containing protein tyrosine phosphatase either before or following the addition of the tyrosine phosphorylated protein under conditions suitable for maintaining the mutant phosphatase and tyrosine phosphorylated protein in a conformation appropriate for formation of a combination. Experimental conditions for evaluating test substances, such as buffer or media, concentration and temperature requirements, can, initially, be similar to those described in Example 3. One of ordinary skill in the art can determine empirically how to vary experimental conditions depending upon the biochemical nature of the test substance. The concentration at which the test substance can be evaluated can be similar, more, or less than concentrations employed by the native ligand to bind the wildtype phosphatase.

The substances which alter the activity of the mutant SH2-containing protein tyrosine phosphatases of the invention can be stimulators/enhancers (e.g., agonists) or inhibitors (e.g., antagonists) of the tyrosine phosphatase activity. The substances can be polypeptides (including post-translationally modified proteins), peptides, or small molecules (including carbohydrates, steroids, lipids, other organic molecules, anions or cations).

The term "inhibitor", as used herein, refers to a substance which blocks, diminishes, antagonizes, hinders, limits, decreases, reduces, restricts or interferes with SH2-containing protein tyrosine phosphatase activity, or alternatively and additionally, prevents or impedes the binding of the protein tyrosine phosphatase with a substrate thereby preventing the phosphatase from acting. By way of example, an inhibitor of SH2-containing protein tyrosine phosphatase can decrease in vitro phosphatase activity as described herein (See Example 3) and lead to diminished in vivo effects attributed to phosphatases such as phenotypic (e.g., prevention or diminished animal cap elongation Xenopus explants) and molecular (e.g., decreased transcription of mesoderm-specific cardiac muscle actin in Xenopus explants) changes (See Example 5).

The term "stimulator" or enhancer as used herein, refers to a substance which agonizes, augments, enhances, increases, intensifies or strengthens SH2-containing protein tyrosine phosphatases, or alternatively and additionally, mimics or enhances the effect of binding of the protein tyrosine phosphatase to a substrate thereby further activating the protein phosphatase. In the case of SHP-2 activated mutants such as the D61A and E76A mutants described herein, a substance possessing stimulatory activity can increase the extent of animal cap elongation in the absence of exogenous growth hormone (e.g., bFGF); or can induce mesoderm-specific marker muscle actin beyond that observed in the absence of exogenous growth hormone.

Inhibitors or stimulators/enhancers of SH2-domain containing protein tyrosine phosphatase of the present invention can include any molecule that binds the catalytic domain or interferes with (inhibitor) or facilitates (stimulates) tyrosine phosphoprotein substrate binding at the binding site. Encompassed by the present invention are inhibitor molecules that mimic the structure and conformation of the phosphotyrosine protein substrate when bound to the catalytic site. The inhibitors or stimulators of SH2-domain-containing protein tyrosine phosphatases can be naturally occurring or synthesized using standard laboratory methods that are well known to those of skill in the art.

In one embodiment of the present invention the test substances are compounds comprising proteins, polypeptides and peptides. The proteins, polypeptides and peptides of the present invention comprise naturally-occurring amino acids (e.g., L-amino acids), non-naturally amino acids (e.g., D-amino acids), and small molecules that biologically and biochemically mimic the inhibitor or stimulation peptides, referred to herein as peptide analogs, derivatives or mimetics. (Saragovi, H. U., et al., *BioTechnology*, 10:773–778 (1992)). The protein, polypeptide or peptide inhibitors of the present invention can be in linear or cyclic conformation.

The test substances of the present invention (e.g., inhibitors or stimulators) can be synthesized using standard laboratory methods that are well-known to those of skill in the art, including standard solid phase techniques. Test substances comprising polypeptides of naturally occurring amino acids can also be produced by recombinant DNA techniques known to those of skill, and subsequently phosphorylated.

The test substances of the present invention can comprise either the 20 naturally occurring amino acids or other synthetic amino acids. Synthetic amino acids encompassed by the present invention include, for example, naphthylalanine, L-hydroxypropylglycine, L-3,4-dihydroxyphenylalanyl, α-amino acids such as L-α-hydroxylysyl and D-α-methylalanyl, L-α-methyl-alanyl, β amino-acids such as β-analine, and isoquinolyl.

D-amino acids and other non-naturally occurring synthetic amino acids can also be incorporated into the test substances of the present invention. Such other non-naturally occurring synthetic amino acids include those where the naturally occurring side chains of the 20 genetically encoded amino acids (or any L or D amino acid) are replaced with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

As used herein, "lower alkyl" refers to straight and branched chain alkyl groups having from 1 to 6 carbon atoms, such as methyl, ethyl propyl, butyl and so on. "Lower alkoxy" encompasses straight and branched chain alkoxy groups having from 1 to 6 carbon atoms, such as methoxy, ethoxy and so on.

Cyclic groups can be saturated or unsaturated, and if unsaturated, can be aromatic or non-aromatic. Heterocyclic groups typically contain one or more nitrogen, oxygen, and/or sulphur heteroatoms, e.g., furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. The heterocyclic groups can be substituted or unsubstituted. Where a group is substituted, the substituent can be alkyl, alkoxy, halogen, oxygen, or substituted or unsubstituted phenyl. (See U.S. Pat. No. 5,654, 276 and U.S. Pat. No. 5,643,873, the teachings of which are herein incorporated by reference).

Biologically active derivatives or analogs of the above-described test substances (e.g., inhibitors or stimulators), referred to herein as peptide mimetics, can be designed and produced by techniques known to those of skill in the art.

(See e.g., U.S. Pat. Nos. 4,612,132; 5,643,873 and 5,654,276, the teachings of which are herein incorporated by reference). These mimetics can be based, for example, on a specific peptide phosphatase inhibitor sequences and maintain the relative positions in space of the corresponding peptide inhibitor. These peptide mimetics possess biologically activity (e.g., phosphatase inhibiting or stimulating activity) similar to the biological activity of the corresponding peptide compound, but possess a "biological advantage" over the corresponding peptide inhibitor or stimulation with respect to one, or more, of the following properties: solubility, stability, and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor. Modifications of peptides to produce peptide mimetics are described in U.S. Pat. Nos. 5,643,873 and 5,654,276, the teachings of which are incorporated herein by reference.

Where the test substances of present invention comprise amino acids, the test substance can also be cyclic protein, peptides and cyclic peptide mimetics. Such cyclic test substances can be produced using known laboratory techniques (e.g., as described in U.S. Pat. No. 5,654,276, the teachings of which are herein incorporated in their entirety by reference).

The test substances identified as inhibitors or stimulators as described herein can be used in vitro to study cell cycle regulation, mitotic events and embryonic development. For example, the inhibitors of the present invention can be used to evaluate mitotic events in mammalian cells by inhibiting a specific phosphatase and evaluating the effects on the cell cycle.

The present invention also provides methods of identifying binding partners for SH2-domain-containing protein tyrosine phosphatases, comprising combining the candidate binding partner and an activated compound mutant protein tyrosine phosphatase under conditions suitable for interaction between the binding partner and phosphatase, resulting in the formation of a complex, thereby producing a combination; and determining the presence or absence of a complex in the combination wherein the presence of a complex in the combination indicates that the binding partner binds the activated compound mutant SH2-domain-containing protein tyrosine phosphatase with which it forms a complex. The term "binding partner" refers to any molecule (e.g., polypeptide, peptidomimetic, lipid, anion or cation, small organic molecule, carbohydrate) which interacts with a SH2-domain-containing protein tyrosine phosphatase. The binding partner can, or cannot be acted upon by the SH2-containing protein tyrosine phosphatase (e.g., dephosphorylation). Candidate binding partners can be obtained from cells, isolated from natural sources, or manufactured synthetically as described for test substances (e.g., inhibitors or stimulators). Binding of a partner to a SH2-containing phosphatase can be determined using standard experimental techniques (Garton, A. J., et al., *Molec. Cell. Biol.* 16:6408–6418 (1996); Klingmüller, U., et al., U.S. Pat. No. 5,659,012 (1997)), the teachings of which are incorporated herein in their entirety. Methods include, for example, the use of labeled (e.g., fluorescent, biotin, radioactive, luminescent) activated compound mutants and detection techniques such as solid-phase plate assays; immunoprecipitation; and microinjection and tracing of labeled activated compound phosphatases in cells. Such technologies are well established and within the technical expertise of one of ordinary skill in the art.

For example, the activated compound mutant SH2-containing protein tyrosine phosphatase, preferably a mutant of SHP-2 (e.g., the D61A/D425A mutant described in Example 8; SEQ ID NO: 12), SHP-1 or corkscrew can be used as described herein. The activated compound mutant phosphatase is combined with a candidate binding partner under conditions suitable for interaction and for maintaining the activated mutant phosphatase and binding partner in a conformation appropriate for interaction and formation of a complex. The term "interaction" or "interact" as used herein is intended to refer to binding between a binding partner and phosphatase or an alteration in the phosphorylation status of a binding partner (e.g., dephosphorylation). Experimental conditions (e.g., buffers, pH, temperatures) can be similar to those described for interaction of wildtype SH2-containing protein tyrosine phosphatases and known substrates (e.g., SHP-2 and PDGFR, respectively). The skilled artisan would know how to alter conditions for experimental evaluation of different putative binding partners. The extent of interaction which includes binding and phosphorylation of the binding partner can be determined and compared to the amount of interaction in the presence of the wildtype SH2-domain-containing protein tyrosine phosphatase using art-recognized techniques as described herein.

The activated compound mutant can retain the ability to interact with a binding partner, yet be unable to dephosphorylate the binding partner due to a mutation in the catalytic domain. Hence, the method described herein can be useful in identifying unknown binding partners for wildtype SH2-domain-containing protein tyrosine phosphatases. Therefore, a tyrosine phosphorylated substrate for a SH2-domain-containing protein tyrosine phosphatase can be captured by the activated compound mutant thereby providing a screening method for previously unknown substrates.

Over-expression and activation of certain growth factors, which are substrates for SH2-containing protein tyrosine phosphatases and disruptions in their cell signaling components have been implicated in the genesis of human tumors (Kolibaba, K. S., et al., *Biochim. Biophys. Acta.* 1333:217–248 (1997), Bos, J. L., *Mutat. Res.* 195:255–271 (1988); Birchmeier, W., et al., *Curr. Top. Microbiol. Immunol.* 213:117–135 (1996); Bracke, M. E., et al., *Curr. Top. Microbiol. Immunol.* 213:123–161 (1996)). The identification of substances which alter (e.g., inhibit or stimulate) protein tyrosine phosphatase activity as identified herein can be important in defining pathways which lead to carcinogenesis and to the development of novel, specific and more effective treatment regimens. SH2-domain-containing protein tyrosine phosphatases can act as positive signal transducers in certain receptor protein-tyrosine kinase pathways, for example, growth factor signaling (Tang, T. L., et al., *Cell* 80:473–483 (1995); Neel, B. G., et al., *Curr. Opinion Cell Biol.* 9:193–204 (1997)). Inhibitors of phosphatase activity as identified herein can be used to in vivo or in vitro antagonize such growth promoting effects in certain tumors.

SH2-containing protein tyrosine phosphatases play a key role in transducing extracellular matrix (e.g., vitronectin, integrin, fibronectin, laminin, collagen, hyaluronic acid) signaling pathways to mediate, for example, cell spreading, adhesion and prevention of apoptosis. It is further envisioned that the activated mutant SH2-containing protein tyrosine phosphatases of the present invention and substances which alter their activity can be used to evaluate, interfere and treat extracellular matrix events such as cell spreading in metastatic cancers.

As another example, because SHP-2 is critical for vertebrate development (Tang, T. L., et al., *Cell* 80:473–483 (1995); Arrandale, J. M., et al., *J. Biol. Chem.* 271:21353–21358 (1996); Saxton, T. M., et al., *EMBO J.* 16:2352–2364 (1997)) substances which alter (e.g., inhibit) the activity of an SH2-containing protein tyrosine phosphatases can be used to discern the mechanisms for certain aspects of embryonic development such as mesodermal migration, somite patterning, or blood vessel formation. Targeted disruption of the SHP-2 gene in mice results in embryonic lethality in homozygotic mutants (Arrandale, J. M., et al., *J. Biol. Chem.* 271:21353–21358 (1996); Saxton, T. M., et al., *EMBO J.* 16:2352–2364 (1997)). Analysis of homozygotic mutant embryos reveals a range of abnormalities including failure to initiate turning, posterior truncation, fewer somites, disorganized neuroectoderm, abnormal midline structures, disorganized vasculature, and loss of anterior/posterior axis determination. The identification of substrates for and substances which alter SH2-containing protein tyrosine phosphatases can be useful for the study of the embryonic process and cause of developmental anomalies.

Also encompassed by the invention are the use of inhibitors of phosphatase activity as identified herein to inhibit the enzymatic activity of other non-SH2-containing protein tyrosine phosphatases. For example, the inhibitors of the present invention can be used to inhibit the de-phosphorylation of erythropoietin receptors thereby maintaining activation of the erythropoietin receptor and effector molecules leading to prolonged biological effects attributed to erythropoietin (e.g., hematopoiesis). For example, the inhibitors of the present invention are useful to treat recipients of bone marrow transplants, or diabetics (e.g., inhibitors of phophatase activity regulating the insulin receptor).

The inhibitors or stimulators of the activated mutant SH2-domain containing protein tyrosine phosphatase of the present invention can be used to interfere with eukaryotic cell growth and to treat hyperplastic and neoplastic disorders in mammals. As defined herein, mammals include rodents (such as rats, mice or guinea pigs), domesticated animals (such as dogs or cats), ruminant animals (such as horses, cows) and primates (such as monkeys or humans). For example, a stimulation of SHP-1, which attenuates some cell signaling pathways, can be useful in anti-neoplastic therapies for the treatment of diseases such as leukemia. Certain neoplasms have been attributed to an augmentation in the phosphorylation of cellular effectors which can be offset or neutralized by activated mutants of SHP-1 thereby turning off or controlling the unregulated cellular growth or pathway.

Neoplastic and hyperplastic disorders include all forms of malignancies, psoriasis, retinosis, atherosclerosis resulting from plaque formation, leukemias and benign tumor growth. For example, such disorders include lymphomas, papilomas, pulmonary fibrosis, rheumatoid arthritis and multiple sclerosis.

The inhibitors or stimulators identified by screening methods of the present invention can be formulated into compositions with an effective amount of the inhibitor or stimulation as the active ingredient. Such compositions can also comprise a pharmaceutically acceptable carrier, and are referred to herein as pharmaceutical compositions. The inhibitor or stimulation compositions of the present invention can be administered intravenously, parenterally, orally, nasally, by inhalation, by implant, by injection, or by suppository. The mode of administration is preferably at the location of the target cells. The inhibitor or stimulation composition can be administered in a single dose or in more than one dose over a period of time to achieve a level of inhibitor which is sufficient to confer the desired effect.

Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampules are convenient unit dosages.

It will be appreciated that the actual effective amounts of an inhibitor or stimulation in a specific case can vary according to the specific inhibitor compound being utilized, the particular composition formulated, the mode of administration and the age, weight and condition of the patient, for example. As used herein, an effective amount of inhibitor is an amount of inhibitor which is capable of inhibiting the phosphatase activity of the phosphatase of interest, thereby inhibiting target cell growth and resulting in target cell death, for example. Dosages for a particular patient can be determined by one of ordinary skill in the art using conventional considerations, (e.g. by means of an appropriate, conventional pharmacological protocol).

Thus, the invention also relates to a method of altering SH2-domain-containing protein tyrosine phosphatase activity in a target cell comprising introducing an activated mutant SH2-domain-containing protein tyrosine phosphatase, or a nucleic acid encoding an activated mutant phosphatase, into the target cell, wherein the amount of activated mutant phosphatase introduced effectively alters the phosphatase activity of the target cell. Techniques to introduce the activated mutants or nucleic acids encoding the activated mutants described herein, to monitor expression of the exogenous nucleic acids and to assess phosphatase activity in target cells are well-known to one of ordinary skill in the art. (See Examples 3, 8 and 9).

A further aspect of the invention relates to a method of altering SH2-domain-containing protein tyrosine phosphatase activity in a target cell, comprising introducing into the target cell a substance, wherein the amount of the substance introduced effectively alters the phosphatase activity. In one embodiment the substance inhibits, completely or partially, phosphatase activity, or enhances, phosphatase activity in the target cell.

The present invention further relates to a method of treating a protein tyrosine phosphatase-mediated condition in a mammal, wherein the condition results from alteration in the regulation of SH2-domain containing protein tyrosine phosphatase activity, comprising introducing into the mammal an amount of substance effective to regulate the SH2-domain containing phosphatase activity in the mammal, thereby alleviating the condition. Regulation of phosphatase activity can be up-regulation (e.g., an increase or enhancement in phosphatase activity) or down-regulation (e.g., a decrease or inhibition in phosphatase activity).

The novel activated mutant SH2-domain containing protein tyrosine phosphatases of the present invention can be used to treat a protein tyrosine phosphatase-mediated condition or disease in a mammal wherein the condition results from an alteration in the regulation of SH2-domain-containing protein tyrosine phosphatase activity, comprising delivering to target cells the activated mutant phosphatase described herein, or a nucleic acid sequence encoding the activated phosphatase, in vitro or in vivo, wherein the amount of activated mutant phosphatase introduced effectively alters the phosphatase activity in a target cell in a mammal. The phrase "protein tyrosine phosphatase-mediated disease or condition" is intended to refer to a cellular process wherein the endogenous phosphatase activity is not sufficiently regulated, for example, as a result of inadequate cellular levels or activity of a phosphatase or alternatively and additionally, a condition wherein the levels or activity of a protein tyrosine kinase exceeds the capacity of the endogenous phosphatase thereby resulting in a cell in which the delicate balance of phosphorylation and dephosphorylation events is disturbed. For example, an activated mutant of SHP-1 can be used to negatively regulate a condition arising from unrestricted B-cell proliferation. Likewise an activated mutant of SHP-2 can be used to treat a condition in a cell arising from overstimulation or production of PDGF receptor and resulting cell growth. Thus, the activated mutant phosphatases of the invention can be used experimentally or therapeutically to reduce the activity of tyrosine phosphorylated proteins or to enhance and attenuate cell signaling mediated by tyrosyl phosphorylation. Protein tyrosine phosphatase mediated diseases or conditions can be, for example, uncontrolled cell growth or proliferation such as neoplastic disorders. In addition, for example, the activity of SHP-2 can be regulated to treat conditions of obesity and to inhibit angiogenesis. Diseases requiring the promotion of angiogenesis can be treated by regulating SHP-1 activity.

The activated mutant phosphatases of the invention can be delivered to a cell by the use of vectors comprising one or more nucleic acid sequences encoding the activated mutant SH2-containing protein tyrosine phosphatases. Vectors, as used herein, can include viral and non-viral vectors. Examples of nonviral vectors are lipids or liposomes (U.S. Pat. No. 5,676,954, the teachings of which are incorporated herein by reference). Alternatively, DNA can be introduced into cells via a gene gun, as described in Tynan, E. F., et al., *Proc. Natl. Acad. Sci. USA.*, 90:11478–11482 (1993). The nucleic acid sequence can be been incorporated into the genome of the viral vector. In vitro, the viral vector containing the activated mutant phosphatases described herein or nucleic acid sequences encoding the mutant phosphatases can be contacted with a cell and infectivity can occur. The cell can then be used experimentally to study, for example, unrestricted cell growth in vitro or be implanted into a patient for therapeutic use. The cell can be migratory, such as hematopoietic cells, or non-migratory such as a solid tumor or fibroblast. The cell can be present in a biological sample obtained from the patient (e.g., blood, bone marrow) and used in the treatment of disease, or can be obtained from cell culture and used to dissect cell proliferation pathways in in vivo and in vitro systems.

After contact with the viral vector comprising the activated mutant SH2-containing protein tyrosine phosphatase protein or a nucleic acid sequence encoding the activated mutant, the sample can be returned or readministered to a cell or patient according to methods known to those practiced in the art. In the case of delivery to a patient or experimental animal model (e.g., rat, mouse, monkey, chimpanzee), such a treatment procedure is sometimes referred to as ex vivo treatment or therapy. Frequently the cell is targeted from the patient or animal and returned to the patient or animal once contacted with the viral vector comprising the activated mutant of the present invention. Ex vivo gene therapy has been described, for example, in Kasid, et al., *Proc. Natl. Acad. Sci. USA* 87:473 (1990); Rosenberg, et al., *New Engl. J. Med.* 323:570 (1990); Williams, et al., *Nature* 310476 (1984); Dick, et al., *Cell* 42:71 (1985); Keller, et al., *Nature* 318:149 (1985) and Anderson, et al., U.S. Pat. No. 5,399,346 (1994).

Where a cell is contacted in vitro, the cell incorporating the viral vector comprising a nucleic acid sequence of an activated mutant SH2-containing protein tyrosine phosphatase can be implanted into a patient or experimental animal model for delivery or used in in vitro experimentation to study cellular events mediated by protein tyrosine kinase and phosphatase signal transduction -mechanisms such as certain aspects of cell growth and embryo development.

Where the viral vector comprising the activated mutant phosphatase of the invention or an isolated nucleic acid sequence encoding the activated mutant phosphatase is delivered to a patient or experimental animal, the mode of administration is preferably at the location of the cells which are to be treated. As such, the administration can be nasally (e.g., as in administering a vector expressing ADA), orally (e.g., as in an inhalant or spray as in administering a vector expressing the cystic fibrosis transmembrane conductance regulator (CFTR)) or by injection (e.g., as in administering a vector expressing a suicide gene to a tumor). Other modes of administration (e.g., parenteral, mucosal, systemic, implant or intraperitoneal) are generally known in the art. The substances can, preferably, be administered in a pharmaceutically acceptable carrier, such as saline, sterile water, Ringer's solution, and isotonic sodium chloride solution.

Generally, viral vectors which can be used therapeutically and experimentally are known in the art. Examples include the vectors described by Srivastava, A., U.S. Pat. No. 5,252,479 (1993); Anderson, W. F., et al., U.S. Pat. No. 5,399,346 (1994); Ausubel et al., "Current Protocols in Molecular Biology", John Wiley & Sons, Inc. (1998). Suitable viral vectors for the delivery of nucleic acids to cells include, for example, replication defective retrovirus, adenovirus, parvovirus (e.g., adeno-associated viruses), and coronavirus. Examples of retroviruses include avian leukosis-arcoma, mammalian C-type, B-type viruses, lentiviruses (Coffin, J. M., "Retroviridae: The Viruses and Their Replication", In: *Fundamental Virology*, Third Edition, B. N. Fields, et al., eds., Lippincott-Raven Publishers, Philadelphia, Pa., (1996)). Viral vectors infect cells by known mechanisms thereby delivery the activated mutant protein tyrosine phosphatase or the nucleic acid encoding the activated phosphatase. The mechanism of infectivity depends upon the viral vector and target cell. For example, adenoviral infectivity of HeLa cells occurs by binding to a viral surface receptor, followed by receptor-mediated endocytosis and extrachromasomally replication (Horwitz, M. S., "Adenoviruses" In: *Fundamental Virology*, Third Edition, B. N. Fields, et al., eds., Lippincott-Raven Publishers, Philadelphia, Pa., (1996)).

The following Examples are offered for the purpose of illustrating the present invention and are not to be construed to limit the scope of this invention. The teachings of all references cited herein are hereby incorporated by reference.

EXAMPLE 1

Generation and Purification of Activated Mutant Protein Tyrosine SHP-2 Phosphatases Activated mutants (D61A and E76A) of SHP-2 were generated by recombinant DNA techniques and evaluated biochemically for phosphatase activity and biologically for effects on SHP-2 mediated cellular events.

To construct the D61A (SEQ ID NOS: 1 and 2) and E76A (SEQ ID NOS: 3 and 4) activated mutants, point mutations in the amino-SH2 domain of SHP-2 phosphatases were made by overlap extension PCR (O'Reilly, A. M., et al., *Molec. Cell. Biol.* 18:161–177 (1998)). The D61A mutant designates replacement of aspartic acid at position 61 in the wildtype SHP-2 with an alanine residue. The E76A mutant designates replacement of glutamic acid at position 76 in the wildtype SHP-2 with alanine.

To construct the mutant D61A, the oligonucleotide primers 5'-GGTCATAGTAAGCACTGTTC-3' (SEQ ID NO: 51) (referred to as D61Aa) and 5'-CGGAATTCAACATGACATCGCGGAG-3' (SEQ ID NO: 52) (referred to as Ekls) were used with human SHP-2 as a template to generate a 0.2 kb fragment containing the 5' end of the D61A construct. The oligonucleotide primers 5'-GAACACTGGTGCTTACTATGACC-3' (SEQ ID NO: 53) (referred to as D61As) and the standard T3 primer 5'-ATTAACCCTCACTAAAG-3' (SEQ ID NO: 54) were used with human SHP-2 as a template to generate a 1.8 kilobase 3' end of the D61A construct. The 0.2 kb and 1.8 kb products were purified and used as templates in a second round of PCR in conjunction with the Ekls and T3 primers to generate the full length 2.0 kb D61A PCR product. The PCR product was blunt-end cloned into pBSKS and then subcloned as an EcoRI fragment into EcoR1 linearized pSp64R1 (Tang, T. L., et al., *Cell* 80:473–483 (1995)). The resulting D61A phosphatase contains D61 mutated to alanine.

The E76A mutant was cloned in a similar manner as that described for D61A using the oligonucleotide primers 5'-CTGGACCAACGCAGCCAAAGT G-3' (SEQ ID NO: 55) (referred to as E76Aa), Ekls (SEQ ID NO: 52), 5'-CACTTTGGCTGCGTTGGTCCAG-3' (SEQ ID NO: 56) (E76As), and T3 (SEQ ID NO: 54) with human SHP-2 as a template for the first round reactions. The products of the first round were purified and used in a second round of PCR with the Ekls (SEQ ID NO: 52) and T3 (SEQ ID NO: 54) oligonucleotides to generate the full length 2.0 kb E76 PCR product. The fragment was cloned and subcloned as described above for the D61A mutant. The resulting E76A phosphatase contains E76 mutated to alanine.

The E61A and D61A mutants were sequenced in their entirety to verify the absence of additional mutations and presence of single point mutations.

EXAMPLE 2

Production and Purification of SHP-2 Mutants

*Escherichia Coli* BL21 (DE3) cells were transformed with pGEX 4T-2 encoding either wild type SHP-2, or the activated SHP-2 mutants D61A or E76A. Following induction, harvesting and cell lysis the expressed proteins were initially fractionated by passage over a glutathione Sepharose column. Bound proteins were eluted with 20 mM glutathione and dialyzed in a buffer containing 25 mM Tris pH 8.0, 150 mM NaCl and 10 mM dithiothreitol. Cleavage of the glutathione tag from the expressed proteins was performed by adding thrombin and $Ca^{2+}$ to a final concentration of 2.5 mM. The eluted proteins were purified by FPLC over a Mono S HR column. Expressed protein was purified to greater than 97% homogeneity.

EXAMPLE 3
Phosphatase Activity of SHP-2 Mutants

Wildtype, D61A and E76A mutant SHP-2 proteins were expressed in *E. coli*, purified as described above and used to assess phosphatase activity with a lysozyme substrate in the presence and absence of phosphotyrosine peptides.

Phosphopeptides were synthesized following a modified $N^\alpha$-FLOC protecting group strategy (Piccione, E., et al., *Biochemistry* 32:3197–3202 (1993)). Due to difficulties encountered in synthesizing peptides containing two phosphotyrosines, a polyethylene glycol-polystryrene resin (Millipore Corp., Bedford, Mass.) was used, and problematic couplings were with o-(7-azabenzotriazol-1-yl)-1,1,3,3,-tetramethyluronium hexafluorophosphate (HATU) rather than 1-benzotriazolyloxytris (dimethyl amino)-phosphonium hexafluorophosphate (BOP). The peptides were purified by reverse phase HPLC and characterized by amino acid analysis and mass spectrometry. The sequence of the peptide DIT[pY]ADLNLPKGKKPAPQAAEPNNHTE[pY]ASIQTS-$_{NH2}$ (SEQ ID NO: 69) where pY designates a phosphotyrosine was derived from SHPS-1, a known target for wildtype SHP-2.

The [$^{32}$P]reduced carboxyamidomethylated and maleylated-lysozyme (RCM-lysozyme) substrate was prepared by phosphorylating RCM-lysozyme (Sigma Chemical Co., St. Louis, Mo.) on a unique tyrosine using recombinant full length Src kinase (provided by W. Xu, Harvard Medical School, Boston, Mass.). The Src kinase (200 mM) and RCM-lysozyme (200 mM) were incubated with 500 mM [$\gamma$-$^{32}$P] ATP (700 mCi/ml) in 50 mM Hepes buffer, pH 7.5, containing 10 mM MgCl$_2$ and 2 mM sodium vanadate for 14 hours at 30° C. The product was precipitated with trichloroacetic acid to yield [$^{32}$P]RCM-lysozyme having a specific activity of approximately 2000 cpm/pmol (Tonks, N. K., et al., *J. Biol. Chem.* 263:6731–6737 (1988).

The substrate [$^{32}$P] RCM-lysozyme (2 $\mu$M) and SHPS-1 phosphotyrosine peptides (0–33 $\mu$M) were incubated in 25 mM Hepes, pH 7.4 containing 150 mM NaCl, 0.125 mg/ml bovine serum albumin, 5 mM EDTA, and 10 mM dithiothreitol. Protein tyrosine phosphatase reactions (30 $\mu$l) were initiated by adding wildtype SHP-2 or SHP-2 mutants D61A or E76A to a final enzyme concentration ranging from 1–5 nM (Pluskey, S., et al., *J. Biol. Chem.* 270:2897–2900 (1995)). After 1 minute at 30° C., reactions were terminated by adding a suspension of activated charcoal. Following centrifugation, product release was measured as [32P] phosphate in the supernatant solution by gamma counting. Linear rates for phosphate release were observed consistent with previous results for known protein tyrosine phosphatases (Sugimoto, S., et al., *J. Biol. Chem.* 268:22771–22776 (1993); Sugimoto, S., et al., *J. Biol. Chem.* 269:13614–13622 (1994)).

The D61A and E76A SHP-2 mutants differ in phosphatase activity compared to each other and to wildtype SHP-2 (FIG. 30). The D61A mutant displays a 15–20 fold increase in basal phosphatase activity compared to wildtype SHP-2 in the absence of phosphotyrosine peptides. The D61A mutant is further activated (approximately 5-fold higher than wildtype SHP-2) by amino-SH2 binding to an appropriate phosphotyrosine peptide. These data provide strong evidence that the D61A mutation does not alter the integrity of the amino-SH2 phosphotyrosine peptide binding pocket, but disrupts interaction of the "backside loop" with the catalytic domain of the phosphatase protein thereby accounting for phosphatase activity in the absence of phosphotyrosine peptide binding and an increase in phosphatase activity following peptide binding. Thus, D61A mutant is a partially active mutant.

The E76A mutant is fully or constitutively active (e.g., 100 pmol/min-pmol of [$^{32}$P]RCM-lysozyme liberated), in the absence of phosphotyrosine peptide. No further increase in phosphatase activity was observed following the addition of phosphotyrosine peptides (FIG. 30). Binding studies show that the amino-SH2 domain of the E76A mutant retains the ability to bind phosphotyrosine.

A partially active (e.g., D61A) or constitutively (e.g., E76A) mutant of an SH2-containing protein tyrosine phosphatase can be used to discern distinct functions of the phosphatases (e.g., SHP-2) in cell signaling pathways, for example, the FGFR pathway, which leads to cellular reorganization such as animal cap elongation or mesodermal gene expression (e.g., cardiac actin) in Xenopus explants. It is possible that a more activated, "activated mutant" can be generated by fusing the myristoylation signal from c-Src to the N-terminus of D61A and E76A, generating a MyrD61A and MyrE76A mutant, respectively. The effects of the D61A and E76A activated mutants as well as MyrD61A and MyrE76A can be compared to effects of bFGF, providing a further assessment of the role of SHP-2 in bFGF signaling pathways in cells.

EXAMPLE 4
Embryo Cultures

Fertilization and embryo cultures were performed as previously described (Newport, J., et al., *Cell* 30:675–686 (1982)). Embryos were transferred to 0.5× MMR media (100 mM NaCl, 2 mM KCl, 2 mM CaCl$_2$, 1 MM MgCl$_2$, 5 mM HEPES), 3% Ficoll (Pharmacia, Piscataway, N.J.) and micro-injected, using standard procedures, with 10 nL of mRNA in the animal pole of both cells of two-cell stage embryos. Controls consisted of embryos which were not injected with SHP-2 mutants (negative controls) and embryos injected with bFGF (positive controls). Following microinjection, embryos were transferred to 0.1× MMR and allowed to develop at room temperature. Developing embryos were staged according to the criteria of Nieuwkoop, P. D., et al., "Normal Table of *Xenopus laevis*", Daudin, North Hollan, Amsterdam (1967). Animal pole explants were excised at stage 7.5–8.5 and analyzed as described previously (Tang, T. L., et al., *Cell* 80:473–483 (1995)). Briefly, explants were fixed in 3.7% formaldehyde in PBS for 1 hour at room temperature and examined histologically.

EXAMPLE 5
Effects of SHP-2 Mutants E76A and D61A on Xenopus Explants

The bioactivity of the D61A (SEQ ID NO: 2) and E76A (SEQ ID NO: 4) SHP-2 mutants was assessed using a Xenopus "danimal cap assay" (Nieuwkoop, P. D., Wilhelm Roux'Arch 162:341–373 (1969); Nieuwkoop, P. D. *J. Embryol. Exp. Morph.* 89 Suppl.:333–347 (1985); Klein, P. S., et al., *Endocrine Rev.* 15:326–341 (1994); Smith, J. C. *Curr. Opin. Cell Biol.* 7:856–861 (1995)). Xenopus animal cap explants that were not injected with SHP-2 mutants elongate in response to bFGF treatment. Remarkably, animal caps from Xenopus embryos injected with either the D61A or E76A mutant elongate significantly in the complete absence of bFGF (although not to the same extent as bFGF-treated caps). No elongation occurs in animal caps injected with the wildtype SHP-2. Thus, the D61A and E76A activated mutants evoke aspects of the bFGF-induced elongation pathway in Xenopus animal caps.

Embryos micro-injected with the D61A activated mutant exhibit a more elongated animal cap than embryos injected with the E76A activated mutant. Different mesodermal tissues differentially mediate elongation events (Shih, J. et al., *Development* 116:901–914 (1992); Shih, J, Keller, et al., *Development* 116:915–930 (1992); Smith, J. C., et al., *Development Supplement:* 127–136. (1992)), and varying doses of bFGF induce different types of mesoderm (Smith, J. C., et al., *Curr. Opin. Cell Biol.* 7:856–861 (1995); Isaacs, H. V., *Cell. Mol. Life Sci.* 53:350–361 (1997); Smith, J. C., et al., *Development Supplement:* 127–136 (1997); Smith, J. C., et al., *EMBO J.* 12:4463–4470 (1993)). The D61A and E76A mutants differentially induce the late embryonic stage mesodermal cardiac actin. The D61A activated mutant weakly induces expression of cardiac actin mRNA as determined by Northern blotting, and the E76A activated mutant strongly induces expression of cardiac actin mRNA. Both the D61A and E76A mutants are less effective than bFGF in promoting actin mRNA expression. The differential ability of D61A and E76A to promote elongation of animal caps and actin mesoderm specific marker induction can be a consequence of varying extents of activation; and thus a difference in the effective "dose" or intensity (constitutive versus partially activated mutant) of an activating signal delivered to the bFGF pathway. For example, the E76A mutant due to its constitutively active nature can direct transcription at a "higher dose" or intensity than the partially active D61A mutant. For example, the amino SH2 domain does not associate with the protein tyrosine phosphatase domain in the E76A mutant resulting in an accessible phosphotyrosine binding site and a catalytically available enzyme always available for SHP-2 substrates, whereas the partially active D61A is only partially available to access substrates. Similarly, the weaker effect of the activated mutants compared with bFGF may indicate that SHP-2 mediates only some aspects of the bFGF signal and/or that only a small amount of each mutant gets to the correct place in the cell in the absence of bFGF signaling (and generation of SHP-2 binding proteins).

The D61A activated mutant, not the E76A mutant, is temperature-sensitive in its ability to induce animal cap elongation and expression of mesoderm specific cardiac actin. Xenopus animal caps can elongate when maintained at temperatures from 13–22° C. Basic FGF (bFGF) and the E76A mutant induce elongation at a full range of temperatures (e.g., 13–22° C.); however, the D61A mutant promotes elongation well at 22° C., poorly at 18° C., and not at all at 13° C. Protein crystallography of wildtype SHP-2 has shown that the aspartic acid at position 61 of the amino-SH2 domain forms a hydrogen bond through a water molecule with the catalytic cystine at position 459 (Hof, P., et al, *Cell* 92:441–450 (1998)). Thus, the backside loop/protein tyrosine phosphatase domain interactions are mediated by hydrogen bonds and should be temperature sensitive. The temperature-sensitive nature of the D61A mutant can be due to disruption of hydrogen bonds between the amino SH2-domain and the protein tyrosine phosphatase (catalytic) domain at lower temperatures as a result of substitution of the aspartic acid at position 61 with an alanine residue.

EXAMPLE 6
Plasmid Constructs and In Vitro Transcription

For in vitro transcription, constructs were subcloned into the pSp64R1 vector which contains a polylinker flanked by Xenopus β-globin 5' and 3' untranslated sequences. In vitro transcription of linearized plasmids was carried out using SP6 polymerase and the MEGAscript™ kit (Ambion, Austin, Tex.).

EXAMPLE 7
RNA and Protein Analysis

RNA extraction and Northern blot analysis of cellular markers characteristic of late embryonic development were performed as previously described (Itoh, K., et al., *Development* 121:2703–2711 (1994)). For XMAP kinase assays, animals caps were isolated at stage 7.5–8 and dissociated in calcium-free, magnesium-free normal amphibian media (Green, J. B. A., et al., *Nature* 347:391–394 (1990)). Dissociated cells were collected and stimulated for 5 minutes at 25° C. with 100 ng/ml Xenopus bFGF (XbFGF), and then pelleted for 10 seconds at 14,000 rpm. Pellets were lysed immediately in 1% NP40 lysis buffer (1% NP40, 150 mM NaCl, 50 mM Tris pH 7.4) containing protease inhibitors, (10 mg/ml leupeptin, 1 μg/ml aprotinin, 1 μg/ml pepstatin A, 1 μg/ml antipain, and 20 μg/ml phenylmethylsulfonyl fluoride), and phosphatase inhibitors (1 mM sodium vanadate) and incubated for 10 minutes on ice. Lysates were clarified for 10 minutes at 14,000 rpm at 4° C., electrophoresed and transferred to Immobilon P (Millipore Corp., Bedford, Mass.). Immunoblots were probed with C-terminal anti-Xenopus MAPK rabbit polyclonal antibodies (gift of James Maller). Protein levels of SHP-2 were analyzed by probing total NP40 lysates from animal caps or embryos at stage 8–9 with mouse monoclonal antibodies against the amino SH2 domain of SHP-2 (Transduction Labs, Lexington, Ky.).

EXAMPLE 8
Generation and Purification of an Activated Compound Mutant Protein Tyrosine SHP-2 Phosphatase The activated compound double mutant D61A/D425A (SEQ ID NOS: 11 and 12) was generated by excising a 0.6 kb and 1.4 kb EcoRI, BglII fragment from the SHP-2 D61A and D425A mutants, respectively, in pSP64RI. The D61A mutant was made as described in Example 1. The D425A mutant of SHP-2 was generated by substituting aspartic acid at position 425 with alanine using PCR. To construct the D425A mutant, the oligonucleotide primers 5'-CACGCCGTGGGCCGGCCAG-3' (SEQ ID NO: 57) (referred to a D425Aa) and the Ekls primer (SEQ ID NO: 52, described in Example 1) were used with human SHP-2 as a template to generate a 1.3 kb fragment containing the 5' end of the construct. The oligonucleotide primer 5'-CTGGCCGGCCCACGGCGTG-3' (SEQ ID NO: 58) (referred to as D425As) and the standard T3 primer (SEQ ID NO: 54, described in Example 1) were used with human SHP-2 as a template to generate the 0.7 kb 3' end of the construct. The 1.3 kb and 0.7 kb products were purified and used as templates in the second round of PCR in conjunction with the Ekls (SEQ ID NO: 52) and T3 (SEQ ID NO: 54) primers to generate the full length 2.0 kb product. The PCR product was blunt-end cloned into pBSKS and then subcloned as an EcoRI fragment into EcoR1 linearized pSp64R1 (Tang, T. L., et al., *Cell,* 80:473–483 (1995)). The resulting D425A phosphatase contains D425 mutated to alanine.

A 2.0 kb insert encoding the D61A/D425A mutant was made employing a three-way ligation strategy with EcoRI digested and alkaline phosphatase treated pSp64RI vector as a backbone, the 0.6 kb D61A fragment and the 1.4 kb D425A fragment. Resulting clones were analyzed by restriction-digestion with EcoRI (2.0 kb), BglII (1.6 kb) and PstI (0.8 kb). Clones which generated a 2.0 kb fragment following EcoRI digestion are the activated compound double -D61A/D425A mutants. Experimental conditions for ligation, restriction digests, PCR, and selection and propagation of clones are well known to one of ordinary skill in the art.

To construct the activated compound triple SHP-2 mutant, R32K/R138K/D61A (SEQ ID NOS: 19 and 20), the D61Aa (SEQ ID NO: 51, Example 1) and Ekls (SEQ ID NO: 52, Example 1) primers were used with human SHP-2 R32K/R138K (Sugimoto, S., et al., *J. Biol. Chem.*, 268:2733–2736 (1993)) as a template to generate a 0.2 kb fragment containing the 5' end of the construct. The D61As (SEQ ID NO: 53, Example 1) and the T3 (SEQ ID NO: 54, Example 1) primers were used with human SHP-2 R32K/138K as a template to generate the 1.8 kb 3' end of the construct. The 0.2 kb and the 1.8 kb products were purified and used as templates in a second round of PCR in conjunction with Ekls and T3 primers to generate the full length 2.0 kb product. The PCR product was blunt-end cloned into pBSKS and then subcloned as an EcoRI fragment into EcoR1 linearized pSp64R1 (Tang, T. L., et al., *Cell,* 80:475–483 (1995)). The resulting R32K/R138K/D61A phosphatase contains R32 mutated to lysine, R138 mutated to lysine, and D61 mutated to alanine.

EXAMPLE 9
Effects of Activated Compound SHP-2 Triple Mutant R32K/R138K/D61A on Xenopus Explants The biological activity of the R32K/R138K/D61A triple mutant (SEQ ID NO: 20) was determined using a Xenopus animal cap assay as described in Example 5.

Briefly, two-cell embryos were microinjected with varying amounts of R32K/R138K/D61A mRNA and phosphatase expression monitored by Western blotting. At relatively low expression levels (approximately equivalent to the E16A or E76A single activated mutants), the R32K/R138K/D61A activated compound triple mutant did not induce elongation of animal cap explants or cardiac mesoderm actin expression. However, at higher levels of expression the R32K/R138K/D61A did induce animal cap elongation and actin expression.

These data suggest that the R32K/R138K/D61A triple mutant does not bind SH2 ligand (e.g., phosphotyrosine ligand in Xenopus explants) since it does not signal equivalently to the D61A single mutant (see Example 5); yet it appears that the requirement for ligand binding can be over-come or bypassed at very high levels of expression of the activated compound triple mutant phosphatase.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An activated SHP-2 protein tyrosine phosphatase mutant having a mutation in the SH2 domain, wherein the mutation is a substitution of an amino acid at position 4, 8, 9, 58, 59, 61, 62, 63, 69, 70, 71, 72, 74, 75, 76, and/or 77 of SEQ ID NO: 6, wherein an alanine residue substitutes the amino acid at positions 4, 8, 9, 58, 59, 61, 62, 63, 69, 70, 71, 72, 74, 75, 76 and/or 77.

2. An activated SHP-2 protein tyrosine phosphatase mutant comprising a mutation in the SH2 domain, wherein the mutation comprises a substitution of an aspartic acid at position 61 in SEQ ID NO: 6, wherein an alanine residue substitutes the aspartic acid at position 61.

3. An activated SHP-2 protein tyrosine phosphatase mutant comprising the amino acid sequence of SEQ ID NO: 2.

4. An activated SHP-2 protein tyrosine phosphatase mutant comprising a mutation in the SH2 domain, wherein the mutation comprises a substitution of a glutamic acid at position 76 in SEQ ID NO: 6, wherein an alanine residue substitutes the glutamic acid at position 76.

5. An activated SHP-2 protein tyrosine phosphatase mutant comprising the amino acid sequence of SEQ ID NO: 4.

6. An activated SHP-1 protein tyrosine phosphatase mutant having a mutation in the SH2 domain, wherein the mutation is a substitution of an amino acid at position 2, 5, 6, 56, 58, 59, 61, 67, 68, 69, 71, 72, 74, and/or 75 of SEQ ID NO: 8, wherein an alanine residue substitutes the amino acid at positions 2, 5, 6, 56, 58, 59, 61, 67, 69, 71, 72, 74 and/or 77.

7. An activated SHP-1 protein tyrosine phosphatase mutant comprising a mutation in the SH2 domain, wherein the mutation comprises a substitution at an aspartic acid at position 59 in SEQ ID NO: 8, wherein an alanine residue substitutes the aspartic acid at position 59.

8. An activated SHP-1 protein tyrosine phosphatase, mutant comprising a mutation in the SH2 domain, wherein the mutation comprises a substitution of glutamic acid at position 74 in SEQ ID NO: 8, wherein an alanine residue substitutes the glutamic acid at position 74.

9. An activated SHP-2 protein tyrosine phosphatase compound mutant comprising a compound mutation, wherein the compound mutation is a substitution of an aspartic acid at position 61 and a cysteine at position 459 of SEQ ID NO: 6, wherein an alanine residue substitutes the aspartic acid at position 61 and an alanine residue or serine residue substitutes the cysteine at position 459.

10. An activated SHP-2 protein tyrosine phosphatase compound mutant comprising a compound mutation, wherein the compound mutation is a substitution of an aspartic acid at positions 61 and 425 of SEQ ID NO: 6, wherein an alanine residue substitutes the aspartic acid at positions 61 and 425.

11. An activated SHP-2 protein tyrosine phosphatase compound mutant comprising the amino acid sequence of SEQ ID NO: 12.

12. An activated SHP-2 protein tyrosine phosphatase compound mutant comprising a compound mutation, wherein the compound mutation is a substitution of an arginine at positions 32 and 138 and an aspartic acid at position 61 of SEQ ID NO: 6, wherein a lysine residue substitutes the arginine at positions 32 and 138 and an alanine residue substitutes the aspartic acid at position 61.

13. An activated SHP-2 protein tyrosine phosphatase compound mutant comprising the amino acid sequence of SEQ ID NO: 20.

14. An activated SHP-2 protein tyrosine phosphatase compound mutant comprising a compound mutation, wherein the compound mutation is a substitution of an arginine at positions 32 and 138 and a glutamic acid at position 76 of SEQ ID NO: 6, wherein a lysine residue substitutes the arginine at positions 32 and 138; and an alanine residue substitutes the glutamic acid at position 76.

15. An activated SHP-2 protein tyrosine phosphatase compound mutant comprising the amino acid sequence of SEQ ID NO: 22.

16. An activated SHP-2 protein tyrosine phosphatase compound mutant comprising a compound mutation, wherein the compound mutation is a substitution of an arginine at positions 32 and 138 and an aspartic acid at positions 61 and 425 of SEQ ID NO: 6, wherein a lysine residue substitutes the arginine at positions 32; and 138 and an alanine residue substitutes the aspartic acid at positions 61 and 425.

17. An activated SHP-2 protein tyrosine phosphatase compound mutant comprising the amino acid sequence of SEQ ID NO: 26.

18. An activated SHP-2 protein tyrosine phosphatase compound mutant comprising a compound mutation, wherein the compound mutation is a substitution of an arginine at positions 32 and 138, an aspartic acid at position 61 and a cysteine at position 459 of SEQ ID NO: 6, wherein a lysine residue substitutes the arginine at positions 32 and 138; an alanine residue substitutes the aspartic acid at positions 61; and a serine residue substitutes the cysteine at position 459.

19. An activated SHP-2 protein tyrosine phosphatase compound mutant comprising the amino acid sequence of SEQ ID NO: 24.

20. An activated SHP-2 protein tyrosine phosphatase compound mutant comprising a compound mutation, wherein the compound mutation is a substitution of an arginine at positions 32 and 138, a glutamic acid at position 76 and an aspartic acid at position 425 of SEQ ID NO: 6, wherein a lysine residue substitutes the arginine at positions 32 and 138; an alanine residue substitutes the glutamic acid at positions 76; and an alanine residue substitutes the aspartic acid at position 425.

21. An activated SHP-2 protein tyrosine phosphatase compound mutant comprising the amino acid sequence of SEQ ID NO: 30.

22. An activated SHP-2 protein tyrosine phosphatase compound mutant comprising a compound mutation, wherein the compound mutation is a substitution of an arginine at positions 32 and 138, a glutamic acid at position 76, and a cysteine at position 459 of SEQ ID NO: 6, wherein a lysine residue substitutes the arginine at positions 32 and 138; an alanine residue substitutes the glutamic acid at positions 76; and a serine residue substitutes the cysteine at position 459.

23. An activated SHP-2 protein tyrosine phosphatase compound mutant comprising the amino acid sequence of SEQ ID NO: 28.

24. An activated SHP-1 protein tyrosine phosphatase compound mutant comprising a compound mutation, wherein the compound mutation is a substitution of an aspartic acid at position 59 and a cysteine at position 453 of SEQ ID NO: 8, wherein an alanine residue substitutes the aspartic acid at position 59; and a serine or an alanine residue substitute the cysteine at position 453.

25. An activated SHP-1 protein tyrosine phosphatase compound mutant comprising a compound mutation, wherein the compound mutation is substitution of an aspartic acid at positions 59 and 419 of SEQ ID NO: 8, wherein an alanine residue substitutes the aspartic acid at positions 59 and 419.

26. An activated SHP-1 protein tyrosine phosphatase compound mutant comprising a compound mutation, wherein the compound mutation is a substitution of an arginine at positions 30 and 136 and an aspartic acid at position 59 of SEQ ID NO: 8, wherein a lysine residue substitutes the arginine at positions 30 and 136; and an alanine residue substitutes the aspartic acid at position 59.

27. An activated SHP-1 protein tyrosine phosphatase compound mutant comprising the amino acid sequence of SEQ ID NO: 40.

28. An activated SHP-1 protein tyrosine phosphatase compound mutant, wherein the compound mutation is a substitution of an arginine at positions 30 and 136 and a glutamic acid at position 74 of SEQ ID NO: 8, wherein a lysine residue substitutes the arginine at positions 30 and 136; and an alanine residue substitutes the glutamic acid at position 74.

29. An activated SHP-1 protein tyrosine phosphatase compound mutant comprising the amino acid sequence of SEQ ID NO: 42.

30. An activated SHP-1 protein tyrosine phosphatase compound mutant, wherein the compound mutation is a substitution of an arginine at positions 30 and 136, an aspartic acid at position 59, and a cysteine at position 453 of SEQ ID NO: 8, wherein a lysine residue substitutes the arginine at positions 30 and 136; an alanine residue substitutes the aspartic acid at position 59; and a serine residue substitutes the cysteine at position 453.

31. An activated SHP-1 protein tyrosine phosphatase compound mutant comprising the amino acid sequence of SEQ ID NO: 44.

32. An activated SHP-1 protein tyrosine phosphatase compound mutant, wherein the compound mutation is a substitution of an arginine at positions 30 and 136; and an aspartic acid at positions 59 and 419 of SEQ ID NO: 8, wherein a lysine residue substitutes the arginine at positions 30 and 136; and an alanine residue substitutes the aspartic acid at positions 59 and 419.

33. An activated SHP-1 protein tyrosine phosphatase compound mutant comprising the amino acid sequence of SEQ ID NO: 46.

34. An activated SHP-1 protein tyrosine phosphatase compound mutant, wherein the compound mutation is a substitution of an arginine at positions 30 and 136, a glutamic acid at position 74 and a cysteine at position 453 of SEQ ID NO: 8, wherein a lysine residue substitutes the arginine at positions 30 and 136; an alanine residue substitutes the glutamic acid at position 74; and a serine residue substitutes the cysteine at position 453.

35. An activated SHP-1 protein tyrosine phosphatase compound mutant comprising the amino acid sequence of SEQ ID NO: 48.

36. An activated SHP-1 protein tyrosine phosphatase compound mutant, wherein the compound mutation is a substitution of an arginine at positions 30 and 136, a glutamic acid at position 74, and an aspartic acid at position 419 of SEQ ID NO: 8, wherein a lysine residue substitutes the arginine at positions 30 and 136; an alanine residue substitutes the glutamic acid at position 74; and an alanine residue substitute the aspartic acid at position 419.

37. An activated SHP-1 protein tyrosine phosphatase compound mutant comprising the amino acid sequence of SEQ ID NO: 50.

38. An activated mutant comprising amino acid SEQ ID NO: 60.

39. An activated mutant comprising amino acid SEQ ID NO: 62.

40. An activated SHP-2 protein tyrosine phosphatase compound mutant comprising the amino acid sequence of SEQ ID NO: 14.

41. An activated SHP-1 protein tyrosine phosphatase compound mutant comprising the amino acid sequence of SEQ ID NO: 34.

42. An activated SHP-1 protein tyrosine phosphatase compound mutant comprising a compound mutation, wherein the compound mutation is a substitution of a glutamic acid at position 74 and a cysteine at position 453 of SEQ ID NO: 8, wherein an alanine residue substitutes the glutamic acid at position 74 and a serine residue substitutes the cysteine at position 453.

43. An activated SHP-1 protein tyrosine phosphatase compound mutant comprising the amino acid sequence of SEQ ID NO: 36.

44. An activated SHP-1 protein tyrosine phosphatase compound mutant comprising a compound mutation, wherein the compound mutation is a substitution of a glutamic acid at position 74 and an aspartic acid at position 419 of SEQ ID NO: 8, wherein an alanine residue substitutes the glutamic acid at position 74; and an alanine residue substitutes the aspartic acid at position 419.

45. An activated SHP-1 protein tyrosine phosphatase compound mutant comprising the amino acid sequence of SEQ ID NO: 38.

46. An activated SHP-1 protein tyrosine phosphatase compound mutant comprising the amino acid sequence of SEQ ID NO: 32.

47. An activated SHP-2 protein tyrosine phosphatase compound mutant comprising a compound mutation, wherein the compound mutation is a substitution of a glutamic acid at position 76 and a cysteine at position 459 of SEQ ID NO: 6, wherein an alanine residue substitutes the glutainic acid at position 76 and a serine residue substitutes the cysteine at position 459.

48. An activated SHP-2 protein tyrosine phosphatase compound mutant comprising the amino acid sequence of SEQ ID NO: 16.

49. An activated SHP-2 protein tyrosine phosphatase compound mutant comprising a compound mutation, wherein the compound mutation is a substitution of a glutamic acid at position 76 and an aspartic acid at position 425 of SEQ ID NO: 6, wherein an alanine residue substitutes the glutainic acid at position 76 and an alanine residue substitutes the aspartic acid at position 425.

50. An activated SHP-2 protein tyrosine phosphatase compound mutant comprising the amino acid sequence of SEQ ID NO: 18.

51. An activated SHP-2 protein tyrosine phosphatase mutant having a mutation in the SH2 domain, wherein the mutation is a substitution of an amino acid at position 4, 8, 9, 58, 59, 61, 62, 63, 69, 70, 71, 72, 74, 75, 76, and/or 77 of SEQ ID NO: 6, wherein a threonine residue substitutes the amino acid at positions 4, 8, 9, 58, 59, 61, 62, 63, 69, 70, 71, 72, 74, 75, 76 and/or 77.

52. An activated SHP-2 protein tyro sine phosphatase mutant having a mutation in the SH2 domain, wherein the mutation is a substitution of an amino acid at position 4, 8, 9, 58, 59, 61, 62, 63, 69, 70, 71, 72, 74, 75, 76, and/or 77 of SEQ ID NO: 6, wherein a serine residue substitutes the amino acid at positions 4, 8, 9, 58, 59, 61, 62, 63, 69, 70, 71, 72, 74, 75, 76 and/or 77.

53. An activated SHP-2 protein tyrosine phosphatase mutant having a mutation in the SH2 domain, wherein the mutation is a substitution of an amino acid at position 4, 8, 9, 58, 59, 61, 62, 63, 69, 70, 71, 72, 74, 75, 76, and/or 77 of SEQ ID NO: 6, wherein a glycine residue substitutes the amino acid at positions 4, 8, 9, 58, 59, 61, 62, 63, 69, 70, 71, 72, 74, 75, 76 and/or 77.

54. An activated SHP-1 protein tyrosine phosphatase mutant having a mutation in the SH2 domain, wherein the mutation is a substitution of an amino acid at position 2, 5, 6, 56, 58, 59, 61, 67, 68, 69, 71, 72, 74, and/or 75 of SEQ ID NO: 8, wherein a threonine residue substitutes the amino acid at positions 2, 5, 6, 56, 58, 59, 61, 67, 69, 71, 72, 74 and/or 77.

55. An activated SHP-1 protein tyrosine phosphatase mutant having a mutation in the SH2 domain, wherein the mutation is a substitution of an amino acid at position 2, 5, 6, 56, 58, 59, 61, 67, 68, 69, 71, 72, 74, and/or 75 of SEQ ID NO: 8, wherein a serine residue substitutes the amino acid at positions 2, 5, 6, 56, 58, 59, 61, 67, 69, 71, 72, 74 and/or 77.

56. An activated SHP-1 protein tyrosine phosphatase mutant having a mutation in the SH2 domain, wherein the mutation is a substitution of an amino acid at position 2, 5, 6, 56, 58, 59, 61, 67, 68, 69, 71, 72, 74, and/or 75 of SEQ ID NO: 8, wherein a glycine residue substitutes the amino acid at positions 2, 5, 6, 56, 58, 59, 61, 67, 69, 71, 72, 74 and/or 77.

57. An activated SHP-2 protein tyrosine phosphatase mutant comprising a mutation in the SH2 domain of SEQ ID NO: 6, wherein the mutation is a substitution of an amino acid at position 61 or 76.

58. An activated SHP-1 protein tyrosine phosphatase mutant comprising a mutation in the SH2 domain of SEQ ID NO: 8, wherein the mutation is a substitution of an amino acid at position 59 or 74.

* * * * *

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
      (A) LENGTH: 1782 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..1779

(xi) SEQUENCE DESCRIPTION: SEQ ID NO:1:

```
ATG ACA TCG CGG AGA TGG TTT CAC CCA AAT ATC ACT GGT GTG GAG GCA      48
Met Thr Ser Arg Arg Trp Phe His Pro Asn Ile Thr Gly Val Glu Ala
 1               5                  10                  15

GAA AAC CTA CTG TTG ACA AGA GGA GTT GAT GGC AGT TTT TTG GCA AGG      96
Glu Asn Leu Leu Leu Thr Arg Gly Val Asp Gly Ser Phe Leu Ala Arg
                20                  25                  30

CCT AGT AAA AGT AAC CCT GGA GAC TTC ACA CTT TCC GTT AGA AGA AAT     144
Pro Ser Lys Ser Asn Pro Gly Asp Phe Thr Leu Ser Val Arg Arg Asn
             35                  40                  45

GGA GCT GTC ACC CAC ATC AAG ATT CAG AAC ACT GGT GAT TAC TAT GAC     192
Gly Ala Val Thr His Ile Lys Ile Gln Asn Thr Gly Asp Tyr Tyr Asp
         50                  55                  60

CTG TAT GGA GGG GAG AAA TTT GCC ACT TTG GCT GCG TTG GTC CAG TAT     240
Leu Tyr Gly Gly Glu Lys Phe Ala Thr Leu Ala Ala Leu Val Gln Tyr
 65                  70                  75                  80
```

```
TAC ATG GAA CAT CAC GGG CAA TTA AAA GAG AAG AAT GGA GAT GTC ATT        288
Tyr Met Glu His His Gly Gln Leu Lys Glu Lys Asn Gly Asp Val Ile
             85                  90                  95

GAG CTT AAA TAT CCT CTG AAC TGT GCA GAT CCT ACC TCT GAA AGG TGG        336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA        384
Phe His Gly His Leu Ser Gly Lys Glu Ala Glu Lys Leu Leu Thr Glu
            115                 120                 125

AAA GGA AAA CAT GGT AGT TTT CTT GTA CGA GAG AGC CAG AGC CAC CCT        432
Lys Gly Lys His Gly Ser Phe Leu Val Arg Glu Ser Gln Ser His Pro
130                 135                 140

GGA GAT TTT GTT CTT TCT GTG CGC ACT GGT GAT GAC AAA GGG GAG AGC        480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA        528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT        576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA        624
Leu Val Glu His Tyr Lys Lys Asn Pro Met Val Glu Thr Leu Gly Thr
            195                 200                 205

GTA CTA CAA CTC AAG CAG CCC CTT AAC ACG ACT CGT ATA AAT GCT GCT        672
Val Leu Gln Leu Lys Gln Pro Leu Asn Thr Thr Arg Ile Asn Ala Ala
210                 215                 220

GAA ATA GAA AGC AGA GTT CGA GAA CTA AGC AAA TTA GCT GAG ACC ACA        720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA        768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA        816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC        864
Asn Lys Asn Lys Asn Arg Tyr Lys Asn Ile Leu Pro Phe Asp His Thr
            275                 280                 285

AGG GTT GTC CTA CAC GAT GGT GAT CCC AAT GAG CCT GTT TCA GAT TAC        912
Arg Val Val Leu His Asp Gly Asp Pro Asn Glu Pro Val Ser Asp Tyr
290                 295                 300

ATC AAT GCA AAT ATC ATC ATG CCT GAA TTT GAA ACC AAG TGC AAC AAT        960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC       1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG       1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC       1104
Ile Val Met Thr Thr Lys Glu Val Glu Arg Gly Lys Ser Lys Cys Val
            355                 360                 365

AAA TAC TGG CCT GAT GAG TAT GCT CTA AAA GAA TAT GGC GTC ATG CGT       1152
Lys Tyr Trp Pro Asp Glu Tyr Ala Leu Lys Glu Tyr Gly Val Met Arg
370                 375                 380

GTT AGG AAC GTC AAA GAA AGC GCC GCT CAT GAC TAT ACG CTA AGA GAA       1200
Val Arg Asn Val Lys Glu Ser Ala Ala His Asp Tyr Thr Leu Arg Glu
385                 390                 395                 400
```

```
CTT AAA CTT TCA AAG GTT GGA CAA GGG AAT ACG GAG AGA ACG GTC TGG       1248
Leu Lys Leu Ser Lys Val Gly Gln Gly Asn Thr Glu Arg Thr Val Trp
            405                 410                 415

CAA TAC CAC TTT CGG ACC TGG CCG GAC CAC GGC GTG CCC AGC GAC CCT       1296
Gln Tyr His Phe Arg Thr Trp Pro Asp His Gly Val Pro Ser Asp Pro
            420                 425                 430

GGG GGC GTG CTG GAC TTC CTG GAG GAG GTG CAC CAT AAG CAG GAG AGC       1344
Gly Gly Val Leu Asp Phe Leu Glu Glu Val His His Lys Gln Glu Ser
            435                 440                 445

ATC ATG GAT GCA GGG CCG GTC GTG GTG CAC TGC AGT GCT GGA ATT GGC       1392
Ile Met Asp Ala Gly Pro Val Val Val His Cys Ser Ala Gly Ile Gly
450                 455                 460

CGG ACA GGG ACG TTC ATT GTG ATT GAT ATT CTT ATT GAC ATC ATC AGA       1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG       1488
Glu Lys Gly Val Asp Cys Asp Ile Asp Val Pro Lys Thr Ile Gln Met
            485                 490                 495

GTG CGG TCT CAG AGG TCA GGG ATG GTC CAG ACA GAA GCA CAG TAC CGA       1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG       1584
Phe Ile Tyr Met Ala Val Gln His Tyr Ile Glu Thr Leu Gln Arg Arg
            515                 520                 525

ATT GAA GAA GAG CAG AAA AGC AAG AGG AAA GGG CAC GAA TAT ACA AAT       1632
Ile Glu Glu Glu Gln Lys Ser Lys Arg Lys Gly His Glu Tyr Thr Asn
        530                 535                 540

ATT AAG TAT TCT CTA GCG GAC CAG ACG AGT GGA GAT CAG AGC CCT CTC       1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT       1728
Pro Pro Cys Thr Pro Thr Pro Pro Cys Ala Glu Met Arg Glu Asp Ser
            565                 570                 575

GCT AGA GTC TAT GAA AAC GTG GGC CTG ATG CAA CAG CAG AAA AGT TTC       1776
Ala Arg Val Tyr Glu Asn Val Gly Leu Met Gln Gln Gln Lys Ser Phe
            580                 585                 590

AGA TGA                                                               1782
Arg (2) INFORMATION FOR SEQ ID NO:2:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Arg
                20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
        50                  55                  60

Leu Tyr Gly Gly Glu Lys Phe Ala Thr Leu Ala Ala Leu Val Gln Tyr
65                  70                  75                  80
```

```
Tyr Met Glu His His Gly Gln Leu Lys Glu Lys Asn Gly Asp Val Ile
                 85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
```

```
                     500                 505                 510
Phe Ile Tyr Met Ala Val Gln His Tyr Ile Glu Thr Leu Gln Arg Arg
            515                 520                 525

Ile Glu Glu Gln Lys Ser Lys Arg Lys Gly His Glu Tyr Thr Asn
    530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Lys Ser Phe
            580                 585                 590

Arg
```

(2) INFORMATION FOR SEQ ID NO:3:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:3:

```
ATG ACA TCG CGG AGA TGG TTT CAC CCA AAT ATC ACT GGT GTG GAG GCA        48
Met Thr Ser Arg Arg Trp Phe His Pro Asn Ile Thr Gly Val Glu Ala
 1               5                  10                  15

GAA AAC CTA CTG TTG ACA AGA GGA GTT GAT GGC AGT TTT TTG GCA AGG        96
Glu Asn Leu Leu Leu Thr Arg Gly Val Asp Gly Ser Phe Leu Ala Arg
                20                  25                  30

CCT AGT AAA AGT AAC CCT GGA GAC TTC ACA CTT TCC GTT AGA AGA AAT       144
Pro Ser Lys Ser Asn Pro Gly Asp Phe Thr Leu Ser Val Arg Arg Asn
            35                  40                  45

GGA GCT GTC ACC CAC ATC AAG ATT CAG AAC ACT GGT GAT TAC TAT GAC       192
Gly Ala Val Thr His Ile Lys Ile Gln Asn Thr Gly Asp Tyr Tyr Asp
        50                  55                  60

CTG TAT GGA GGG GAG AAA TTT GCC ACT TTG GCT GCG TTG GTC CAG TAT       240
Leu Tyr Gly Gly Glu Lys Phe Ala Thr Leu Ala Ala Leu Val Gln Tyr
 65                  70                  75                  80

TAC ATG GAA CAT CAC GGG CAA TTA AAA GAG AAG AAT GGA GAT GTC ATT       288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG       336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA       384
Phe His Gly His Leu Ser Gly Lys Glu Ala Glu Lys Leu Leu Thr Glu
        115                 120                 125

AAA GGA AAA CAT GGT AGT TTT CTT GTA CGA GAG AGC CAG AGC CAC CCT       432
Lys Gly Lys His Gly Ser Phe Leu Val Arg Glu Ser Gln Ser His Pro
    130                 135                 140

GGA GAT TTT GTT CTT TCT GTG CGC ACT GGT GAT GAC AAA GGG GAG AGC       480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA       528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT       576
```

```
                Leu Lys Tyr Asp Val Gly Gly Gly Glu Arg Phe Asp Ser Leu Thr Asp
                                180                 185                 190

CTT GTG GAA CAT TAT AAG AAG AAT CCT ATG GTG GAA ACA TTG GGT ACA            624
Leu Val Glu His Tyr Lys Lys Asn Pro Met Val Glu Thr Leu Gly Thr
            195                 200                 205

GTA CTA CAA CTC AAG CAG CCC CTT AAC ACG ACT CGT ATA AAT GCT GCT            672
Val Leu Gln Leu Lys Gln Pro Leu Asn Thr Thr Arg Ile Asn Ala Ala
210                 215                 220

GAA ATA GAA AGC AGA GTT CGA GAA CTA AGC AAA TTA GCT GAG ACC ACA            720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA            768
Asp Lys Val Lys Gln Gly Phe Trp Glu Glu Phe Glu Thr Leu Gln Gln
            245                 250                 255

CAG GAG TGC AAA CTT CTC TAC AGC CGA AAA GAG GGT CAA AGG CAA GAA            816
Gln Glu Cys Lys Leu Leu Tyr Ser Arg Lys Glu Gly Gln Arg Gln Glu
        260                 265                 270

AAC AAA AAC AAA AAT AGA TAT AAA AAC ATC CTG CCC TTT GAT CAT ACC            864
Asn Lys Asn Lys Asn Arg Tyr Lys Asn Ile Leu Pro Phe Asp His Thr
275                 280                 285

AGG GTT GTC CTA CAC GAT GGT GAT CCC AAT GAG CCT GTT TCA GAT TAC            912
Arg Val Val Leu His Asp Gly Asp Pro Asn Glu Pro Val Ser Asp Tyr
        290                 295                 300

ATC AAT GCA AAT ATC ATC ATG CCT GAA TTT GAA ACC AAG TGC AAC AAT            960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC           1008
Ser Lys Pro Lys Lys Ser Tyr Ile Ala Thr Gln Gly Cys Leu Gln Asn
            325                 330                 335

ACG GTG AAT GAC TTT TGG CGG ATG GTG TTC CAA GAA AAC TCC CGA GTG           1056
Thr Val Asn Asp Phe Trp Arg Met Val Phe Gln Glu Asn Ser Arg Val
        340                 345                 350

ATT GTC ATG ACA ACG AAA GAA GTG GAG AGA GGA AAG AGT AAA TGT GTC           1104
Ile Val Met Thr Thr Lys Glu Val Glu Arg Gly Lys Ser Lys Cys Val
                355                 360                 365

AAA TAC TGG CCT GAT GAG TAT GCT CTA AAA GAA TAT GGC GTC ATG CGT           1152
Lys Tyr Trp Pro Asp Glu Tyr Ala Leu Lys Glu Tyr Gly Val Met Arg
        370                 375                 380

GTT AGG AAC GTC AAA GAA AGC GCC GCT CAT GAC TAT ACG CTA AGA GAA           1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG           1248
Leu Lys Leu Ser Lys Val Gly Gln Gly Asn Thr Glu Arg Thr Val Trp
            405                 410                 415

CAA TAC CAC TTT CGG ACC TGG CCG GAC CAC GGC GTG CCC AGC GAC CCT           1296
Gln Tyr His Phe Arg Thr Trp Pro Asp His Gly Val Pro Ser Asp Pro
        420                 425                 430

GGG GGC GTG CTG GAC TTC CTG GAG GAG GTG CAC CAT AAG CAG GAG AGC           1344
Gly Gly Val Leu Asp Phe Leu Glu Glu Val His His Lys Gln Glu Ser
                435                 440                 445

ATC ATG GAT GCA GGG CCG GTC GTG GTG CAC TGC AGT GCT GGA ATT GGC           1392
Ile Met Asp Ala Gly Pro Val Val Val His Cys Ser Ala Gly Ile Gly
        450                 455                 460

CGG ACA GGG ACG TTC ATT GTG ATT GAT ATT CTT ATT GAC ATC ATC AGA           1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG           1488
Glu Lys Gly Val Asp Cys Asp Ile Asp Val Pro Lys Thr Ile Gln Met
            485                 490                 495
```

-continued

```
GTG CGG TCT CAG AGG TCA GGG ATG GTC CAG ACA GAA GCA CAG TAC CGA    1536
Val Arg Ser Gln Arg Ser Gly Met Val Gln Thr Glu Ala Gln Tyr Arg
        500                 505                 510

TTT ATC TAT ATG GCG GTC CAG CAT TAT ATT GAA ACA CTA CAG CGC AGG    1584
Phe Ile Tyr Met Ala Val Gln His Tyr Ile Glu Thr Leu Gln Arg Arg
            515                 520                 525

ATT GAA GAA GAG CAG AAA AGC AAG AGG AAA GGG CAC GAA TAT ACA AAT    1632
Ile Glu Glu Glu Gln Lys Ser Lys Arg Lys Gly His Glu Tyr Thr Asn
530                 535                 540

ATT AAG TAT TCT CTA GCG GAC CAG ACG AGT GGA GAT CAG AGC CCT CTC    1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT    1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC    1776
Ala Arg Val Tyr Glu Asn Val Gly Leu Met Gln Gln Gln Lys Ser Phe
            580                 585                 590

AGA TGA                                                            1782
Arg
```

(2) INFORMATION FOR SEQ ID NO:4:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Ala Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
```

-continued

```
                210                 215                 220
Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
                260                 265                 270

Asn Lys Asn Lys Asn Arg Tyr Lys Asn Ile Leu Pro Phe Asp His Thr
                275                 280                 285

Arg Val Val Leu His Asp Gly Asp Pro Asn Glu Pro Val Ser Asp Tyr
                290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
                340                 345                 350

Ile Val Met Thr Thr Lys Glu Val Glu Arg Gly Lys Ser Lys Cys Val
                355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
                420                 425                 430

Gly Gly Val Leu Asp Phe Leu Glu Glu Val His His Lys Gln Glu Ser
                435                 440                 445

Ile Met Asp Ala Gly Pro Val Val His Cys Ser Ala Gly Ile Gly
450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
                500                 505                 510

Phe Ile Tyr Met Ala Val Gln His Tyr Ile Glu Thr Leu Gln Arg Arg
                515                 520                 525

Ile Glu Glu Glu Gln Lys Ser Lys Arg Lys Gly His Glu Tyr Thr Asn
                530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Cys Ala Glu Met Arg Glu Asp Ser
                565                 570                 575

Ala Arg Val Tyr Glu Asn Val Gly Leu Met Gln Gln Gln Lys Ser Phe
                580                 585                 590

Arg
```

(2) INFORMATION FOR SEQ ID NO:5:

(i) SEQUENCE CHARACTERISTICS:
        (A) LENGTH: 1782 base pairs
        (B) TYPE: nucleic acid (C) STRANDEDNESS: single
(D) TOPOLOGY: linear (ix) FEATURE:
    (A) NAME/KEY: CDS
    (B) LOCATION: 1..1779

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | ACA | TCG | CGG | AGA | TGG | TTT | CAC | CCA | AAT | ATC | ACT | GGT | GTG | GAG | GCA | 48 |
| Met | Thr | Ser | Arg | Arg | Trp | Phe | His | Pro | Asn | Ile | Thr | Gly | Val | Glu | Ala | |
| 1 | | | | 5 | | | | | 10 | | | | | 15 | | |
| GAA | AAC | CTA | CTG | TTG | ACA | AGA | GGA | GTT | GAT | GGC | AGT | TTT | TTG | GCA | AGG | 96 |
| Glu | Asn | Leu | Leu | Leu | Thr | Arg | Gly | Val | Asp | Gly | Ser | Phe | Leu | Ala | Arg | |
| | | | 20 | | | | | 25 | | | | | 30 | | | |
| CCT | AGT | AAA | AGT | AAC | CCT | GGA | GAC | TTC | ACA | CTT | TCC | GTT | AGA | AGA | AAT | 144 |
| Pro | Ser | Lys | Ser | Asn | Pro | Gly | Asp | Phe | Thr | Leu | Ser | Val | Arg | Arg | Asn | |
| | | | 35 | | | | | 40 | | | | | 45 | | | |
| GGA | GCT | GTC | ACC | CAC | ATC | AAG | ATT | CAG | AAC | ACT | GGT | GAT | TAC | TAT | GAC | 192 |
| Gly | Ala | Val | Thr | His | Ile | Lys | Ile | Gln | Asn | Thr | Gly | Asp | Tyr | Tyr | Asp | |
| | | 50 | | | | | 55 | | | | | 60 | | | | |
| CTG | TAT | GGA | GGG | GAG | AAA | TTT | GCC | ACT | TTG | GCT | GAG | TTG | GTC | CAG | TAT | 240 |
| Leu | Tyr | Gly | Gly | Glu | Lys | Phe | Ala | Thr | Leu | Ala | Glu | Leu | Val | Gln | Tyr | |
| 65 | | | | | 70 | | | | | 75 | | | | | 80 | |
| TAC | ATG | GAA | CAT | CAC | GGG | CAA | TTA | AAA | GAG | AAG | AAT | GGA | GAT | GTC | ATT | 288 |
| Tyr | Met | Glu | His | His | Gly | Gln | Leu | Lys | Glu | Lys | Asn | Gly | Asp | Val | Ile | |
| | | | | 85 | | | | | 90 | | | | | 95 | | |
| GAG | CTT | AAA | TAT | CCT | CTG | AAC | TGT | GCA | GAT | CCT | ACC | TCT | GAA | AGG | TGG | 336 |
| Glu | Leu | Lys | Tyr | Pro | Leu | Asn | Cys | Ala | Asp | Pro | Thr | Ser | Glu | Arg | Trp | |
| | | | 100 | | | | | 105 | | | | | 110 | | | |
| TTT | CAT | GGA | CAT | CTC | TCT | GGG | AAA | GAA | GCA | GAG | AAA | TTA | TTA | ACT | GAA | 384 |
| Phe | His | Gly | His | Leu | Ser | Gly | Lys | Glu | Ala | Glu | Lys | Leu | Leu | Thr | Glu | |
| | | | 115 | | | | | 120 | | | | | 125 | | | |
| AAA | GGA | AAA | CAT | GGT | AGT | TTT | CTT | GTA | CGA | GAG | AGC | CAG | AGC | CAC | CCT | 432 |
| Lys | Gly | Lys | His | Gly | Ser | Phe | Leu | Val | Arg | Glu | Ser | Gln | Ser | His | Pro | |
| | | 130 | | | | | 135 | | | | | 140 | | | | |
| GGA | GAT | TTT | GTT | CTT | TCT | GTG | CGC | ACT | GGT | GAT | GAC | AAA | GGG | GAG | AGC | 480 |
| Gly | Asp | Phe | Val | Leu | Ser | Val | Arg | Thr | Gly | Asp | Asp | Lys | Gly | Glu | Ser | |
| 145 | | | | | 150 | | | | | 155 | | | | | 160 | |
| AAT | GAC | GGC | AAG | TCT | AAA | GTG | ACC | CAT | GTT | ATG | ATT | CGC | TGT | CAG | GAA | 528 |
| Asn | Asp | Gly | Lys | Ser | Lys | Val | Thr | His | Val | Met | Ile | Arg | Cys | Gln | Glu | |
| | | | | 165 | | | | | 170 | | | | | 175 | | |
| CTG | AAA | TAC | GAC | GTT | GGT | GGA | GGA | GAA | CGG | TTT | GAT | TCT | TTG | ACA | GAT | 576 |
| Leu | Lys | Tyr | Asp | Val | Gly | Gly | Gly | Glu | Arg | Phe | Asp | Ser | Leu | Thr | Asp | |
| | | | 180 | | | | | 185 | | | | | 190 | | | |
| CTT | GTG | GAA | CAT | TAT | AAG | AAG | AAT | CCT | ATG | GTG | GAA | ACA | TTG | GGT | ACA | 624 |
| Leu | Val | Glu | His | Tyr | Lys | Lys | Asn | Pro | Met | Val | Glu | Thr | Leu | Gly | Thr | |
| | | | 195 | | | | | 200 | | | | | 205 | | | |
| GTA | CTA | CAA | CTC | AAG | CAG | CCC | CTT | AAC | ACG | ACT | CGT | ATA | AAT | GCT | GCT | 672 |
| Val | Leu | Gln | Leu | Lys | Gln | Pro | Leu | Asn | Thr | Thr | Arg | Ile | Asn | Ala | Ala | |
| | | 210 | | | | | 215 | | | | | 220 | | | | |
| GAA | ATA | GAA | AGC | AGA | GTT | CGA | GAA | CTA | AGC | AAA | TTA | GCT | GAG | ACC | ACA | 720 |
| Glu | Ile | Glu | Ser | Arg | Val | Arg | Glu | Leu | Ser | Lys | Leu | Ala | Glu | Thr | Thr | |
| 225 | | | | | 230 | | | | | 235 | | | | | 240 | |
| GAT | AAA | GTC | AAA | CAA | GGC | TTT | TGG | GAA | GAA | TTT | GAG | ACA | CTA | CAA | CAA | 768 |
| Asp | Lys | Val | Lys | Gln | Gly | Phe | Trp | Glu | Glu | Phe | Glu | Thr | Leu | Gln | Gln | |
| | | | | 245 | | | | | 250 | | | | | 255 | | |
| CAG | GAG | TGC | AAA | CTT | CTC | TAC | AGC | CGA | AAA | GAG | GGT | CAA | AGG | CAA | GAA | 816 |
| Gln | Glu | Cys | Lys | Leu | Leu | Tyr | Ser | Arg | Lys | Glu | Gly | Gln | Arg | Gln | Glu | |
| | | | 260 | | | | | 265 | | | | | 270 | | | |
| AAC | AAA | AAC | AAA | AAT | AGA | TAT | AAA | AAC | ATC | CTG | CCC | TTT | GAT | CAT | ACC | 864 |
| Asn | Lys | Asn | Lys | Asn | Arg | Tyr | Lys | Asn | Ile | Leu | Pro | Phe | Asp | His | Thr | |

-continued

```
                275                 280                 285
AGG GTT GTC CTA CAC GAT GGT GAT CCC AAT GAG CCT GTT TCA GAT TAC       912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT       960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC      1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG      1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC      1104
Ile Val Met Thr Thr Lys Glu Val Glu Arg Gly Lys Ser Lys Cys Val
        355                 360                 365

AAA TAC TGG CCT GAT GAG TAT GCT CTA AAA GAA TAT GGC GTC ATG CGT      1152
Lys Tyr Trp Pro Asp Glu Tyr Ala Leu Lys Glu Tyr Gly Val Met Arg
    370                 375                 380

GTT AGG AAC GTC AAA GAA AGC GCC GCT CAT GAC TAT ACG CTA AGA GAA      1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG      1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT      1296
Gln Tyr His Phe Arg Thr Trp Pro Asp His Gly Val Pro Ser Asp Pro
            420                 425                 430

GGG GGC GTG CTG GAC TTC CTG GAG GAG GTG CAC CAT AAG CAG GAG AGC      1344
Gly Gly Val Leu Asp Phe Leu Glu Glu Val His His Lys Gln Glu Ser
        435                 440                 445

ATC ATG GAT GCA GGG CCG GTC GTG GTG CAC TGC AGT GCT GGA ATT GGC      1392
Ile Met Asp Ala Gly Pro Val Val Val His Cys Ser Ala Gly Ile Gly
    450                 455                 460

CGG ACA GGG ACG TTC ATT GTG ATT GAT ATT CTT ATT GAC ATC ATC AGA      1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG      1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA      1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG      1584
Phe Ile Tyr Met Ala Val Gln His Tyr Ile Glu Thr Leu Gln Arg Arg
        515                 520                 525

ATT GAA GAA GAG CAG AAA AGC AAG AGG AAA GGG CAC GAA TAT ACA AAT      1632
Ile Glu Glu Glu Gln Lys Ser Lys Arg Lys Gly His Glu Tyr Thr Asn
    530                 535                 540

ATT AAG TAT TCT CTA GCG GAC CAG ACG AGT GGA GAT CAG AGC CCT CTC      1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT      1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC      1776
Ala Arg Val Tyr Glu Asn Val Gly Leu Met Gln Gln Gln Lys Ser Phe
            580                 585                 590

AGA TGA                                                              1782
```

Arg (2) INFORMATION FOR SEQ ID NO:6:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Arg
             20                  25                  30

Pro Ser Lys Ser Asn Pro Gly Asp Phe Thr Leu Ser Val Arg Arg Asn
         35                  40                  45

Gly Ala Val Thr His Ile Lys Ile Gln Asn Thr Gly Asp Tyr Tyr Asp
     50                  55                  60

Leu Tyr Gly Gly Glu Lys Phe Ala Thr Leu Ala Glu Leu Val Gln Tyr
 65                  70                  75                  80

Tyr Met Glu His His Gly Gln Leu Lys Glu Lys Asn Gly Asp Val Ile
                 85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350
```

-continued

```
Ile Val Met Thr Thr Lys Glu Val Glu Arg Gly Lys Ser Lys Cys Val
            355                 360                 365
Lys Tyr Trp Pro Asp Glu Tyr Ala Leu Lys Glu Tyr Gly Val Met Arg
    370                 375                 380
Val Arg Asn Val Lys Glu Ser Ala Ala His Asp Tyr Thr Leu Arg Glu
385                 390                 395                 400
Leu Lys Leu Ser Lys Val Gly Gln Gly Asn Thr Glu Arg Thr Val Trp
                405                 410                 415
Gln Tyr His Phe Arg Thr Trp Pro Asp His Gly Val Pro Ser Asp Pro
            420                 425                 430
Gly Gly Val Leu Asp Phe Leu Glu Glu Val His His Lys Gln Glu Ser
            435                 440                 445
Ile Met Asp Ala Gly Pro Val Val His Cys Ser Ala Gly Ile Gly
    450                 455                 460
Arg Thr Gly Thr Phe Ile Val Ile Asp Ile Leu Ile Asp Ile Ile Arg
465                 470                 475                 480
Glu Lys Gly Val Asp Cys Asp Ile Asp Val Pro Lys Thr Ile Gln Met
                485                 490                 495
Val Arg Ser Gln Arg Ser Gly Met Val Gln Thr Glu Ala Gln Tyr Arg
            500                 505                 510
Phe Ile Tyr Met Ala Val Gln His Tyr Ile Glu Thr Leu Gln Arg Arg
    515                 520                 525
Ile Glu Glu Glu Gln Lys Ser Lys Arg Lys Gly His Glu Tyr Thr Asn
530                 535                 540
Ile Lys Tyr Ser Leu Ala Asp Gln Thr Ser Gly Asp Gln Ser Pro Leu
545                 550                 555                 560
Pro Pro Cys Thr Pro Thr Pro Pro Cys Ala Glu Met Arg Glu Asp Ser
            565                 570                 575
Ala Arg Val Tyr Glu Asn Val Gly Leu Met Gln Gln Lys Ser Phe
            580                 585                 590
Arg
```

(2) INFORMATION FOR SEQ ID NO:7:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:7:

```
ATG GTG AGG TGG TTT CAC CGA GAC CTC AGT GGG CTG GAT GCA GAG ACC    48
Met Val Arg Trp Phe His Arg Asp Leu Ser Gly Leu Asp Ala Glu Thr
1               5                   10                  15

CTC CTC AAG GGC CGA GGT GTC CAC GGT AGC TTC CTG GCT CGG CCC AGT    96
Leu Leu Lys Gly Arg Gly Val His Gly Ser Phe Leu Ala Arg Pro Ser
                20                  25                  30

CGC AAG AAC CAG GGT GAC TTC TCG CTC TCC GTC AGG GTG GGG GAT CAG   144
Arg Lys Asn Gln Gly Asp Phe Ser Leu Ser Val Arg Val Gly Asp Gln
            35                  40                  45

GTG ACC CAT ATT CGG ATC CAG AAC TCA GGG GAT TTC TAT GAC CTG TAT   192
Val Thr His Ile Arg Ile Gln Asn Ser Gly Asp Phe Tyr Asp Leu Tyr
        50                  55                  60
```

```
GGA GGG GAG AAG TTT GCG ACT CTG ACA GAG CTG GTG GAG TAC TAC ACT       240
Gly Gly Glu Lys Phe Ala Thr Leu Thr Glu Leu Val Glu Tyr Tyr Thr
 65              70                  75                  80

CAG CAG CAG GGT GTG GTG CAG GAC CGC GAC GGC ACC ATC ATC CAC CTC       288
Gln Gln Gln Gly Val Val Gln Asp Arg Asp Gly Thr Ile Ile His Leu
                 85                  90                  95

AAG TAC CCG CTG AAC TGC TCC GAT CCC ACT AGT GAG AGG TGG TAC CAT       336
Lys Tyr Pro Leu Asn Cys Ser Asp Pro Thr Ser Glu Arg Trp Tyr His
             100                 105                 110

GGC CAC ATG TCT GGC GGG CAG GCA GAG ACG CTG CTG CAG GCC AAG GGC       384
Gly His Met Ser Gly Gly Gln Ala Glu Thr Leu Leu Gln Ala Lys Gly
                 115                 120                 125

GAG CCC TGG ACG TTT CTT GTG CGT GAG AGC CTC AGC CAG CCT GGA GAC       432
Glu Pro Trp Thr Phe Leu Val Arg Glu Ser Leu Ser Gln Pro Gly Asp
130                 135                 140

TTC GTG CTT TCT GTG CTC AGT GAC CAG CCC AAG GCT GGC CCA GGC TCC       480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC       528
Pro Leu Arg Val Thr His Ile Lys Val Met Cys Glu Gly Gly Arg Tyr
                 165                 170                 175

ACA GTG GGT GGT TTG GAG ACC TTC GAC AGC CTC ACG GAC CTG GTG GAG       576
Thr Val Gly Gly Leu Glu Thr Phe Asp Ser Leu Thr Asp Leu Val Glu
             180                 185                 190

CAT TTC AAG AAG ACG GGG ATT GAG GAG GCC TCA GGC GCC TTT GTC TAC       624
His Phe Lys Lys Thr Gly Ile Glu Glu Ala Ser Gly Ala Phe Val Tyr
         195                 200                 205

CTG CGG CAG CCG TAC TAT GCC ACG AGG GTG AAT GCG GCT GAC ATT GAG       672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC       720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG       768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC       816
Lys Asn Leu His Gln Arg Leu Glu Gly Gln Arg Pro Glu Asn Lys Gly
             260                 265                 270

AAG AAC CGC TAC AAG AAC ATT CTC CCC TTT GAC CAC AGC CGA GTG ATC       864
Lys Asn Arg Tyr Lys Asn Ile Leu Pro Phe Asp His Ser Arg Val Ile
         275                 280                 285

CTG CAG GGA CGG GAC AGT AAC ATC CCC GGG TCC GAC TAC ATC AAT GCC       912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC       960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG      1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA      1056
Gln Met Ala Trp Gln Glu Asn Ser Arg Val Ile Val Met Thr Thr Arg
             340                 345                 350

GAG GTG GAG AAA GGC CGG AAC AAA TGC GTC CCA TAC TGG CCC GAG GTG      1104
Glu Val Glu Lys Gly Arg Asn Lys Cys Val Pro Tyr Trp Pro Glu Val
         355                 360                 365

GGC ATG CAG CGT GCT TAT GGG CCC TAC TCT GTG ACC AAC TGC GGG GAG      1152
Gly Met Gln Arg Ala Tyr Gly Pro Tyr Ser Val Thr Asn Cys Gly Glu
    370                 375                 380
```

```
CAT GAC ACA ACC GAA TAC AAA CTC CGT ACC TTA CAG GTC TCC CCG CTG        1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC        1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC        1296
Trp Pro Asp His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC        1344
Leu Asp Gln Ile Asn Gln Arg Gln Glu Ser Leu Pro His Ala Gly Pro
        435                 440                 445

ATC ATC GTG CAC TGC AGC GCC GGC ATC GGC CGC ACA GGC ACC ATC ATT        1392
Ile Ile Val His Cys Ser Ala Gly Ile Gly Arg Thr Gly Thr Ile Ile
    450                 455                 460

GTC ATC GAC ATG CTC ATG GAG AAC ATC TCC ACC AAG GGC CTG GAC TGT        1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG        1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC        1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG        1584
Ala Gln Phe Ile Glu Thr Thr Lys Lys Lys Leu Glu Val Leu Gln Ser
        515                 520                 525

CAG AAG GGC CAG GAG TCG GAG TAC GGG AAC ATC ACC TAT CCC CCA GCC        1632
Gln Lys Gly Gln Glu Ser Glu Tyr Gly Asn Ile Thr Tyr Pro Pro Ala
    530                 535                 540

ATG AAG AAT GCC CAT GCC AAG GCC TCC CGC ACC TCG TCC AAA CAC AAG        1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA        1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC        1776
Val Lys Lys Gln Arg Ser Ala Asp Lys Glu Lys Ser Lys Gly Ser Leu
            580                 585                 590

AAG AGG AAG TGA                                                        1788
Lys Arg Lys
        595

(2) INFORMATION FOR SEQ ID NO:8:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:8:

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
```

-continued

```
                  50                     55                     60
Gly Gly Glu Lys Phe Ala Thr Leu Thr Glu Leu Val Glu Tyr Tyr Thr
 65                     70                     75                     80
Gln Gln Gln Gly Val Val Gln Asp Arg Asp Gly Thr Ile Ile His Leu
                        85                     90                     95
Lys Tyr Pro Leu Asn Cys Ser Asp Pro Thr Ser Glu Arg Trp Tyr His
                    100                    105                    110
Gly His Met Ser Gly Gly Gln Ala Glu Thr Leu Leu Gln Ala Lys Gly
                115                    120                    125
Glu Pro Trp Thr Phe Leu Val Arg Glu Ser Leu Ser Gln Pro Gly Asp
            130                    135                    140
Phe Val Leu Ser Val Leu Ser Asp Gln Pro Lys Ala Gly Pro Gly Ser
145                    150                    155                    160
Pro Leu Arg Val Thr His Ile Lys Val Met Cys Glu Gly Gly Arg Tyr
                    165                    170                    175
Thr Val Gly Gly Leu Glu Thr Phe Asp Ser Leu Thr Asp Leu Val Glu
                180                    185                    190
His Phe Lys Lys Thr Gly Ile Glu Glu Ala Ser Gly Ala Phe Val Tyr
            195                    200                    205
Leu Arg Gln Pro Tyr Tyr Ala Thr Arg Val Asn Ala Ala Asp Ile Glu
        210                    215                    220
Asn Arg Val Leu Glu Leu Asn Lys Lys Gln Glu Ser Glu Asp Thr Ala
225                    230                    235                    240
Lys Ala Gly Phe Trp Glu Glu Phe Glu Ser Leu Gln Lys Gln Glu Val
                    245                    250                    255
Lys Asn Leu His Gln Arg Leu Glu Gly Gln Arg Pro Glu Asn Lys Gly
                260                    265                    270
Lys Asn Arg Tyr Lys Asn Ile Leu Pro Phe Asp His Ser Arg Val Ile
            275                    280                    285
Leu Gln Gly Arg Asp Ser Asn Ile Pro Gly Ser Asp Tyr Ile Asn Ala
        290                    295                    300
Asn Tyr Ile Lys Asn Gln Leu Leu Gly Pro Asp Glu Asn Ala Lys Thr
305                    310                    315                    320
Tyr Ile Ala Ser Gln Gly Cys Leu Glu Ala Thr Val Asn Asp Phe Trp
                    325                    330                    335
Gln Met Ala Trp Gln Glu Asn Ser Arg Val Ile Val Met Thr Thr Arg
                340                    345                    350
Glu Val Glu Lys Gly Arg Asn Lys Cys Val Pro Tyr Trp Pro Glu Val
            355                    360                    365
Gly Met Gln Arg Ala Tyr Gly Pro Tyr Ser Val Thr Asn Cys Gly Glu
        370                    375                    380
His Asp Thr Thr Glu Tyr Lys Leu Arg Thr Leu Gln Val Ser Pro Leu
385                    390                    395                    400
Asp Asn Gly Asp Leu Ile Arg Glu Ile Trp His Tyr Gln Tyr Leu Ser
                    405                    410                    415
Trp Pro Asp His Gly Val Pro Ser Glu Pro Gly Gly Val Leu Ser Phe
                420                    425                    430
Leu Asp Gln Ile Asn Gln Arg Gln Glu Ser Leu Pro His Ala Gly Pro
            435                    440                    445
Ile Ile Val His Cys Ser Ala Gly Ile Gly Arg Thr Gly Thr Ile Ile
        450                    455                    460
Val Ile Asp Met Leu Met Glu Asn Ile Ser Thr Lys Gly Leu Asp Cys
465                    470                    475                    480
```

```
Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
        530                 535                 540

Met Lys Asn Ala His Ala Lys Ala Ser Arg Thr Ser Lys His Lys
545                 550                 555                 560

Glu Asp Val Tyr Glu Asn Leu His Thr Lys Asn Lys Arg Glu Lys
                565                 570                 575

Val Lys Lys Gln Arg Ser Ala Asp Lys Glu Lys Ser Lys Gly Ser Leu
            580                 585                 590

Lys Arg Lys
        595
```

(2) INFORMATION FOR SEQ ID NO:9:

(i) SEQUENCE CHARACTERISTICS:
        (A) LENGTH: 2526 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..2523

(xi) SEQUENCE DESCRIPTION: SEQ ID NO:9:

```
ATG TCA TCG CGA AGA TGG TTC CAC CCA ACG ATA TCT GGC ATC GAA GCT      48
Met Ser Ser Arg Arg Trp Phe His Pro Thr Ile Ser Gly Ile Glu Ala
1               5                   10                  15

GAG AAA CTG CTG CAG GAG CAG GGA TTC GAC GGC TCC TTC CTC GCC CGC      96
Glu Lys Leu Leu Gln Glu Gln Gly Phe Asp Gly Ser Phe Leu Ala Arg
            20                  25                  30

CTC TCC TCC TCG AAT CCG GGC GCC TTC ACG CTC TCC GTG CGC CGC GGC     144
Leu Ser Ser Ser Asn Pro Gly Ala Phe Thr Leu Ser Val Arg Arg Gly
        35                  40                  45

AAC GAG GTG ACC CAC ATC AAA ATC CAA AAC AAT GGC GAC TTC TTT GAT     192
Asn Glu Val Thr His Ile Lys Ile Gln Asn Asn Gly Asp Phe Phe Asp
50                  55                  60

CTC TAC GGT GGT GAA AAG TTC GCC ACA CTG CCG GAA CTG GTA CAA TAC     240
Leu Tyr Gly Gly Glu Lys Phe Ala Thr Leu Pro Glu Leu Val Gln Tyr
65                  70                  75                  80

TAC ATG GAG AAT GGC GAG CTA AAG GAG AAG AAC GGC CAG GCC ATC GAA     288
Tyr Met Glu Asn Gly Glu Leu Lys Glu Lys Asn Gly Gln Ala Ile Glu
                85                  90                  95

CTC AAG CAG CCG CTG ATC TGC GCC GAG CCC ACC ACG GAA AGA TGG TTT     336
Leu Lys Gln Pro Leu Ile Cys Ala Glu Pro Thr Thr Glu Arg Trp Phe
            100                 105                 110

CAT GGC AAT CTT TCC GGA AAG GAA GCG GAA AAA TTG ATC CTG GAG CGG     384
His Gly Asn Leu Ser Gly Lys Glu Ala Glu Lys Leu Ile Leu Glu Arg
        115                 120                 125

GGC AAG AAT GGT TCG TTT CTC GTC CGT GAA TCT CAG AGC AAG CCT GGC     432
Gly Lys Asn Gly Ser Phe Leu Val Arg Glu Ser Gln Ser Lys Pro Gly
    130                 135                 140

GAC TTC GTC CTT TCC GTG CGC ACG GAC GAC AAA GTA ACG CAT GTC ATG     480
Asp Phe Val Leu Ser Val Arg Thr Asp Asp Lys Val Thr His Val Met
145                 150                 155                 160
```

```
ATT CGA TGG CAG GAC AAG AAG TAC GAC GTC GGC GGC GGG GAA TCC TTT       528
Ile Arg Trp Gln Asp Lys Lys Tyr Asp Val Gly Gly Gly Glu Ser Phe
                165                 170                 175

GGC ACC TTG TCG GAA CTG ATC GAT CAC TAC AAG CGT AAT CCC ATG GTG       576
Gly Thr Leu Ser Glu Leu Ile Asp His Tyr Lys Arg Asn Pro Met Val
            180                 185                 190

GAG ACG TGC GGA ACC GTG GTG CAT CTG CGA CAG CCA TTC AAC GCC ACA       624
Glu Thr Cys Gly Thr Val Val His Leu Arg Gln Pro Phe Asn Ala Thr
        195                 200                 205

CGA ATC ACG GCG GCC GGC ATC AAT GCC CGG GTG GAA CAG CTG GTC AAG       672
Arg Ile Thr Ala Ala Gly Ile Asn Ala Arg Val Glu Gln Leu Val Lys
    210                 215                 220

GGA GGT TTC TGG GAG GAA TTC GAA TCG CTG CAA CAG GAC AGT CGG GAC       720
Gly Gly Phe Trp Glu Glu Phe Glu Ser Leu Gln Gln Asp Ser Arg Asp
225                 230                 235                 240

ACA TTC TCG CGC AAC GAG GGC TAC AAA CAG GAG AAC CGC CTC AAG AAT       768
Thr Phe Ser Arg Asn Glu Gly Tyr Lys Gln Glu Asn Arg Leu Lys Asn
                245                 250                 255

CGC TAC CGC AAC ATA TTG CCA TAC GAC CAC ACG CGC GTC AAG CTG CTG       816
Arg Tyr Arg Asn Ile Leu Pro Tyr Asp His Thr Arg Val Lys Leu Leu
                260                 265                 270

GAC GTG GAG CAT AGC GTG GCC GGA GCC GAG TAC ATC AAT GCC AAC TAC       864
Asp Val Glu His Ser Val Ala Gly Ala Glu Tyr Ile Asn Ala Asn Tyr
            275                 280                 285

ATA CGG CTG CCC ACC GAC GGC GAC CTG TAC AAC ATG AGC AGC TCG TCG       912
Ile Arg Leu Pro Thr Asp Gly Asp Leu Tyr Asn Met Ser Ser Ser Ser
        290                 295                 300

GAG AGC CTG AAC AGC TCG GTG CCC TCG TGC CCC GCC TGC ACG GCT GCC       960
Glu Ser Leu Asn Ser Ser Val Pro Ser Cys Pro Ala Cys Thr Ala Ala
305                 310                 315                 320

CAG ACA CAG CGG AAC TGC TCC AAC TGC CAG CTG CAA AAC AAG ACG TGC      1008
Gln Thr Gln Arg Asn Cys Ser Asn Cys Gln Leu Gln Asn Lys Thr Cys
                325                 330                 335

GTG CAG TGC GCC GTG AAG AGC GCC ATT CTG CCG TAT AGC AAC TGT GCC      1056
Val Gln Cys Ala Val Lys Ser Ala Ile Leu Pro Tyr Ser Asn Cys Ala
                340                 345                 350

ACC TGC AGC CGC AAG TCA GAC TCC CTG AGC AAG CAC AAG CGG AGC GAA      1104
Thr Cys Ser Arg Lys Ser Asp Ser Leu Ser Lys His Lys Arg Ser Glu
            355                 360                 365

TCC TCG GCC TCT TCA TCG CCC TCC TCC GGC TCT GGG TCC GGA CCA GGA      1152
Ser Ser Ala Ser Ser Ser Pro Ser Ser Gly Ser Gly Ser Gly Pro Gly
        370                 375                 380

TCG TCG GGC ACC AGC GGA GTG AGC AGC GTC AAT GGA CCC GGC ACA CCC      1200
Ser Ser Gly Thr Ser Gly Val Ser Ser Val Asn Gly Pro Gly Thr Pro
385                 390                 395                 400

ACC AAT CTC ACG AGC GGC ACA GCC GGA TGT CTG GTC GGC CTG CTG AAG      1248
Thr Asn Leu Thr Ser Gly Thr Ala Gly Cys Leu Val Gly Leu Leu Lys
                405                 410                 415

AGA CAC TCG AAC GAC TCG TCC GGA GCT GTT TCT ATA TCG ATG GCC GAA      1296
Arg His Ser Asn Asp Ser Ser Gly Ala Val Ser Ile Ser Met Ala Glu
                420                 425                 430

CGG GAA CGC GAG AGG GAG CGC GAG ATG TTT AAG ACC TAC ATC GCC ACC      1344
Arg Glu Arg Glu Arg Glu Arg Glu Met Phe Lys Thr Tyr Ile Ala Thr
            435                 440                 445

CAG GGC TGT CTG CTC ACC CAG CAA GTG AAC ACG GTG ACG GAC TTC TGG      1392
Gln Gly Cys Leu Leu Thr Gln Gln Val Asn Thr Val Thr Asp Phe Trp
        450                 455                 460

AAC ATG GTC TGG CAG GAG AAC ACG CGG GTG ATC GTC ATG ACC ACC AAG      1440
Asn Met Val Trp Gln Glu Asn Thr Arg Val Ile Val Met Thr Thr Lys
```

```
465                 470                 475                 480
GAG TAC GAG CGC GGC AAA GAA AAG TGC GCC CGC TAC TGG CCG GAC GAG        1488
Glu Tyr Glu Arg Gly Lys Glu Lys Cys Ala Arg Tyr Trp Pro Asp Glu
                    485                 490                 495

GGT AGA TCG GAG CAG TTC GGC CAC GCG CGG ATA CAG TGC GTC TCG GAG        1536
Gly Arg Ser Glu Gln Phe Gly His Ala Arg Ile Gln Cys Val Ser Glu
            500                 505                 510

AAC TCG ACC AGT GAC TAT ACG CTG CGC GAG TTC CTC GTC TCG TGG CGG        1584
Asn Ser Thr Ser Asp Tyr Thr Leu Arg Glu Phe Leu Val Ser Trp Arg
        515                 520                 525

GAT CAG CCG GCG CGC CGG ATC TTT CAC TAC CAT TTC CAG GTG TGG CCG        1632
Asp Gln Pro Ala Arg Arg Ile Phe His Tyr His Phe Gln Val Trp Pro
    530                 535                 540

GAT CAC GGA GTG CCC GCC GAT CCG GGC TGT GTG CTC AAC TTC CTG CAA        1680
Asp His Gly Val Pro Ala Asp Pro Gly Cys Val Leu Asn Phe Leu Gln
545                 550                 555                 560

GAT GTC AAC ACG CGT CAG AGT CAC CTG GCT CAA GCG GGC GAG AAG CCG        1728
Asp Val Asn Thr Arg Gln Ser His Leu Ala Gln Ala Gly Glu Lys Pro
                565                 570                 575

GGT CCG ATC TGC GTG CAC TGC TCT GCG GGC ATC GGT CGC ACT GGC ACC        1776
Gly Pro Ile Cys Val His Cys Ser Ala Gly Ile Gly Arg Thr Gly Thr
            580                 585                 590

TTT ATT GTG ATC GAT ATG ATT CTC GAT CAG ATT GTG CGC AAT GGA TTG        1824
Phe Ile Val Ile Asp Met Ile Leu Asp Gln Ile Val Arg Asn Gly Leu
        595                 600                 605

GAT ACT GAA ATC GAC ATC CAG CGC ACC ATT CAG ATG GTC CGA TCG CAG        1872
Asp Thr Glu Ile Asp Ile Gln Arg Thr Ile Gln Met Val Arg Ser Gln
    610                 615                 620

CGT TCC GGT CTT GTG CAA ACC GAG GCG CAA TAC AAG TTC GTC TAC TAT        1920
Arg Ser Gly Leu Val Gln Thr Glu Ala Gln Tyr Lys Phe Val Tyr Tyr
625                 630                 635                 640

GCG GTG CAG CAC TAT ATA CAG ACC CTG ATC GCC CGG AAA CGA GCT GAG        1968
Ala Val Gln His Tyr Ile Gln Thr Leu Ile Ala Arg Lys Arg Ala Glu
                645                 650                 655

GAG CAG AGC CTG CAG GTT GGC CGC GAG TAC ACC AAT ATA AAG TAC ACG        2016
Glu Gln Ser Leu Gln Val Gly Arg Glu Tyr Thr Asn Ile Lys Tyr Thr
            660                 665                 670

GGC GAA ATT GGA AAC GAT TCA CAA AGA TCT CCA TTA CCA CCA GCA ATT        2064
Gly Glu Ile Gly Asn Asp Ser Gln Arg Ser Pro Leu Pro Pro Ala Ile
        675                 680                 685

TCT AGC ATA AGT TTA GTT CCG AGT AAG ACG CCA CTG ACG CCG ACA TCG        2112
Ser Ser Ile Ser Leu Val Pro Ser Lys Thr Pro Leu Thr Pro Thr Ser
    690                 695                 700

GCG GAT TTG GGC ACT GGG ATG GGC CTA AGC ATG GGC GTG GGC ATG GGC        2160
Ala Asp Leu Gly Thr Gly Met Gly Leu Ser Met Gly Val Gly Met Gly
705                 710                 715                 720

GTC GGC AAC AAG CAC GCA TCG AAG CAG CAG CCG CCG TTG CCG GTG GTC        2208
Val Gly Asn Lys His Ala Ser Lys Gln Gln Pro Pro Leu Pro Val Val
                725                 730                 735

AAC TGC AAC AAT AAT AAC AAC GGC ATT GGC AAT AGC GGC TGC AGC AAC        2256
Asn Cys Asn Asn Asn Asn Asn Gly Ile Gly Asn Ser Gly Cys Ser Asn
            740                 745                 750

GGC GGC GGG AGC AGC ACC ACC AGC AGC AGC AAC GGC AGC AGC AAC GGT        2304
Gly Gly Gly Ser Ser Thr Thr Ser Ser Ser Asn Gly Ser Ser Asn Gly
        755                 760                 765

AAC ATC AAC GCC CTA CTG GGC GGC ATC GGC TTG GGG CTG GGC GGC AAT        2352
Asn Ile Asn Ala Leu Leu Gly Gly Ile Gly Leu Gly Leu Gly Gly Asn
    770                 775                 780

ATG CGC AAG TCG AAC TTT TAC AGC GAC TCG CTG AAG CAG CAA CAG CAG        2400
```

```
Met Arg Lys Ser Asn Phe Tyr Ser Asp Ser Leu Lys Gln Gln Gln Gln
785                 790                 795                 800

CGC GAG GAG CAG GCT CCG GCG GGA GCA GCA AAA TTC AAA AAC ATT CCC    2448
Arg Glu Glu Gln Ala Pro Ala Gly Ala Ala Lys Phe Lys Asn Ile Pro
                    805                 810                 815

AAA GAC ATG ATC GGC TTG CGA CCG CCA AGC CAT GCG CCT GCG TTG CCG    2496
Lys Asp Met Ile Gly Leu Arg Pro Pro Ser His Ala Pro Ala Leu Pro
                820                 825                 830

CCG CCA CCG ACA CCG CCG CGC AAA ACA TGA                            2526
Pro Pro Pro Thr Pro Pro Arg Lys Thr
                835                 840
```

(2) INFORMATION FOR SEQ ID NO:10:

(i) SEQUENCE CHARACTERISTICS:
        (A) LENGTH: 841 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Ser Arg Arg Trp Phe His Pro Thr Ile Ser Gly Ile Glu Ala
 1               5                  10                  15

Glu Lys Leu Leu Gln Glu Gln Gly Phe Asp Gly Ser Phe Leu Ala Arg
            20                  25                  30

Leu Ser Ser Ser Asn Pro Gly Ala Phe Thr Leu Ser Val Arg Arg Gly
        35                  40                  45

Asn Glu Val Thr His Ile Lys Ile Gln Asn Asn Gly Asp Phe Phe Asp
    50                  55                  60

Leu Tyr Gly Gly Glu Lys Phe Ala Thr Leu Pro Glu Leu Val Gln Tyr
65                  70                  75                  80

Tyr Met Glu Asn Gly Glu Leu Lys Glu Lys Asn Gly Gln Ala Ile Glu
                85                  90                  95

Leu Lys Gln Pro Leu Ile Cys Ala Glu Pro Thr Thr Glu Arg Trp Phe
            100                 105                 110

His Gly Asn Leu Ser Gly Lys Glu Ala Glu Lys Leu Ile Leu Glu Arg
        115                 120                 125

Gly Lys Asn Gly Ser Phe Leu Val Arg Glu Ser Gln Ser Lys Pro Gly
    130                 135                 140

Asp Phe Val Leu Ser Val Arg Thr Asp Asp Lys Val Thr His Val Met
145                 150                 155                 160

Ile Arg Trp Gln Asp Lys Lys Tyr Asp Val Gly Gly Gly Glu Ser Phe
                165                 170                 175

Gly Thr Leu Ser Glu Leu Ile Asp His Tyr Lys Arg Asn Pro Met Val
            180                 185                 190

Glu Thr Cys Gly Thr Val Val His Leu Arg Gln Pro Phe Asn Ala Thr
        195                 200                 205

Arg Ile Thr Ala Ala Gly Ile Asn Ala Arg Val Glu Gln Leu Val Lys
    210                 215                 220

Gly Gly Phe Trp Glu Glu Phe Glu Ser Leu Gln Gln Asp Ser Arg Asp
225                 230                 235                 240

Thr Phe Ser Arg Asn Glu Gly Tyr Lys Gln Glu Asn Arg Leu Lys Asn
                245                 250                 255

Arg Tyr Arg Asn Ile Leu Pro Tyr Asp His Thr Arg Val Lys Leu Leu
            260                 265                 270

Asp Val Glu His Ser Val Ala Gly Ala Glu Tyr Ile Asn Ala Asn Tyr
```

-continued

```
                275                 280                 285
Ile Arg Leu Pro Thr Asp Gly Asp Leu Tyr Asn Met Ser Ser Ser
290                 295                 300

Glu Ser Leu Asn Ser Ser Val Pro Ser Cys Pro Ala Cys Thr Ala Ala
305                 310                 315                 320

Gln Thr Gln Arg Asn Cys Ser Asn Cys Gln Leu Gln Asn Lys Thr Cys
                325                 330                 335

Val Gln Cys Ala Val Lys Ser Ala Ile Leu Pro Tyr Ser Asn Cys Ala
            340                 345                 350

Thr Cys Ser Arg Lys Ser Asp Ser Leu Ser Lys His Lys Arg Ser Glu
        355                 360                 365

Ser Ser Ala Ser Ser Ser Pro Ser Ser Gly Ser Gly Ser Gly Pro Gly
370                 375                 380

Ser Ser Gly Thr Ser Gly Val Ser Ser Val Asn Gly Pro Gly Thr Pro
385                 390                 395                 400

Thr Asn Leu Thr Ser Gly Thr Ala Gly Cys Leu Val Gly Leu Leu Lys
                405                 410                 415

Arg His Ser Asn Asp Ser Ser Gly Ala Val Ser Ile Ser Met Ala Glu
            420                 425                 430

Arg Glu Arg Glu Arg Glu Arg Glu Met Phe Lys Thr Tyr Ile Ala Thr
        435                 440                 445

Gln Gly Cys Leu Leu Thr Gln Gln Val Asn Thr Val Thr Asp Phe Trp
450                 455                 460

Asn Met Val Trp Gln Glu Asn Thr Arg Val Ile Val Met Thr Thr Lys
465                 470                 475                 480

Glu Tyr Glu Arg Gly Lys Glu Lys Cys Ala Arg Tyr Trp Pro Asp Glu
                485                 490                 495

Gly Arg Ser Glu Gln Phe Gly His Ala Arg Ile Gln Cys Val Ser Glu
            500                 505                 510

Asn Ser Thr Ser Asp Tyr Thr Leu Arg Glu Phe Leu Val Ser Trp Arg
        515                 520                 525

Asp Gln Pro Ala Arg Arg Ile Phe His Tyr His Phe Gln Val Trp Pro
530                 535                 540

Asp His Gly Val Pro Ala Asp Pro Gly Cys Val Leu Asn Phe Leu Gln
545                 550                 555                 560

Asp Val Asn Thr Arg Gln Ser His Leu Ala Gln Ala Gly Glu Lys Pro
                565                 570                 575

Gly Pro Ile Cys Val His Cys Ser Ala Gly Ile Gly Arg Thr Gly Thr
            580                 585                 590

Phe Ile Val Ile Asp Met Ile Leu Asp Gln Ile Val Arg Asn Gly Leu
        595                 600                 605

Asp Thr Glu Ile Asp Ile Gln Arg Thr Ile Gln Met Val Arg Ser Gln
610                 615                 620

Arg Ser Gly Leu Val Gln Thr Glu Ala Gln Tyr Lys Phe Val Tyr Tyr
625                 630                 635                 640

Ala Val Gln His Tyr Ile Gln Thr Leu Ile Ala Arg Lys Arg Ala Glu
                645                 650                 655

Glu Gln Ser Leu Gln Val Gly Arg Glu Tyr Thr Asn Ile Lys Tyr Thr
            660                 665                 670

Gly Glu Ile Gly Asn Asp Ser Gln Arg Ser Pro Leu Pro Pro Ala Ile
        675                 680                 685

Ser Ser Ile Ser Leu Val Pro Ser Lys Thr Pro Leu Thr Pro Thr Ser
690                 695                 700
```

```
Ala Asp Leu Gly Thr Gly Met Gly Leu Ser Met Gly Val Gly Met Gly
705                 710                 715                 720

Val Gly Asn Lys His Ala Ser Lys Gln Gln Pro Pro Leu Pro Val Val
            725                 730                 735

Asn Cys Asn Asn Asn Asn Gly Ile Gly Asn Ser Gly Cys Ser Asn
            740                 745                 750

Gly Gly Gly Ser Ser Thr Thr Ser Ser Ser Asn Gly Ser Ser Asn Gly
            755                 760                 765

Asn Ile Asn Ala Leu Leu Gly Gly Ile Gly Leu Gly Leu Gly Gly Asn
770                 775                 780

Met Arg Lys Ser Asn Phe Tyr Ser Asp Ser Leu Lys Gln Gln Gln Gln
785                 790                 795                 800

Arg Glu Glu Gln Ala Pro Ala Gly Ala Ala Lys Phe Lys Asn Ile Pro
                805                 810                 815

Lys Asp Met Ile Gly Leu Arg Pro Pro Ser His Ala Pro Ala Leu Pro
            820                 825                 830

Pro Pro Pro Thr Pro Pro Arg Lys Thr
            835                 840

(2) INFORMATION FOR SEQ ID NO:11:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:11:

ATG ACA TCG CGG AGA TGG TTT CAC CCA AAT ATC ACT GGT GTG GAG GCA        48
Met Thr Ser Arg Arg Trp Phe His Pro Asn Ile Thr Gly Val Glu Ala
1               5                   10                  15

GAA AAC CTA CTG TTG ACA AGA GGA GTT GAT GGC AGT TTT TTG GCA AGG        96
Glu Asn Leu Leu Leu Thr Arg Gly Val Asp Gly Ser Phe Leu Ala Arg
                20                  25                  30

CCT AGT AAA AGT AAC CCT GGA GAC TTC ACA CTT TCC GTT AGA AGA AAT       144
Pro Ser Lys Ser Asn Pro Gly Asp Phe Thr Leu Ser Val Arg Arg Asn
            35                  40                  45

GGA GCT GTC ACC CAC ATC AAG ATT CAG AAC ACT GGT GCT TAC TAT GAC       192
Gly Ala Val Thr His Ile Lys Ile Gln Asn Thr Gly Ala Tyr Tyr Asp
        50                  55                  60

CTG TAT GGA GGG GAG AAA TTT GCC ACT TTG GCT GAG TTG GTC CAG TAT       240
Leu Tyr Gly Gly Glu Lys Phe Ala Thr Leu Ala Glu Leu Val Gln Tyr
65                  70                  75                  80

TAC ATG GAA CAT CAC GGG CAA TTA AAA GAG AAG AAT GGA GAT GTC ATT       288
Tyr Met Glu His His Gly Gln Leu Lys Glu Lys Asn Gly Asp Val Ile
                85                  90                  95

GAG CTT AAA TAT CCT CTG AAC TGT GCA GAT CCT ACC TCT GAA AGG TGG       336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA       384
Phe His Gly His Leu Ser Gly Lys Glu Ala Glu Lys Leu Leu Thr Glu
        115                 120                 125

AAA GGA AAA CAT GGT AGT TTT CTT GTA CGA GAG AGC CAG AGC CAC CCT       432
Lys Gly Lys His Gly Ser Phe Leu Val Arg Glu Ser Gln Ser His Pro
130                 135                 140
```

```
GGA GAT TTT GTT CTT TCT GTG CGC ACT GGT GAT GAC AAA GGG GAG AGC      480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA      528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT      576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA      624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT      672
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA      720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA      768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA      816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC      864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC      912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT      960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC     1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG     1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC     1104
Ile Val Met Thr Thr Lys Glu Val Glu Arg Gly Lys Ser Lys Cys Val
        355                 360                 365

AAA TAC TGG CCT GAT GAG TAT GCT CTA AAA GAA TAT GGC GTC ATG CGT     1152
Lys Tyr Trp Pro Asp Glu Tyr Ala Leu Lys Glu Tyr Gly Val Met Arg
    370                 375                 380

GTT AGG AAC GTC AAA GAA AGC GCC GCT CAT GAC TAT ACG CTA AGA GAA     1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG     1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT     1296
Gln Tyr His Phe Arg Thr Trp Pro Asp His Gly Val Pro Ser Asp Pro
            420                 425                 430

GGG GGC GTG CTG GAC TTC CTG GAG GAG GTG CAC CAT AAG CAG GAG AGC     1344
Gly Gly Val Leu Asp Phe Leu Glu Glu Val His His Lys Gln Glu Ser
        435                 440                 445

ATC ATG GAT GCA GGG CCG GTC GTG GTG CAC TGC AGT GCT GGA ATT GGC     1392
Ile Met Asp Ala Gly Pro Val Val Val His Cys Ser Ala Gly Ile Gly
450                 455                 460
```

```
CGG ACA GGG ACG TTC ATT GTG ATT GAT ATT CTT ATT GAC ATC ATC AGA     1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG     1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA     1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG     1584
Phe Ile Tyr Met Ala Val Gln His Tyr Ile Glu Thr Leu Gln Arg Arg
        515                 520                 525

ATT GAA GAA GAG CAG AAA AGC AAG AGG AAA GGG CAC GAA TAT ACA AAT     1632
Ile Glu Glu Glu Gln Lys Ser Lys Arg Lys Gly His Glu Tyr Thr Asn
    530                 535                 540

ATT AAG TAT TCT CTA GCG GAC CAG ACG AGT GGA GAT CAG AGC CCT CTC     1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT     1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC     1776
Ala Arg Val Tyr Glu Asn Val Gly Leu Met Gln Gln Gln Lys Ser Phe
            580                 585                 590

AGA TGA                                                             1782
Arg
```

(2) INFORMATION FOR SEQ ID NO:12:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:12:

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
                20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Ala Tyr Tyr Asp
        50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
```

-continued

```
                165                 170                 175
Leu Lys Tyr Asp Val Gly Gly Glu Arg Phe Asp Ser Leu Thr Asp
                    180                 185                 190
Leu Val Glu His Tyr Lys Lys Asn Pro Met Val Glu Thr Leu Gly Thr
            195                 200                 205
Val Leu Gln Leu Lys Gln Pro Leu Asn Thr Thr Arg Ile Asn Ala Ala
        210                 215                 220
Glu Ile Glu Ser Arg Val Arg Glu Leu Ser Lys Leu Ala Glu Thr Thr
225                 230                 235                 240
Asp Lys Val Lys Gln Gly Phe Trp Glu Glu Phe Glu Thr Leu Gln Gln
                    245                 250                 255
Gln Glu Cys Lys Leu Leu Tyr Ser Arg Lys Glu Gly Gln Arg Gln Glu
                260                 265                 270
Asn Lys Asn Lys Asn Arg Tyr Lys Asn Ile Leu Pro Phe Asp His Thr
            275                 280                 285
Arg Val Val Leu His Asp Gly Asp Pro Asn Glu Pro Val Ser Asp Tyr
        290                 295                 300
Ile Asn Ala Asn Ile Ile Met Pro Glu Phe Glu Thr Lys Cys Asn Asn
305                 310                 315                 320
Ser Lys Pro Lys Lys Ser Tyr Ile Ala Thr Gln Gly Cys Leu Gln Asn
                    325                 330                 335
Thr Val Asn Asp Phe Trp Arg Met Val Phe Gln Glu Asn Ser Arg Val
                340                 345                 350
Ile Val Met Thr Thr Lys Glu Val Glu Arg Gly Lys Ser Lys Cys Val
            355                 360                 365
Lys Tyr Trp Pro Asp Glu Tyr Ala Leu Lys Glu Tyr Gly Val Met Arg
        370                 375                 380
Val Arg Asn Val Lys Glu Ser Ala Ala His Asp Tyr Thr Leu Arg Glu
385                 390                 395                 400
Leu Lys Leu Ser Lys Val Gly Gln Gly Asn Thr Glu Arg Thr Val Trp
                    405                 410                 415
Gln Tyr His Phe Arg Thr Trp Pro Asp His Gly Val Pro Ser Asp Pro
                420                 425                 430
Gly Gly Val Leu Asp Phe Leu Glu Glu Val His His Lys Gln Glu Ser
            435                 440                 445
Ile Met Asp Ala Gly Pro Val Val His Cys Ser Ala Gly Ile Gly
        450                 455                 460
Arg Thr Gly Thr Phe Ile Val Ile Asp Ile Leu Ile Asp Ile Ile Arg
465                 470                 475                 480
Glu Lys Gly Val Asp Cys Asp Ile Asp Val Pro Lys Thr Ile Gln Met
                    485                 490                 495
Val Arg Ser Gln Arg Ser Gly Met Val Gln Thr Glu Ala Gln Tyr Arg
                500                 505                 510
Phe Ile Tyr Met Ala Val Gln His Tyr Ile Glu Thr Leu Gln Arg Arg
            515                 520                 525
Ile Glu Glu Gln Lys Ser Lys Arg Lys Gly His Glu Tyr Thr Asn
        530                 535                 540
Ile Lys Tyr Ser Leu Ala Asp Gln Thr Ser Gly Asp Gln Ser Pro Leu
545                 550                 555                 560
Pro Pro Cys Thr Pro Thr Pro Cys Ala Glu Met Arg Glu Asp Ser
                    565                 570                 575
Ala Arg Val Tyr Glu Asn Val Gly Leu Met Gln Gln Gln Lys Ser Phe
                580                 585                 590
```

Arg (2) INFORMATION FOR SEQ ID NO:13:

(i) SEQUENCE CHARACTERISTICS:
    (A) LENGTH: 1782 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 1..1779

(xi) SEQUENCE DESCRIPTION: SEQ ID NO:13:

```
ATG ACA TCG CGG AGA TGG TTT CAC CCA AAT ATC ACT GGT GTG GAG GCA       48
Met Thr Ser Arg Arg Trp Phe His Pro Asn Ile Thr Gly Val Glu Ala
  1               5                  10                  15

GAA AAC CTA CTG TTG ACA AGA GGA GTT GAT GGC AGT TTT TTG GCA AGG       96
Glu Asn Leu Leu Leu Thr Arg Gly Val Asp Gly Ser Phe Leu Ala Arg
             20                  25                  30

CCT AGT AAA AGT AAC CCT GGA GAC TTC ACA CTT TCC GTT AGA AGA AAT      144
Pro Ser Lys Ser Asn Pro Gly Asp Phe Thr Leu Ser Val Arg Arg Asn
         35                  40                  45

GGA GCT GTC ACC CAC ATC AAG ATT CAG AAC ACT GGT GCT TAC TAT GAC      192
Gly Ala Val Thr His Ile Lys Ile Gln Asn Thr Gly Ala Tyr Tyr Asp
     50                  55                  60

CTG TAT GGA GGG GAG AAA TTT GCC ACT TTG GCT GAG TTG GTC CAG TAT      240
Leu Tyr Gly Gly Glu Lys Phe Ala Thr Leu Ala Glu Leu Val Gln Tyr
 65                  70                  75                  80

TAC ATG GAA CAT CAC GGG CAA TTA AAA GAG AAG AAT GGA GAT GTC ATT      288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG      336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA      384
Phe His Gly His Leu Ser Gly Lys Glu Ala Glu Lys Leu Leu Thr Glu
        115                 120                 125

AAA GGA AAA CAT GGT AGT TTT CTT GTA CGA GAG AGC CAG AGC CAC CCT      432
Lys Gly Lys His Gly Ser Phe Leu Val Arg Glu Ser Gln Ser His Pro
    130                 135                 140

GGA GAT TTT GTT CTT TCT GTG CGC ACT GGT GAT GAC AAA GGG GAG AGC      480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA      528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT      576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA      624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT      672
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA      720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA      768
```

```
        Asp Lys Val Lys Gln Gly Phe Trp Glu Glu Phe Glu Thr Leu Gln Gln
                    245                 250                 255

CAG GAG TGC AAA CTT CTC TAC AGC CGA AAA GAG GGT CAA AGG CAA GAA             816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC             864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC             912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT             960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC            1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG            1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC            1104
Ile Val Met Thr Thr Lys Glu Val Glu Arg Gly Lys Ser Lys Cys Val
        355                 360                 365

AAA TAC TGG CCT GAT GAG TAT GCT CTA AAA GAA TAT GGC GTC ATG CGT            1152
Lys Tyr Trp Pro Asp Glu Tyr Ala Leu Lys Glu Tyr Gly Val Met Arg
    370                 375                 380

GTT AGG AAC GTC AAA GAA AGC GCC GCT CAT GAC TAT ACG CTA AGA GAA            1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG            1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT            1296
Gln Tyr His Phe Arg Thr Trp Pro Asp His Gly Val Pro Ser Asp Pro
            420                 425                 430

GGG GGC GTG CTG GAC TTC CTG GAG GAG GTG CAC CAT AAG CAG GAG AGC            1344
Gly Gly Val Leu Asp Phe Leu Glu Glu Val His His Lys Gln Glu Ser
        435                 440                 445

ATC ATG GAT GCA GGG CCG GTC GTG GTG CAC TCG AGT GCT GGA ATT GGC            1392
Ile Met Asp Ala Gly Pro Val Val Val His Ser Ser Ala Gly Ile Gly
    450                 455                 460

CGG ACA GGG ACG TTC ATT GTG ATT GAT ATT CTT ATT GAC ATC ATC AGA            1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG            1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA            1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG            1584
Phe Ile Tyr Met Ala Val Gln His Tyr Ile Glu Thr Leu Gln Arg Arg
        515                 520                 525

ATT GAA GAA GAG CAG AAA AGC AAG AGG AAA GGG CAC GAA TAT ACA AAT            1632
Ile Glu Glu Glu Gln Lys Ser Lys Arg Lys Gly His Glu Tyr Thr Asn
    530                 535                 540

ATT AAG TAT TCT CTA GCG GAC CAG ACG AGT GGA GAT CAG AGC CCT CTC            1680
Ile Lys Tyr Ser Leu Ala Asp Gln Thr Ser Gly Asp Gln Ser Pro Leu
545                 550                 555                 560
```

```
CCG CCT TGT ACT CCA ACG CCA CCC TGT GCA GAA ATG AGA GAA GAC AGT      1728
Pro Pro Cys Thr Pro Thr Pro Pro Cys Ala Glu Met Arg Glu Asp Ser
            565                 570                 575

GCT AGA GTC TAT GAA AAC GTG GGC CTG ATG CAA CAG CAG AAA AGT TTC      1776
Ala Arg Val Tyr Glu Asn Val Gly Leu Met Gln Gln Gln Lys Ser Phe
        580                 585                 590

AGA TGA                                                              1782
Arg (2) INFORMATION FOR SEQ ID NO:14:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:14:

Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Ala Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300
```

```
Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
            325                 330                 335

Thr Val Asn Asp Phe Trp Arg Met Val Phe Gln Glu Asn Ser Arg Val
                340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
            405                 410                 415

Gln Tyr His Phe Arg Thr Trp Pro Asp His Gly Val Pro Ser Asp Pro
                420                 425                 430

Gly Gly Val Leu Asp Phe Leu Glu Glu Val His His Lys Gln Glu Ser
            435                 440                 445

Ile Met Asp Ala Gly Pro Val Val His Ser Ser Ala Gly Ile Gly
450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
            515                 520                 525

Ile Glu Glu Glu Gln Lys Ser Lys Arg Lys Gly His Glu Tyr Thr Asn
530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
            565                 570                 575

Ala Arg Val Tyr Glu Asn Val Gly Leu Met Gln Gln Gln Lys Ser Phe
            580                 585                 590

Arg (2) INFORMATION FOR SEQ ID NO:15:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:15:

ATG ACA TCG CGG AGA TGG TTT CAC CCA AAT ATC ACT GGT GTG GAG GCA     48
Met Thr Ser Arg Arg Trp Phe His Pro Asn Ile Thr Gly Val Glu Ala
  1               5                  10                  15

GAA AAC CTA CTG TTG ACA AGA GGA GTT GAT GGC AGT TTT TTG GCA AGG     96
Glu Asn Leu Leu Leu Thr Arg Gly Val Asp Gly Ser Phe Leu Ala Arg
             20                  25                  30
```

```
CCT AGT AAA AGT AAC CCT GGA GAC TTC ACA CTT TCC GTT AGA AGA AAT        144
Pro Ser Lys Ser Asn Pro Gly Asp Phe Thr Leu Ser Val Arg Arg Asn
        35                  40                  45

GGA GCT GTC ACC CAC ATC AAG ATT CAG AAC ACT GGT GAT TAC TAT GAC        192
Gly Ala Val Thr His Ile Lys Ile Gln Asn Thr Gly Asp Tyr Tyr Asp
 50                  55                  60

CTG TAT GGA GGG GAG AAA TTT GCC ACT TTG GCT GCG TTG GTC CAG TAT        240
Leu Tyr Gly Gly Glu Lys Phe Ala Thr Leu Ala Ala Leu Val Gln Tyr
 65              70                  75                  80

TAC ATG GAA CAT CAC GGG CAA TTA AAA GAG AAG AAT GGA GAT GTC ATT        288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG        336
Glu Leu Lys Tyr Pro Leu Asn Cys Ala Asp Pro Thr Ser Glu Arg Trp
             100                 105                 110

TTT CAT GGA CAT CTC TCT GGG AAA GAA GCA GAG AAA TTA TTA ACT GAA        384
Phe His Gly His Leu Ser Gly Lys Glu Ala Glu Lys Leu Leu Thr Glu
             115                 120                 125

AAA GGA AAA CAT GGT AGT TTT CTT GTA CGA GAG AGC CAG AGC CAC CCT        432
Lys Gly Lys His Gly Ser Phe Leu Val Arg Glu Ser Gln Ser His Pro
130                 135                 140

GGA GAT TTT GTT CTT TCT GTG CGC ACT GGT GAT GAC AAA GGG GAG AGC        480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA        528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT        576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA        624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT        672
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA        720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA        768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA        816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC        864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC        912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT        960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC       1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG       1056
Thr Val Asn Asp Phe Trp Arg Met Val Phe Gln Glu Asn Ser Arg Val
```

```
                    340                 345                 350
ATT GTC ATG ACA ACG AAA GAA GTG GAG AGA GGA AAG AGT AAA TGT GTC      1104
Ile Val Met Thr Thr Lys Glu Val Glu Arg Gly Lys Ser Lys Cys Val
            355                 360                 365

AAA TAC TGG CCT GAT GAG TAT GCT CTA AAA GAA TAT GGC GTC ATG CGT      1152
Lys Tyr Trp Pro Asp Glu Tyr Ala Leu Lys Glu Tyr Gly Val Met Arg
    370                 375                 380

GTT AGG AAC GTC AAA GAA AGC GCC GCT CAT GAC TAT ACG CTA AGA GAA      1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG      1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT      1296
Gln Tyr His Phe Arg Thr Trp Pro Asp His Gly Val Pro Ser Asp Pro
            420                 425                 430

GGG GGC GTG CTG GAC TTC CTG GAG GAG GTG CAC CAT AAG CAG GAG AGC      1344
Gly Gly Val Leu Asp Phe Leu Glu Glu Val His His Lys Gln Glu Ser
        435                 440                 445

ATG ATG GAT GCA GGG CCG GTC GTG GTG CAC TCG AGT GCT GGA ATT GGC      1392
Ile Met Asp Ala Gly Pro Val Val Val His Ser Ser Ala Gly Ile Gly
    450                 455                 460

CGG ACA GGG ACG TTC ATT GTG ATT GAT ATT CTT ATT GAC ATC ATC AGA      1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG      1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA      1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG      1584
Phe Ile Tyr Met Ala Val Gln His Tyr Ile Glu Thr Leu Gln Arg Arg
        515                 520                 525

ATT GAA GAA GAG CAG AAA AGC AAG AGG AAA GGG CAC GAA TAT ACA AAT      1632
Ile Glu Glu Glu Gln Lys Ser Lys Arg Lys Gly His Glu Tyr Thr Asn
    530                 535                 540

ATT AAG TAT TCT CTA GCG GAC CAG ACG AGT GGA GAT CAG AGC CCT CTC      1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT      1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC      1776
Ala Arg Val Tyr Glu Asn Val Gly Leu Met Gln Gln Gln Lys Ser Phe
            580                 585                 590

AGA TGA                                                              1782
Arg (2) INFORMATION FOR SEQ ID NO:16:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:16:

Met Thr Ser Arg Arg Trp Phe His Pro Asn Ile Thr Gly Val Glu Ala
 1               5                  10                  15
```

-continued

```
Glu Asn Leu Leu Leu Thr Arg Gly Val Asp Gly Ser Phe Leu Ala Arg
             20                  25                  30

Pro Ser Lys Ser Asn Pro Gly Asp Phe Thr Leu Ser Val Arg Arg Asn
         35                  40                  45

Gly Ala Val Thr His Ile Lys Ile Gln Asn Thr Gly Asp Tyr Tyr Asp
     50                  55                  60

Leu Tyr Gly Gly Glu Lys Phe Ala Thr Leu Ala Ala Leu Val Gln Tyr
 65                  70                  75                  80

Tyr Met Glu His His Gly Gln Leu Lys Glu Lys Asn Gly Asp Val Ile
                 85                  90                  95

Glu Leu Lys Tyr Pro Leu Asn Cys Ala Asp Pro Thr Ser Glu Arg Trp
             100                 105                 110

Phe His Gly His Leu Ser Gly Lys Glu Ala Glu Lys Leu Leu Thr Glu
         115                 120                 125

Lys Gly Lys His Gly Ser Phe Leu Val Arg Glu Ser Gln Ser His Pro
     130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430
```

```
Gly Gly Val Leu Asp Phe Leu Glu Glu Val His His Lys Gln Glu Ser
            435                 440                 445

Ile Met Asp Ala Gly Pro Val Val His Ser Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                    485                 490                 495

Val Arg Ser Gln Arg Ser Gly Met Val Gln Thr Glu Ala Gln Tyr Arg
                500                 505                 510

Phe Ile Tyr Met Ala Val Gln His Tyr Ile Glu Thr Leu Gln Arg Arg
            515                 520                 525

Ile Glu Glu Gln Lys Ser Lys Arg Lys Gly His Glu Tyr Thr Asn
    530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Gln Lys Ser Phe
                580                 585                 590

Arg
```

(2) INFORMATION FOR SEQ ID NO:17:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:17:

```
ATG ACA TCG CGG AGA TGG TTT CAC CCA AAT ATC ACT GGT GTG GAG GCA        48
Met Thr Ser Arg Arg Trp Phe His Pro Asn Ile Thr Gly Val Glu Ala
1               5                   10                  15

GAA AAC CTA CTG TTG ACA AGA GGA GTT GAT GGC AGT TTT TTG GCA AGG        96
Glu Asn Leu Leu Leu Thr Arg Gly Val Asp Gly Ser Phe Leu Ala Arg
                20                  25                  30

CCT AGT AAA AGT AAC CCT GGA GAC TTC ACA CTT TCC GTT AGA AGA AAT       144
Pro Ser Lys Ser Asn Pro Gly Asp Phe Thr Leu Ser Val Arg Arg Asn
            35                  40                  45

GGA GCT GTC ACC CAC ATC AAG ATT CAG AAC ACT GGT GAT TAC TAT GAC       192
Gly Ala Val Thr His Ile Lys Ile Gln Asn Thr Gly Asp Tyr Tyr Asp
50                  55                  60

CTG TAT GGA GGG GAG AAA TTT GCC ACT TTG GCT GCG TTG GTC CAG TAT       240
Leu Tyr Gly Gly Glu Lys Phe Ala Thr Leu Ala Ala Leu Val Gln Tyr
65                  70                  75                  80

TAC ATG GAA CAT CAC GGG CAA TTA AAA GAG AAG AAT GGA GAT GTC ATT       288
Tyr Met Glu His His Gly Gln Leu Lys Glu Lys Asn Gly Asp Val Ile
                85                  90                  95

GAG CTT AAA TAT CCT CTG AAC TGT GCA GAT CCT ACC TCT GAA AGG TGG       336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA       384
Phe His Gly His Leu Ser Gly Lys Glu Ala Glu Lys Leu Leu Thr Glu
        115                 120                 125
```

```
AAA GGA AAA CAT GGT AGT TTT CTT GTA CGA GAG AGC CAG AGC CAC CCT          432
Lys Gly Lys His Gly Ser Phe Leu Val Arg Glu Ser Gln Ser His Pro
        130                 135                 140

GGA GAT TTT GTT CTT TCT GTG CGC ACT GGT GAT GAC AAA GGG GAG AGC          480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA          528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT          576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA          624
Leu Val Glu His Tyr Lys Lys Asn Pro Met Val Glu Thr Leu Gly Thr
                195                 200                 205

GTA CTA CAA CTC AAG CAG CCC CTT AAC ACG ACT CGT ATA AAT GCT GCT          672
Val Leu Gln Leu Lys Gln Pro Leu Asn Thr Thr Arg Ile Asn Ala Ala
210                 215                 220

GAA ATA GAA AGC AGA GTT CGA GAA CTA AGC AAA TTA GCT GAG ACC ACA          720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA          768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA          816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC          864
Asn Lys Asn Lys Asn Arg Tyr Lys Asn Ile Leu Pro Phe Asp His Thr
                275                 280                 285

AGG GTT GTC CTA CAC GAT GGT GAT CCC AAT GAG CCT GTT TCA GAT TAC          912
Arg Val Val Leu His Asp Gly Asp Pro Asn Glu Pro Val Ser Asp Tyr
290                 295                 300

ATC AAT GCA AAT ATC ATC ATG CCT GAA TTT GAA ACC AAG TGC AAC AAT          960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC         1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG         1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC         1104
Ile Val Met Thr Thr Lys Glu Val Glu Arg Gly Lys Ser Lys Cys Val
                355                 360                 365

AAA TAC TGG CCT GAT GAG TAT GCT CTA AAA GAA TAT GGC GTC ATG CGT         1152
Lys Tyr Trp Pro Asp Glu Tyr Ala Leu Lys Glu Tyr Gly Val Met Arg
370                 375                 380

GTT AGG AAC GTC AAA GAA AGC GCC GCT CAT GAC TAT ACG CTA AGA GAA         1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG         1248
Leu Lys Leu Ser Lys Val Gly Gln Gly Asn Thr Glu Arg Thr Val Trp
                405                 410                 415

CAA TAC CAC TTT CGG ACC TGG CCG GCC CAC GGC GTG CCC AGC GAC CCT         1296
Gln Tyr His Phe Arg Thr Trp Pro Ala His Gly Val Pro Ser Asp Pro
            420                 425                 430

GGG GGC GTG CTG GAC TTC CTG GAG GAG GTG CAC CAT AAG CAG GAG AGC         1344
Gly Gly Val Leu Asp Phe Leu Glu Glu Val His His Lys Gln Glu Ser
                435                 440                 445
```

-continued

```
ATC ATG GAT GCA GGG CCG GTC GTG GTG CAC TGC AGT GCT GGA ATT GGC    1392
Ile Met Asp Ala Gly Pro Val Val Val His Cys Ser Ala Gly Ile Gly
    450                 455                 460

CGG ACA GGG ACG TTC ATT GTG ATT GAT ATT CTT ATT GAC ATC ATC AGA    1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG    1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA    1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG    1584
Phe Ile Tyr Met Ala Val Gln His Tyr Ile Glu Thr Leu Gln Arg Arg
        515                 520                 525

ATT GAA GAA GAG CAG AAA AGC AAG AGG AAA GGG CAC GAA TAT ACA AAT    1632
Ile Glu Glu Glu Gln Lys Ser Lys Arg Lys Gly His Glu Tyr Thr Asn
    530                 535                 540

ATT AAG TAT TCT CTA GCG GAC CAG ACG AGT GGA GAT CAG AGC CCT CTC    1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT    1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC    1776
Ala Arg Val Tyr Glu Asn Val Gly Leu Met Gln Gln Gln Lys Ser Phe
            580                 585                 590

AGA TGA                                                             1782
Arg
```

(2) INFORMATION FOR SEQ ID NO:18:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:18:

```
Met Thr Ser Arg Arg Trp Phe His Pro Asn Ile Thr Gly Val Glu Ala
  1               5                  10                  15

Glu Asn Leu Leu Leu Thr Arg Gly Val Asp Gly Ser Phe Leu Ala Arg
                 20                  25                  30

Pro Ser Lys Ser Asn Pro Gly Asp Phe Thr Leu Ser Val Arg Arg Asn
             35                  40                  45

Gly Ala Val Thr His Ile Lys Ile Gln Asn Thr Gly Asp Tyr Tyr Asp
         50                  55                  60

Leu Tyr Gly Gly Glu Lys Phe Ala Thr Leu Ala Leu Val Gln Tyr
 65                  70                  75                  80

Tyr Met Glu His His Gly Gln Leu Lys Glu Lys Asn Gly Asp Val Ile
                     85                  90                  95

Glu Leu Lys Tyr Pro Leu Asn Cys Ala Asp Pro Thr Ser Glu Arg Trp
                100                 105                 110

Phe His Gly His Leu Ser Gly Lys Glu Ala Glu Lys Leu Leu Thr Glu
            115                 120                 125

Lys Gly Lys His Gly Ser Phe Leu Val Arg Glu Ser Gln Ser His Pro
        130                 135                 140
```

```
Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
            165                 170                 175

Leu Lys Tyr Asp Val Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Ala His Gly Val Pro Ser Asp Pro
            420                 425                 430

Gly Gly Val Leu Asp Phe Leu Glu Glu Val His His Lys Gln Glu Ser
            435                 440                 445

Ile Met Asp Ala Gly Pro Val Val His Cys Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Ser Lys Arg Lys Gly His Glu Tyr Thr Asn
    530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Cys Ala Glu Met Arg Glu Asp Ser
```

```
                565                 570                 575
Ala Arg Val Tyr Glu Asn Val Gly Leu Met Gln Gln Gln Lys Ser Phe
                580                 585                 590

Arg (2) INFORMATION FOR SEQ ID NO:19:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:19:

ATG ACA TCG CGG AGA TGG TTT CAC CCA AAT ATC ACT GGT GTG GAG GCA        48
Met Thr Ser Arg Arg Trp Phe His Pro Asn Ile Thr Gly Val Glu Ala
 1               5                  10                  15

GAA AAC CTA CTG TTG ACA AGA GGA GTT GAT GGC AGT TTT TTG GCA AAG        96
Glu Asn Leu Leu Leu Thr Arg Gly Val Asp Gly Ser Phe Leu Ala Lys
                20                  25                  30

CCT AGT AAA AGT AAC CCT GGA GAC TTC ACA CTT TCC GTT AGA AGA AAT       144
Pro Ser Lys Ser Asn Pro Gly Asp Phe Thr Leu Ser Val Arg Arg Asn
            35                  40                  45

GGA GCT GTC ACC CAC ATC AAG ATT CAG AAC ACT GGT GCT TAC TAT GAC       192
Gly Ala Val Thr His Ile Lys Ile Gln Asn Thr Gly Ala Tyr Tyr Asp
        50                  55                  60

CTG TAT GGA GGG GAG AAA TTT GCC ACT TTG GCT GAG TTG GTC CAG TAT       240
Leu Tyr Gly Gly Glu Lys Phe Ala Thr Leu Ala Glu Leu Val Gln Tyr
 65                 70                  75                  80

TAC ATG GAA CAT CAC GGG CAA TTA AAA GAG AAG AAT GGA GAT GTC ATT       288
Tyr Met Glu His His Gly Gln Leu Lys Glu Lys Asn Gly Asp Val Ile
                85                  90                  95

GAG CTT AAA TAT CCT CTG AAC TGT GCA GAT CCT ACC TCT GAA AGG TGG       336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA       384
Phe His Gly His Leu Ser Gly Lys Glu Ala Glu Lys Leu Leu Thr Glu
        115                 120                 125

AAA GGA AAA CAT GGT AGT TTT CTT GTA AAA GAG AGC CAG AGC CAC CCT       432
Lys Gly Lys His Gly Ser Phe Leu Val Lys Glu Ser Gln Ser His Pro
    130                 135                 140

GGA GAT TTT GTT CTT TCT GTG CGC ACT GGT GAT GAC AAA GGG GAG AGC       480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA       528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT       576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA       624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT       672
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA       720
```

-continued

```
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA         768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA         816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC         864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC         912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT         960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC        1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG        1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC        1104
Ile Val Met Thr Thr Lys Glu Val Glu Arg Gly Lys Ser Lys Cys Val
        355                 360                 365

AAA TAC TGG CCT GAT GAG TAT GCT CTA AAA GAA TAT GGC GTC ATG CGT        1152
Lys Tyr Trp Pro Asp Glu Tyr Ala Leu Lys Glu Tyr Gly Val Met Arg
    370                 375                 380

GTT AGG AAC GTC AAA GAA AGC GCC GCT CAT GAC TAT ACG CTA AGA GAA        1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG        1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT        1296
Gln Tyr His Phe Arg Thr Trp Pro Asp His Gly Val Pro Ser Asp Pro
            420                 425                 430

GGG GGC GTG CTG GAC TTC CTG GAG GAG GTG CAC CAT AAG CAG GAG AGC        1344
Gly Gly Val Leu Asp Phe Leu Glu Glu Val His His Lys Gln Glu Ser
        435                 440                 445

ATC ATG GAT GCA GGG CCG GTC GTG GTG CAC TGC AGT GCT GGA ATT GGC        1392
Ile Met Asp Ala Gly Pro Val Val Val His Cys Ser Ala Gly Ile Gly
    450                 455                 460

CGG ACA GGG ACG TTC ATT GTG ATT GAT ATT CTT ATT GAC ATC ATC AGA        1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG        1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA        1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG        1584
Phe Ile Tyr Met Ala Val Gln His Tyr Ile Glu Thr Leu Gln Arg Arg
        515                 520                 525

ATT GAA GAA GAG CAG AAA AGC AAG AGG AAA GGG CAC GAA TAT ACA AAT        1632
Ile Glu Glu Glu Gln Lys Ser Lys Arg Lys Gly His Glu Tyr Thr Asn
    530                 535                 540
```

```
ATT AAG TAT TCT CTA GCG GAC CAG ACG AGT GGA GAT CAG AGC CCT CTC      1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT      1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC      1776
Ala Arg Val Tyr Glu Asn Val Gly Leu Met Gln Gln Gln Lys Ser Phe
            580                 585                 590

AGA TGA                                                              1782
Arg
```

(2) INFORMATION FOR SEQ ID NO:20:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:20:

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Lys
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Ala Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Lys Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
```

-continued

```
                275                 280                 285
Arg Val Val Leu His Asp Gly Asp Pro Asn Glu Pro Val Ser Asp Tyr
        290                 295                 300
Ile Asn Ala Asn Ile Ile Met Pro Glu Phe Glu Thr Lys Cys Asn Asn
305                 310                 315                 320
Ser Lys Pro Lys Lys Ser Tyr Ile Ala Thr Gln Gly Cys Leu Gln Asn
                325                 330                 335
Thr Val Asn Asp Phe Trp Arg Met Val Phe Gln Glu Asn Ser Arg Val
            340                 345                 350
Ile Val Met Thr Thr Lys Glu Val Glu Arg Gly Lys Ser Lys Cys Val
                355                 360                 365
Lys Tyr Trp Pro Asp Glu Tyr Ala Leu Lys Glu Tyr Gly Val Met Arg
370                 375                 380
Val Arg Asn Val Lys Glu Ser Ala Ala His Asp Tyr Thr Leu Arg Glu
385                 390                 395                 400
Leu Lys Leu Ser Lys Val Gly Gln Gly Asn Thr Glu Arg Thr Val Trp
                405                 410                 415
Gln Tyr His Phe Arg Thr Trp Pro Asp His Gly Val Pro Ser Asp Pro
            420                 425                 430
Gly Gly Val Leu Asp Phe Leu Glu Glu Val His His Lys Gln Glu Ser
                435                 440                 445
Ile Met Asp Ala Gly Pro Val Val His Cys Ser Ala Gly Ile Gly
450                 455                 460
Arg Thr Gly Thr Phe Ile Val Ile Asp Ile Leu Ile Asp Ile Ile Arg
465                 470                 475                 480
Glu Lys Gly Val Asp Cys Asp Ile Asp Val Pro Lys Thr Ile Gln Met
                485                 490                 495
Val Arg Ser Gln Arg Ser Gly Met Val Gln Thr Glu Ala Gln Tyr Arg
            500                 505                 510
Phe Ile Tyr Met Ala Val Gln His Tyr Ile Glu Thr Leu Gln Arg Arg
            515                 520                 525
Ile Glu Glu Glu Gln Lys Ser Lys Arg Lys Gly His Glu Tyr Thr Asn
            530                 535                 540
Ile Lys Tyr Ser Leu Ala Asp Gln Thr Ser Gly Asp Gln Ser Pro Leu
545                 550                 555                 560
Pro Pro Cys Thr Pro Thr Pro Cys Ala Glu Met Arg Glu Asp Ser
                565                 570                 575
Ala Arg Val Tyr Glu Asn Val Gly Leu Met Gln Gln Gln Lys Ser Phe
            580                 585                 590
Arg
```

(2) INFORMATION FOR SEQ ID NO:21:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:21:

```
ATG ACA TCG CGG AGA TGG TTT CAC CCA AAT ATC ACT GGT GTG GAG GCA      48
Met Thr Ser Arg Arg Trp Phe His Pro Asn Ile Thr Gly Val Glu Ala
 1               5                  10                  15
```

-continued

```
GAA AAC CTA CTG TTG ACA AGA GGA GTT GAT GGC AGT TTT TTG GCA AAG        96
Glu Asn Leu Leu Leu Thr Arg Gly Val Asp Gly Ser Phe Leu Ala Lys
         20                  25                  30

CCT AGT AAA AGT AAC CCT GGA GAC TTC ACA CTT TCC GTT AGA AGA AAT       144
Pro Ser Lys Ser Asn Pro Gly Asp Phe Thr Leu Ser Val Arg Arg Asn
             35                  40                  45

GGA GCT GTC ACC CAC ATC AAG ATT CAG AAC ACT GGT GAT TAC TAT GAC       192
Gly Ala Val Thr His Ile Lys Ile Gln Asn Thr Gly Asp Tyr Tyr Asp
     50                  55                  60

CTG TAT GGA GGG GAG AAA TTT GCC ACT TTG GCT GCG TTG GTC CAG TAT       240
Leu Tyr Gly Gly Glu Lys Phe Ala Thr Leu Ala Ala Leu Val Gln Tyr
 65                  70                  75                  80

TAC ATG GAA CAT CAC GGG CAA TTA AAA GAG AAG AAT GGA GAT GTC ATT       288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG       336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA       384
Phe His Gly His Leu Ser Gly Lys Glu Ala Glu Lys Leu Leu Thr Glu
        115                 120                 125

AAA GGA AAA CAT GGT AGT TTT CTT GTA AAA GAG AGC CAG AGC CAC CCT       432
Lys Gly Lys His Gly Ser Phe Leu Val Lys Glu Ser Gln Ser His Pro
    130                 135                 140

GGA GAT TTT GTT CTT TCT GTG CGC ACT GGT GAT GAC AAA GGG GAG AGC       480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA       528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT       576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA       624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT       672
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA       720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA       768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA       816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC       864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC       912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT       960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC      1008
Ser Lys Pro Lys Lys Ser Tyr Ile Ala Thr Gln Gly Cys Leu Gln Asn
```

```
                    325                 330                 335
ACG GTG AAT GAC TTT TGG CGG ATG GTG TTC CAA GAA AAC TCC CGA GTG        1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC        1104
Ile Val Met Thr Thr Lys Glu Val Glu Arg Gly Lys Ser Lys Cys Val
                355                 360                 365

AAA TAC TGG CCT GAT GAG TAT GCT CTA AAA GAA TAT GGC GTC ATG CGT        1152
Lys Tyr Trp Pro Asp Glu Tyr Ala Leu Lys Glu Tyr Gly Val Met Arg
370                 375                 380

GTT AGG AAC GTC AAA GAA AGC GCC GCT CAT GAC TAT ACG CTA AGA GAA        1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG        1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT        1296
Gln Tyr His Phe Arg Thr Trp Pro Asp His Gly Val Pro Ser Asp Pro
                420                 425                 430

GGG GGC GTG CTG GAC TTC CTG GAG GAG GTG CAC CAT AAG CAG GAG AGC        1344
Gly Gly Val Leu Asp Phe Leu Glu Glu Val His His Lys Gln Glu Ser
            435                 440                 445

ATC ATG GAT GCA GGG CCG GTC GTG GTG CAC TGC AGT GCT GGA ATT GGC        1392
Ile Met Asp Ala Gly Pro Val Val Val His Cys Ser Ala Gly Ile Gly
450                 455                 460

CGG ACA GGG ACG TTC ATT GTG ATT GAT ATT CTT ATT GAC ATC ATC AGA        1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG        1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA        1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG        1584
Phe Ile Tyr Met Ala Val Gln His Tyr Ile Glu Thr Leu Gln Arg Arg
            515                 520                 525

ATT GAA GAA GAG CAG AAA AGC AAG AGG AAA GGG CAC GAA TAT ACA AAT        1632
Ile Glu Glu Glu Gln Lys Ser Lys Arg Lys Gly His Glu Tyr Thr Asn
        530                 535                 540

ATT AAG TAT TCT CTA GCG GAC CAG ACG AGT GGA GAT CAG AGC CCT CTC        1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT        1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC        1776
Ala Arg Val Tyr Glu Asn Val Gly Leu Met Gln Gln Gln Lys Ser Phe
            580                 585                 590

AGA TGA                                                                1782
Arg (2) INFORMATION FOR SEQ ID NO:22:

(i) SEQUENCE CHARACTERISTICS:
        (A) LENGTH: 593 amino acids
        (B) TYPE: amino acid
        (D) TOPOLOGY: linear (ii) MOLECULE TYPE: protein
```

(xi) SEQUENCE DESCRIPTION: SEQ ID NO:22:

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Lys
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Ala Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Lys Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415
```

```
Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Gln Lys Ser Lys Arg Lys Gly His Glu Tyr Thr Asn
    530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
                565                 570                 575

Ala Arg Val Tyr Glu Asn Val Gly Leu Met Gln Gln Gln Lys Ser Phe
            580                 585                 590

Arg (2) INFORMATION FOR SEQ ID NO:23:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:23:

ATG ACA TCG CGG AGA TGG TTT CAC CCA AAT ATC ACT GGT GTG GAG GCA       48
Met Thr Ser Arg Arg Trp Phe His Pro Asn Ile Thr Gly Val Glu Ala
  1               5                  10                  15

GAA AAC CTA CTG TTG ACA AGA GGA GTT GAT GGC AGT TTT TTG GCA AAG       96
Glu Asn Leu Leu Leu Thr Arg Gly Val Asp Gly Ser Phe Leu Ala Lys
             20                  25                  30

CCT AGT AAA AGT AAC CCT GGA GAC TTC ACA CTT TCC GTT AGA AGA AAT      144
Pro Ser Lys Ser Asn Pro Gly Asp Phe Thr Leu Ser Val Arg Arg Asn
         35                  40                  45

GGA GCT GTC ACC CAC ATC AAG ATT CAG AAC ACT GGT GCT TAC TAT GAC      192
Gly Ala Val Thr His Ile Lys Ile Gln Asn Thr Gly Ala Tyr Tyr Asp
     50                  55                  60

CTG TAT GGA GGG GAG AAA TTT GCC ACT TTG GCT GAG TTG GTC CAG TAT      240
Leu Tyr Gly Gly Glu Lys Phe Ala Thr Leu Ala Glu Leu Val Gln Tyr
 65                  70                  75                  80

TAC ATG GAA CAT CAC GGG CAA TTA AAA GAG AAG AAT GGA GAT GTC ATT      288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG      336
Glu Leu Lys Tyr Pro Leu Asn Cys Ala Asp Pro Thr Ser Glu Arg Trp
            100                 105                 110
```

```
TTT CAT GGA CAT CTC TCT GGG AAA GAA GCA GAG AAA TTA TTA ACT GAA      384
Phe His Gly His Leu Ser Gly Lys Glu Ala Glu Lys Leu Leu Thr Glu
        115                 120                 125

AAA GGA AAA CAT GGT AGT TTT CTT GTA AAA GAG AGC CAG AGC CAC CCT      432
Lys Gly Lys His Gly Ser Phe Leu Val Lys Glu Ser Gln Ser His Pro
130                 135                 140

GGA GAT TTT GTT CTT TCT GTG CGC ACT GGT GAT GAC AAA GGG GAG AGC      480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA      528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT      576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA      624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT      672
Val Leu Gln Leu Lys Gln Pro Leu Asn Thr Thr Arg Ile Asn Ala Ala
210                 215                 220

GAA ATA GAA AGC AGA GTT CGA GAA CTA AGC AAA TTA GCT GAG ACC ACA      720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA      768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA      816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC      864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC      912
Arg Val Val Leu His Asp Gly Asp Pro Asn Glu Pro Val Ser Asp Tyr
290                 295                 300

ATC AAT GCA AAT ATC ATC ATG CCT GAA TTT GAA ACC AAG TGC AAC AAT      960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC     1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG     1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC     1104
Ile Val Met Thr Thr Lys Glu Val Glu Arg Gly Lys Ser Lys Cys Val
        355                 360                 365

AAA TAC TGG CCT GAT GAG TAT GCT CTA AAA GAA TAT GGC GTC ATG CGT     1152
Lys Tyr Trp Pro Asp Glu Tyr Ala Leu Lys Glu Tyr Gly Val Met Arg
370                 375                 380

GTT AGG AAC GTC AAA GAA AGC GCC GCT CAT GAC TAT ACG CTA AGA GAA     1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG     1248
Leu Lys Leu Ser Lys Val Gly Gln Gly Asn Thr Glu Arg Thr Val Trp
                405                 410                 415

CAA TAC CAC TTT CGG ACC TGG CCG GAC CAC GGC GTG CCC AGC GAC CCT     1296
Gln Tyr His Phe Arg Thr Trp Pro Asp His Gly Val Pro Ser Asp Pro
            420                 425                 430
```

```
GGG GGC GTG CTG GAC TTC CTG GAG GAG GTG CAC CAT AAG CAG GAG AGC    1344
Gly Gly Val Leu Asp Phe Leu Glu Glu Val His His Lys Gln Glu Ser
            435                 440                 445

ATC ATG GAT GCA GGG CCG GTC GTG GTG CAC TCG AGT GCT GGA ATT GGC    1392
Ile Met Asp Ala Gly Pro Val Val Val His Ser Ser Ala Gly Ile Gly
            450                 455                 460

CGG ACA GGG ACG TTC ATT GTG ATT GAT ATT CTT ATT GAC ATC ATC AGA    1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG    1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA    1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG    1584
Phe Ile Tyr Met Ala Val Gln His Tyr Ile Glu Thr Leu Gln Arg Arg
            515                 520                 525

ATT GAA GAA GAG CAG AAA AGC AAG AGG AAA GGG CAC GAA TAT ACA AAT    1632
Ile Glu Glu Glu Gln Lys Ser Lys Arg Lys Gly His Glu Tyr Thr Asn
            530                 535                 540

ATT AAG TAT TCT CTA GCG GAC CAG ACG AGT GGA GAT CAG AGC CCT CTC    1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT    1728
Pro Pro Cys Thr Pro Thr Pro Pro Cys Ala Glu Met Arg Glu Asp Ser
                565                 570                 575

GCT AGA GTC TAT GAA AAC GTG GGC CTG ATG CAA CAG CAG AAA AGT TTC    1776
Ala Arg Val Tyr Glu Asn Val Gly Leu Met Gln Gln Gln Lys Ser Phe
            580                 585                 590

AGA TGA                                                             1782
Arg (2) INFORMATION FOR SEQ ID NO:24:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:24:

Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Lys
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Ala Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125
```

```
Lys Gly Lys His Gly Ser Phe Leu Val Lys Glu Ser Gln Ser His Pro
130                 135                 140
Gly Asp Phe Val Leu Ser Val Arg Thr Gly Asp Asp Lys Gly Glu Ser
145                 150                 155                 160
Asn Asp Gly Lys Ser Lys Val Thr His Val Met Ile Arg Cys Gln Glu
                165                 170                 175
Leu Lys Tyr Asp Val Gly Gly Glu Arg Phe Asp Ser Leu Thr Asp
            180                 185                 190
Leu Val Glu His Tyr Lys Lys Asn Pro Met Val Glu Thr Leu Gly Thr
                195                 200                 205
Val Leu Gln Leu Lys Gln Pro Leu Asn Thr Thr Arg Ile Asn Ala Ala
210                 215                 220
Glu Ile Glu Ser Arg Val Arg Glu Leu Ser Lys Leu Ala Glu Thr Thr
225                 230                 235                 240
Asp Lys Val Lys Gln Gly Phe Trp Glu Glu Phe Glu Thr Leu Gln Gln
                245                 250                 255
Gln Glu Cys Lys Leu Leu Tyr Ser Arg Lys Glu Gly Gln Arg Gln Glu
                260                 265                 270
Asn Lys Asn Lys Asn Arg Tyr Lys Asn Ile Leu Pro Phe Asp His Thr
                275                 280                 285
Arg Val Val Leu His Asp Gly Asp Pro Asn Glu Pro Val Ser Asp Tyr
290                 295                 300
Ile Asn Ala Asn Ile Ile Met Pro Glu Phe Glu Thr Lys Cys Asn Asn
305                 310                 315                 320
Ser Lys Pro Lys Lys Ser Tyr Ile Ala Thr Gln Gly Cys Leu Gln Asn
                325                 330                 335
Thr Val Asn Asp Phe Trp Arg Met Val Phe Gln Glu Asn Ser Arg Val
                340                 345                 350
Ile Val Met Thr Thr Lys Glu Val Glu Arg Gly Lys Ser Lys Cys Val
                355                 360                 365
Lys Tyr Trp Pro Asp Glu Tyr Ala Leu Lys Glu Tyr Gly Val Met Arg
                370                 375                 380
Val Arg Asn Val Lys Glu Ser Ala Ala His Asp Tyr Thr Leu Arg Glu
385                 390                 395                 400
Leu Lys Leu Ser Lys Val Gly Gln Gly Asn Thr Glu Arg Thr Val Trp
                405                 410                 415
Gln Tyr His Phe Arg Thr Trp Pro Asp His Gly Val Pro Ser Asp Pro
                420                 425                 430
Gly Gly Val Leu Asp Phe Leu Glu Glu Val His His Lys Gln Glu Ser
                435                 440                 445
Ile Met Asp Ala Gly Pro Val Val His Ser Ser Ala Gly Ile Gly
                450                 455                 460
Arg Thr Gly Thr Phe Ile Val Ile Asp Ile Leu Ile Asp Ile Ile Arg
465                 470                 475                 480
Glu Lys Gly Val Asp Cys Asp Ile Asp Val Pro Lys Thr Ile Gln Met
                485                 490                 495
Val Arg Ser Gln Arg Ser Gly Met Val Gln Thr Glu Ala Gln Tyr Arg
                500                 505                 510
Phe Ile Tyr Met Ala Val Gln His Tyr Ile Glu Thr Leu Gln Arg Arg
                515                 520                 525
Ile Glu Glu Glu Gln Lys Ser Lys Arg Lys Gly His Glu Tyr Thr Asn
530                 535                 540
```

-continued

```
Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
            565                 570                 575

Ala Arg Val Tyr Glu Asn Val Gly Leu Met Gln Gln Gln Lys Ser Phe
            580                 585                 590

Arg
```

(2) INFORMATION FOR SEQ ID NO:25:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:25:

```
ATG ACA TCG CGG AGA TGG TTT CAC CCA AAT ATC ACT GGT GTG GAG GCA    48
Met Thr Ser Arg Arg Trp Phe His Pro Asn Ile Thr Gly Val Glu Ala
 1               5                  10                  15

GAA AAC CTA CTG TTG ACA AGA GGA GTT GAT GGC AGT TTT TTG GCA AAG    96
Glu Asn Leu Leu Leu Thr Arg Gly Val Asp Gly Ser Phe Leu Ala Lys
             20                  25                  30

CCT AGT AAA AGT AAC CCT GGA GAC TTC ACA CTT TCC GTT AGA AGA AAT   144
Pro Ser Lys Ser Asn Pro Gly Asp Phe Thr Leu Ser Val Arg Arg Asn
         35                  40                  45

GGA GCT GTC ACC CAC ATC AAG ATT CAG AAC ACT GGT GCT TAC TAT GAC   192
Gly Ala Val Thr His Ile Lys Ile Gln Asn Thr Gly Ala Tyr Tyr Asp
     50                  55                  60

CTG TAT GGA GGG GAG AAA TTT GCC ACT TTG GCT GAG TTG GTC CAG TAT   240
Leu Tyr Gly Gly Glu Lys Phe Ala Thr Leu Ala Glu Leu Val Gln Tyr
 65                  70                  75                  80

TAC ATG GAA CAT CAC GGG CAA TTA AAA GAG AAG AAT GGA GAT GTC ATT   288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG   336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA   384
Phe His Gly His Leu Ser Gly Lys Glu Ala Glu Lys Leu Leu Thr Glu
        115                 120                 125

AAA GGA AAA CAT GGT AGT TTT CTT GTA AAA GAG AGC CAG AGC CAC CCT   432
Lys Gly Lys His Gly Ser Phe Leu Val Lys Glu Ser Gln Ser His Pro
    130                 135                 140

GGA GAT TTT GTT CTT TCT GTG CGC ACT GGT GAT GAC AAA GGG GAG AGC   480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA   528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT   576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA   624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT   672
```

```
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA         720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA         768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA         816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC         864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC         912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT         960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC         1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG         1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC         1104
Ile Val Met Thr Thr Lys Glu Val Glu Arg Gly Lys Ser Lys Cys Val
        355                 360                 365

AAA TAC TGG CCT GAT GAG TAT GCT CTA AAA GAA TAT GGC GTC ATG CGT         1152
Lys Tyr Trp Pro Asp Glu Tyr Ala Leu Lys Glu Tyr Gly Val Met Arg
    370                 375                 380

GTT AGG AAC GTC AAA GAA AGC GCC GCT CAT GAC TAT ACG CTA AGA GAA         1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG         1248
Leu Lys Leu Ser Lys Val Gly Gln Gly Asn Thr Glu Arg Thr Val Trp
                405                 410                 415

CAA TAC CAC TTT CGG ACC TGG CCG GCC CAC GGC GTG CCC AGC GAC CCT         1296
Gln Tyr His Phe Arg Thr Trp Pro Ala His Gly Val Pro Ser Asp Pro
            420                 425                 430

GGG GGC GTG CTG GAC TTC CTG GAG GAG GTG CAC CAT AAG CAG GAG AGC         1344
Gly Gly Val Leu Asp Phe Leu Glu Glu Val His His Lys Gln Glu Ser
        435                 440                 445

ATC ATG GAT GCA GGG CCG GTC GTG GTG CAC TGC AGT GCT GGA ATT GGC         1392
Ile Met Asp Ala Gly Pro Val Val Val His Cys Ser Ala Gly Ile Gly
    450                 455                 460

CGG ACA GGG ACG TTC ATT GTG ATT GAT ATT CTT ATT GAC ATC ATC AGA         1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG         1488
Glu Lys Gly Val Asp Cys Asp Ile Asp Val Pro Lys Thr Ile Gln Met
                485                 490                 495

GTG CGG TCT CAG AGG TCA GGG ATG GTC CAG ACA GAA GCA CAG TAC CGA         1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG         1584
Phe Ile Tyr Met Ala Val Gln His Tyr Ile Glu Thr Leu Gln Arg Arg
        515                 520                 525
```

```
ATT GAA GAA GAG CAG AAA AGC AAG AGG AAA GGG CAC GAA TAT ACA AAT     1632
Ile Glu Glu Glu Gln Lys Ser Lys Arg Lys Gly His Glu Tyr Thr Asn
530                     535                     540

ATT AAG TAT TCT CTA GCG GAC CAG ACG AGT GGA GAT CAG AGC CCT CTC     1680
Ile Lys Tyr Ser Leu Ala Asp Gln Thr Ser Gly Asp Gln Ser Pro Leu
545                     550                     555             560

CCG CCT TGT ACT CCA ACG CCA CCC TGT GCA GAA ATG AGA GAA GAC AGT     1728
Pro Pro Cys Thr Pro Thr Pro Pro Cys Ala Glu Met Arg Glu Asp Ser
                565                     570                     575

GCT AGA GTC TAT GAA AAC GTG GGC CTG ATG CAA CAG CAG AAA AGT TTC     1776
Ala Arg Val Tyr Glu Asn Val Gly Leu Met Gln Gln Gln Lys Ser Phe
            580                     585                     590

AGA TGA                                                             1782
Arg
```

(2) INFORMATION FOR SEQ ID NO:26:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:26:

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Lys
                20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Ala Tyr Tyr Asp
        50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Lys Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255
```

```
Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Ala His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
    450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

Ile Glu Glu Glu Gln Lys Ser Lys Arg Lys Gly His Glu Tyr Thr Asn
530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
            565                 570                 575

Ala Arg Val Tyr Glu Asn Val Gly Leu Met Gln Gln Gln Lys Ser Phe
        580                 585                 590

Arg
```

(2) INFORMATION FOR SEQ ID NO:27:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:27:

```
ATG ACA TCG CGG AGA TGG TTT CAC CCA AAT ATC ACT GGT GTG GAG GCA      48
Met Thr Ser Arg Arg Trp Phe His Pro Asn Ile Thr Gly Val Glu Ala
 1               5                  10                  15

GAA AAC CTA CTG TTG ACA AGA GGA GTT GAT GGC AGT TTT TTG GCA AAG      96
Glu Asn Leu Leu Leu Thr Arg Gly Val Asp Gly Ser Phe Leu Ala Lys
                20                  25                  30

CCT AGT AAA AGT AAC CCT GGA GAC TTC ACA CTT TCC GTT AGA AGA AAT     144
Pro Ser Lys Ser Asn Pro Gly Asp Phe Thr Leu Ser Val Arg Arg Asn
         35                  40                  45

GGA GCT GTC ACC CAC ATC AAG ATT CAG AAC ACT GGT GAT TAC TAT GAC     192
Gly Ala Val Thr His Ile Lys Ile Gln Asn Thr Gly Asp Tyr Tyr Asp
     50                  55                  60

CTG TAT GGA GGG GAG AAA TTT GCC ACT TTG GCT GCG TTG GTC CAG TAT     240
Leu Tyr Gly Gly Glu Lys Phe Ala Thr Leu Ala Ala Leu Val Gln Tyr
 65                  70                  75                  80

TAC ATG GAA CAT CAC GGG CAA TTA AAA GAG AAG AAT GGA GAT GTC ATT     288
Tyr Met Glu His His Gly Gln Leu Lys Glu Lys Asn Gly Asp Val Ile
                 85                  90                  95

GAG CTT AAA TAT CCT CTG AAC TGT GCA GAT CCT ACC TCT GAA AGG TGG     336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA     384
Phe His Gly His Leu Ser Gly Lys Glu Ala Glu Lys Leu Leu Thr Glu
            115                 120                 125

AAA GGA AAA CAT GGT AGT TTT CTT GTA AAA GAG AGC CAG AGC CAC CCT     432
Lys Gly Lys His Gly Ser Phe Leu Val Lys Glu Ser Gln Ser His Pro
        130                 135                 140

GGA GAT TTT GTT CTT TCT GTG CGC ACT GGT GAT GAC AAA GGG GAG AGC     480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA     528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT     576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA     624
Leu Val Glu His Tyr Lys Lys Asn Pro Met Val Glu Thr Leu Gly Thr
        195                 200                 205

GTA CTA CAA CTC AAG CAG CCC CTT AAC ACG ACT CGT ATA AAT GCT GCT     672
Val Leu Gln Leu Lys Gln Pro Leu Asn Thr Thr Arg Ile Asn Ala Ala
    210                 215                 220

GAA ATA GAA AGC AGA GTT CGA GAA CTA AGC AAA TTA GCT GAG ACC ACA     720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA     768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA     816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC     864
Asn Lys Asn Lys Asn Arg Tyr Lys Asn Ile Leu Pro Phe Asp His Thr
        275                 280                 285

AGG GTT GTC CTA CAC GAT GGT GAT CCC AAT GAG CCT GTT TCA GAT TAC     912
Arg Val Val Leu His Asp Gly Asp Pro Asn Glu Pro Val Ser Asp Tyr
    290                 295                 300

ATC AAT GCA AAT ATC ATC ATG CCT GAA TTT GAA ACC AAG TGC AAC AAT     960
Ile Asn Ala Asn Ile Ile Met Pro Glu Phe Glu Thr Lys Cys Asn Asn
```

```
                305               310               315               320
     TCA AAG CCC AAA AAG AGT TAC ATT GCC ACA CAA GGC TGC CTG CAA AAC     1008
     Ser Lys Pro Lys Lys Ser Tyr Ile Ala Thr Gln Gly Cys Leu Gln Asn
                     325               330               335

ACG GTG AAT GAC TTT TGG CGG ATG GTG TTC CAA GAA AAC TCC CGA GTG     1056
     Thr Val Asn Asp Phe Trp Arg Met Val Phe Gln Glu Asn Ser Arg Val
                     340               345               350

ATT GTC ATG ACA ACG AAA GAA GTG GAG AGA GGA AAG AGT AAA TGT GTC     1104
     Ile Val Met Thr Thr Lys Glu Val Glu Arg Gly Lys Ser Lys Cys Val
                     355               360               365

AAA TAC TGG CCT GAT GAG TAT GCT CTA AAA GAA TAT GGC GTC ATG CGT     1152
     Lys Tyr Trp Pro Asp Glu Tyr Ala Leu Lys Glu Tyr Gly Val Met Arg
             370               375               380

GTT AGG AAC GTC AAA GAA AGC GCC GCT CAT GAC TAT ACG CTA AGA GAA     1200
     Val Arg Asn Val Lys Glu Ser Ala Ala His Asp Tyr Thr Leu Arg Glu
     385               390               395               400

CTT AAA CTT TCA AAG GTT GGA CAA GGG AAT ACG GAG AGA ACG GTC TGG     1248
     Leu Lys Leu Ser Lys Val Gly Gln Gly Asn Thr Glu Arg Thr Val Trp
                     405               410               415

CAA TAC CAC TTT CGG ACC TGG CCG GAC CAC GGC GTG CCC AGC GAC CCT     1296
     Gln Tyr His Phe Arg Thr Trp Pro Asp His Gly Val Pro Ser Asp Pro
                     420               425               430

GGG GGC GTG CTG GAC TTC CTG GAG GAG GTG CAC CAT AAG CAG GAG AGC     1344
     Gly Gly Val Leu Asp Phe Leu Glu Glu Val His His Lys Gln Glu Ser
                     435               440               445

ATC ATG GAT GCA GGG CCG GTC GTG GTG CAC TCG AGT GCT GGA ATT GGC     1392
     Ile Met Asp Ala Gly Pro Val Val Val His Ser Ser Ala Gly Ile Gly
             450               455               460

CGG ACA GGG ACG TTC ATT GTG ATT GAT ATT CTT ATT GAC ATC ATC AGA     1440
     Arg Thr Gly Thr Phe Ile Val Ile Asp Ile Leu Ile Asp Ile Ile Arg
     465               470               475               480

GAG AAA GGT GTT GAC TGC GAT ATT GAC GTT CCC AAA ACC ATC CAG ATG     1488
     Glu Lys Gly Val Asp Cys Asp Ile Asp Val Pro Lys Thr Ile Gln Met
                     485               490               495

GTG CGG TCT CAG AGG TCA GGG ATG GTC CAG ACA GAA GCA CAG TAC CGA     1536
     Val Arg Ser Gln Arg Ser Gly Met Val Gln Thr Glu Ala Gln Tyr Arg
                     500               505               510

TTT ATC TAT ATG GCG GTC CAG CAT TAT ATT GAA ACA CTA CAG CGC AGG     1584
     Phe Ile Tyr Met Ala Val Gln His Tyr Ile Glu Thr Leu Gln Arg Arg
             515               520               525

ATT GAA GAA GAG CAG AAA AGC AAG AGG AAA GGG CAC GAA TAT ACA AAT     1632
     Ile Glu Glu Glu Gln Lys Ser Lys Arg Lys Gly His Glu Tyr Thr Asn
             530               535               540

ATT AAG TAT TCT CTA GCG GAC CAG ACG AGT GGA GAT CAG AGC CCT CTC     1680
     Ile Lys Tyr Ser Leu Ala Asp Gln Thr Ser Gly Asp Gln Ser Pro Leu
     545               550               555               560

CCG CCT TGT ACT CCA ACG CCA CCC TGT GCA GAA ATG AGA GAA GAC AGT     1728
     Pro Pro Cys Thr Pro Thr Pro Pro Cys Ala Glu Met Arg Glu Asp Ser
                     565               570               575

GCT AGA GTC TAT GAA AAC GTG GGC CTG ATG CAA CAG CAG AAA AGT TTC     1776
     Ala Arg Val Tyr Glu Asn Val Gly Leu Met Gln Gln Gln Lys Ser Phe
                     580               585               590

AGA TGA                                                             1782
     Arg (2) INFORMATION FOR SEQ ID NO:28:

(i) SEQUENCE CHARACTERISTICS:
        (A) LENGTH: 593 amino acids
        (B) TYPE: amino acid
```

(D) TOPOLOGY: linear (ii) MOLECULE TYPE: protein (xi) SEQUENCE DESCRIPTION: SEQ ID NO:28:

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Lys
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Lys Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
```

```
385                 390                 395                 400
Leu Lys Leu Ser Lys Val Gly Gln Gly Asn Thr Glu Arg Thr Val Trp
            405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
            435                 440                 445

Ile Met Asp Ala Gly Pro Val Val His Ser Ser Ala Gly Ile Gly
            450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
            485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
            515                 520                 525

Ile Glu Glu Gln Lys Ser Lys Arg Lys Gly His Glu Tyr Thr Asn
            530                 535                 540

Ile Lys Tyr Ser Leu Ala Asp Gln Thr Ser Gly Asp Gln Ser Pro Leu
545                 550                 555                 560

Pro Pro Cys Thr Pro Thr Pro Pro Cys Ala Glu Met Arg Glu Asp Ser
            565                 570                 575

Ala Arg Val Tyr Glu Asn Val Gly Leu Met Gln Gln Lys Ser Phe
            580                 585                 590

Arg (2) INFORMATION FOR SEQ ID NO:29:

(i) SEQUENCE CHARACTERISTICS:
        (A) LENGTH: 1782 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1779

(xi) SEQUENCE DESCRIPTION: SEQ ID NO:29:

ATG ACA TCG CGG AGA TGG TTT CAC CCA AAT ATC ACT GGT GTG GAG GCA    48
Met Thr Ser Arg Arg Trp Phe His Pro Asn Ile Thr Gly Val Glu Ala
1               5                  10                  15

GAA AAC CTA CTG TTG ACA AGA GGA GTT GAT GGC AGT TTT TTG GCA AAG    96
Glu Asn Leu Leu Leu Thr Arg Gly Val Asp Gly Ser Phe Leu Ala Lys
            20                  25                  30

CCT AGT AAA AGT AAC CCT GGA GAC TTC ACA CTT TCC GTT AGA AGA AAT    144
Pro Ser Lys Ser Asn Pro Gly Asp Phe Thr Leu Ser Val Arg Arg Asn
        35                  40                  45

GGA GCT GTC ACC CAC ATC AAG ATT CAG AAC ACT GGT GAT TAC TAT GAC    192
Gly Ala Val Thr His Ile Lys Ile Gln Asn Thr Gly Asp Tyr Tyr Asp
    50                  55                  60

CTG TAT GGA GGG GAG AAA TTT GCC ACT TTG GCT GCG TTG GTC CAG TAT    240
Leu Tyr Gly Gly Glu Lys Phe Ala Thr Leu Ala Ala Leu Val Gln Tyr
65                  70                  75                  80

TAC ATG GAA CAT CAC GGG CAA TTA AAA GAG AAG AAT GGA GAT GTC ATT    288
Tyr Met Glu His His Gly Gln Leu Lys Glu Lys Asn Gly Asp Val Ile
            85                  90                  95
```

```
GAG CTT AAA TAT CCT CTG AAC TGT GCA GAT CCT ACC TCT GAA AGG TGG        336
Glu Leu Lys Tyr Pro Leu Asn Cys Ala Asp Pro Thr Ser Glu Arg Trp
            100                 105                 110

TTT CAT GGA CAT CTC TCT GGG AAA GAA GCA GAG AAA TTA TTA ACT GAA        384
Phe His Gly His Leu Ser Gly Lys Glu Ala Glu Lys Leu Leu Thr Glu
            115                 120                 125

AAA GGA AAA CAT GGT AGT TTT CTT GTA AAA GAG AGC CAG AGC CAC CCT        432
Lys Gly Lys His Gly Ser Phe Leu Val Lys Glu Ser Gln Ser His Pro
        130                 135                 140

GGA GAT TTT GTT CTT TCT GTG CGC ACT GGT GAT GAC AAA GGG GAG AGC        480
Gly Asp Phe Val Leu Ser Val Arg Thr Gly Asp Asp Lys Gly Glu Ser
145                 150                 155                 160

AAT GAC GGC AAG TCT AAA GTG ACC CAT GTT ATG ATT CGC TGT CAG GAA        528
Asn Asp Gly Lys Ser Lys Val Thr His Val Met Ile Arg Cys Gln Glu
                165                 170                 175

CTG AAA TAC GAC GTT GGT GGA GGA GAA CGG TTT GAT TCT TTG ACA GAT        576
Leu Lys Tyr Asp Val Gly Gly Gly Glu Arg Phe Asp Ser Leu Thr Asp
            180                 185                 190

CTT GTG GAA CAT TAT AAG AAG AAT CCT ATG GTG GAA ACA TTG GGT ACA        624
Leu Val Glu His Tyr Lys Lys Asn Pro Met Val Glu Thr Leu Gly Thr
            195                 200                 205

GTA CTA CAA CTC AAG CAG CCC CTT AAC ACG ACT CGT ATA AAT GCT GCT        672
Val Leu Gln Leu Lys Gln Pro Leu Asn Thr Thr Arg Ile Asn Ala Ala
        210                 215                 220

GAA ATA GAA AGC AGA GTT CGA GAA CTA AGC AAA TTA GCT GAG ACC ACA        720
Glu Ile Glu Ser Arg Val Arg Glu Leu Ser Lys Leu Ala Glu Thr Thr
225                 230                 235                 240

GAT AAA GTC AAA CAA GGC TTT TGG GAA GAA TTT GAG ACA CTA CAA CAA        768
Asp Lys Val Lys Gln Gly Phe Trp Glu Glu Phe Glu Thr Leu Gln Gln
                245                 250                 255

CAG GAG TGC AAA CTT CTC TAC AGC CGA AAA GAG GGT CAA AGG CAA GAA        816
Gln Glu Cys Lys Leu Leu Tyr Ser Arg Lys Glu Gly Gln Arg Gln Glu
            260                 265                 270

AAC AAA AAC AAA AAT AGA TAT AAA AAC ATC CTG CCC TTT GAT CAT ACC        864
Asn Lys Asn Lys Asn Arg Tyr Lys Asn Ile Leu Pro Phe Asp His Thr
            275                 280                 285

AGG GTT GTC CTA CAC GAT GGT GAT CCC AAT GAG CCT GTT TCA GAT TAC        912
Arg Val Val Leu His Asp Gly Asp Pro Asn Glu Pro Val Ser Asp Tyr
        290                 295                 300

ATC AAT GCA AAT ATC ATC ATG CCT GAA TTT GAA ACC AAG TGC AAC AAT        960
Ile Asn Ala Asn Ile Ile Met Pro Glu Phe Glu Thr Lys Cys Asn Asn
305                 310                 315                 320

TCA AAG CCC AAA AAG AGT TAC ATT GCC ACA CAA GGC TGC CTG CAA AAC       1008
Ser Lys Pro Lys Lys Ser Tyr Ile Ala Thr Gln Gly Cys Leu Gln Asn
                325                 330                 335

ACG GTG AAT GAC TTT TGG CGG ATG GTG TTC CAA GAA AAC TCC CGA GTG       1056
Thr Val Asn Asp Phe Trp Arg Met Val Phe Gln Glu Asn Ser Arg Val
            340                 345                 350

ATT GTC ATG ACA ACG AAA GAA GTG GAG AGA GGA AAG AGT AAA TGT GTC       1104
Ile Val Met Thr Thr Lys Glu Val Glu Arg Gly Lys Ser Lys Cys Val
            355                 360                 365

AAA TAC TGG CCT GAT GAG TAT GCT CTA AAA GAA TAT GGC GTC ATG CGT       1152
Lys Tyr Trp Pro Asp Glu Tyr Ala Leu Lys Glu Tyr Gly Val Met Arg
        370                 375                 380

GTT AGG AAC GTC AAA GAA AGC GCC GCT CAT GAC TAT ACG CTA AGA GAA       1200
Val Arg Asn Val Lys Glu Ser Ala Ala His Asp Tyr Thr Leu Arg Glu
385                 390                 395                 400

CTT AAA CTT TCA AAG GTT GGA CAA GGG AAT ACG GAG AGA ACG GTC TGG       1248
Leu Lys Leu Ser Lys Val Gly Gln Gly Asn Thr Glu Arg Thr Val Trp
                405                 410                 415
```

```
CAA TAC CAC TTT CGG ACC TGG CCG GCC CAC GGC GTG CCC AGC GAC CCT    1296
Gln Tyr His Phe Arg Thr Trp Pro Ala His Gly Val Pro Ser Asp Pro
            420                 425                 430

GGG GGC GTG CTG GAC TTC CTG GAG GAG GTG CAC CAT AAG CAG GAG AGC    1344
Gly Gly Val Leu Asp Phe Leu Glu Glu Val His His Lys Gln Glu Ser
            435                 440                 445

ATC ATG GAT GCA GGG CCG GTC GTG GTG CAC TGC AGT GCT GGA ATT GGC    1392
Ile Met Asp Ala Gly Pro Val Val Val His Cys Ser Ala Gly Ile Gly
            450                 455                 460

CGG ACA GGG ACG TTC ATT GTG ATT GAT ATT CTT ATT GAC ATC ATC AGA    1440
Arg Thr Gly Thr Phe Ile Val Ile Asp Ile Leu Ile Asp Ile Ile Arg
465                 470                 475                 480

GAG AAA GGT GTT GAC TGC GAT ATT GAC GTT CCC AAA ACC ATC CAG ATG    1488
Glu Lys Gly Val Asp Cys Asp Ile Asp Val Pro Lys Thr Ile Gln Met
            485                 490                 495

GTG CGG TCT CAG AGG TCA GGG ATG GTC CAG ACA GAA GCA CAG TAC CGA    1536
Val Arg Ser Gln Arg Ser Gly Met Val Gln Thr Glu Ala Gln Tyr Arg
            500                 505                 510

TTT ATC TAT ATG GCG GTC CAG CAT TAT ATT GAA ACA CTA CAG CGC AGG    1584
Phe Ile Tyr Met Ala Val Gln His Tyr Ile Glu Thr Leu Gln Arg Arg
            515                 520                 525

ATT GAA GAA GAG CAG AAA AGC AAG AGG AAA GGG CAC GAA TAT ACA AAT    1632
Ile Glu Glu Glu Gln Lys Ser Lys Arg Lys Gly His Glu Tyr Thr Asn
530                 535                 540

ATT AAG TAT TCT CTA GCG GAC CAG ACG AGT GGA GAT CAG AGC CCT CTC    1680
Ile Lys Tyr Ser Leu Ala Asp Gln Thr Ser Gly Asp Gln Ser Pro Leu
545                 550                 555                 560

CCG CCT TGT ACT CCA ACG CCA CCC TGT GCA GAA ATG AGA GAA GAC AGT    1728
Pro Pro Cys Thr Pro Thr Pro Pro Cys Ala Glu Met Arg Glu Asp Ser
            565                 570                 575

GCT AGA GTC TAT GAA AAC GTG GGC CTG ATG CAA CAG CAG AAA AGT TTC    1776
Ala Arg Val Tyr Glu Asn Val Gly Leu Met Gln Gln Gln Lys Ser Phe
            580                 585                 590

AGA TGA                                                             1782
Arg
```

(2) INFORMATION FOR SEQ ID NO:30:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:30:

```
Met Thr Ser Arg Arg Trp Phe His Pro Asn Ile Thr Gly Val Glu Ala
 1               5                  10                  15

Glu Asn Leu Leu Leu Thr Arg Gly Val Asp Gly Ser Phe Leu Ala Lys
                20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Ala Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
```

```
                100                 105                 110
    Phe His Gly His Leu Ser Gly Lys Glu Ala Glu Lys Leu Leu Thr Glu
                115                 120                 125

Lys Gly Lys His Gly Ser Phe Leu Val Lys Glu Ser Gln Ser His Pro
                130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Glu Arg Phe Asp Ser Leu Thr Asp
                180                 185                 190

Leu Val Glu His Tyr Lys Lys Asn Pro Met Val Glu Thr Leu Gly Thr
                195                 200                 205

Val Leu Gln Leu Lys Gln Pro Leu Asn Thr Thr Arg Ile Asn Ala Ala
                210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
                260                 265                 270

Asn Lys Asn Lys Asn Arg Tyr Lys Asn Ile Leu Pro Phe Asp His Thr
                275                 280                 285

Arg Val Val Leu His Asp Gly Asp Pro Asn Glu Pro Val Ser Asp Tyr
                290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
                340                 345                 350

Ile Val Met Thr Thr Lys Glu Val Glu Arg Gly Lys Ser Lys Cys Val
                355                 360                 365

Lys Tyr Trp Pro Asp Glu Tyr Ala Leu Lys Glu Tyr Gly Val Met Arg
                370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Ala His Gly Val Pro Ser Asp Pro
                420                 425                 430

Gly Gly Val Leu Asp Phe Leu Glu Glu Val His His Lys Gln Glu Ser
                435                 440                 445

Ile Met Asp Ala Gly Pro Val Val His Cys Ser Ala Gly Ile Gly
                450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
                500                 505                 510

Phe Ile Tyr Met Ala Val Gln His Tyr Ile Glu Thr Leu Gln Arg Arg
                515                 520                 525
```

-continued

```
Ile Glu Glu Glu Gln Lys Ser Lys Arg Lys Gly His Glu Tyr Thr Asn
    530                 535                 540
Ile Lys Tyr Ser Leu Ala Asp Gln Thr Ser Gly Asp Gln Ser Pro Leu
545                 550                 555                 560
Pro Pro Cys Thr Pro Thr Pro Pro Cys Ala Glu Met Arg Glu Asp Ser
                565                 570                 575
Ala Arg Val Tyr Glu Asn Val Gly Leu Met Gln Gln Gln Lys Ser Phe
            580                 585                 590
Arg
```

(2) INFORMATION FOR SEQ ID NO:31:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:31:

```
ATG GTG AGG TGG TTT CAC CGA GAC CTC AGT GGG CTG GAT GCA GAG ACC        48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT CGG CCC AGT        96
Leu Leu Lys Gly Arg Gly Val His Gly Ser Phe Leu Ala Arg Pro Ser
            20                  25                  30

CGC AAG AAC CAG GGT GAC TTC TCG CTC TCC GTC AGG GTG GGG GAT CAG       144
Arg Lys Asn Gln Gly Asp Phe Ser Leu Ser Val Arg Val Gly Asp Gln
        35                  40                  45

GTG ACC CAT ATT CGG ATC CAG AAC TCA GGG GCT TTC TAT GAC CTG TAT       192
Val Thr His Ile Arg Ile Gln Asn Ser Gly Ala Phe Tyr Asp Leu Tyr
    50                  55                  60

GGA GGG GAG AAG TTT GCG ACT CTG ACA GAG CTG GTG GAG TAC TAC ACT       240
Gly Gly Glu Lys Phe Ala Thr Leu Thr Glu Leu Val Glu Tyr Tyr Thr
65                  70                  75                  80

CAG CAG CAG GGT GTG GTG CAG GAC CGC GAC GGC ACC ATC ATC CAC CTC       288
Gln Gln Gln Gly Val Val Gln Asp Arg Asp Gly Thr Ile Ile His Leu
                85                  90                  95

AAG TAC CCG CTG AAC TGC TCC GAT CCC ACT AGT GAG AGG TGG TAC CAT       336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC       384
Gly His Met Ser Gly Gly Gln Ala Glu Thr Leu Leu Gln Ala Lys Gly
        115                 120                 125

GAG CCC TGG ACG TTT CTT GTG CGT GAG AGC CTC AGC CAG CCT GGA GAC       432
Glu Pro Trp Thr Phe Leu Val Arg Glu Ser Leu Ser Gln Pro Gly Asp
    130                 135                 140

TTC GTG CTT TCT GTG CTC AGT GAC CAG CCC AAG GCT GGC CCA GGC TCC       480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC       528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG       576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC       624
```

-continued

```
            His Phe Lys Lys Thr Gly Ile Glu Glu Ala Ser Gly Ala Phe Val Tyr
                195                 200                 205

CTG CGG CAG CCG TAC TAT GCC ACG AGG GTG AAT GCG GCT GAC ATT GAG            672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC            720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG            768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC            816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC            864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC            912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC            960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG           1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA           1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG           1104
Glu Val Glu Lys Gly Arg Asn Lys Cys Val Pro Tyr Trp Pro Glu Val
        355                 360                 365

GGC ATG CAG CGT GCT TAT GGG CCC TAC TCT GTG ACC AAC TGC GGG GAG           1152
Gly Met Gln Arg Ala Tyr Gly Pro Tyr Ser Val Thr Asn Cys Gly Glu
    370                 375                 380

CAT GAC ACA ACC GAA TAC AAA CTC CGT ACC TTA CAG GTC TCC CCG CTG           1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC           1248
Asp Asn Gly Asp Leu Ile Arg Glu Ile Trp His Tyr Gln Tyr Leu Ser
                405                 410                 415

TGG CCC GCC CAT GGG GTC CCC AGT GAG CCT GGG GGT GTC CTC AGC TTC           1296
Trp Pro Ala His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC           1344
Leu Asp Gln Ile Asn Gln Arg Gln Glu Ser Leu Pro His Ala Gly Pro
        435                 440                 445

ATC ATC GTG CAC TGC AGC GCC GGC ATC GGC CGC ACA GGC ACC ATC ATT           1392
Ile Ile Val His Cys Ser Ala Gly Ile Gly Arg Thr Gly Thr Ile Ile
    450                 455                 460

GTC ATC GAC ATG CTC ATG GAG AAC ATC TCC ACC AAG GGC CTG GAC TGT           1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG           1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC           1536
Gly Met Val Gln Thr Glu Ala Gln Tyr Lys Phe Ile Tyr Val Ala Ile
            500                 505                 510
```

```
GCC CAG TTC ATT GAA ACC ACT AAG AAG AAG CTG GAG GTC CTG CAG TCG    1584
Ala Gln Phe Ile Glu Thr Thr Lys Lys Lys Leu Glu Val Leu Gln Ser
            515                 520                 525

CAG AAG GGC CAG GAG TCG GAG TAC GGG AAC ATC ACC TAT CCC CCA GCC    1632
Gln Lys Gly Gln Glu Ser Glu Tyr Gly Asn Ile Thr Tyr Pro Pro Ala
        530                 535                 540

ATG AAG AAT GCC CAT GCC AAG GCC TCC CGC ACC TCG TCC AAA CAC AAG    1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA    1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC    1776
Val Lys Lys Gln Arg Ser Ala Asp Lys Glu Lys Ser Lys Gly Ser Leu
            580                 585                 590

AAG AGG AAG TGA                                                    1788
Lys Arg Lys
        595
```

(2) INFORMATION FOR SEQ ID NO:32:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:32:

```
Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Arg Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Ala Phe Tyr Asp Leu Tyr
        50                  55                  60

Gly Gly Glu Lys Phe Ala Thr Leu Thr Glu Leu Val Glu Tyr Tyr Thr
 65                 70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
                100                 105                 110

Gly His Met Ser Gly Gly Gln Ala Glu Thr Leu Leu Gln Ala Lys Gly
            115                 120                 125

Glu Pro Trp Thr Phe Leu Val Arg Glu Ser Leu Ser Gln Pro Gly Asp
        130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
        210                 215                 220

Asn Arg Val Leu Glu Leu Asn Lys Lys Gln Glu Ser Glu Asp Thr Ala
```

```
              225                 230                 235                 240
         Lys Ala Gly Phe Trp Glu Glu Phe Glu Ser Leu Gln Lys Gln Glu Val
                         245                 250                 255

Lys Asn Leu His Gln Arg Leu Glu Gly Gln Arg Pro Glu Asn Lys Gly
                         260                 265                 270

Lys Asn Arg Tyr Lys Asn Ile Leu Pro Phe Asp His Ser Arg Val Ile
                         275                 280                 285

Leu Gln Gly Arg Asp Ser Asn Ile Pro Gly Ser Asp Tyr Ile Asn Ala
                         290                 295                 300

Asn Tyr Ile Lys Asn Gln Leu Leu Gly Pro Asp Glu Asn Ala Lys Thr
         305                 310                 315                 320

Tyr Ile Ala Ser Gln Gly Cys Leu Glu Ala Thr Val Asn Asp Phe Trp
                         325                 330                 335

Gln Met Ala Trp Gln Glu Asn Ser Arg Val Ile Val Met Thr Thr Arg
                         340                 345                 350

Glu Val Glu Lys Gly Arg Asn Lys Cys Val Pro Tyr Trp Pro Glu Val
                         355                 360                 365

Gly Met Gln Arg Ala Tyr Gly Pro Tyr Ser Val Thr Asn Cys Gly Glu
                         370                 375                 380

His Asp Thr Thr Glu Tyr Lys Leu Arg Thr Leu Gln Val Ser Pro Leu
         385                 390                 395                 400

Asp Asn Gly Asp Leu Ile Arg Glu Ile Trp His Tyr Gln Tyr Leu Ser
                         405                 410                 415

Trp Pro Ala His Gly Val Pro Ser Glu Pro Gly Gly Val Leu Ser Phe
                         420                 425                 430

Leu Asp Gln Ile Asn Gln Arg Gln Glu Ser Leu Pro His Ala Gly Pro
                         435                 440                 445

Ile Ile Val His Cys Ser Ala Gly Ile Gly Arg Thr Gly Thr Ile Ile
         450                 455                 460

Val Ile Asp Met Leu Met Glu Asn Ile Ser Thr Lys Gly Leu Asp Cys
         465                 470                 475                 480

Asp Ile Asp Ile Gln Lys Thr Ile Gln Met Val Arg Ala Gln Arg Ser
                         485                 490                 495

Gly Met Val Gln Thr Glu Ala Gln Tyr Lys Phe Ile Tyr Val Ala Ile
                         500                 505                 510

Ala Gln Phe Ile Glu Thr Thr Lys Lys Lys Leu Glu Val Leu Gln Ser
                         515                 520                 525

Gln Lys Gly Gln Glu Ser Glu Tyr Gly Asn Ile Thr Tyr Pro Pro Ala
                         530                 535                 540

Met Lys Asn Ala His Ala Lys Ala Ser Arg Thr Ser Ser Lys His Lys
         545                 550                 555                 560

Glu Asp Val Tyr Glu Asn Leu His Thr Lys Asn Lys Arg Glu Glu Lys
                         565                 570                 575

Val Lys Lys Gln Arg Ser Ala Asp Lys Glu Lys Ser Lys Gly Ser Leu
                         580                 585                 590

Lys Arg Lys
                595

(2) INFORMATION FOR SEQ ID NO:33:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear
```

(ix) FEATURE:
    (A) NAME/KEY: CDS
    (B) LOCATION: 1..1785

(xi) SEQUENCE DESCRIPTION: SEQ ID NO:33:

```
ATG GTG AGG TGG TTT CAC CGA GAC CTC AGT GGG CTG GAT GCA GAG ACC       48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT CGG CCC AGT       96
Leu Leu Lys Gly Arg Gly Val His Gly Ser Phe Leu Ala Arg Pro Ser
            20                  25                  30

CGC AAG AAC CAG GGT GAC TTC TCG CTC TCC GTC AGG GTG GGG GAT CAG      144
Arg Lys Asn Gln Gly Asp Phe Ser Leu Ser Val Arg Val Gly Asp Gln
        35                  40                  45

GTG ACC CAT ATT CGG ATC CAG AAC TCA GGG GCT TTC TAT GAC CTG TAT      192
Val Thr His Ile Arg Ile Gln Asn Ser Gly Ala Phe Tyr Asp Leu Tyr
    50                  55                  60

GGA GGG GAG AAG TTT GCG ACT CTG ACA GAG CTG GTG GAG TAC TAC ACT      240
Gly Gly Glu Lys Phe Ala Thr Leu Thr Glu Leu Val Glu Tyr Tyr Thr
 65                 70                  75                  80

CAG CAG CAG GGT GTG GTG CAG GAC CGC GAC GGC ACC ATC ATC CAC CTC      288
Gln Gln Gln Gly Val Val Gln Asp Arg Asp Gly Thr Ile Ile His Leu
                85                  90                  95

AAG TAC CCG CTG AAC TGC TCC GAT CCC ACT AGT GAG AGG TGG TAC CAT      336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC      384
Gly His Met Ser Gly Gly Gln Ala Glu Thr Leu Leu Gln Ala Lys Gly
        115                 120                 125

GAG CCC TGG ACG TTT CTT GTG CGT GAG AGC CTC AGC CAG CCT GGA GAC      432
Glu Pro Trp Thr Phe Leu Val Arg Glu Ser Leu Ser Gln Pro Gly Asp
    130                 135                 140

TTC GTG CTT TCT GTG CTC AGT GAC CAG CCC AAG GCT GGC CCA GGC TCC      480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC      528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG      576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC      624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG      672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC      720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG      768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC      816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC      864
Lys Asn Arg Tyr Lys Asn Ile Leu Pro Phe Asp His Ser Arg Val Ile
        275                 280                 285
```

```
CTG CAG GGA CGG GAC AGT AAC ATC CCC GGG TCC GAC TAC ATC AAT GCC    912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC    960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG   1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA   1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG   1104
Glu Val Glu Lys Gly Arg Asn Lys Cys Val Pro Tyr Trp Pro Glu Val
        355                 360                 365

GGC ATG CAG CGT GCT TAT GGG CCC TAC TCT GTG ACC AAC TGC GGG GAG   1152
Gly Met Gln Arg Ala Tyr Gly Pro Tyr Ser Val Thr Asn Cys Gly Glu
    370                 375                 380

CAT GAC ACA ACC GAA TAC AAA CTC CGT ACC TTA CAG GTC TCC CCG CTG   1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC   1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC   1296
Trp Pro Asp His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC   1344
Leu Asp Gln Ile Asn Gln Arg Gln Glu Ser Leu Pro His Ala Gly Pro
        435                 440                 445

ATC ATC GTG CAC TCC AGC GCC GGC ATC GGC CGC ACA GGC ACC ATC ATT   1392
Ile Ile Val His Ser Ser Ala Gly Ile Gly Arg Thr Gly Thr Ile Ile
    450                 455                 460

GTC ATC GAC ATG CTC ATG GAG AAC ATC TCC ACC AAG GGC CTG GAC TGT   1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG   1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC   1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG   1584
Ala Gln Phe Ile Glu Thr Thr Lys Lys Lys Leu Glu Val Leu Gln Ser
        515                 520                 525

CAG AAG GGC CAG GAG TCG GAG TAC GGG AAC ATC ACC TAT CCC CCA GCC   1632
Gln Lys Gly Gln Glu Ser Glu Tyr Gly Asn Ile Thr Tyr Pro Pro Ala
    530                 535                 540

ATG AAG AAT GCC CAT GCC AAG GCC TCC CGC ACC TCG TCC AAA CAC AAG   1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA   1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC   1776
Val Lys Lys Gln Arg Ser Ala Asp Lys Glu Lys Ser Lys Gly Ser Leu
            580                 585                 590

AAG AGG AAG TGA                                                   1788
Lys Arg Lys
        595
```

(2) INFORMATION FOR SEQ ID NO:34:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:34:

```
Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Arg Pro Ser
             20                  25                  30

Arg Lys Asn Gln Gly Asp Phe Ser Leu Ser Val Arg Val Gly Asp Gln
         35                  40                  45

Val Thr His Ile Arg Ile Gln Asn Ser Gly Ala Phe Tyr Asp Leu Tyr
     50                  55                  60

Gly Gly Glu Lys Phe Ala Thr Leu Thr Glu Leu Val Glu Tyr Tyr Thr
 65                  70                  75                  80

Gln Gln Gln Gly Val Val Gln Asp Arg Asp Gly Thr Ile Ile His Leu
                 85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
            340                 345                 350
```

```
Glu Val Glu Lys Gly Arg Asn Lys Cys Val Pro Tyr Trp Pro Glu Val
            355                 360                 365

Gly Met Gln Arg Ala Tyr Gly Pro Tyr Ser Val Thr Asn Cys Gly Glu
    370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
                420                 425                 430

Leu Asp Gln Ile Asn Gln Arg Gln Glu Ser Leu Pro His Ala Gly Pro
            435                 440                 445

Ile Ile Val His Ser Ser Ala Gly Ile Gly Arg Thr Gly Thr Ile Ile
        450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
    595

(2) INFORMATION FOR SEQ ID NO:35:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:35:

ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
1               5                   10                  15

CTG CTC AAG GGC CGA GGT GTC CAC GGT AGC TTC CTG GCT CGG CCC AGT      96
Leu Leu Lys Gly Arg Gly Val His Gly Ser Phe Leu Ala Arg Pro Ser
                20                  25                  30

CGC AAG AAC CAG GGT GAC TTC TCG CTC TCC GTC AGG GTG GGG GAT CAG     144
Arg Lys Asn Gln Gly Asp Phe Ser Leu Ser Val Arg Val Gly Asp Gln
            35                  40                  45

GTG ACC CAT ATT CGG ATC CAG AAC TCA GGG GAT TTC TAT GAC CTG TAT     192
Val Thr His Ile Arg Ile Gln Asn Ser Gly Asp Phe Tyr Asp Leu Tyr
        50                  55                  60
```

-continued

```
GGA GGG GAG AAG TTT GCG ACT CTG ACA GCG CTG GTG GAG TAC TAC ACT       240
Gly Gly Glu Lys Phe Ala Thr Leu Thr Ala Leu Val Glu Tyr Tyr Thr
 65              70                  75                  80

CAG CAG CAG GGT GTG GTG CAG GAC CGC GAC GGC ACC ATC ATC CAC CTC       288
Gln Gln Gln Gly Val Val Gln Asp Arg Asp Gly Thr Ile Ile His Leu
                 85                  90                  95

AAG TAC CCG CTG AAC TGC TCC GAT CCC ACT AGT GAG AGG TGG TAC CAT       336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC       384
Gly His Met Ser Gly Gly Gln Ala Glu Thr Leu Leu Gln Ala Lys Gly
                115                 120                 125

GAG CCC TGG ACG TTT CTT GTG CGT GAG AGC CTC AGC CAG CCT GGA GAC       432
Glu Pro Trp Thr Phe Leu Val Arg Glu Ser Leu Ser Gln Pro Gly Asp
130                 135                 140

TTC GTG CTT TCT GTG CTC AGT GAC CAG CCC AAG GCT GGC CCA GGC TCC       480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC       528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG       576
Thr Val Gly Gly Leu Glu Thr Phe Asp Ser Leu Thr Asp Leu Val Glu
                180                 185                 190

CAT TTC AAG AAG ACG GGG ATT GAG GAG GCC TCA GGC GCC TTT GTC TAC       624
His Phe Lys Lys Thr Gly Ile Glu Glu Ala Ser Gly Ala Phe Val Tyr
            195                 200                 205

CTG CGG CAG CCG TAC TAT GCC ACG AGG GTG AAT GCG GCT GAC ATT GAG       672
Leu Arg Gln Pro Tyr Tyr Ala Thr Arg Val Asn Ala Ala Asp Ile Glu
210                 215                 220

AAC CGA GTG TTG GAA CTG AAC AAG AAG CAG GAG TCC GAG GAT ACA GCC       720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG       768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC       816
Lys Asn Leu His Gln Arg Leu Glu Gly Gln Arg Pro Glu Asn Lys Gly
                260                 265                 270

AAG AAC CGC TAC AAG AAC ATT CTC CCC TTT GAC CAC AGC CGA GTG ATC       864
Lys Asn Arg Tyr Lys Asn Ile Leu Pro Phe Asp His Ser Arg Val Ile
            275                 280                 285

CTG CAG GGA CGG GAC AGT AAC ATC CCC GGG TCC GAC TAC ATC AAT GCC       912
Leu Gln Gly Arg Asp Ser Asn Ile Pro Gly Ser Asp Tyr Ile Asn Ala
            290                 295                 300

AAC TAC ATC AAG AAC CAG CTG CTA GGC CCT GAT GAG AAC GCT AAG ACC       960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG      1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA      1056
Gln Met Ala Trp Gln Glu Asn Ser Arg Val Ile Val Met Thr Thr Arg
                340                 345                 350

GAG GTG GAG AAA GGC CGG AAC AAA TGC GTC CCA TAC TGG CCC GAG GTG      1104
Glu Val Glu Lys Gly Arg Asn Lys Cys Val Pro Tyr Trp Pro Glu Val
            355                 360                 365

GGC ATG CAG CGT GCT TAT GGG CCC TAC TCT GTG ACC AAC TGC GGG GAG      1152
Gly Met Gln Arg Ala Tyr Gly Pro Tyr Ser Val Thr Asn Cys Gly Glu
            370                 375                 380
```

```
CAT GAC ACA ACC GAA TAC AAA CTC CGT ACC TTA CAG GTC TCC CCG CTG        1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC        1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC        1296
Trp Pro Asp His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC        1344
Leu Asp Gln Ile Asn Gln Arg Gln Glu Ser Leu Pro His Ala Gly Pro
        435                 440                 445

ATC ATC GTG CAC TCC AGC GCC GGC ATC GGC CGC ACA GGC ACC ATC ATT        1392
Ile Ile Val His Ser Ser Ala Gly Ile Gly Arg Thr Gly Thr Ile Ile
    450                 455                 460

GTC ATC GAC ATG CTC ATG GAG AAC ATC TCC ACC AAG GGC CTG GAC TGT        1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG        1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC        1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG        1584
Ala Gln Phe Ile Glu Thr Thr Lys Lys Lys Leu Glu Val Leu Gln Ser
        515                 520                 525

CAG AAG GGC CAG GAG TCG GAG TAC GGG AAC ATC ACC TAT CCC CCA GCC        1632
Gln Lys Gly Gln Glu Ser Glu Tyr Gly Asn Ile Thr Tyr Pro Pro Ala
    530                 535                 540

ATG AAG AAT GCC CAT GCC AAG GCC TCC CGC ACC TCG TCC AAA CAC AAG        1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA        1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC        1776
Val Lys Lys Gln Arg Ser Ala Asp Lys Glu Lys Ser Lys Gly Ser Leu
            580                 585                 590

AAG AGG AAG TGA                                                        1788
Lys Arg Lys
        595

(2) INFORMATION FOR SEQ ID NO:36:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:36:

Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Arg Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Asp Phe Tyr Asp Leu Tyr
```

```
             50                  55                  60
Gly Gly Glu Lys Phe Ala Thr Leu Thr Ala Leu Val Glu Tyr Tyr Thr
 65                  70                  75                  80

Gln Gln Gln Gly Val Val Gln Asp Arg Asp Gly Thr Ile Ile His Leu
                 85                  90                  95

Lys Tyr Pro Leu Asn Cys Ser Asp Pro Thr Ser Glu Arg Trp Tyr His
                100                 105                 110

Gly His Met Ser Gly Gly Gln Ala Glu Thr Leu Leu Gln Ala Lys Gly
                115                 120                 125

Glu Pro Trp Thr Phe Leu Val Arg Glu Ser Leu Ser Gln Pro Gly Asp
        130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                    165                 170                 175

Thr Val Gly Gly Leu Glu Thr Phe Asp Ser Leu Thr Asp Leu Val Glu
                180                 185                 190

His Phe Lys Lys Thr Gly Ile Glu Glu Ala Ser Gly Ala Phe Val Tyr
                195                 200                 205

Leu Arg Gln Pro Tyr Tyr Ala Thr Arg Val Asn Ala Ala Asp Ile Glu
        210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                    245                 250                 255

Lys Asn Leu His Gln Arg Leu Glu Gly Gln Arg Pro Glu Asn Lys Gly
                260                 265                 270

Lys Asn Arg Tyr Lys Asn Ile Leu Pro Phe Asp His Ser Arg Val Ile
                275                 280                 285

Leu Gln Gly Arg Asp Ser Asn Ile Pro Gly Ser Asp Tyr Ile Asn Ala
        290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                    325                 330                 335

Gln Met Ala Trp Gln Glu Asn Ser Arg Val Ile Val Met Thr Thr Arg
                340                 345                 350

Glu Val Glu Lys Gly Arg Asn Lys Cys Val Pro Tyr Trp Pro Glu Val
                355                 360                 365

Gly Met Gln Arg Ala Tyr Gly Pro Tyr Ser Val Thr Asn Cys Gly Glu
        370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                    405                 410                 415

Trp Pro Asp His Gly Val Pro Ser Glu Pro Gly Gly Val Leu Ser Phe
                420                 425                 430

Leu Asp Gln Ile Asn Gln Arg Gln Glu Ser Leu Pro His Ala Gly Pro
        435                 440                 445

Ile Ile Val His Ser Ser Ala Gly Ile Gly Arg Thr Gly Thr Ile Ile
            450                 455                 460

Val Ile Asp Met Leu Met Glu Asn Ile Ser Thr Lys Gly Leu Asp Cys
465                 470                 475                 480
```

-continued

```
Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
        500                 505                 510

Ala Gln Phe Ile Glu Thr Thr Lys Lys Lys Leu Glu Val Leu Gln Ser
        515                 520                 525

Gln Lys Gly Gln Glu Ser Glu Tyr Gly Asn Ile Thr Tyr Pro Pro Ala
        530                 535                 540

Met Lys Asn Ala His Ala Lys Ala Ser Arg Thr Ser Lys His Lys
545                 550                 555                 560

Glu Asp Val Tyr Glu Asn Leu His Thr Lys Asn Lys Arg Glu Glu Lys
            565                 570                 575

Val Lys Lys Gln Arg Ser Ala Asp Lys Glu Lys Ser Lys Gly Ser Leu
        580                 585                 590

Lys Arg Lys
        595
```

(2) INFORMATION FOR SEQ ID NO:37:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:37:

```
ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT CGG CCC AGT      96
Leu Leu Lys Gly Arg Gly Val His Gly Ser Phe Leu Ala Arg Pro Ser
            20                  25                  30

CGC AAG AAC CAG GGT GAC TTC TCG CTC TCC GTC AGG GTG GGG GAT CAG     144
Arg Lys Asn Gln Gly Asp Phe Ser Leu Ser Val Arg Val Gly Asp Gln
        35                  40                  45

GTG ACC CAT ATT CGG ATC CAG AAC TCA GGG GAT TTC TAT GAC CTG TAT     192
Val Thr His Ile Arg Ile Gln Asn Ser Gly Asp Phe Tyr Asp Leu Tyr
 50                  55                  60

GGA GGG GAG AAG TTT GCG ACT CTG ACA GCG CTG GTG GAG TAC TAC ACT     240
Gly Gly Glu Lys Phe Ala Thr Leu Thr Ala Leu Val Glu Tyr Tyr Thr
 65                  70                  75                  80

CAG CAG CAG GGT GTG GTG CAG GAC CGC GAC GGC ACC ATC ATC CAC CTC     288
Gln Gln Gln Gly Val Val Gln Asp Arg Asp Gly Thr Ile Ile His Leu
            85                  90                  95

AAG TAC CCG CTG AAC TGC TCC GAT CCC ACT AGT GAG AGG TGG TAC CAT     336
Lys Tyr Pro Leu Asn Cys Ser Asp Pro Thr Ser Glu Arg Trp Tyr His
        100                 105                 110

GGC CAC ATG TCT GGC GGG CAG GCA GAG ACG CTG CTG CAG GCC AAG GGC     384
Gly His Met Ser Gly Gly Gln Ala Glu Thr Leu Leu Gln Ala Lys Gly
        115                 120                 125

GAG CCC TGG ACG TTT CTT GTG CGT GAG AGC CTC AGC CAG CCT GGA GAC     432
Glu Pro Trp Thr Phe Leu Val Arg Glu Ser Leu Ser Gln Pro Gly Asp
        130                 135                 140

TTC GTG CTT TCT GTG CTC AGT GAC CAG CCC AAG GCT GGC CCA GGC TCC     480
Phe Val Leu Ser Val Leu Ser Asp Gln Pro Lys Ala Gly Pro Gly Ser
145                 150                 155                 160
```

```
CCG CTC AGG GTC ACC CAC ATC AAG GTC ATG TGC GAG GGT GGA CGC TAC      528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG      576
Thr Val Gly Gly Leu Glu Thr Phe Asp Ser Leu Thr Asp Leu Val Glu
                180                 185                 190

CAT TTC AAG AAG ACG GGG ATT GAG GAG GCC TCA GGC GCC TTT GTC TAC      624
His Phe Lys Lys Thr Gly Ile Glu Glu Ala Ser Gly Ala Phe Val Tyr
                195                 200                 205

CTG CGG CAG CCG TAC TAT GCC ACG AGG GTG AAT GCG GCT GAC ATT GAG      672
Leu Arg Gln Pro Tyr Tyr Ala Thr Arg Val Asn Ala Ala Asp Ile Glu
        210                 215                 220

AAC CGA GTG TTG GAA CTG AAC AAG AAG CAG GAG TCC GAG GAT ACA GCC      720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG      768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC      816
Lys Asn Leu His Gln Arg Leu Glu Gly Gln Arg Pro Glu Asn Lys Gly
                260                 265                 270

AAG AAC CGC TAC AAG AAC ATT CTC CCC TTT GAC CAC AGC CGA GTG ATC      864
Lys Asn Arg Tyr Lys Asn Ile Leu Pro Phe Asp His Ser Arg Val Ile
                275                 280                 285

CTG CAG GGA CGG GAC AGT AAC ATC CCC GGG TCC GAC TAC ATC AAT GCC      912
Leu Gln Gly Arg Asp Ser Asn Ile Pro Gly Ser Asp Tyr Ile Asn Ala
        290                 295                 300

AAC TAC ATC AAG AAC CAG CTG CTA GGC CCT GAT GAG AAC GCT AAG ACC      960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG     1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA     1056
Gln Met Ala Trp Gln Glu Asn Ser Arg Val Ile Val Met Thr Thr Arg
                340                 345                 350

GAG GTG GAG AAA GGC CGG AAC AAA TGC GTC CCA TAC TGG CCC GAG GTG     1104
Glu Val Glu Lys Gly Arg Asn Lys Cys Val Pro Tyr Trp Pro Glu Val
                355                 360                 365

GGC ATG CAG CGT GCT TAT GGG CCC TAC TCT GTG ACC AAC TGC GGG GAG     1152
Gly Met Gln Arg Ala Tyr Gly Pro Tyr Ser Val Thr Asn Cys Gly Glu
        370                 375                 380

CAT GAC ACA ACC GAA TAC AAA CTC CGT ACC TTA CAG GTC TCC CCG CTG     1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC     1248
Asp Asn Gly Asp Leu Ile Arg Glu Ile Trp His Tyr Gln Tyr Leu Ser
                405                 410                 415

TGG CCC GCC CAT GGG GTC CCC AGT GAG CCT GGG GGT GTC CTC AGC TTC     1296
Trp Pro Ala His Gly Val Pro Ser Glu Pro Gly Gly Val Leu Ser Phe
                420                 425                 430

CTG GAC CAG ATC AAC CAG CGG CAG GAA AGT CTG CCT CAC GCA GGG CCC     1344
Leu Asp Gln Ile Asn Gln Arg Gln Glu Ser Leu Pro His Ala Gly Pro
        435                 440                 445

ATC ATC GTG CAC TGC AGC GCC GGC ATC GGC CGC ACA GGC ACC ATC ATT     1392
Ile Ile Val His Cys Ser Ala Gly Ile Gly Arg Thr Gly Thr Ile Ile
450                 455                 460

GTC ATC GAC ATG CTC ATG GAG AAC ATC TCC ACC AAG GGC CTG GAC TGT     1440
Val Ile Asp Met Leu Met Glu Asn Ile Ser Thr Lys Gly Leu Asp Cys
```

```
                465                 470                 475                 480
GAC ATT GAC ATC CAG AAG ACC ATC CAG ATG GTG CGG GCG CAG CGC TCG                  1488
Asp Ile Asp Ile Gln Lys Thr Ile Gln Met Val Arg Ala Gln Arg Ser
                        485                 490                 495

GGC ATG GTG CAG ACG GAG GCG CAG TAC AAG TTC ATC TAC GTG GCC ATC                  1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG                  1584
Ala Gln Phe Ile Glu Thr Thr Lys Lys Lys Leu Glu Val Leu Gln Ser
            515                 520                 525

CAG AAG GGC CAG GAG TCG GAG TAC GGG AAC ATC ACC TAT CCC CCA GCC                  1632
Gln Lys Gly Gln Glu Ser Glu Tyr Gly Asn Ile Thr Tyr Pro Pro Ala
        530                 535                 540

ATG AAG AAT GCC CAT GCC AAG GCC TCC CGC ACC TCG TCC AAA CAC AAG                  1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA                  1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC                  1776
Val Lys Lys Gln Arg Ser Ala Asp Lys Glu Lys Ser Lys Gly Ser Leu
            580                 585                 590

AAG AGG AAG TGA                                                                  1788
Lys Arg Lys
        595
```

(2) INFORMATION FOR SEQ ID NO:38:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:38:

```
Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Ala Leu Val Glu Tyr Tyr Thr
65                  70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175
```

-continued

```
Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
            195                 200                 205

Leu Arg Gln Pro Tyr Tyr Ala Thr Arg Val Asn Ala Ala Asp Ile Glu
            210                 215                 220

Asn Arg Val Leu Glu Leu Asn Lys Lys Gln Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
                260                 265                 270

Lys Asn Arg Tyr Lys Asn Ile Leu Pro Phe Asp His Ser Arg Val Ile
                275                 280                 285

Leu Gln Gly Arg Asp Ser Asn Ile Pro Gly Ser Asp Tyr Ile Asn Ala
                290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
                340                 345                 350

Glu Val Glu Lys Gly Arg Asn Lys Cys Val Pro Tyr Trp Pro Glu Val
                355                 360                 365

Gly Met Gln Arg Ala Tyr Gly Pro Tyr Ser Val Thr Asn Cys Gly Glu
                370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Ala His Gly Val Pro Ser Glu Pro Gly Gly Val Leu Ser Phe
                420                 425                 430

Leu Asp Gln Ile Asn Gln Arg Gln Glu Ser Leu Pro His Ala Gly Pro
                435                 440                 445

Ile Ile Val His Cys Ser Ala Gly Ile Gly Arg Thr Gly Thr Ile Ile
                450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
                500                 505                 510

Ala Gln Phe Ile Glu Thr Thr Lys Lys Lys Leu Glu Val Leu Gln Ser
                515                 520                 525

Gln Lys Gly Gln Glu Ser Glu Tyr Gly Asn Ile Thr Tyr Pro Pro Ala
                530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
                580                 585                 590

Lys Arg Lys
```

(2) INFORMATION FOR SEQ ID NO:39:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:39:

```
ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT AAG CCC AGT      96
Leu Leu Lys Gly Arg Gly Val His Gly Ser Phe Leu Ala Lys Pro Ser
             20                  25                  30

CGC AAG AAC CAG GGT GAC TTC TCG CTC TCC GTC AGG GTG GGG GAT CAG     144
Arg Lys Asn Gln Gly Asp Phe Ser Leu Ser Val Arg Val Gly Asp Gln
         35                  40                  45

GTG ACC CAT ATT CGG ATC CAG AAC TCA GGG GCT TTC TAT GAC CTG TAT     192
Val Thr His Ile Arg Ile Gln Asn Ser Gly Ala Phe Tyr Asp Leu Tyr
     50                  55                  60

GGA GGG GAG AAG TTT GCG ACT CTG ACA GAG CTG GTG GAG TAC TAC ACT     240
Gly Gly Glu Lys Phe Ala Thr Leu Thr Glu Leu Val Glu Tyr Tyr Thr
 65                  70                  75                  80

CAG CAG CAG GGT GTG GTG CAG GAC CGC GAC GGC ACC ATC ATC CAC CTC     288
Gln Gln Gln Gly Val Val Gln Asp Arg Asp Gly Thr Ile Ile His Leu
                 85                  90                  95

AAG TAC CCG CTG AAC TGC TCC GAT CCC ACT AGT GAG AGG TGG TAC CAT     336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC     384
Gly His Met Ser Gly Gly Gln Ala Glu Thr Leu Leu Gln Ala Lys Gly
        115                 120                 125

GAG CCC TGG ACG TTT CTT GTG AAG GAG AGC CTC AGC CAG CCT GGA GAC     432
Glu Pro Trp Thr Phe Leu Val Lys Glu Ser Leu Ser Gln Pro Gly Asp
    130                 135                 140

TTC GTG CTT TCT GTG CTC AGT GAC CAG CCC AAG GCT GGC CCA GGC TCC     480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC     528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG     576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC     624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG     672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC     720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG     768
Lys Ala Gly Phe Trp Glu Glu Phe Glu Ser Leu Gln Lys Gln Glu Val
```

-continued

```
                     245                 250                     255
AAG AAC TTG CAC CAG CGT CTG GAA GGG CAA CGG CCA GAG AAC AAG GGC      816
Lys Asn Leu His Gln Arg Leu Glu Gly Gln Arg Pro Glu Asn Lys Gly
                260                 265                 270

AAG AAC CGC TAC AAG AAC ATT CTC CCC TTT GAC CAC AGC CGA GTG ATC      864
Lys Asn Arg Tyr Lys Asn Ile Leu Pro Phe Asp His Ser Arg Val Ile
                275                 280                 285

CTG CAG GGA CGG GAC AGT AAC ATC CCC GGG TCC GAC TAC ATC AAT GCC      912
Leu Gln Gly Arg Asp Ser Asn Ile Pro Gly Ser Asp Tyr Ile Asn Ala
        290                 295                 300

AAC TAC ATC AAG AAC CAG CTG CTA GGC CCT GAT GAG AAC GCT AAG ACC      960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG     1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA     1056
Gln Met Ala Trp Gln Glu Asn Ser Arg Val Ile Val Met Thr Thr Arg
                340                 345                 350

GAG GTG GAG AAA GGC CGG AAC AAA TGC GTC CCA TAC TGG CCC GAG GTG     1104
Glu Val Glu Lys Gly Arg Asn Lys Cys Val Pro Tyr Trp Pro Glu Val
                355                 360                 365

GGC ATG CAG CGT GCT TAT GGG CCC TAC TCT GTG ACC AAC TGC GGG GAG     1152
Gly Met Gln Arg Ala Tyr Gly Pro Tyr Ser Val Thr Asn Cys Gly Glu
        370                 375                 380

CAT GAC ACA ACC GAA TAC AAA CTC CGT ACC TTA CAG GTC TCC CCG CTG     1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC     1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC     1296
Trp Pro Asp His Gly Val Pro Ser Glu Pro Gly Gly Val Leu Ser Phe
                420                 425                 430

CTG GAC CAG ATC AAC CAG CGG CAG GAA AGT CTG CCT CAC GCA GGG CCC     1344
Leu Asp Gln Ile Asn Gln Arg Gln Glu Ser Leu Pro His Ala Gly Pro
        435                 440                 445

ATC ATC GTG CAC TGC AGC GCC GGC ATC GGC CGC ACA GGC ACC ATC ATT     1392
Ile Ile Val His Cys Ser Ala Gly Ile Gly Arg Thr Gly Thr Ile Ile
        450                 455                 460

GTC ATC GAC ATG CTC ATG GAG AAC ATC TCC ACC AAG GGC CTG GAC TGT     1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG     1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC     1536
Gly Met Val Gln Thr Glu Ala Gln Tyr Lys Phe Ile Tyr Val Ala Ile
                500                 505                 510

GCC CAG TTC ATT GAA ACC ACT AAG AAG AAG CTG GAG GTC CTG CAG TCG     1584
Ala Gln Phe Ile Glu Thr Thr Lys Lys Lys Leu Glu Val Leu Gln Ser
        515                 520                 525

CAG AAG GGC CAG GAG TCG GAG TAC GGG AAC ATC ACC TAT CCC CCA GCC     1632
Gln Lys Gly Gln Glu Ser Glu Tyr Gly Asn Ile Thr Tyr Pro Pro Ala
        530                 535                 540

ATG AAG AAT GCC CAT GCC AAG GCC TCC CGC ACC TCG TCC AAA CAC AAG     1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA     1728
```

```
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC      1776
Val Lys Lys Gln Arg Ser Ala Asp Lys Glu Lys Ser Lys Gly Ser Leu
            580                 585                 590

AAG AGG AAG TGA                                                      1788
Lys Arg Lys
        595
```

(2) INFORMATION FOR SEQ ID NO:40:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:40:

```
Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Lys Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Ala Phe Tyr Asp Leu Tyr
        50                  55                  60

Gly Gly Glu Lys Phe Ala Thr Leu Thr Glu Leu Val Glu Tyr Tyr Thr
 65                  70                  75                  80

Gln Gln Gln Gly Val Val Gln Asp Arg Asp Gly Thr Ile Ile His Leu
                 85                  90                  95

Lys Tyr Pro Leu Asn Cys Ser Asp Pro Thr Ser Glu Arg Trp Tyr His
                100                 105                 110

Gly His Met Ser Gly Gly Gln Ala Glu Thr Leu Leu Gln Ala Lys Gly
            115                 120                 125

Glu Pro Trp Thr Phe Leu Val Lys Glu Ser Leu Ser Gln Pro Gly Asp
        130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300
```

```
Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
            325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
            355                 360                 365

Gly Met Gln Arg Ala Tyr Gly Pro Tyr Ser Val Thr Asn Cys Gly Glu
370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
            405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
            530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
            565                 570                 575

Val Lys Lys Gln Arg Ser Ala Asp Lys Glu Lys Ser Lys Gly Ser Leu
            580                 585                 590

Lys Arg Lys
    595

(2) INFORMATION FOR SEQ ID NO:41:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:41:

ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
  1               5                  10                  15

CTG CTC AAG GGC CGA GGT GTC CAC GGT AGC TTC CTG GCT AAG CCC AGT      96
Leu Leu Lys Gly Arg Gly Val His Gly Ser Phe Leu Ala Lys Pro Ser
```

```
                    20                      25                      30
CGC AAG AAC CAG GGT GAC TTC TCG CTC TCC GTC AGG GTG GGG GAT CAG       144
Arg Lys Asn Gln Gly Asp Phe Ser Leu Ser Val Arg Val Gly Asp Gln
                    35                      40                      45

GTG ACC CAT ATT CGG ATC CAG AAC TCA GGG GAT TTC TAT GAC CTG TAT       192
Val Thr His Ile Arg Ile Gln Asn Ser Gly Asp Phe Tyr Asp Leu Tyr
                    50                      55                      60

GGA GGG GAG AAG TTT GCG ACT CTG ACA GCG CTG GTG GAG TAC TAC ACT       240
Gly Gly Glu Lys Phe Ala Thr Leu Thr Ala Leu Val Glu Tyr Tyr Thr
65                      70                      75                      80

CAG CAG CAG GGT GTG GTG CAG GAC CGC GAC GGC ACC ATC ATC CAC CTC       288
Gln Gln Gln Gly Val Val Gln Asp Arg Asp Gly Thr Ile Ile His Leu
                    85                      90                      95

AAG TAC CCG CTG AAC TGC TCC GAT CCC ACT AGT GAG AGG TGG TAC CAT       336
Lys Tyr Pro Leu Asn Cys Ser Asp Pro Thr Ser Glu Arg Trp Tyr His
                    100                     105                     110

GGC CAC ATG TCT GGC GGG CAG GCA GAG ACG CTG CTG CAG GCC AAG GGC       384
Gly His Met Ser Gly Gly Gln Ala Glu Thr Leu Leu Gln Ala Lys Gly
                    115                     120                     125

GAG CCC TGG ACG TTT CTT GTG AAG GAG AGC CTC AGC CAG CCT GGA GAC       432
Glu Pro Trp Thr Phe Leu Val Lys Glu Ser Leu Ser Gln Pro Gly Asp
            130                     135                     140

TTC GTG CTT TCT GTG CTC AGT GAC CAG CCC AAG GCT GGC CCA GGC TCC       480
Phe Val Leu Ser Val Leu Ser Asp Gln Pro Lys Ala Gly Pro Gly Ser
145                     150                     155                     160

CCG CTC AGG GTC ACC CAC ATC AAG GTC ATG TGC GAG GGT GGA CGC TAC       528
Pro Leu Arg Val Thr His Ile Lys Val Met Cys Glu Gly Gly Arg Tyr
                    165                     170                     175

ACA GTG GGT GGT TTG GAG ACC TTC GAC AGC CTC ACG GAC CTG GTG GAG       576
Thr Val Gly Gly Leu Glu Thr Phe Asp Ser Leu Thr Asp Leu Val Glu
                    180                     185                     190

CAT TTC AAG AAG ACG GGG ATT GAG GAG GCC TCA GGC GCC TTT GTC TAC       624
His Phe Lys Lys Thr Gly Ile Glu Glu Ala Ser Gly Ala Phe Val Tyr
            195                     200                     205

CTG CGG CAG CCG TAC TAT GCC ACG AGG GTG AAT GCG GCT GAC ATT GAG       672
Leu Arg Gln Pro Tyr Tyr Ala Thr Arg Val Asn Ala Ala Asp Ile Glu
    210                     215                     220

AAC CGA GTG TTG GAA CTG AAC AAG AAG CAG GAG TCC GAG GAT ACA GCC       720
Asn Arg Val Leu Glu Leu Asn Lys Lys Gln Glu Ser Glu Asp Thr Ala
225                     230                     235                     240

AAG GCT GGC TTC TGG GAG GAG TTT GAG AGT TTG CAG AAG CAG GAG GTG       768
Lys Ala Gly Phe Trp Glu Glu Phe Glu Ser Leu Gln Lys Gln Glu Val
                    245                     250                     255

AAG AAC TTG CAC CAG CGT CTG GAA GGG CAA CGG CCA GAG AAC AAG GGC       816
Lys Asn Leu His Gln Arg Leu Glu Gly Gln Arg Pro Glu Asn Lys Gly
            260                     265                     270

AAG AAC CGC TAC AAG AAC ATT CTC CCC TTT GAC CAC AGC CGA GTG ATC       864
Lys Asn Arg Tyr Lys Asn Ile Leu Pro Phe Asp His Ser Arg Val Ile
        275                     280                     285

CTG CAG GGA CGG GAC AGT AAC ATC CCC GGG TCC GAC TAC ATC AAT GCC       912
Leu Gln Gly Arg Asp Ser Asn Ile Pro Gly Ser Asp Tyr Ile Asn Ala
            290                     295                     300

AAC TAC ATC AAG AAC CAG CTG CTA GGC CCT GAT GAG AAC GCT AAG ACC       960
Asn Tyr Ile Lys Asn Gln Leu Leu Gly Pro Asp Glu Asn Ala Lys Thr
305                     310                     315                     320

TAC ATC GCC AGC CAG GGC TGT CTG GAG GCC ACG GTC AAT GAC TTC TGG       1008
Tyr Ile Ala Ser Gln Gly Cys Leu Glu Ala Thr Val Asn Asp Phe Trp
                    325                     330                     335

CAG ATG GCG TGG CAG GAG AAC AGC CGT GTC ATC GTC ATG ACC ACC CGA       1056
```

```
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG      1104
Glu Val Glu Lys Gly Arg Asn Lys Cys Val Pro Tyr Trp Pro Glu Val
            355                 360                 365

GGC ATG CAG CGT GCT TAT GGG CCC TAC TCT GTG ACC AAC TGC GGG GAG      1152
Gly Met Gln Arg Ala Tyr Gly Pro Tyr Ser Val Thr Asn Cys Gly Glu
        370                 375                 380

CAT GAC ACA ACC GAA TAC AAA CTC CGT ACC TTA CAG GTC TCC CCG CTG      1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC      1248
Asp Asn Gly Asp Leu Ile Arg Glu Ile Trp His Tyr Gln Tyr Leu Ser
            405                 410                 415

TGG CCC GAC CAT GGG GTC CCC AGT GAG CCT GGG GGT GTC CTC AGC TTC      1296
Trp Pro Asp His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC      1344
Leu Asp Gln Ile Asn Gln Arg Gln Glu Ser Leu Pro His Ala Gly Pro
            435                 440                 445

ATC ATC GTG CAC TGC AGC GCC GGC ATC GGC CGC ACA GGC ACC ATC ATT      1392
Ile Ile Val His Cys Ser Ala Gly Ile Gly Arg Thr Gly Thr Ile Ile
            450                 455                 460

GTC ATC GAC ATG CTC ATG GAG AAC ATC TCC ACC AAG GGC CTG GAC TGT      1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG      1488
Asp Ile Asp Ile Gln Lys Thr Ile Gln Met Val Arg Ala Gln Arg Ser
            485                 490                 495

GGC ATG GTG CAG ACG GAG GCG CAG TAC AAG TTC ATC TAC GTG GCC ATC      1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG      1584
Ala Gln Phe Ile Glu Thr Thr Lys Lys Lys Leu Glu Val Leu Gln Ser
            515                 520                 525

CAG AAG GGC CAG GAG TCG GAG TAC GGG AAC ATC ACC TAT CCC CCA GCC      1632
Gln Lys Gly Gln Glu Ser Glu Tyr Gly Asn Ile Thr Tyr Pro Pro Ala
        530                 535                 540

ATG AAG AAT GCC CAT GCC AAG GCC TCC CGC ACC TCG TCC AAA CAC AAG      1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA      1728
Glu Asp Val Tyr Glu Asn Leu His Thr Lys Asn Lys Arg Glu Glu Lys
            565                 570                 575

GTG AAG AAG CAG CGG TCA GCA GAC AAG GAG AAG AGC AAG GGT TCC CTC      1776
Val Lys Lys Gln Arg Ser Ala Asp Lys Glu Lys Ser Lys Gly Ser Leu
            580                 585                 590

AAG AGG AAG TGA                                                       1788
Lys Arg Lys
        595

(2) INFORMATION FOR SEQ ID NO:42:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:42:
```

```
Met Val Arg Trp Phe His Arg Asp Leu Ser Gly Leu Asp Ala Glu Thr
  1               5                  10                  15

Leu Leu Lys Gly Arg Gly Val His Gly Ser Phe Leu Ala Lys Pro Ser
             20                  25                  30

Arg Lys Asn Gln Gly Asp Phe Ser Leu Ser Val Arg Val Gly Asp Gln
         35                  40                  45

Val Thr His Ile Arg Ile Gln Asn Ser Gly Asp Phe Tyr Asp Leu Tyr
     50                  55                  60

Gly Gly Glu Lys Phe Ala Thr Leu Thr Ala Leu Val Glu Tyr Tyr Thr
 65                  70                  75                  80

Gln Gln Gln Gly Val Val Gln Asp Arg Asp Gly Thr Ile Ile His Leu
                 85                  90                  95

Lys Tyr Pro Leu Asn Cys Ser Asp Pro Thr Ser Glu Arg Trp Tyr His
             100                 105                 110

Gly His Met Ser Gly Gly Gln Ala Glu Thr Leu Leu Gln Ala Lys Gly
             115                 120                 125

Glu Pro Trp Thr Phe Leu Val Lys Glu Ser Leu Ser Gln Pro Gly Asp
             130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                 165                 170                 175

Thr Val Gly Gly Leu Glu Thr Phe Asp Ser Leu Thr Asp Leu Val Glu
             180                 185                 190

His Phe Lys Lys Thr Gly Ile Glu Glu Ala Ser Gly Ala Phe Val Tyr
             195                 200                 205

Leu Arg Gln Pro Tyr Tyr Ala Thr Arg Val Asn Ala Ala Asp Ile Glu
     210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
             245                 250                 255

Lys Asn Leu His Gln Arg Leu Glu Gly Gln Arg Pro Glu Asn Lys Gly
             260                 265                 270

Lys Asn Arg Tyr Lys Asn Ile Leu Pro Phe Asp His Ser Arg Val Ile
             275                 280                 285

Leu Gln Gly Arg Asp Ser Asn Ile Pro Gly Ser Asp Tyr Ile Asn Ala
     290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
             325                 330                 335

Gln Met Ala Trp Gln Glu Asn Ser Arg Val Ile Val Met Thr Thr Arg
             340                 345                 350

Glu Val Glu Lys Gly Arg Asn Lys Cys Val Pro Tyr Trp Pro Glu Val
             355                 360                 365

Gly Met Gln Arg Ala Tyr Gly Pro Tyr Ser Val Thr Asn Cys Gly Glu
             370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
             405                 410                 415

Trp Pro Asp His Gly Val Pro Ser Glu Pro Gly Gly Val Leu Ser Phe
```

-continued

```
                       420                 425                 430
Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
    450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
            530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
        595
```

(2) INFORMATION FOR SEQ ID NO:43:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:43:

```
ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
1               5                  10                  15

CTC CTC AAG GGC CGA GGT GTC CAC GGT AGC TTC CTG GCT AAG CCC AGT      96
Leu Leu Lys Gly Arg Gly Val His Gly Ser Phe Leu Ala Lys Pro Ser
                20                  25                  30

CGC AAG AAC CAG GGT GAC TTC TCG CTC TCC GTC AGG GTG GGG GAT CAG     144
Arg Lys Asn Gln Gly Asp Phe Ser Leu Ser Val Arg Val Gly Asp Gln
            35                  40                  45

GTG ACC CAT ATT CGG ATC CAG AAC TCA GGG GCT TTC TAT GAC CTG TAT     192
Val Thr His Ile Arg Ile Gln Asn Ser Gly Ala Phe Tyr Asp Leu Tyr
        50                  55                  60

GGA GGG GAG AAG TTT GCG ACT CTG ACA GAG CTG GTG GAG TAC TAC ACT     240
Gly Gly Glu Lys Phe Ala Thr Leu Thr Glu Leu Val Glu Tyr Tyr Thr
65                  70                  75                  80

CAG CAG CAG GGT GTG GTG CAG GAC CGC GAC GGC ACC ATC ATC CAC CTC     288
Gln Gln Gln Gly Val Val Gln Asp Arg Asp Gly Thr Ile Ile His Leu
                85                  90                  95

AAG TAC CCG CTG AAC TGC TCC GAT CCC ACT AGT GAG AGG TGG TAC CAT     336
Lys Tyr Pro Leu Asn Cys Ser Asp Pro Thr Ser Glu Arg Trp Tyr His
                100                 105                 110

GGC CAC ATG TCT GGC GGG CAG GCA GAG ACG CTG CTG CAG GCC AAG GGC     384
```

-continued

```
Gly His Met Ser Gly Gly Gln Ala Glu Thr Leu Leu Gln Ala Lys Gly
        115                 120                 125

GAG CCC TGG ACG TTT CTT GTG AAG GAG AGC CTC AGC CAG CCT GGA GAC        432
Glu Pro Trp Thr Phe Leu Val Lys Glu Ser Leu Ser Gln Pro Gly Asp
    130                 135                 140

TTC GTG CTT TCT GTG CTC AGT GAC CAG CCC AAG GCT GGC CCA GGC TCC        480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC        528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG        576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC        624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG        672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC        720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG        768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC        816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC        864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC        912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC        960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG       1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA       1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG       1104
Glu Val Glu Lys Gly Arg Asn Lys Cys Val Pro Tyr Trp Pro Glu Val
        355                 360                 365

GGC ATG CAG CGT GCT TAT GGG CCC TAC TCT GTG ACC AAC TGC GGG GAG       1152
Gly Met Gln Arg Ala Tyr Gly Pro Tyr Ser Val Thr Asn Cys Gly Glu
    370                 375                 380

CAT GAC ACA ACC GAA TAC AAA CTC CGT ACC TTA CAG GTC TCC CCG CTG       1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC       1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC       1296
Trp Pro Asp His Gly Val Pro Ser Glu Pro Gly Gly Val Leu Ser Phe
            420                 425                 430
```

```
CTG GAC CAG ATC AAC CAG CGG CAG GAA AGT CTG CCT CAC GCA GGG CCC      1344
Leu Asp Gln Ile Asn Gln Arg Gln Glu Ser Leu Pro His Ala Gly Pro
        435                 440                 445

ATC ATC GTG CAC TCC AGC GCC GGC ATC GGC CGC ACA GGC ACC ATC ATT      1392
Ile Ile Val His Ser Ser Ala Gly Ile Gly Arg Thr Gly Thr Ile Ile
450                 455                 460

GTC ATC GAC ATG CTC ATG GAG AAC ATC TCC ACC AAG GGC CTG GAC TGT      1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG      1488
Asp Ile Asp Ile Gln Lys Thr Ile Gln Met Val Arg Ala Gln Arg Ser
            485                 490                 495

GGC ATG GTG CAG ACG GAG GCG CAG TAC AAG TTC ATC TAC GTG GCC ATC      1536
Gly Met Val Gln Thr Glu Ala Gln Tyr Lys Phe Ile Tyr Val Ala Ile
        500                 505                 510

GCC CAG TTC ATT GAA ACC ACT AAG AAG AAG CTG GAG GTC CTG CAG TCG      1584
Ala Gln Phe Ile Glu Thr Thr Lys Lys Lys Leu Glu Val Leu Gln Ser
        515                 520                 525

CAG AAG GGC CAG GAG TCG GAG TAC GGG AAC ATC ACC TAT CCC CCA GCC      1632
Gln Lys Gly Gln Glu Ser Glu Tyr Gly Asn Ile Thr Tyr Pro Pro Ala
    530                 535                 540

ATG AAG AAT GCC CAT GCC AAG GCC TCC CGC ACC TCG TCC AAA CAC AAG      1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA      1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC      1776
Val Lys Lys Gln Arg Ser Ala Asp Lys Glu Lys Ser Lys Gly Ser Leu
            580                 585                 590

AAG AGG AAG TGA                                                      1788
Lys Arg Lys
        595

(2) INFORMATION FOR SEQ ID NO:44:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:44:

Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Lys Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Ala Phe Tyr Asp Leu Tyr
        50                  55                  60

Gly Gly Glu Lys Phe Ala Thr Leu Thr Glu Leu Val Glu Tyr Tyr Thr
 65                 70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125
```

```
Glu Pro Trp Thr Phe Leu Val Lys Glu Ser Leu Ser Gln Pro Gly Asp
    130                 135                 140
Phe Val Leu Ser Val Leu Ser Asp Gln Pro Lys Ala Gly Pro Gly Ser
145                 150                 155                 160
Pro Leu Arg Val Thr His Ile Lys Val Met Cys Glu Gly Gly Arg Tyr
                165                 170                 175
Thr Val Gly Gly Leu Glu Thr Phe Asp Ser Leu Thr Asp Leu Val Glu
                180                 185                 190
His Phe Lys Lys Thr Gly Ile Glu Glu Ala Ser Gly Ala Phe Val Tyr
                195                 200                 205
Leu Arg Gln Pro Tyr Tyr Ala Thr Arg Val Asn Ala Ala Asp Ile Glu
    210                 215                 220
Asn Arg Val Leu Glu Leu Asn Lys Lys Gln Glu Ser Glu Asp Thr Ala
225                 230                 235                 240
Lys Ala Gly Phe Trp Glu Glu Phe Glu Ser Leu Gln Lys Gln Glu Val
                245                 250                 255
Lys Asn Leu His Gln Arg Leu Glu Gly Gln Arg Pro Glu Asn Lys Gly
                260                 265                 270
Lys Asn Arg Tyr Lys Asn Ile Leu Pro Phe Asp His Ser Arg Val Ile
                275                 280                 285
Leu Gln Gly Arg Asp Ser Asn Ile Pro Gly Ser Asp Tyr Ile Asn Ala
    290                 295                 300
Asn Tyr Ile Lys Asn Gln Leu Leu Gly Pro Asp Glu Asn Ala Lys Thr
305                 310                 315                 320
Tyr Ile Ala Ser Gln Gly Cys Leu Glu Ala Thr Val Asn Asp Phe Trp
                325                 330                 335
Gln Met Ala Trp Gln Glu Asn Ser Arg Val Ile Val Met Thr Thr Arg
                340                 345                 350
Glu Val Glu Lys Gly Arg Asn Lys Cys Val Pro Tyr Trp Pro Glu Val
                355                 360                 365
Gly Met Gln Arg Ala Tyr Gly Pro Tyr Ser Val Thr Asn Cys Gly Glu
    370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                405                 410                 415
Trp Pro Asp His Gly Val Pro Ser Glu Pro Gly Gly Val Leu Ser Phe
                420                 425                 430
Leu Asp Gln Ile Asn Gln Arg Gln Glu Ser Leu Pro His Ala Gly Pro
    435                 440                 445
Ile Ile Val His Ser Ser Ala Gly Ile Gly Arg Thr Gly Thr Ile Ile
450                 455                 460
Val Ile Asp Met Leu Met Glu Asn Ile Ser Thr Lys Gly Leu Asp Cys
465                 470                 475                 480
Asp Ile Asp Ile Gln Lys Thr Ile Gln Met Val Arg Ala Gln Arg Ser
                485                 490                 495
Gly Met Val Gln Thr Glu Ala Gln Tyr Lys Phe Ile Tyr Val Ala Ile
                500                 505                 510
Ala Gln Phe Ile Glu Thr Thr Lys Lys Lys Leu Glu Val Leu Gln Ser
    515                 520                 525
Gln Lys Gly Gln Glu Ser Glu Tyr Gly Asn Ile Thr Tyr Pro Pro Ala
    530                 535                 540
```

```
Met Lys Asn Ala His Ala Lys Ala Ser Arg Thr Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
                580                 585                 590

Lys Arg Lys
    595

(2) INFORMATION FOR SEQ ID NO:45:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:45:

ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
1               5                   10                  15

CTG CTC AAG GGC CGA GGT GTC CAC GGT AGC TTC CTG GCT AAG CCC AGT      96
Leu Leu Lys Gly Arg Gly Val His Gly Ser Phe Leu Ala Lys Pro Ser
                20                  25                  30

CGC AAG AAC CAG GGT GAC TTC TCG CTC TCC GTC AGG GTG GGG GAT CAG     144
Arg Lys Asn Gln Gly Asp Phe Ser Leu Ser Val Arg Val Gly Asp Gln
            35                  40                  45

GTG ACC CAT ATT CGG ATC CAG AAC TCA GGG GCT TTC TAT GAC CTG TAT     192
Val Thr His Ile Arg Ile Gln Asn Ser Gly Ala Phe Tyr Asp Leu Tyr
        50                  55                  60

GGA GGG GAG AAG TTT GCG ACT CTG ACA GAG CTG GTG GAG TAC TAC ACT     240
Gly Gly Glu Lys Phe Ala Thr Leu Thr Glu Leu Val Glu Tyr Tyr Thr
65                  70                  75                  80

CAG CAG CAG GGT GTG GTG CAG GAC CGC GAC GGC ACC ATC ATC CAC CTC     288
Gln Gln Gln Gly Val Val Gln Asp Arg Asp Gly Thr Ile Ile His Leu
                85                  90                  95

AAG TAC CCG CTG AAC TGC TCC GAT CCC ACT AGT GAG AGG TGG TAC CAT     336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC     384
Gly His Met Ser Gly Gly Gln Ala Glu Thr Leu Leu Gln Ala Lys Gly
        115                 120                 125

GAG CCC TGG ACG TTT CTT GTG AAG GAG AGC CTC AGC CAG CCT GGA GAC     432
Glu Pro Trp Thr Phe Leu Val Lys Glu Ser Leu Ser Gln Pro Gly Asp
130                 135                 140

TTC GTG CTT TCT GTG CTC AGT GAC CAG CCC AAG GCT GGC CCA GGC TCC     480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC     528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG     576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC     624
His Phe Lys Lys Thr Gly Ile Glu Glu Ala Ser Gly Ala Phe Val Tyr
        195                 200                 205
```

```
CTG CGG CAG CCG TAC TAT GCC ACG AGG GTG AAT GCG GCT GAC ATT GAG      672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC      720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG      768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC      816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC      864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC      912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC      960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG     1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA     1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG     1104
Glu Val Glu Lys Gly Arg Asn Lys Cys Val Pro Tyr Trp Pro Glu Val
        355                 360                 365

GGC ATG CAG CGT GCT TAT GGG CCC TAC TCT GTG ACC AAC TGC GGG GAG     1152
Gly Met Gln Arg Ala Tyr Gly Pro Tyr Ser Val Thr Asn Cys Gly Glu
    370                 375                 380

CAT GAC ACA ACC GAA TAC AAA CTC CGT ACC TTA CAG GTC TCC CCG CTG     1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC     1248
Asp Asn Gly Asp Leu Ile Arg Glu Ile Trp His Tyr Gln Tyr Leu Ser
                405                 410                 415

TGG CCC GCC CAT GGG GTC CCC AGT GAG CCT GGG GGT GTC CTC AGC TTC     1296
Trp Pro Ala His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC     1344
Leu Asp Gln Ile Asn Gln Arg Gln Glu Ser Leu Pro His Ala Gly Pro
        435                 440                 445

ATC ATC GTG CAC TGC AGC GCC GGC ATC GGC CGC ACA GGC ACC ATC ATT     1392
Ile Ile Val His Cys Ser Ala Gly Ile Gly Arg Thr Gly Thr Ile Ile
    450                 455                 460

GTC ATC GAC ATG CTC ATG GAG AAC ATC TCC ACC AAG GGC CTG GAC TGT     1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG     1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC     1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG     1584
Ala Gln Phe Ile Glu Thr Thr Lys Lys Lys Leu Glu Val Leu Gln Ser
        515                 520                 525
```

```
CAG AAG GGC CAG GAG TCG GAG TAC GGG AAC ATC ACC TAT CCC CCA GCC    1632
Gln Lys Gly Gln Glu Ser Glu Tyr Gly Asn Ile Thr Tyr Pro Pro Ala
        530                 535                 540

ATG AAG AAT GCC CAT GCC AAG GCC TCC CGC ACC TCG TCC AAA CAC AAG    1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA    1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC    1776
Val Lys Lys Gln Arg Ser Ala Asp Lys Glu Lys Ser Lys Gly Ser Leu
            580                 585                 590

AAG AGG AAG TGA                                                     1788
Lys Arg Lys
        595
```

(2) INFORMATION FOR SEQ ID NO:46:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:46:

```
Met Val Arg Trp Phe His Arg Asp Leu Ser Gly Leu Asp Ala Glu Thr
1               5                  10                  15

Leu Leu Lys Gly Arg Gly Val His Gly Ser Phe Leu Ala Lys Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Ala Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Lys Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
```

```
                    245                 250                 255
Lys Asn Leu His Gln Arg Leu Glu Gly Gln Arg Pro Glu Asn Lys Gly
                260                 265                 270

Lys Asn Arg Tyr Lys Asn Ile Leu Pro Phe Asp His Ser Arg Val Ile
            275                 280                 285

Leu Gln Gly Arg Asp Ser Asn Ile Pro Gly Ser Asp Tyr Ile Asn Ala
        290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
                340                 345                 350

Glu Val Glu Lys Gly Arg Asn Lys Cys Val Pro Tyr Trp Pro Glu Val
                355                 360                 365

Gly Met Gln Arg Ala Tyr Gly Pro Tyr Ser Val Thr Asn Cys Gly Glu
            370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Ala His Gly Val Pro Ser Glu Pro Gly Gly Val Leu Ser Phe
                420                 425                 430

Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
        450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
                500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
        530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
        595

(2) INFORMATION FOR SEQ ID NO:47:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
```

(B) LOCATION: 1..1785

(xi) SEQUENCE DESCRIPTION: SEQ ID NO:47:

```
ATG GTG AGG TGG TTT CAC CGA GAC CTC AGT GGG CTG GAT GCA GAG ACC        48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT AAG CCC AGT        96
Leu Leu Lys Gly Arg Gly Val His Gly Ser Phe Leu Ala Lys Pro Ser
             20                  25                  30

CGC AAG AAC CAG GGT GAC TTC TCG CTC TCC GTC AGG GTG GGG GAT CAG       144
Arg Lys Asn Gln Gly Asp Phe Ser Leu Ser Val Arg Val Gly Asp Gln
         35                  40                  45

GTG ACC CAT ATT CGG ATC CAG AAC TCA GGG GAT TTC TAT GAC CTG TAT       192
Val Thr His Ile Arg Ile Gln Asn Ser Gly Asp Phe Tyr Asp Leu Tyr
     50                  55                  60

GGA GGG GAG AAG TTT GCG ACT CTG ACA GCG CTG GTG GAG TAC TAC ACT       240
Gly Gly Glu Lys Phe Ala Thr Leu Thr Ala Leu Val Glu Tyr Tyr Thr
 65                  70                  75                  80

CAG CAG CAG GGT GTG GTG CAG GAC CGC GAC GGC ACC ATC ATC CAC CTC       288
Gln Gln Gln Gly Val Val Gln Asp Arg Asp Gly Thr Ile Ile His Leu
                 85                  90                  95

AAG TAC CCG CTG AAC TGC TCC GAT CCC ACT AGT GAG AGG TGG TAC CAT       336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC       384
Gly His Met Ser Gly Gly Gln Ala Glu Thr Leu Leu Gln Ala Lys Gly
        115                 120                 125

GAG CCC TGG ACG TTT CTT GTG AAG GAG AGC CTC AGC CAG CCT GGA GAC       432
Glu Pro Trp Thr Phe Leu Val Lys Glu Ser Leu Ser Gln Pro Gly Asp
    130                 135                 140

TTC GTG CTT TCT GTG CTC AGT GAC CAG CCC AAG GCT GGC CCA GGC TCC       480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC       528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG       576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC       624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG       672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC       720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG       768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC       816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC       864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC       912
Leu Gln Gly Arg Asp Ser Asn Ile Pro Gly Ser Asp Tyr Ile Asn Ala
    290                 295                 300
```

```
AAC TAC ATC AAG AAC CAG CTG CTA GGC CCT GAT GAG AAC GCT AAG ACC      960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG     1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA     1056
Gln Met Ala Trp Gln Glu Asn Ser Arg Val Ile Val Met Thr Thr Arg
                340                 345                 350

GAG GTG GAG AAA GGC CGG AAC AAA TGC GTC CCA TAC TGG CCC GAG GTG     1104
Glu Val Glu Lys Gly Arg Asn Lys Cys Val Pro Tyr Trp Pro Glu Val
            355                 360                 365

GGC ATG CAG CGT GCT TAT GGG CCC TAC TCT GTG ACC AAC TGC GGG GAG     1152
Gly Met Gln Arg Ala Tyr Gly Pro Tyr Ser Val Thr Asn Cys Gly Glu
        370                 375                 380

CAT GAC ACA ACC GAA TAC AAA CTC CGT ACC TTA CAG GTC TCC CCG CTG     1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC     1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC     1296
Trp Pro Asp His Gly Val Pro Ser Glu Pro Gly Gly Val Leu Ser Phe
                420                 425                 430

CTG GAC CAG ATC AAC CAG CGG CAG GAA AGT CTG CCT CAC GCA GGG CCC     1344
Leu Asp Gln Ile Asn Gln Arg Gln Glu Ser Leu Pro His Ala Gly Pro
                435                 440                 445

ATC ATC GTG CAC TCC AGC GCC GGC ATC GGC CGC ACA GGC ACC ATC ATT     1392
Ile Ile Val His Ser Ser Ala Gly Ile Gly Arg Thr Gly Thr Ile Ile
            450                 455                 460

GTC ATC GAC ATG CTC ATG GAG AAC ATC TCC ACC AAG GGC CTG GAC TGT     1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG     1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC     1536
Gly Met Val Gln Thr Glu Ala Gln Tyr Lys Phe Ile Tyr Val Ala Ile
                500                 505                 510

GCC CAG TTC ATT GAA ACC ACT AAG AAG AAG CTG GAG GTC CTG CAG TCG     1584
Ala Gln Phe Ile Glu Thr Thr Lys Lys Lys Leu Glu Val Leu Gln Ser
            515                 520                 525

CAG AAG GGC CAG GAG TCG GAG TAC GGG AAC ATC ACC TAT CCC CCA GCC     1632
Gln Lys Gly Gln Glu Ser Glu Tyr Gly Asn Ile Thr Tyr Pro Pro Ala
530                 535                 540

ATG AAG AAT GCC CAT GCC AAG GCC TCC CGC ACC TCG TCC AAA CAC AAG     1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA     1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC     1776
Val Lys Lys Gln Arg Ser Ala Asp Lys Glu Lys Ser Lys Gly Ser Leu
                580                 585                 590

AAG AGG AAG TGA                                                     1788
Lys Arg Lys
        595
```

(2) INFORMATION FOR SEQ ID NO:48:

(i) SEQUENCE CHARACTERISTICS:
    (A) LENGTH: 595 amino acids
    (B) TYPE: amino acid
    (D) TOPOLOGY: linear (ii) MOLECULE TYPE: protein (xi) SEQUENCE DESCRIPTION: SEQ ID NO:48:

```
Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Lys Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Ala Leu Val Glu Tyr Tyr Thr
65                  70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Lys Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
        355                 360                 365
```

```
Gly Met Gln Arg Ala Tyr Gly Pro Tyr Ser Val Thr Asn Cys Gly Glu
        370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
        435                 440                 445

Ile Ile Val His Ser Ser Ala Gly Ile Gly Arg Thr Gly Thr Ile Ile
    450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
    595

(2) INFORMATION FOR SEQ ID NO:49:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:49:

ATG GTG AGG TGG TTT CAC CGA GAC CTC AGT GGG CTG GAT GCA GAG ACC      48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT AAG CCC AGT      96
Leu Leu Lys Gly Arg Gly Val His Gly Ser Phe Leu Ala Lys Pro Ser
            20                  25                  30

CGC AAG AAC CAG GGT GAC TTC TCG CTC TCC GTC AGG GTG GGG GAT CAG     144
Arg Lys Asn Gln Gly Asp Phe Ser Leu Ser Val Arg Val Gly Asp Gln
        35                  40                  45

GTG ACC CAT ATT CGG ATC CAG AAC TCA GGG GAT TTC TAT GAC CTG TAT     192
Val Thr His Ile Arg Ile Gln Asn Ser Gly Asp Phe Tyr Asp Leu Tyr
     50                  55                  60

GGA GGG GAG AAG TTT GCG ACT CTG ACA GCG CTG GTG GAG TAC TAC ACT     240
Gly Gly Glu Lys Phe Ala Thr Leu Thr Ala Leu Val Glu Tyr Tyr Thr
 65                  70                  75                  80
```

-continued

```
CAG CAG CAG GGT GTG GTG CAG GAC CGC GAC GGC ACC ATC ATC CAC CTC      288
Gln Gln Gln Gly Val Val Gln Asp Arg Asp Gly Thr Ile Ile His Leu
                85                  90                  95

AAG TAC CCG CTG AAC TGC TCC GAT CCC ACT AGT GAG AGG TGG TAC CAT      336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC      384
Gly His Met Ser Gly Gly Gln Ala Glu Thr Leu Leu Gln Ala Lys Gly
        115                 120                 125

GAG CCC TGG ACG TTT CTT GTG AAG GAG AGC CTC AGC CAG CCT GGA GAC      432
Glu Pro Trp Thr Phe Leu Val Lys Glu Ser Leu Ser Gln Pro Gly Asp
    130                 135                 140

TTC GTG CTT TCT GTG CTC AGT GAC CAG CCC AAG GCT GGC CCA GGC TCC      480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC      528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG      576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC      624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG      672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC      720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG      768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC      816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC      864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC      912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC      960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG     1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA     1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG     1104
Glu Val Glu Lys Gly Arg Asn Lys Cys Val Pro Tyr Trp Pro Glu Val
        355                 360                 365

GGC ATG CAG CGT GCT TAT GGG CCC TAC TCT GTG ACC AAC TGC GGG GAG     1152
Gly Met Gln Arg Ala Tyr Gly Pro Tyr Ser Val Thr Asn Cys Gly Glu
    370                 375                 380

CAT GAC ACA ACC GAA TAC AAA CTC CGT ACC TTA CAG GTC TCC CCG CTG     1200
His Asp Thr Thr Glu Tyr Lys Leu Arg Thr Leu Gln Val Ser Pro Leu
```

```
                    385                 390                 395                 400
GAC AAT GGA GAC CTG ATT CGG GAG ATC TGG CAT TAC CAG TAC CTG AGC          1248
Asp Asn Gly Asp Leu Ile Arg Glu Ile Trp His Tyr Gln Tyr Leu Ser
                        405                 410                 415

TGG CCC GCC CAT GGG GTC CCC AGT GAG CCT GGG GGT GTC CTC AGC TTC          1296
Trp Pro Ala His Gly Val Pro Ser Glu Pro Gly Gly Val Leu Ser Phe
                420                 425                 430

CTG GAC CAG ATC AAC CAG CGG CAG GAA AGT CTG CCT CAC GCA GGG CCC          1344
Leu Asp Gln Ile Asn Gln Arg Gln Glu Ser Leu Pro His Ala Gly Pro
            435                 440                 445

ATC ATC GTG CAC TGC AGC GCC GGC ATC GGC CGC ACA GGC ACC ATC ATT          1392
Ile Ile Val His Cys Ser Ala Gly Ile Gly Arg Thr Gly Thr Ile Ile
        450                 455                 460

GTC ATC GAC ATG CTC ATG GAG AAC ATC TCC ACC AAG GGC CTG GAC TGT          1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG          1488
Asp Ile Asp Ile Gln Lys Thr Ile Gln Met Val Arg Ala Gln Arg Ser
                    485                 490                 495

GGC ATG GTG CAG ACG GAG GCG CAG TAC AAG TTC ATC TAC GTG GCC ATC          1536
Gly Met Val Gln Thr Glu Ala Gln Tyr Lys Phe Ile Tyr Val Ala Ile
                500                 505                 510

GCC CAG TTC ATT GAA ACC ACT AAG AAG AAG CTG GAG GTC CTG CAG TCG          1584
Ala Gln Phe Ile Glu Thr Thr Lys Lys Lys Leu Glu Val Leu Gln Ser
            515                 520                 525

CAG AAG GGC CAG GAG TCG GAG TAC GGG AAC ATC ACC TAT CCC CCA GCC          1632
Gln Lys Gly Gln Glu Ser Glu Tyr Gly Asn Ile Thr Tyr Pro Pro Ala
        530                 535                 540

ATG AAG AAT GCC CAT GCC AAG GCC TCC CGC ACC TCG TCC AAA CAC AAG          1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA          1728
Glu Asp Val Tyr Glu Asn Leu His Thr Lys Asn Lys Arg Glu Glu Lys
                    565                 570                 575

GTG AAG AAG CAG CGG TCA GCA GAC AAG GAG AAG AGC AAG GGT TCC CTC          1776
Val Lys Lys Gln Arg Ser Ala Asp Lys Glu Lys Ser Lys Gly Ser Leu
                580                 585                 590

AAG AGG AAG TGA                                                          1788
Lys Arg Lys
        595

(2) INFORMATION FOR SEQ ID NO:50:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:50:

Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Ala Lys Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Ala Leu Val Glu Tyr Tyr Thr
```

```
              65                  70                  75                  80
         Gln Gln Gln Gly Val Val Gln Asp Arg Asp Gly Thr Ile Ile His Leu
                         85                  90                  95
         Lys Tyr Pro Leu Asn Cys Ser Asp Pro Thr Ser Glu Arg Trp Tyr His
                     100                 105                 110
         Gly His Met Ser Gly Gly Gln Ala Glu Thr Leu Leu Gln Ala Lys Gly
                     115                 120                 125
         Glu Pro Trp Thr Phe Leu Val Lys Glu Ser Leu Ser Gln Pro Gly Asp
                     130                 135                 140
         Phe Val Leu Ser Val Leu Ser Asp Gln Pro Lys Ala Gly Pro Gly Ser
         145                 150                 155                 160
         Pro Leu Arg Val Thr His Ile Lys Val Met Cys Glu Gly Gly Arg Tyr
                         165                 170                 175
         Thr Val Gly Gly Leu Glu Thr Phe Asp Ser Leu Thr Asp Leu Val Glu
                     180                 185                 190
         His Phe Lys Lys Thr Gly Ile Glu Glu Ala Ser Gly Ala Phe Val Tyr
                     195                 200                 205
         Leu Arg Gln Pro Tyr Tyr Ala Thr Arg Val Asn Ala Ala Asp Ile Glu
             210                 215                 220
         Asn Arg Val Leu Glu Leu Asn Lys Lys Gln Glu Ser Glu Asp Thr Ala
         225                 230                 235                 240
         Lys Ala Gly Phe Trp Glu Glu Phe Glu Ser Leu Gln Lys Gln Glu Val
                         245                 250                 255
         Lys Asn Leu His Gln Arg Leu Glu Gly Gln Arg Pro Glu Asn Lys Gly
                     260                 265                 270
         Lys Asn Arg Tyr Lys Asn Ile Leu Pro Phe Asp His Ser Arg Val Ile
                     275                 280                 285
         Leu Gln Gly Arg Asp Ser Asn Ile Pro Gly Ser Asp Tyr Ile Asn Ala
             290                 295                 300
         Asn Tyr Ile Lys Asn Gln Leu Leu Gly Pro Asp Glu Asn Ala Lys Thr
         305                 310                 315                 320
         Tyr Ile Ala Ser Gln Gly Cys Leu Glu Ala Thr Val Asn Asp Phe Trp
                         325                 330                 335
         Gln Met Ala Trp Gln Glu Asn Ser Arg Val Ile Val Met Thr Thr Arg
                     340                 345                 350
         Glu Val Glu Lys Gly Arg Asn Lys Cys Val Pro Tyr Trp Pro Glu Val
                     355                 360                 365
         Gly Met Gln Arg Ala Tyr Gly Pro Tyr Ser Val Thr Asn Cys Gly Glu
                     370                 375                 380
         His Asp Thr Thr Glu Tyr Lys Leu Arg Thr Leu Gln Val Ser Pro Leu
         385                 390                 395                 400
         Asp Asn Gly Asp Leu Ile Arg Glu Ile Trp His Tyr Gln Tyr Leu Ser
                         405                 410                 415
         Trp Pro Ala His Gly Val Pro Ser Glu Pro Gly Gly Val Leu Ser Phe
                     420                 425                 430
         Leu Asp Gln Ile Asn Gln Arg Gln Glu Ser Leu Pro His Ala Gly Pro
                     435                 440                 445
         Ile Ile Val His Cys Ser Ala Gly Ile Gly Arg Thr Gly Thr Ile Ile
                     450                 455                 460
         Val Ile Asp Met Leu Met Glu Asn Ile Ser Thr Lys Gly Leu Asp Cys
         465                 470                 475                 480
         Asp Ile Asp Ile Gln Lys Thr Ile Gln Met Val Arg Ala Gln Arg Ser
                         485                 490                 495
```

```
Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
        595

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:51:

GGTCATAGTA AGCACTGTTC                                              20

(2) INFORMATION FOR SEQ ID NO:52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:52:

CGGAATTCAA CATGACATCG CGGAG                                        25

(2) INFORMATION FOR SEQ ID NO:53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:53:

GAACACTGGT GCTTACTATG ACC                                          23

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:54:

ATTAACCCTC ACTAAAG                                                 17

(2) INFORMATION FOR SEQ ID NO:55:

(i) SEQUENCE CHARACTERISTICS:
        (A) LENGTH: 21 base pairs
```

(B) TYPE: nucleic acid
            (C) STRANDEDNESS: single
            (D) TOPOLOGY: linear (xi) SEQUENCE DESCRIPTION: SEQ ID NO:55:

CTGGACCAAC GCAGCCAAAG T                                              21

(2) INFORMATION FOR SEQ ID NO:56:

(i) SEQUENCE CHARACTERISTICS:
            (A) LENGTH: 22 amino acids
            (B) TYPE: amino acid
            (C) STRANDEDNESS: single
            (D) TOPOLOGY: linear (xi) SEQUENCE DESCRIPTION: SEQ ID NO:56:

Cys Ala Cys Thr Thr Thr Gly Gly Cys Thr Gly Cys Gly Thr Thr Gly
1               5                   10                  15

Gly Thr Cys Cys Ala Gly
            20

(2) INFORMATION FOR SEQ ID NO:57:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:57:

CACGCCGTGG GCCGGCCAG                                                 19

(2) INFORMATION FOR SEQ ID NO:58:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:58:

CTGGCCGGCC CACGGCGTG                                                 19

(2) INFORMATION FOR SEQ ID NO:59:

(i) SEQUENCE CHARACTERISTICS:
            (A) LENGTH: 1788 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 1..1785

(xi) SEQUENCE DESCRIPTION: SEQ ID NO:59:

ATG GTG AGG TGG TTT CAC CGA GAC CTC AGT GGG CTG GAT GCA GAG ACC        48
Met Val Arg Trp Phe His Arg Asp Leu Ser Gly Leu Asp Ala Glu Thr
1               5                   10                  15

CTG CTC AAG GGC CGA GGT GTC CAC GGT AGC TTC CTG GCT CGG CCC AGT        96
Leu Leu Lys Gly Arg Gly Val His Gly Ser Phe Leu Ala Arg Pro Ser
            20                  25                  30

CGC AAG AAC CAG GGT GAC TTC TCG CTC TCC GTC AGG GTG GGG GAT CAG       144
Arg Lys Asn Gln Gly Asp Phe Ser Leu Ser Val Arg Val Gly Asp Gln
        35                  40                  45

GTG ACC CAT ATT CGG ATC CAG AAC TCA GGG CTT TAT GAC CTG TAT           192

-continued

```
Val Thr His Ile Arg Ile Gln Asn Ser Gly Ala Phe Tyr Asp Leu Tyr
 50                  55                  60

GGA GGG GAG AAG TTT GCG ACT CTG ACA GAG CTG GTG GAG TAC TAC ACT        240
Gly Gly Glu Lys Phe Ala Thr Leu Thr Glu Leu Val Glu Tyr Tyr Thr
 65                  70                  75                  80

CAG CAG CAG GGT GTG GTG CAG GAC CGC GAC GGC ACC ATC ATC CAC CTC        288
Gln Gln Gln Gly Val Val Gln Asp Arg Asp Gly Thr Ile Ile His Leu
                 85                  90                  95

AAG TAC CCG CTG AAC TGC TCC GAT CCC ACT AGT GAG AGG TGG TAC CAT        336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC        384
Gly His Met Ser Gly Gly Gln Ala Glu Thr Leu Leu Gln Ala Lys Gly
        115                 120                 125

GAG CCC TGG ACG TTT CTT GTG CGT GAG AGC CTC AGC CAG CCT GGA GAC        432
Glu Pro Trp Thr Phe Leu Val Arg Glu Ser Leu Ser Gln Pro Gly Asp
130                 135                 140

TTC GTG CTT TCT GTG CTC AGT GAC CAG CCC AAG GCT GGC CCA GGC TCC        480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC        528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG        576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC        624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG        672
Leu Arg Gln Pro Tyr Tyr Ala Thr Arg Val Asn Ala Ala Asp Ile Glu
210                 215                 220

AAC CGA GTG TTG GAA CTG AAC AAG AAG CAG GAG TCC GAG GAT ACA GCC        720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG        768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC        816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC        864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC        912
Leu Gln Gly Arg Asp Ser Asn Ile Pro Gly Ser Asp Tyr Ile Asn Ala
290                 295                 300

AAC TAC ATC AAG AAC CAG CTG CTA GGC CCT GAT GAG AAC GCT AAG ACC        960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG       1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA       1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG       1104
Glu Val Glu Lys Gly Arg Asn Lys Cys Val Pro Tyr Trp Pro Glu Val
        355                 360                 365
```

```
GGC ATG CAG CGT GCT TAT GGG CCC TAC TCT GTG ACC AAC TGC GGG GAG      1152
Gly Met Gln Arg Ala Tyr Gly Pro Tyr Ser Val Thr Asn Cys Gly Glu
        370                 375                 380

CAT GAC ACA ACC GAA TAC AAA CTC CGT ACC TTA CAG GTC TCC CCG CTG      1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC      1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC      1296
Trp Pro Asp His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC      1344
Leu Asp Gln Ile Asn Gln Arg Gln Glu Ser Leu Pro His Ala Gly Pro
                435                 440                 445

ATC ATC GTG CAC TGC AGC GCC GGC ATC GGC CGC ACA GGC ACC ATC ATT      1392
Ile Ile Val His Cys Ser Ala Gly Ile Gly Arg Thr Gly Thr Ile Ile
        450                 455                 460

GTC ATC GAC ATG CTC ATG GAG AAC ATC TCC ACC AAG GGC CTG GAC TGT      1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG      1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC      1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG      1584
Ala Gln Phe Ile Glu Thr Thr Lys Lys Lys Leu Glu Val Leu Gln Ser
            515                 520                 525

CAG AAG GGC CAG GAG TCG GAG TAC GGG AAC ATC ACC TAT CCC CCA GCC      1632
Gln Lys Gly Gln Glu Ser Glu Tyr Gly Asn Ile Thr Tyr Pro Pro Ala
530                 535                 540

ATG AAG AAT GCC CAT GCC AAG GCC TCC CGC ACC TCG TCC AAA CAC AAG      1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA      1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC      1776
Val Lys Lys Gln Arg Ser Ala Asp Lys Glu Lys Ser Lys Gly Ser Leu
            580                 585                 590

AAG AGG AAG TGA                                                      1788
Lys Arg Lys
595
```

(2) INFORMATION FOR SEQ ID NO:60:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:60:

```
Met Val Arg Trp Phe His Arg Asp Leu Ser Gly Leu Asp Ala Glu Thr
1               5                  10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
```

-continued

```
                35                  40                  45
Val Thr His Ile Arg Ile Gln Asn Ser Gly Ala Phe Tyr Asp Leu Tyr
         50                  55                  60
Gly Gly Glu Lys Phe Ala Thr Leu Thr Glu Leu Val Glu Tyr Tyr Thr
 65                  70                  75                  80
Gln Gln Gln Gly Val Val Gln Asp Arg Asp Gly Thr Ile Ile His Leu
                 85                  90                  95
Lys Tyr Pro Leu Asn Cys Ser Asp Pro Thr Ser Glu Arg Trp Tyr His
            100                 105                 110
Gly His Met Ser Gly Gln Ala Glu Thr Leu Leu Gln Ala Lys Gly
            115                 120                 125
Glu Pro Trp Thr Phe Leu Val Arg Glu Ser Leu Ser Gln Pro Gly Asp
        130                 135                 140
Phe Val Leu Ser Val Leu Ser Asp Gln Pro Lys Ala Gly Pro Gly Ser
145                 150                 155                 160
Pro Leu Arg Val Thr His Ile Lys Val Met Cys Glu Gly Gly Arg Tyr
                165                 170                 175
Thr Val Gly Gly Leu Glu Thr Phe Asp Ser Leu Thr Asp Leu Val Glu
            180                 185                 190
His Phe Lys Lys Thr Gly Ile Glu Glu Ala Ser Gly Ala Phe Val Tyr
            195                 200                 205
Leu Arg Gln Pro Tyr Tyr Ala Thr Arg Val Asn Ala Ala Asp Ile Glu
    210                 215                 220
Asn Arg Val Leu Glu Leu Asn Lys Lys Gln Glu Ser Glu Asp Thr Ala
225                 230                 235                 240
Lys Ala Gly Phe Trp Glu Glu Phe Glu Ser Leu Gln Lys Gln Glu Val
                245                 250                 255
Lys Asn Leu His Gln Arg Leu Glu Gly Gln Arg Pro Glu Asn Lys Gly
            260                 265                 270
Lys Asn Arg Tyr Lys Asn Ile Leu Pro Phe Asp His Ser Arg Val Ile
            275                 280                 285
Leu Gln Gly Arg Asp Ser Asn Ile Pro Gly Ser Asp Tyr Ile Asn Ala
    290                 295                 300
Asn Tyr Ile Lys Asn Gln Leu Leu Gly Pro Asp Glu Asn Ala Lys Thr
305                 310                 315                 320
Tyr Ile Ala Ser Gln Gly Cys Leu Glu Ala Thr Val Asn Asp Phe Trp
                325                 330                 335
Gln Met Ala Trp Gln Glu Asn Ser Arg Val Ile Val Met Thr Thr Arg
            340                 345                 350
Glu Val Glu Lys Gly Arg Asn Lys Cys Val Pro Tyr Trp Pro Glu Val
            355                 360                 365
Gly Met Gln Arg Ala Tyr Gly Pro Tyr Ser Val Thr Asn Cys Gly Glu
    370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                405                 410                 415
Trp Pro Asp His Gly Val Pro Ser Glu Pro Gly Gly Val Leu Ser Phe
            420                 425                 430
Leu Asp Gln Ile Asn Gln Arg Gln Glu Ser Leu Pro His Ala Gly Pro
            435                 440                 445
Ile Ile Val His Cys Ser Ala Gly Ile Gly Arg Thr Gly Thr Ile Ile
    450                 455                 460
```

```
Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Lys His Lys
545                 550                 555                 560

Glu Asp Val Tyr Glu Asn Leu His Thr Lys Asn Lys Arg Glu Glu Lys
            565                 570                 575

Val Lys Lys Gln Arg Ser Ala Asp Lys Glu Lys Ser Lys Gly Ser Leu
            580                 585                 590

Lys Arg Lys
        595
```

(2) INFORMATION FOR SEQ ID NO:61:

(i) SEQUENCE CHARACTERISTICS:
        (A) LENGTH: 1788 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1785

(xi) SEQUENCE DESCRIPTION: SEQ ID NO:61:

```
ATG GTG AGG TGG TTT CAC CGA GAC CTC AGT GGG CTG GAT GCA GAG ACC        48
Met Val Arg Trp Phe His Arg Asp Leu Ser Gly Leu Asp Ala Glu Thr
 1               5                  10                  15

CTG CTC AAG GGC CGA GGT GTC CAC GGT AGC TTC CTG GCT CGG CCC AGT        96
Leu Leu Lys Gly Arg Gly Val His Gly Ser Phe Leu Ala Arg Pro Ser
                20                  25                  30

CGC AAG AAC CAG GGT GAC TTC TCG CTC TCC GTC AGG GTG GGG GAT CAG       144
Arg Lys Asn Gln Gly Asp Phe Ser Leu Ser Val Arg Val Gly Asp Gln
            35                  40                  45

GTG ACC CAT ATT CGG ATC CAG AAC TCA GGG GAT TTC TAT GAC CTG TAT       192
Val Thr His Ile Arg Ile Gln Asn Ser Gly Asp Phe Tyr Asp Leu Tyr
     50                  55                  60

GGA GGG GAG AAG TTT GCG ACT CTG ACA GCG CTG GTG GAG TAC TAC ACT       240
Gly Gly Glu Lys Phe Ala Thr Leu Thr Ala Leu Val Glu Tyr Tyr Thr
 65                  70                  75                  80

CAG CAG CAG GGT GTG GTG CAG GAC CGC GAC GGC ACC ATC ATC CAC CTC       288
Gln Gln Gln Gly Val Val Gln Asp Arg Asp Gly Thr Ile Ile His Leu
                 85                  90                  95

AAG TAC CCG CTG AAC TGC TCC GAT CCC ACT AGT GAG AGG TGG TAC CAT       336
Lys Tyr Pro Leu Asn Cys Ser Asp Pro Thr Ser Glu Arg Trp Tyr His
            100                 105                 110

GGC CAC ATG TCT GGC GGG CAG GCA GAG ACG CTG CTG CAG GCC AAG GGC       384
Gly His Met Ser Gly Gly Gln Ala Glu Thr Leu Leu Gln Ala Lys Gly
        115                 120                 125

GAG CCC TGG ACG TTT CTT GTG CGT GAG AGC CTC AGC CAG CCT GGA GAC       432
Glu Pro Trp Thr Phe Leu Val Arg Glu Ser Leu Ser Gln Pro Gly Asp
    130                 135                 140
```

```
TTC GTG CTT TCT GTG CTC AGT GAC CAG CCC AAG GCT GGC CCA GGC TCC    480
Phe Val Leu Ser Val Leu Ser Asp Gln Pro Lys Ala Gly Pro Gly Ser
145                 150                 155                 160

CCG CTC AGG GTC ACC CAC ATC AAG GTC ATG TGC GAG GGT GGA CGC TAC    528
Pro Leu Arg Val Thr His Ile Lys Val Met Cys Glu Gly Gly Arg Tyr
                165                 170                 175

ACA GTG GGT GGT TTG GAG ACC TTC GAC AGC CTC ACG GAC CTG GTG GAG    576
Thr Val Gly Gly Leu Glu Thr Phe Asp Ser Leu Thr Asp Leu Val Glu
            180                 185                 190

CAT TTC AAG AAG ACG GGG ATT GAG GAG GCC TCA GGC GCC TTT GTC TAC    624
His Phe Lys Lys Thr Gly Ile Glu Glu Ala Ser Gly Ala Phe Val Tyr
        195                 200                 205

CTG CGG CAG CCG TAC TAT GCC ACG AGG GTG AAT GCG GCT GAC ATT GAG    672
Leu Arg Gln Pro Tyr Tyr Ala Thr Arg Val Asn Ala Ala Asp Ile Glu
    210                 215                 220

AAC CGA GTG TTG GAA CTG AAC AAG AAG CAG GAG TCC GAG GAT ACA GCC    720
Asn Arg Val Leu Glu Leu Asn Lys Lys Gln Glu Ser Glu Asp Thr Ala
225                 230                 235                 240

AAG GCT GGC TTC TGG GAG GAG TTT GAG AGT TTG CAG AAG CAG GAG GTG    768
Lys Ala Gly Phe Trp Glu Glu Phe Glu Ser Leu Gln Lys Gln Glu Val
                245                 250                 255

AAG AAC TTG CAC CAG CGT CTG GAA GGG CAA CGG CCA GAG AAC AAG GGC    816
Lys Asn Leu His Gln Arg Leu Glu Gly Gln Arg Pro Glu Asn Lys Gly
            260                 265                 270

AAG AAC CGC TAC AAG AAC ATT CTC CCC TTT GAC CAC AGC CGA GTG ATC    864
Lys Asn Arg Tyr Lys Asn Ile Leu Pro Phe Asp His Ser Arg Val Ile
        275                 280                 285

CTG CAG GGA CGG GAC AGT AAC ATC CCC GGG TCC GAC TAC ATC AAT GCC    912
Leu Gln Gly Arg Asp Ser Asn Ile Pro Gly Ser Asp Tyr Ile Asn Ala
    290                 295                 300

AAC TAC ATC AAG AAC CAG CTG CTA GGC CCT GAT GAG AAC GCT AAG ACC    960
Asn Tyr Ile Lys Asn Gln Leu Leu Gly Pro Asp Glu Asn Ala Lys Thr
305                 310                 315                 320

TAC ATC GCC AGC CAG GGC TGT CTG GAG GCC ACG GTC AAT GAC TTC TGG   1008
Tyr Ile Ala Ser Gln Gly Cys Leu Glu Ala Thr Val Asn Asp Phe Trp
                325                 330                 335

CAG ATG GCG TGG CAG GAG AAC AGC CGT GTC ATC GTC ATG ACC ACC CGA   1056
Gln Met Ala Trp Gln Glu Asn Ser Arg Val Ile Val Met Thr Thr Arg
            340                 345                 350

GAG GTG GAG AAA GGC CGG AAC AAA TGC GTC CCA TAC TGG CCC GAG GTG   1104
Glu Val Glu Lys Gly Arg Asn Lys Cys Val Pro Tyr Trp Pro Glu Val
        355                 360                 365

GGC ATG CAG CGT GCT TAT GGG CCC TAC TCT GTG ACC AAC TGC GGG GAG   1152
Gly Met Gln Arg Ala Tyr Gly Pro Tyr Ser Val Thr Asn Cys Gly Glu
    370                 375                 380

CAT GAC ACA ACC GAA TAC AAA CTC CGT ACC TTA CAG GTC TCC CCG CTG   1200
His Asp Thr Thr Glu Tyr Lys Leu Arg Thr Leu Gln Val Ser Pro Leu
385                 390                 395                 400

GAC AAT GGA GAC CTG ATT CGG GAG ATC TGG CAT TAC CAG TAC CTG AGC   1248
Asp Asn Gly Asp Leu Ile Arg Glu Ile Trp His Tyr Gln Tyr Leu Ser
                405                 410                 415

TGG CCC GAC CAT GGG GTC CCC AGT GAG CCT GGG GGT GTC CTC AGC TTC   1296
Trp Pro Asp His Gly Val Pro Ser Glu Pro Gly Gly Val Leu Ser Phe
            420                 425                 430

CTG GAC CAG ATC AAC CAG CGG CAG GAA AGT CTG CCT CAC GCA GGG CCC   1344
Leu Asp Gln Ile Asn Gln Arg Gln Glu Ser Leu Pro His Ala Gly Pro
        435                 440                 445

ATC ATC GTG CAC TGC AGC GCC GGC ATC GGC CGC ACA GGC ACC ATC ATT   1392
Ile Ile Val His Cys Ser Ala Gly Ile Gly Arg Thr Gly Thr Ile Ile
    450                 455                 460
```

```
GTC ATC GAC ATG CTC ATG GAG AAC ATC TCC ACC AAG GGC CTG GAC TGT      1440
Val Ile Asp Met Leu Met Glu Asn Ile Ser Thr Lys Gly Leu Asp Cys
465                 470                 475                 480

GAC ATT GAC ATC CAG AAG ACC ATC CAG ATG GTG CGG GCG CAG CGC TCG      1488
Asp Ile Asp Ile Gln Lys Thr Ile Gln Met Val Arg Ala Gln Arg Ser
                485                 490                 495

GGC ATG GTG CAG ACG GAG GCG CAG TAC AAG TTC ATC TAC GTG GCC ATC      1536
Gly Met Val Gln Thr Glu Ala Gln Tyr Lys Phe Ile Tyr Val Ala Ile
            500                 505                 510

GCC CAG TTC ATT GAA ACC ACT AAG AAG AAG CTG GAG GTC CTG CAG TCG      1584
Ala Gln Phe Ile Glu Thr Thr Lys Lys Lys Leu Glu Val Leu Gln Ser
        515                 520                 525

CAG AAG GGC CAG GAG TCG GAG TAC GGG AAC ATC ACC TAT CCC CCA GCC      1632
Gln Lys Gly Gln Glu Ser Glu Tyr Gly Asn Ile Thr Tyr Pro Pro Ala
    530                 535                 540

ATG AAG AAT GCC CAT GCC AAG GCC TCC CGC ACC TCG TCC AAA CAC AAG      1680
Met Lys Asn Ala His Ala Lys Ala Ser Arg Thr Ser Ser Lys His Lys
545                 550                 555                 560

GAG GAT GTG TAT GAG AAC CTG CAC ACT AAG AAC AAG AGG GAG GAG AAA      1728
Glu Asp Val Tyr Glu Asn Leu His Thr Lys Asn Lys Arg Glu Glu Lys
                565                 570                 575

GTG AAG AAG CAG CGG TCA GCA GAC AAG GAG AAG AGC AAG GGT TCC CTC      1776
Val Lys Lys Gln Arg Ser Ala Asp Lys Glu Lys Ser Lys Gly Ser Leu
            580                 585                 590

AAG AGG AAG TGA                                                      1788
Lys Arg Lys
        595

(2) INFORMATION FOR SEQ ID NO:62:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:62:

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Ala Leu Val Glu Tyr Tyr Thr
65                  70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160
```

-continued

```
Pro Leu Arg Val Thr His Ile Lys Val Met Cys Glu Gly Gly Arg Tyr
            165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
            195                 200                 205

Leu Arg Gln Pro Tyr Tyr Ala Thr Arg Val Asn Ala Ala Asp Ile Glu
            210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
            245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
            275                 280                 285

Leu Gln Gly Arg Asp Ser Asn Ile Pro Gly Ser Asp Tyr Ile Asn Ala
            290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
            325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
            355                 360                 365

Gly Met Gln Arg Ala Tyr Gly Pro Tyr Ser Val Thr Asn Cys Gly Glu
            370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
            405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
            435                 440                 445

Ile Ile Val His Cys Ser Ala Gly Ile Gly Arg Thr Gly Thr Ile Ile
450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
            515                 520                 525

Gln Lys Gly Gln Glu Ser Glu Tyr Gly Asn Ile Thr Tyr Pro Pro Ala
            530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
            565                 570                 575

Val Lys Lys Gln Arg Ser Ala Asp Lys Glu Lys Ser Lys Gly Ser Leu
```

```
                   580                 585                 590
Lys Arg Lys
        595

(2) INFORMATION FOR SEQ ID NO:63:

(i) SEQUENCE CHARACTERISTICS:
        (A) LENGTH: 524 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
```

```
                    325                 330                 335
Thr Val Asn Asp Phe Trp Arg Met Val Phe Gln Glu Asn Ser Arg Val
                340                 345                 350

Ile Val Met Thr Thr Lys Glu Val Glu Arg Gly Lys Ser Lys Cys Val
                355                 360                 365

Lys Tyr Trp Pro Asp Glu Tyr Ala Leu Lys Glu Tyr Gly Val Met Arg
            370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Met
                405                 410                 415

Gln Tyr His Phe Arg Thr Trp Pro Asp His Gly Val Pro Ser Asp Pro
                420                 425                 430

Gly Gly Val Leu Asp Phe Leu Glu Glu Val His His Lys Gln Glu Ser
                435                 440                 445

Ile Met Asp Ala Gly Pro Val Val His Cys Ser Ala Gly Ile Gly
                450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
                500                 505                 510

Phe Ile Tyr Met Ala Val Gln His Tyr Ile Glu Thr
                515                 520

(2) INFORMATION FOR SEQ ID NO:64:

(i) SEQUENCE CHARACTERISTICS:
        (A) LENGTH: 518 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
                20                  25                  30

Arg Lys Asn Gln Gly Asp Phe Ser Leu Ser Val Arg Val Gly Asp Gln
            35                  40                  45

Val Thr His Ile Arg Ile Gln Asn Ser Gly Asp Phe Tyr Asp Leu Tyr
        50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
                100                 105                 110

Gly His Met Ser Gly Gly Gln Ala Glu Thr Leu Leu Gln Ala Lys Gly
            115                 120                 125

Glu Pro Trp Thr Phe Leu Val Arg Glu Ser Leu Ser Gln Pro Gly Asp
        130                 135                 140

Phe Val Leu Ser Val Leu Ser Asp Gln Pro Lys Ala Gly Pro Gly Ser
```

```
                145                 150                 155                 160
Pro Leu Arg Val Thr His Ile Lys Val Met Cys Glu Gly Gly Arg Tyr
                    165                 170                 175
Thr Val Gly Gly Leu Glu Thr Phe Asp Ser Leu Thr Asp Leu Val Glu
                180                 185                 190
His Phe Lys Lys Thr Gly Ile Glu Glu Ala Ser Gly Ala Phe Val Tyr
                195                 200                 205
Leu Arg Gln Pro Tyr Tyr Ala Thr Arg Val Asn Ala Ala Asp Ile Glu
                210                 215                 220
Asn Arg Val Leu Glu Leu Asn Lys Lys Gln Glu Ser Glu Asp Thr Ala
225                 230                 235                 240
Lys Ala Gly Phe Trp Glu Glu Phe Glu Ser Leu Gln Lys Gln Glu Val
                    245                 250                 255
Lys Asn Leu His Gln Arg Leu Glu Gly Gln Arg Pro Glu Asn Lys Gly
                260                 265                 270
Lys Asn Arg Tyr Lys Asn Ile Leu Pro Phe Asp His Ser Arg Val Ile
                275                 280                 285
Leu Gln Gly Arg Asp Ser Asn Ile Pro Gly Ser Asp Tyr Ile Asn Ala
                290                 295                 300
Asn Tyr Ile Lys Asn Gln Leu Leu Gly Pro Asp Glu Asn Ala Lys Thr
305                 310                 315                 320
Tyr Ile Ala Ser Gln Gly Cys Leu Glu Ala Thr Val Asn Asp Phe Trp
                    325                 330                 335
Gln Met Ala Trp Gln Glu Asn Ser Arg Val Ile Val Met Thr Thr Arg
                340                 345                 350
Glu Val Glu Lys Gly Arg Asn Lys Cys Val Pro Tyr Trp Pro Glu Val
                355                 360                 365
Gly Met Gln Arg Ala Tyr Gly Pro Tyr Ser Val Thr Asn Cys Gly Glu
                370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                    405                 410                 415
Trp Pro Asp His Gly Val Pro Ser Glu Pro Gly Gly Val Leu Ser Phe
                420                 425                 430
Leu Asp Gln Ile Asn Gln Arg Gln Glu Ser Leu Pro His Ala Gly Pro
                435                 440                 445
Ile Ile Val His Cys Ser Ala Gly Ile Gly Arg Thr Gly Thr Ile Ile
                450                 455                 460
Val Ile Asp Met Leu Met Glu Asn Ile Ser Thr Lys Gly Leu Asp Cys
465                 470                 475                 480
Asp Ile Asp Ile Gln Lys Thr Ile Gln Met Val Arg Ala Gln Arg Ser
                    485                 490                 495
Gly Met Val Gln Thr Glu Ala Gln Tyr Lys Phe Ile Tyr Val Ala Ile
                500                 505                 510
Ala Gln Phe Ile Glu Thr
            515

(2) INFORMATION FOR SEQ ID NO:65:

(i) SEQUENCE CHARACTERISTICS:
        (A) LENGTH: 491 amino acids
        (B) TYPE: amino acid
        (C) STRANDEDNESS: single
        (D) TOPOLOGY: linear
```

(ii) MOLECULE TYPE: peptide (ix) FEATURE:
    (A) NAME/KEY: Modified-site
    (B) LOCATION: 292
    (D) OTHER INFORMATION: /product= "158 amino acid insert in the PTO domain"

(xi) SEQUENCE DESCRIPTION: SEQ ID NO:65:

```
Met Ser Ser Arg Arg Trp Phe His Pro Thr Ile Ser Gly Ile Glu Ala
1               5                   10                  15

Glu Lys Leu Leu Gln Glu Gln Gly Phe Asp Gly Ser Phe Leu Ala Arg
            20                  25                  30

Leu Ser Ser Asn Pro Gly Ala Phe Thr Leu Ser Val Arg Arg Gly
        35                  40                  45

Asn Glu Val Thr His Ile Lys Ile Gln Asn Asn Gly Asp Phe Phe Asp
    50                  55                  60

Leu Tyr Gly Gly Glu Lys Phe Ala Thr Leu Pro Glu Leu Val Gln Tyr
65              70                  75                  80

Tyr Met Glu Asn Gly Glu Leu Lys Glu Lys Asn Gly Ile Ala Ile Glu
                85                  90                  95

Leu Lys Gln Pro Leu Ile Cys Ala Glu Pro Thr Thr Glu Arg Trp Phe
            100                 105                 110

His Gly Asn Leu Ser Gly Lys Glu Ala Glu Lys Leu Ile Leu Glu Arg
            115                 120                 125

Gly Lys Asn Gly Ser Phe Leu Val Arg Glu Ser Gln Ser Lys Pro Gly
130                 135                 140

Asp Phe Val Leu Ser Val Arg Thr Asp Asp Lys Val Thr His Val Met
145                 150                 155                 160

Ile Arg Trp Gln Asp Lys Lys Tyr Asp Val Gly Gly Gly Glu Ser Phe
                165                 170                 175

Gly Thr Leu Ser Glu Leu Ile Asp His Tyr Lys Arg Asn Pro Met Val
            180                 185                 190

Glu Thr Cys Gly Thr Val Val His Leu Arg Gln Pro Phe Asn Ala Thr
            195                 200                 205

Arg Ile Thr Ala Ala Gly Ile Asn Ala Arg Val Glu Gln Leu Val Lys
210                 215                 220

Gly Gly Phe Trp Glu Glu Phe Glu Ser Leu Gln Gln Asp Ser Arg Asp
225                 230                 235                 240

Thr Phe Ser Arg Asn Glu Gly Tyr Lys Gln Glu Asn Arg Leu Lys Asn
                245                 250                 255

Arg Tyr Arg Asn Ile Leu Pro Tyr Asp His Thr Arg Val Lys Leu Leu
            260                 265                 270

Asp Val Glu His Ser Val Ala Gly Ala Glu Tyr Ile Asn Ala Asn Tyr
            275                 280                 285

Ile Arg Leu Xaa Gly Cys Leu Leu Thr Gln Gln Val Asn Thr Val Thr
290                 295                 300

Asp Phe Trp Asn Met Val Trp Gln Glu Asn Thr Arg Val Ile Val Met
305                 310                 315                 320

Thr Thr Lys Glu Tyr Glu Arg Gly Lys Glu Lys Cys Ala Arg Tyr Trp
                325                 330                 335

Pro Asp Glu Gly Arg Ser Glu Gln Phe Gly His Ala Arg Ile Gln Cys
            340                 345                 350

Val Ser Glu Asn Ser Thr Ser Asp Tyr Thr Leu Arg Glu Phe Leu Val
            355                 360                 365
```

```
Ser Trp Arg Asp Gln Pro Ala Arg Arg Ile Phe His Tyr His Phe Gln
    370                 375                 380
Val Trp Pro Asp His Gly Val Pro Ala Asp Pro Gly Cys Val Leu Asn
385                 390                 395                 400
Phe Leu Gln Asp Val Asn Thr Arg Gln Ser His Leu Ala Gln Ala Gly
                405                 410                 415
Glu Lys Pro Gly Pro Ile Cys Val His Cys Ser Ala Gly Ile Gly Arg
                420                 425                 430
Thr Gly Thr Phe Ile Val Ile Asp Met Ile Leu Asp Gln Ile Val Arg
                435                 440                 445
Asn Gly Leu Asp Thr Glu Ile Asp Ile Gln Arg Thr Ile Gln Met Val
    450                 455                 460
Arg Ser Gln Arg Ser Gly Leu Val Gln Thr Glu Ala Gln Tyr Lys Phe
465                 470                 475                 480
Val Tyr Tyr Ala Val Gln His Tyr Ile Gln Thr
                485                 490

(2) INFORMATION FOR SEQ ID NO:66:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Met Thr Ser Arg Arg Trp Phe His Pro Asn Ile Thr Gly Val Glu Ala
1               5                   10                  15
Glu Asn Leu Leu Leu Thr Arg Gly Val Asp Gly Ser Phe Leu Ala Arg
            20                  25                  30
Pro Ser Lys Ser Asn Pro Gly Asp Phe Thr Leu Ser Val Arg Arg Asn
        35                  40                  45
Gly Ala Val Thr His Ile Lys Ile Gln Asn Thr Gly Asp Tyr Tyr Asp
    50                  55                  60
Leu Tyr Gly Gly Glu Lys Phe Ala Thr Leu Ala Glu Leu Val Gln Tyr
65                  70                  75                  80
Tyr Met Glu His His Gly Gln Leu Lys Glu Lys Asn Gly Asp Val Ile
                85                  90                  95
Glu Leu Lys Tyr Pro Leu Asn Cys
                100

(2) INFORMATION FOR SEQ ID NO:67:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Met Val Arg Trp Phe His Arg Asp Leu Ser Gly Leu Asp Ala Glu Thr
1               5                   10                  15
Leu Leu Lys Gly Arg Gly Val His Gly Ser Phe Leu Ala Arg Pro Ser
            20                  25                  30
Arg Lys Asn Gln Gly Asp Phe Ser Leu Ser Val Arg Val Gly Asp Gln
```

```
                35                  40                  45
Val Thr His Ile Arg Ile Gln Asn Ser Gly Asp Phe Tyr Asp Leu Tyr
 50                  55                  60

Gly Gly Glu Lys Phe Ala Thr Leu Thr Glu Leu Val Glu Tyr Tyr Thr
 65                  70                  75                  80

Gln Gln Gln Gly Val Val Gln Asp Arg Asp Gly Thr Ile Ile His Leu
                 85                  90                  95

Lys Tyr Pro Leu Ile Cys
                100
```

(2) INFORMATION FOR SEQ ID NO:68:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

```
Met Ser Ser Arg Arg Trp Phe His Pro Thr Ile Ser Gly Ile Glu Ala
 1               5                  10                  15

Glu Lys Leu Leu Gln Glu Gln Gly Phe Asp Gly Ser Phe Leu Ala Arg
                20                  25                  30

Leu Ser Ser Asn Pro Gly Ala Phe Thr Leu Ser Val Arg Arg Gly
                35                  40                  45

Asn Glu Val Thr His Ile Lys Ile Gln Asn Asn Gly Asp Phe Phe Asp
 50                  55                  60

Leu Tyr Gly Gly Glu Lys Phe Ala Thr Leu Pro Glu Leu Val Gln Tyr
 65                  70                  75                  80

Tyr Met Glu Asn Gly Glu Leu Lys Glu Lys Asn Gly Gln Ala Ile Glu
                 85                  90                  95

Leu Lys Gln Pro Leu Ile Cys
                100
```

(2) INFORMATION FOR SEQ ID NO:69:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "phosphorylated"

(ix) FEATURE:
        (A) NAME/KEY: Modified-site
        (B) LOCATION: 28
        (D) OTHER INFORMATION: /product= "Phosphorylated"

(xi) SEQUENCE DESCRIPTION: SEQ ID NO:69:

```
Asp Ile Thr Tyr Ala Asp Leu Asn Leu Pro Lys Gly Lys Lys Pro Ala
 1               5                  10                  15

Pro Gln Ala Ala Glu Pro Asn Asn His Thr Glu Tyr Ala Ser Ile Gln
                20                  25                  30

Thr Ser
```

-continued (2) INFORMATION FOR SEQ ID NO:70:

```
    (i) SEQUENCE CHARACTERISTICS:
         (A) LENGTH: 12 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 5
         (D) OTHER INFORMATION: /note= "5 = any amino acid"

(ix) FEATURE:
         (A) NAME/KEY: Modified-site
         (B) LOCATION: 8
         (D) OTHER INFORMATION: /note= "8 = any amino acid"

(ix) FEATURE:
         (A) NAME/KEY: Modified-site
         (B) LOCATION: 9
         (D) OTHER INFORMATION: /note= "9 = any amino acid"

(ix) FEATURE:
         (A) NAME/KEY: Modified-site
         (B) LOCATION: 11
         (D) OTHER INFORMATION: /note= "11 can be serine or
             threonine"

(xi) SEQUENCE DESCRIPTION: SEQ ID NO:70:

Ile Val His Cys Xaa Ala Gly Xaa Xaa Arg Xaa Gly
1               5                   10
```